US012453782B2

(12) United States Patent
Postel et al.

(10) Patent No.: US 12,453,782 B2
(45) **Date of Patent: *Oct. 28, 2025**

(54) ANTIBODY-OLIGONUCLEOTIDE CONJUGATE

(71) Applicant: Sapreme Technologies B.V., Bilthoven (NL)

(72) Inventors: Ruben Postel, Utrecht (NL); Hendrik Fuchs, Berlin (DE)

(73) Assignee: Sapreme Technologies B.V., Bilthoven (NL)

( * ) Notice: Subject to any disclaimer, the term of this patent is extended or adjusted under 35 U.S.C. 154(b) by 872 days.

This patent is subject to a terminal disclaimer.

(21) Appl. No.: 17/312,019

(22) PCT Filed: Dec. 9, 2019

(86) PCT No.: PCT/EP2019/084242

§ 371 (c)(1),
(2) Date: Jun. 9, 2021

(87) PCT Pub. No.: WO2020/126620

PCT Pub. Date: Jun. 25, 2020

(65) Prior Publication Data

US 2022/0313834 A1 Oct. 6, 2022

(30) Foreign Application Priority Data

Dec. 21, 2018 (NL) .................................... 2022283
Jul. 10, 2019 (NL) .................................... 2023468
Jul. 25, 2019 (NL) .................................... 2023568

(51) Int. Cl.

| | |
|---|---|
| ***A61K 47/68*** | (2017.01) |
| ***A61K 47/54*** | (2017.01) |
| ***A61K 47/55*** | (2017.01) |
| ***A61K 47/59*** | (2017.01) |
| ***A61K 47/60*** | (2017.01) |
| ***A61K 47/64*** | (2017.01) |
| ***A61P 35/00*** | (2006.01) |
| ***C12N 15/113*** | (2010.01) |

(52) U.S. Cl.

CPC ........ *A61K 47/6885* (2017.08); *A61K 47/549* (2017.08); *A61K 47/55* (2017.08); *A61K 47/554* (2017.08); *A61K 47/593* (2017.08); *A61K 47/595* (2017.08); *A61K 47/60* (2017.08); *A61K 47/6415* (2017.08); *A61K 47/642* (2017.08); *A61K 47/643* (2017.08); *A61K 47/6807* (2017.08); *A61K 47/6817* (2017.08); *A61K 47/6825* (2017.08); *A61K 47/6845* (2017.08); *A61K 47/6849* (2017.08); *A61K 47/6851* (2017.08); *A61K 47/6855* (2017.08); *A61K 47/6857* (2017.08); *A61K 47/6889* (2017.08); *A61P 35/00* (2018.01); *C12N 15/113* (2013.01); *C12N 2310/11* (2013.01); *C12N 2320/30* (2013.01)

(58) Field of Classification Search

None

See application file for complete search history.

(56) References Cited

U.S. PATENT DOCUMENTS 4,432,969 A 2/1984 Batchelor
5,583,112 A 12/1996 Kensil et al.

(Continued)

FOREIGN PATENT DOCUMENTS

CA 2290646 A1 11/1998
CN 101563090 A 10/2009

(Continued)

OTHER PUBLICATIONS

Fernandez-Tejada et al., Design, synthesis, and immunologic evaluation of vaccine adjuvant conjugates based on QS-21 and tucaresol, Bioorganic & Medicinal Chemistry 22 (2014) 5917-5923, Publication Date: Sep. 17, 2014 (Year: 2914).*

Barr et al., ISCOMs and other saponin based adjuvants, Advanced Drug Delivery Reviews 32, 247-271, Publication Year: 1998 (Year: 1998).*

Muniyan, A., Ravi, K., Mohan, U. et al. Characterization and in vitro antibacterial activity of saponin-conjugated silver nanoparticles against bacteria that cause burn wound infection. World J Microbiol Biotechnol 33, 147 (2017). https://doi.org/10.1007/s11274-017-2309-3. XP036261778.

(Continued)

*Primary Examiner* — Peter J Reddig
*Assistant Examiner* — Cheng Lu
(74) *Attorney, Agent, or Firm* — N.V. Nederlandsch Octrooibureau

(57) ABSTRACT

The invention relates to a ligand-effector moiety provided with at least one saponin and antibody-effector moiety provided with at least one saponin. An aspect of the invention is a composition comprising the ligand-effector moiety provided with at least one saponin or the antibody-effector moiety provided with at least one saponin of the invention. The invention also relates to an antibody-drug conjugate comprising covalently linked saponin and to an antibody-oligonucleotide conjugate comprising covalently linked saponin. An aspect of the invention relates to a pharmaceutical composition comprising the ligand-effector moiety provided with at least one saponin or the antibody-effector moiety provided with at least one saponin of the invention, and optionally further comprising a pharmaceutically acceptable excipient. The invention also relates to the ligand-effector moiety provided with at least one saponin or the antibody-effector moiety provided with at least one saponin, for use as a medicament. The invention also relates to the ligand-effector moiety provided with at least one saponin or the antibody-effector moiety provided with at least one saponin of the invention for use in the treatment or prophylaxis of a cancer.

17 Claims, 84 Drawing Sheets

Specification includes a Sequence Listing.

(56) References Cited

U.S. PATENT DOCUMENTS

| | | | |
|---|---|---|---|
| 5,591,829 | A | 1/1997 | Matsushita |
| 6,262,029 | B1 | 7/2001 | Press et al. |
| 8,795,648 | B2 | 8/2014 | Ding et al. |
| 9,125,835 | B2 | 9/2015 | Sinko |
| 9,127,088 | B2 | 9/2015 | Dimarchi |
| 2004/0242502 | A1 | 12/2004 | Marciani |
| 2008/0064762 | A1 | 3/2008 | Fuchs |
| 2012/0183621 | A1 | 7/2012 | Sinko |
| 2015/0023989 | A1 | 1/2015 | Lerchen |
| 2016/0045595 | A1 | 2/2016 | Morein et al. |

FOREIGN PATENT DOCUMENTS

| | | | |
|---|---|---|---|
| CN | 102652836 | A | 9/2012 |
| CN | 106892957 | A | 6/2017 |
| WO | WO9305789 | A1 | 4/1993 |
| WO | 94/01118 | A1 | 1/1994 |
| WO | WO 9640263 | A2 | 12/1996 |
| WO | 98/52573 | | 11/1998 |
| WO | 03/069997 | A1 | 8/2003 |
| WO | 2004/092329 | A2 | 10/2004 |
| WO | 2006/005581 | A2 | 1/2006 |
| WO | 2006/033766 | | 3/2006 |
| WO | 2009/117828 | | 10/2009 |
| WO | WO2011054811 | A1 | 5/2011 |
| WO | 2014/082065 | A1 | 5/2014 |
| WO | 2015/157595 | A1 | 10/2015 |
| WO | 2015/184451 | A1 | 12/2015 |
| WO | WO 2017214339 | A1 | 12/2017 |
| WO | 2018/057031 | A1 | 3/2018 |
| WO | 2019/011914 | A1 | 1/2019 |
| WO | 2020/126064 | A1 | 6/2020 |
| WO | 2020/126600 | A1 | 6/2020 |
| WO | 2020/126604 | A1 | 6/2020 |
| WO | 2020/126609 | A2 | 6/2020 |
| WO | 2020/126610 | A1 | 6/2020 |
| WO | 2020/126620 | A2 | 6/2020 |
| WO | 2020/126627 | A1 | 6/2020 |
| WO | 2021/014019 | A1 | 1/2021 |
| WO | WO 2022055352 | A1 | 3/2022 |

OTHER PUBLICATIONS

Craven RA, Vasudev NS, Banks RE. Proteomics and the search for biomarkers for renal cancer. Clin Biochem. Apr. 2013;46(6):456-65. doi: 10.1016/j.clinbiochem.2012.11.029. Epub Dec. 7, 2012. PMID: 23228867.

Hill, K.E., Clawson, S.A., Rose, J.W. et al. Cerebellar Purkinje cells incorporate immunoglobulins and immunotoxins in vitro: implications for human neurological disease and immunotherapeutics. J Neuroinflammation 6, 31 (2009). https://doi.org/10.1186/1742-2094-6-31.

Makoto Saito et al: "3[beta]-Hydroxysterol [Delta]24-Reductase on the Surface of Hepatitis C Virus-Related Hepatocellular Carcinoma Cells Can Be a Target for Molecular Targeting Therapy", PLOS One, vol. 10, No. 4, Apr. 13, 2015, p. e0124197.

Dai Xiaojun: "Anti-metastatic Efficacy of Traditional Chinese Medicine (TCM) Ginsenoside Conjugated to a VEFGR-3 Antibody on Human Gastric Cancer in an Orthotopic Mouse Model", Anticancer Research—International Journal of Cancer Research and Treatment, vol. 37, No. 3, Mar. 17, 2017, pp. 979-986.

Roger Gilabert-Oriol et al: "Modified Trastuzumab and Cetuximab Mediate Efficient Toxin Delivery While Retaining Antibody-Dependent Cell-Mediated Cytotoxicity in Target Cells", Molecular Pharmaceutics, vol. 10, No. 11,Oct. 7, 2013, pp. 4347-4357.

Gilabert-Oriol Roger et al: "Dianthin-30 or gelonin versus monomethyl auristatin E, each configured with an anti-calcitonin receptor antibody, are differentially potent in vitro in high-grade glioma cell lines derived from glioblastoma", Cancer Immunology, Immunotherapy, NIH Author Manuscript, Springer, Berlin/Heidelberg vol. 66, No. 9, May 13, 2017, pp. 1217-1228.

Roger Gilabert-Oriol et al: "Combinatorial approach to increase efficacy of Cetuximab, Panitumumab and Trastuzumab by dianthin conjugation and co-application of SOI 861", Biochemical Pharmacology, vol. 97, No. 3, Oct. 1, 2015, pp. 247-255.

Thakur Mayank et al: "High-speed countercurrent chromatographic recovery and off-line electrospray ionization mass spectrometry profiling of bisdesmodic saponins fromSaponaria officinalispossessing synergistic toxicity enhancing properties on targeted antitumor toxins", Journal of Chromatography B: Biomedical Sciences & Applications, Elsevier, Amsterdam, NL, vol. 955, Feb. 19, 2014, pp. 1-9.

Hendrik Fuchs et al: "Glycosylated Triterpenoids as Endosomal Escape Enhancers in Targeted Tumor Therapies", Biomedicines, vol. 5, No. 2, Mar. 29, 2017, p. 14.

Ekladious Iriny et al: "Polymer-drug conjugate therapeutics: advances, insights and prospects", Nature Reviews. Drug Discovery, Nature Publishing Group, GB, vol. 18, No. 4, Dec. 12, 2018, pp. 273-294.

Alexander Weng et al: "The toxin component of targeted anti-tumor toxins determines their efficacy increase by saponins", Molecular Oncology, Elsevier, vol. 6, No. 3, Jan. 12, 2012, pp. 323-332.

Cheenu Bhargava et al: "Targeted dianthin is a powerful toxin to treat pancreatic carcinoma when applied in combination with the glycosylated triterpene SOI 861", Molecular Oncology, vol. 11, No. 11, Sep. 15, 2017, pp. 1527-1543.

Pastan I et al: "Immunotoxins", Cell, Elsevier, Amsterdam, NL, vol. 47, No. 5, Dec. 5, 1986 (Dec. 5, 1986), pp. 641-648.

Endoscape, a clinically applicable non-viral gene delivery technology—Sapreme Technologies.

Alexandre Lancelot et al., "DNA Transfection to Mesenchymal Stem Cells Using a Novel Type of Pseudodendrimer Based on 2,2-Bis(hydroxymethyl)propionic Acid", Bioconjugate Chemistry, Mar. 13, 2017, vol. 28, No. 4, p. 1135-1150, DOI: 10.1021/acs.bioconjchem.7b00037.

Böttger, S. Untersuchungen zur synergistischen Zytotoxizität zwischen Saponinen und Ribosomen inaktivierenden Proteinen Typ I. Ph.D. Thesis, Freie Universität Berlin, Berlin, Germany, 2013.

Sama S et al. Structure-Activity Relationship of Transfection-Modulating Saponins—A Pursuit for the Optimal Gene Trafficker Planta Med 2019; 85: 513-518.

Böttger, S.; Westhof, E.; Siems, K.; Melzig, M.F. Structure-activity relationships of saponins enhancing the cytotoxicity of ribosome-inactivating proteins type I (RIP-I). Toxicon 2013, 73, 144-150.

Bachran, C.; Sutherland, M.; Heisler, I.; Hebestreit, P.; Melzig, M.F.; Fuchs, H. The saponin-mediated enhanced uptake of targeted saporin-based drugs is strongly dependent on the saponin structure. Exp Biol Med (Maywood) 2006, 231, 412-420.

Dirk C. van Setten, Gerrit van de Werken, Gijsbert Zomer and Gideon F. A. Kersten, Glycosyl Compositions and Structural Characteristics of the Potential Immuno-adjuvant Active Saponins in the Quillaja saponaria Molina Extract Quil A, Rapid Communications in Mass Spectrometry, vol. 9,660-666 (1995).

Gilabert-Oriol, Roger—Doctoral Thesis—2014 Development of a platform technology for enhanced endo/lysosomal escape of targeted toxins by structurally specific oleanane saponins.

Emirda-ğ-Öztürk, S., Karayildirim, T., Çapci-Karagöz, A., Alankuş-Çalişkan, Ö., Özmen, A. and Poyrazoğlu-Çoban, E., 2014. Synthesis, antimicrobial and cytotoxic activities, and structure-activity relationships of gypsogenin derivatives against human cancer cells. European Journal of Medicinal Chemistry, 82, pp. 565-573.

Ruzicka, L. and Wirz, W., 1940. Zur Kenntnis der Triterpene. (Mitteilung) Umwandlung der α—Boswellinsäure in β—Amyrin. Helvetica Chimica Acta, 23(1), pp. 132-135.

Ruzicka, L. and Schellenberg, H., 1937. Polyterpene und Polyterpenoide CXX. Umwandlung der Oleanolsäure in β—Amyrin und Erythro—diol. Helvetica Chimica Acta, 20(1), pp. 1553-1556.

Elliott, D.F., Kon, G.A. and Soper, H.R., 1940. 113. Sapogenins. Part VII. The structure of quillaic acid and its relation to echinocystic acid. Journal of the Chemical Society (Resumed), pp. 612-617.

Xu, R., Fazio, G.C. and Matsuda, S.P., 2004. On the origins of triterpenoid skeletal diversity. Phytochemistry, 65(3), pp. 261-291.

(56) References Cited

OTHER PUBLICATIONS

Frøkiær, H., Sørensen, H., Sørensen, J.C. and Sørensen, S., 1995. Optimization of hapten-protein conjugation by high-performance capillary electrophoresis. Journal of Chromatography A, 717(1-2), pp. 75-81.
Zdraveva, P., Pencheva, I., Popova, P., Ionkova, I. and Krasteva, I., 2015. Production of saponarin in in vitro cultures of *Gypsophila* species. Journal of Chemical and Pharmaceutical Research, 7(1), pp. 829-832.
Van Dongen, M.A., Dougherty, C.A. and Banaszak Holl, M.M., 2014. Multivalent polymers for drug delivery and imaging: the challenges of conjugation. Biomacromolecules, 15(9), pp. 3215-3234.
Wang, D., Zhao, T., Zhu, X., Yan, D. and Wang, W., 2015. Bioapplications of hyperbranched polymers. Chemical Society Reviews, 44(12), pp. 4023-4071.
Martin, J.T., Douaisi, M., Arsiwala, A., Arha, M. and Kane, R.S., 2018. Synthesis of multivalent polymer-aptamer conjugates with enhanced inhibitory potency. International Journal of Nanomedicine, pp. 5249-5253.
Borchmann, D.E., Carberry, T.P. and Weck, M., 2014. "Bio"-macromolecules: polymer-protein conjugates as emerging scaffolds for therapeutics. Macromolecular rapid communications, 35(1), pp. 27-43.
Bande et al, Synthesis and Characterization of Chitosan-Saponin Nanoparticle for Application in Plasmid DNA Delivery, Journal of Nanomaterials 2015, 1, 1-8. XP55608212.
Zhang et al. Designing polymers with sugar-based advantages for bioactive delivery applications, Journal of Controlled Release 2015, 219, 355-368. XP029303679.
Fuchs et al, Glycosylated Triterpenoids as Endosomal Escape Enhancers in Targeted Tumor Therapies 2017, Biomedicines, 5:14.
Sama, "Untersuchung von Saponinen als neuartige Verstarker der Transfektion", Dissertation Freie Universität Berlin, Jun. 6, 2018, XP55608281.
Endoscape, project ID 825790: "A clinically applicable non-viral gene delivery technology", Dec. 10, 2018, XP055608309.
Ekladious et al, Polymer-drug conjugate therapeutics: advances, insights and prospects, Nature Reviews Drug Discovery 2019, 18, 273-294. XP036746043.
Pola et al: "Click chemistry as a powerful and chemoselective tool for the attachment of targeting ligands to polymer drug carriers", Polymer Chemistry, vol. 5(4), Jan. 1, 2014, pp. 1340-1350, XP55608257.
Chopdey et al, Glycyrrhizin Conjugated Dendrimer and Multi-Walled Carbon Nanotubes for Liver Specific Delivery of Doxorubicin, Journal of Nanoscience and Nanotechnology 2015, 15, 1088-1100. XP009519412.
Pulido et al, Controlling Multivalency and Multimodality: Up to Pentamodal Dendritic Platforms Based on Diethylenetriaminepentaacetic Acid Cores, Organic Letters 2014, 16:1318-1321, XP055677348.
Steffensen et al, Synthesis and manipulation of orthogonally protected dendrimers: building blocks for library synthesis, Angewandte Chemie, International Edition in English 2004, 5177-5180. XP002469507.
Saito et al, 3β-hydroxysterol δ24-reductase on the surface of hepatitis C virus-related hepatocellular carcinoma cells can be a target for molecular targeting therapy, PLoS One 2015, 10:e0124197. XP055677053.
Dai et al, Anti-metastatic Efficacy of Traditional Chinese Medicine (TCM) Ginsenoside Conjugated to a VEFGR-3 Antibody on Human Gastric Cancer in an Orthotopic Mouse Model, Anticancer Research 2017, 37, 979-986. XP055677059.
Gilabert-Oriol et al, Modified trastuzumab and cetuximab mediate efficient toxin delivery while retaining antibody-dependent cell-mediated cytotoxicity in target cells. Molecular pharmaceutics 2013, 10, 4347-4357. XP055677122.
Gilabert-Oriol et al, Dianthin-30 or gelonin versus monomethyl auristatin E, each configured with an anti-calcitonin receptor antibody, are differentially potent in vitro in high-grade glioma cell lines derived from glioblastoma, Cancer Immunology Immunotherapy 2017, 66, 1217-1228. XP036309505.
Gilabert-Oriol et al, Combinatorial approach to increase efficacy of Cetuximab, Panitumumab and Trastuzumab by dianthin conjugation and co-application of SO1861. Biochemical pharmacology 2015, 97, 247-255.
Thakur et al, High-speed countercurrent chromatographic recovery and off-line electrospray ionization mass spectrometry profiling of bisdesmodic saponins from Saponaria officinalis possessing synergistic toxicity enhancing properties on targeted antitumor toxins. Journal of Chromatography. B, Analytical technologies in the biomedical and life sciences 2014, 955-956, 1-9. XP028830726.
Pastan et al, Immunotoxins, Cell 1986, 47, 641-648.
Flavell et al, Gypsophila saponins significantly augment the cytotoxicity of saporin-based anti-CD19,-CD22, -CD38 and -CD71 immunotoxins in human leukemia and lymphoma, Cancer Research 2011, 71: 767. XP055677116.
Delmas et al, How to prepare and stabilize very small nanoemulsions, Langmuir 2011, 27, 1683-1692.
Verstraeten et al, The activity of the saponin ginsenoside Rh2 is enhanced by the interaction with membrane sphingomyelin but depressed by cholesterol. Scientific Reports 2019, 9:7285, doi: 10.1038/s41598-019-43674-w. XP055700637.
Weng et al, The toxin component of targeted antitumor toxins determines their efficacy increase by saponins. Molecular oncology 2012, 6, 323-332. XP028508748.
Holmes et al, Triterpenoid saponin augmention of saporin-based immunotoxin cytotoxicity for human leukaemia and lymphoma cells is partially immunospecific and target molecule dependent. Immunopharmacology and immunotoxicology 2015, 37, 42-55.
Bhargava et al,Targeted dianthin is a powerful toxin to treat pancreatic carcinoma when applied in combination with the glycosylated triterpene SO1861, Molecular Oncology 2017,11, 1527-1543.
Emirdağ-Öztürk et al, Synthesis, characterization and in vitro anti-neoplastic activity of gypsogenin derivatives. Bioorganic Chemistry 2014, 53, 15-23.
Carpino et al, The uronium/guanidinium Peptide coupling reagents: finally the true uronium salts. Angewandte Chemie (International Edition in English) 2002, 41, 441-445.
Ambekar et al, Synthesis of heterobifunctional crosslinking reagents: omega-(N-Maleimido)-alkanoic acid hydrazides. Indian Journal of Chemistry 1996, 3, 184-186.
Kensil et al, Structural and Immunological Characterization of the Vaccine Adjuvant QS-21. Vaccine Design 1995, 6, 525-541.
Dennler et al, Antibody Conjugates: From Heterogeneous Populations to Defined Reagents. Antibodies 2015, 4, 197-224.
Jeon et al, Evaluation of Saponin Loaded Gellan Gum Hydrogel Scaffold for Cartilage Regeneration. Macromolecular Research 2018, 26, 724-729.
Fernández-Tejada et al, Design, synthesis, and immunologic evaluation of vaccine adjuvant conjugates based on QS-21 and tucaresol. Bioorganic & medicinal chemistry 2014, 22, 5917-5923.
Gilabert-Oriol et al, Immunotoxins constructed with ribosome-inactivating proteins and their enhancers: a lethal cocktail with tumor specific efficacy. Current Pharmaceutical Design 2014, 20, 6584-6643.
Weng et al, Saponins modulate the intracellular trafficking of protein toxins. Journal of Controlled Release 2012, 164, 74-86.
Frøkiær et al, High-performance capillary electrophoresis for characterization of hapten-protein conjugates used for production of antibodies against soyasaponin I. Journal of Chromatography A 1994, 680, 437-445.
Dai et al, Bioluminescence imaging evaluation of the inhibitory effect of Ginsenoside Rg3 immune-nanoemulsion (VRIN)on nude mice bearing gastric cancer cell lines. Journal of Yangzhou University (Agricultural and Life Science Edition) 2014, 35, 12-14.
Chetankumar et al, A Comprehensive Approach to Mapping the Interacting Surfaces of Murine Amphotropic and Feline Subgroup B Leukemia Viruses with Their Cell Surface Receptors, Journal of Virology, vol. 74, No. 1, Jan. 1, 2000 (Jan. 1, 2000), pp. 237-244, XP055688498.

(56) References Cited

OTHER PUBLICATIONS

Alvarez-Salas et al, Nucleic Acids as Therapeutic Agents, Current Topics in Medicinal Chemistry, vol. 8, No. 15, Oct. 1, 2008 (Oct. 1, 2008), pp. 1379-1404, XP055302276, NL ISSN: 1568-0266, DOI: 10.2174/156802608786141133.

Mathiyalagan et al, Protopanaxadiol aglycone ginsenosidepolyethylene glycol conjugates: synthesis, physicochemical characterizations, and in vitro studies, Artificial Cells, Nanomedicine and Biotechnology, vol. 44, No. 8, Nov. 5, 2015 (Nov. 5, 2015), pp. 1803-1809, XP055677258, ISSN:2169-1401, DOI: 10.3109/21691401.2015.1105236.

Thakur et al, Macromolecular interactions of triterpenoids and targeted toxins: Role of saponins charge, , vol. 61,Jul. 22, 2013 (Jul. 22, 2013), pp. 285-294, XP028729266, ISSN: 0141-8130, DOI: 10.1016/J.IJBIOMAC.2013.07.008.

Thakur et al, Real time monitoring of the cell viability during treatment with tumor-targeted toxins and saponins using impedance measurement, Biosensors and Bioelectronics, vol. 35, No. 1,Mar. 13, 2012 (Mar. 13, 2012), pp. 503-506, XP028482572.

Weng et al, A Simple Method for Isolation of Gypsophila Saponins for the Combined Application of Targeted Toxins and Saponins in Tumor Therapy, Planta Medica, vol. 75, No. 13, May 18, 2009 (May 18, 2009), pp. 1421-1422, XP055428871, ISSN: 0032-0943, DOI: 10.1055/S0029-1185706.

Bachran et al, The distribution of saponins in vivo affects their synergy with chimeric toxins against tumours expressing human epidermal growth factor receptors in mice, British Journal of Pharmacology, vol. 159, No. 2, Jan. 26, 2010 (Jan. 26, 2010), pp. 345-352, XP055677872, ISSN: 0007-1188, DOI: 10.1111/j.1476-5381.2009.00543.x.

Bhargava et al, Combination therapy of a targeted toxin with SOI 861, A shooting star in the world of pancreatic carcinoma, Naunyn-Schmiedeberg's Archives of Pharmacology, vol. 389, No. 1, Suppl. 1,405, Feb. 2016 (Feb. 2016), p. S96, XP035867017.

Flavell et al, Systematic Comparison of Anti-CD22 Single-chain Fusion Toxin Contructs Containing Saporin or PE40 Produced in Different Microbial Expression Systems, 8th Fabisch-Symposium, 3rd Targeted Tumor Therapies, Berlin 2012, Mar. 23, 2012 (Mar. 23, 2012), pp. 14-15, XP055679073.

Bachran et al, Enhancers of Endosomal Escape for Improved Targeted Drug Delivery, 8th Fabisch-Symposium, 3rd Targeted Tumor Therapies, Berlin 2012, Mar. 23, 2012 (Mar. 23, 2012), pp. 36-37, XP055679037, Retrieved from the Internet: URL:https://www.charite.de/fabish/AbstractsText.html [retrieved on Mar. 24, 2020].

Weng et al, Therapeutic Potential of a Combinatorial Anti-tumor Therapy: Role of the Toxin Moiety, 8th Fabisch-Symposium, 3rd Targeted Tumor Therapies, Berlin 2012, Mar. 23, 2012 (Mar. 23, 2012), pp. 52-53, XP055679033, Retrieved from the Internet: URL:https://fabisch.charite.de/ [retrieved on Mar. 24, 2020].

Balasubramanya, Antibody conjugation, Mater Methods 2018, 8, 2670, XP055700616.

Gwak et al, Production of ginsenoside aglycone (protopanaxatriol) and male sterility of transgenic tobacco co-overexpressing three Panax ginseng genes: PgDDS, CYP716A47, and CYP716A53v2. Journal of Ginseng Research 2019, 43, 261-271. XP055700588.

Wang et al, Synthesizing ginsenoside Rh2 in *Saccharomyces cerevisiae* cell factory at high-efficiency. Cell Discovery 2019, 5:5, doi: 10.1038/s41421-018-0075-5. eCollection 2019. XP055700596.

Ponou et al, Dimeric antioxidant and cytotoxic triterpenoid saponins from Terminalia ivorensis A. Chev. Phytochemistry 2010, 71, 2108-2115. XP027491126.

Frøkiær, H., Møller, P., Sørensen, H. and Sørensen, S., 1994. High-performance capillary electrophoresis for characterization of hapten-protein conjugates used for production of antibodies against soyasaponin I. Journal of Chromatography A, 680(2), pp. 437-445.

Moniuszko-Szajwaj et al., Highly Polar Triterpenoid Saponins from the Roots of Saponaria officinalis L., Helv. Chim. Acta, V99, pp. 347-354, 2016 (doi.org/10.1002/hlca.201500224).

Jason Clochard, Gerold Jerz, Peter Schmieder, Hardy Mitdank, Meike Tröger, Simko Sama, Alexander Weng, A new acetylated triterpene saponin from Agrostemma githago L. modulates gene delivery efficiently and shows a high cellular tolerance, International Journal of Pharmaceutics 589 (2020) 119822.

Thakur M, Mergel K, Weng A, von Mallinckrodt B, Gilabert-Oriol R, Dürkop H, Melzig MF, Fuchs H. Targeted tumor therapy by epidermal growth factor appended toxin and purified saponin: an evaluation of toxicity and therapeutic potential in syngeneic tumor bearing mice. Mol Oncol. Jun. 2013;7(3):475-83.

Soltysik S, Wu JY, Recchia J, Wheeler DA, Newman MJ, Coughlin RT, Kensil CR. Structure/function studies of QS-21 adjuvant: assessment of triterpene aldehyde and glucuronic acid roles in adjuvant function. Vaccine. 1995;13(15):1403-10. doi: 10.1016/0264-410x(95)00077-e. PMID: 8578817.

Zhang, Y., Qu, Z., Kim, S. et al. Down-modulation of cancer targets using locked nucleic acid (LNA)-based antisense oligonucleotides without transfection. Gene Ther 18, 326-333 (2011).

* cited by examiner

A

B

C

A

D

A

A

B

C

D

Intermediate 1:

Intermediate 2

Intermediate 3:

Intermediate 4:

Intermediate 5:

Intermediate 6:

Intermediate 7:

Intermediate 8:

Intermediate 9

Intermediate 10:

Intermediate 11:

Intermediate 1:

Intermediate 2:

Intermediate 3:

Intermediate 4:

Intermediate 5:

Intermediate 1:

Intermediate 2:

Intermediate 3:

Intermediate 4:

Intermediate 5:

A

B

A

SO1861
MW = 1862 Da

SO1861-EMCH
MW = 2070 Da

B

C

A

B

A

PFd-G4-Azide-NH-BOC
MW = 4624 Da

G4-dendron scaffold

A

B

C

D

A

ANTIBODY-OLIGONUCLEOTIDE CONJUGATE

REFERENCE TO AN ELECTRONIC SEQUENCE LISTING

The contents of the electronic sequence listing (sequence-listing; Size: 2.29 Kb; and Date of Creation: Jan. 13, 2020) is herein incorporated by reference in its entirety.

TECHNICAL FIELD

The invention relates to a ligand-effector moiety provided with at least one saponin and to antibody-effector moiety provided with at least one saponin, such as an antibody-drug conjugate and an antibody-oligonucleotide conjugate. An aspect of the invention is a composition comprising the ligand-effector moiety provided with at least one saponin or the antibody-effector moiety provided with at least one saponin of the invention. The invention also relates to an antibody-drug conjugate comprising covalently linked saponin and to an antibody-oligonucleotide conjugate comprising covalently linked saponin. An aspect of the invention relates to a pharmaceutical composition comprising the ligand-effector moiety provided with at least one saponin or the antibody-effector moiety provided with at least one saponin of the invention, and optionally further comprising a pharmaceutically acceptable excipient. The invention also relates to the ligand-effector moiety provided with at least one saponin or the antibody-effector moiety provided with at least one saponin, for use as a medicament. The invention also relates to the ligand-effector moiety provided with at least one saponin or the antibody-effector moiety provided with at least one saponin of the invention for use in the treatment or prophylaxis of a cancer.

BACKGROUND

Molecules with a therapeutic biological activity are in many occasions in theory suitable for application as an effective therapeutic drug for the treatment of a disease such as a cancer in human patients in need thereof. A typical example are small-molecule biologically active moieties. However, many if not all potential drug-like molecules and therapeutics currently used in the clinic suffer from at least one of a plethora of shortcomings and drawbacks. When administered to a human body, therapeutically active molecules may exert off-target effects, in addition to the biologically activity directed to an aspect underlying a to-be-treated disease or health problem. Such off-target effects are undesired and bear a risk for induction of health- or even life-threatening side effects of the administered molecule. It is the occurrence of such adverse events that cause many drug-like compounds and therapeutic moieties to fail phase III clinical trials or even phase IV clinical trials (post-market entry follow-up). Therefore, there is a strong desire to provide drug molecules such as small-molecule therapeutics, wherein the therapeutic effect of the drug molecule should, e.g., (1) be highly specific for a biological factor or biological process driving the disease, (2) be sufficiently safe, (3) be sufficiently efficacious, (4) be sufficiently directed to the diseased cell with little to no off-target activity on non-diseased cells, (5) have a sufficiently timely mode of action (e.g. the administered drug molecule should reach the targeted site in the human patient within a certain time frame and should remain at the targeted site for a certain time frame), and/or (6) have sufficiently long lasting therapeutic activity in the patient's body, amongst others. Unfortunately, to date, 'ideal' therapeutics with many or even all of the beneficial characteristics here above outlined, are not available to the patients, despite already long-lasting and intensive research and despite the impressive progress made in several areas of the individually addressed encountered difficulties and drawbacks.

Chemotherapy is one of the most important therapeutic options for cancer treatment. However, it is often associated with a low therapeutic window because it has no specificity towards cancer cells over dividing cells in healthy tissue. The invention of monoclonal antibodies offered the possibility of exploiting their specific binding properties as a mechanism for the targeted delivery of cytotoxic agents to cancer cells, while sparing normal cells. This can be achieved by chemical conjugation of cytotoxic effectors (also known as payloads or warheads) to antibodies, to create antibody-drug conjugates (ADCs). Typically, very potent payloads such as emtansine (DM1) are used which have a limited therapeutic index (a ratio that compares toxic dose to efficacious dose) in their unconjugated forms. The conjugation of DM1 to trastuzumab (ado-trastuzumab emtansine), also known as Kadcycla, enhances the tolerable dose of DM1 at least two-fold in monkeys. In the past few decades tremendous efforts and investments have been made to develop therapeutic ADCs. However, it remains challenging to bring ADCs into the clinic, despite promising preclinical data. The first ADC approved for clinical use was gemtuzumab ozogamicin (Mylotarg, CD33 targeted, Pfizer/Wyeth) for relapsed acute myelogenous leukemia (AML) in 2000. Mylotarg was however, withdrawn from the market at the request of the Federal Drug Administration (FDA) due to a number of concerns including its safety profile. Patients treated with Mylotarg were more often found to die than patients treated with conventional chemotherapy. Mylotarg was admitted to the market again in 2017 with a lower recommended dose, a different schedule in combination with chemotherapy or on its own, and a new patient population. To date, only five ADCs have been approved for clinical use, and meanwhile clinical development of approximately fifty-five ADCs has been halted. However, interest remains high and approximately eighty ADCs are still in clinical development in nearly six-hundred clinical trials at present.

Despite the potential to use toxic payloads that are normally not tolerated by patients, a low therapeutic index (a ratio that compares toxic dose to efficacious dose) is a major problem accounting for the discontinuance of many ADCs in clinical development, which can be caused by several mechanisms such as off-target toxicity on normal cells, development of resistance against the cytotoxic agents and premature release of drugs in the circulation. A systematic review by the FDA of ADCs found that the toxicity profiles of most ADCs could be categorized according to the payload used, but not the antibody used, suggesting that toxicity is mostly determined by premature release of the payload. Of the approximately fifty-five ADCs that were discontinued, it is estimated that at least twenty-three were due to a poor therapeutic index. For example, development of a trastuzumab tesirine conjugate (ADCT-502, HER-2 targeted, ADC therapeutics) was recently discontinued due to a narrow therapeutic index, possibly due to an on-target, off-tissue effect in pulmonary tissue which expresses considerable levels of HER2. In addition, several ADCs in phase 3 trials have been discontinued due to missing primary endpoint. For example, phase 3 trials of a depatuxizumab mafodotin conjugate (ABT-414, EGFR targeted, AbbVie)

tested in patients with newly diagnosed glioblastoma, and a mirvetuximab soravtansine conjugate (IMGN853, folate receptor alpha (FRα) targeted, ImmunoGen) tested in patients with platinum-resistant ovarian cancer, were recently stopped, showing no survival benefit. It is important to note that the clinically used dose of some ADCs may not be sufficient for its full anticancer activity. For example, ado-trastuzumab emtansine has an MTD of 3.6 mg/kg in humans. In preclinical models of breast cancer, ado-trastuzumab emtansine induced tumor regression at dose levels at or above 3 mg/kg, but more potent efficacy was observed at 15 mg/kg. This suggests that at the clinically administered dose, ado-trastuzumab emtansine may not exert its maximal potential anti-tumor effect.

ADCs are mainly composed of an antibody, a cytotoxic moiety such as a payload, and a linker. Several novel strategies have been proposed and carried out in the design and development of new ADCs to overcome the existing problems, targeting each of the components of ADCs. For example, by identification and validation of adequate antigenic targets for the antibody component, by selecting antigens which have high expression levels in tumor and little or no expression in normal tissues, antigens which are present on the cell surface to be accessible to the circulating ADCs, and antigens which allows internalizing of ADCs into the cell after binding; and alternative mechanisms of activity; design and optimize linkers which enhance the solubility and the drug-to-antibody ratio (DAR) of ADCs and overcome resistance induced by proteins that can transport the chemotherapeutic agent out of the cells; enhance the DAR ratio by inclusion of more payloads, select and optimize antibodies to improve antibody homogeneity and developability. In addition to the technological development of ADCs, new clinical and translational strategies are also being deployed to maximize the therapeutic index, such as, change dosing schedules through fractionated dosing; perform biodistribution studies; include biomarkers to optimize patient selection, to capture response signals early and monitor the duration and depth of response, and to inform combination studies.

An example of ADCs with clinical potential are those ADCs such as brentuximab vedotin, inotuzumab ozogamicin, moxetumomab pasudotox, and polatuzumab vedotin, which are evaluated as a treatment option for lymphoid malignancies and multiple myeloma. Polatuzumab vedotin, binding to CD79b on (malignant) B-cells, and pinatuzumab vedotin, binding to CD22, are tested in clinical trials wherein the ADCs each were combined with co-administered rituximab, a monoclonal antibody binding to CD20 and not provided with a payload [B. Yu and D. Liu, *Antibody-drug conjugates in clinical trials for lymphoid malignancies and multiple myeloma; Journal of Hematology & Oncology* (2019) 12:94]. Combinations of monoclonal antibodies such as these examples are yet a further approach and attempt to arrive at the 'magic bullet' which combines many or even all of the aforementioned desired characteristics of ADCs.

Meanwhile in the past few decades, nucleic acid-based therapeutics are under development. Therapeutic nucleic acids can be based on deoxyribonucleic acid (DNA) or ribonucleic acid (RNA), Anti-sense oligonucleotides (ASOs, AONs), and short interfering RNAs (siRNAs), MicroRNAs, and DNA and RNA aptamers, for approaches such as gene therapy, RNA interference (RNAi). Many of them share the same fundamental basis of action by inhibition of either DNA or RNA expression, thereby preventing expression of disease-related abnormal proteins. The largest number of clinical trials is being carried out in the field of gene therapy, with almost 2600 ongoing or completed clinical trials worldwide but with only about 4% entering phase 3. This is followed by clinical trials with ASOs. Similarly to ADCs, despite the large number of techniques being explored, therapeutic nucleic acids share two major issues during clinical development: delivery into cells and off-target effects. For instance, ASOs such as peptide nucleic acid (PNA), phosphoramidate morpholino oligomer (PMO), locked nucleic acid (LNA) and bridged nucleic acid (BNA), are being investigated as an attractive strategy to inhibit specifically target genes and especially those genes that are difficult to target with small molecules inhibitors or neutralizing antibodies. Currently, the efficacy of different ASOs is being studied in many neurodegenerative diseases such as Huntington's disease, Parkinson's disease, Alzheimer's disease, and amyotrophic lateral sclerosis and also in several cancer stages. The application of ASOs as potential therapeutic agents requires safe and effective methods for their delivery to the cytoplasm and/or nucleus of the target cells and tissues. Although the clinical relevance of ASOs has been demonstrated, inefficient cellular uptake, both in vitro and in vivo, limit the efficacy of ASOs and has been a barrier to therapeutic development. Cellular uptake can be <2% of the dose resulting in too low ASO concentration at the active site for an effective and sustained outcome. This consequently requires an increase of the administered dose which induces off-target effects. Most common side-effects are activation of the complement cascade, the inhibition of the clotting cascade and toll-like receptor mediated stimulation of the immune system.

Chemotherapeutics are most commonly small molecules, however, their efficacy is hampered by the severe off-target side toxicity, as well as their poor solubility, rapid clearance and limited tumor exposure. Scaffold-small-molecule drug conjugates such as polymer-drug conjugates (PDCs) are macromolecular constructs with pharmacologically activity, which comprises one or more molecules of a small-molecule drug bound to a carrier scaffold (e.g. polyethylene glycol (PEG)).

Such conjugate principle has attracted much attention and has been under investigation for several decades. The majority of conjugates of small-molecule drugs under pre-clinical or clinical development are for oncological indications. However, up-to-date only one drug not related to cancer has been approved (Movantik, a PEG oligomer conjugate of opioid antagonist naloxone, AstraZeneca) for opioid-induced constipation in patients with chronic pain in 2014, which is a non-oncology indication.

Translating application of drug-scaffold conjugates into treatment of human subjects provides little clinical success so far. For example, PK1 (N-(2-hydroxypropyl)methacrylamide (HPMA) copolymer doxorubicin; development by Pharmacia, Pfizer) showed great anti-cancer activity in both solid tumors and leukemia in murine models, and was under clinical investigation for oncological indications. Despite that it demonstrated significant reduction of nonspecific toxicity and improved pharmacokinetics in man, improvements in anticancer efficacy turned out to be marginal in patients, and as a consequence further development of PK1 was discontinued.

The failure of scaffold-small-molecule drug conjugates is at least partially attributed to its poor accumulation at the tumor site. For example, while in murine models PK1 showed 45-250 times higher accumulation in the tumor than in healthy tissues (liver, kidney, lung, spleen, and heart), accumulation in tumor was only observed in a small subset of patients in the clinical trial.

A potential solution to the aforementioned problems is application of nanoparticle systems for drug delivery such as liposomes. Liposomes are sphere-shaped vesicles consisting of one or more phospholipid bilayers, which are spontaneously formed when phospholipids are dispersed in water. The amphiphilicity characteristics of the phospholipids provide it with the properties of self-assembly, emulsifying and wetting characteristics, and these properties can be employed in the design of new drugs and new drug delivery systems. Drug encapsulated in a liposomal delivery system may convey several advantages over a direct administration of the drug, such as an improvement and control over pharmacokinetics and pharmacodynamics, tissue targeting property, decreased toxicity and enhanced drug activity. An example of such success is liposome-encapsulated form of a small molecule chemotherapy agent doxorubicin (Doxil: a pegylated liposome-encapsulated form of doxorubicin; Myocet: a non-pegylated liposomal doxorubicin), which have been approved for clinical use.

Therefore, a solution still needs to be found that allows for drug therapies such as anti-tumor therapies, applicable for non-systemic use when desired, wherein the drug has for example an acceptable safety profile, little off-target activity, sufficient efficacy, sufficiently low clearance rate from the patient's body, etc.

SUMMARY

For an embodiment of the present invention, it is a first goal to provide an improved biologically active compound or composition comprising such improved biologically active compound.

It is one of several objectives of embodiments of the current invention to provide a solution to the problem of non-specificity, encountered when administering small-molecule therapeutically active compounds to a human patient in need thereof. It is one of several objectives of embodiments of the current invention to provide a solution to the problem of drugs with non-optimal specificity for a biological factor or biological process driving a disease. It is one of several objectives of embodiments of the current invention to provide a solution to the problem of insufficient safety characteristics of current drugs, when administered to human patients in need thereof. It is one of several objectives of embodiments of the current invention to provide a solution to the problem of current drugs being less efficacious than desired, when administered to human patients in need thereof. It is one of several objectives of embodiments of the current invention to provide a solution to the problem of current drugs being not sufficiently directed to the diseased cell with little to no off-target activity on non-diseased cells, when administered to human patients in need thereof. It is one of several objectives of embodiments of the current invention to provide a solution to the problem that current drugs do not have a sufficiently timely mode of action (e.g. the administered drug molecule should reach the targeted site in the human patient within a certain time frame and should remain at the targeted site for a certain time frame), when administered to human patients in need thereof. It is one of several objectives of embodiments of the current invention to provide a solution to the problem that current drugs have not sufficiently long lasting therapeutic activity in the patient's body, when administered to human patients in need thereof.

At least one of the above objectives of embodiments of the invention is achieved by providing an antibody-drug conjugate (ADC) or an antibody-oligonucleotide (AOC) such as an antibody-BNA covalent complex, of the invention, comprising a cell-targeting moiety and at least one saponin and at least one effector moiety such as a proteinaceous toxin and/or an oligonucleotide such as a BNA, the ADC and/or the AOC also suitable for use as a medicament, according to the invention.

The present invention will be described with respect to particular embodiments but the invention is not limited thereto but only by the claims. The embodiments of the invention described herein can operate in combination and cooperation, unless specified otherwise.

An aspect of the invention relates to a conjugate comprising a cell-surface molecule targeting molecule and at least one effector moiety and further comprising at least one covalently bound saponin.

An embodiment is the conjugate of the invention, wherein the at least one saponin is a triterpenoid saponin and/or a bisdesmosidic triterpene saponin belonging to the type of a 12,13-dehydrooleanane with an aldehyde function in position C-23 and optionally comprising a glucuronic acid function in a carbohydrate substituent at the C-3beta-OH group of the saponin, and/or a saponin isolated from any one or more of a *Gypsophila* species and/or a *Saponaria* species and/or an *Agrostemma* species and/or a *Quillaja* species such as *Quillaja saponaria*.

An embodiment is the conjugate of the invention, wherein the at least one saponin is a single specific saponin or is a mixture of two or more different saponins.

An embodiment is the conjugate of the invention, wherein the at least one saponin has a molecular mass of 3.000 Dalton or less, preferably 2.500 Dalton or less, more preferably 2.300 Dalton or less, most preferably, 2.000 Dalton or less, such as 1.500 Dalton-1.900 Dalton.

An embodiment is the conjugate of the invention, wherein the at least one saponin is one or more of the saponins in Table A1 or Scheme I, SO1861, SA1657, GE1741, SA1641, QS-21, QS-21A, QS-21 A-api, QS-21 A-xyl, QS-21B, QS-21 B-api, QS-21 B-xyl, QS-7-xyl, QS-7-api, QS-17-api, QS-17-xyl, QS1861, QS1862, Quillajasaponin, Saponinum album, QS-18, Quil-A, Gyp1, gypsoside A, AG1, AG2, SO1542, SO1584, SO1658, SO1674, SO1832, or any of their stereomers and/or any combinations thereof, preferably the saponin is SO1861 and/or GE1741 and/or SA1641 and/or QS-21 and/or saponin with a quillaic acid aglycon core, a Gal-(1→2)-[Xyl-(1→3)]-GlcA carbohydrate substituent at the C-3beta-OH group and a Glc-(1→3)-Xyl-(1→4)-Rha-(1→2)-[Xyl-(1→3)-4-OAc-Qui-(1→4)]-Fuc carbohydrate substituent at the C-28-OH group, and/or is 3-O-beta-D-galactopyranosyl-(1→2)-[beta-D-xylopyranosyl-(1→3)]-beta-D-glucuronopyranosyl quillaic acid 28-O-beta-D-glucopyranosyl-(1→3)-beta-D-xylopyranosyl-(1→4)-alpha-L-rhamnopyranosyl-(1→2)-[beta-D-xylopyranosyl-(1→3)-4-OAc-beta-D-quinovopyranosyl-(1→4)]-beta-D-fucopyranoside, more preferably the at least one saponin is SO1861 and/or QS-21.

An embodiment is the conjugate of the invention, wherein the at least one saponin is a bisdesmosidic saponin having a molecular mass of at least 1.500 Dalton and comprising an oleanan-type triterpene containing an aldehyde group at the C-23 position and optionally a hydroxyl group at the C-16 position, with a first branched carbohydrate side chain at the C-3 position which first branched carbohydrate side chain optionally contains glucuronic acid, wherein the saponin contains an ester group with a second branched carbohydrate side chain at the C-28 position which second branched carbohydrate chain preferably comprises at least four carbohydrate units, optionally containing at least one acetyl residue such as two acetyl residues and/or optionally comprising deoxy carbohydrates and/or optionally comprising quinovose and/or optionally comprising glucose and/or optionally comprising 4-methoxycinnamic acid and/or optionally comprising 5-O-[5-O-Ara/Api-3,5-dihydroxy-6-methyl-octanoyl]-3,5-dihydroxy-6-methyl-octanoic acid and/or optionally comprising 5-O-[5-O-Rha-(1→2)-Ara/Api-3,5-dihydroxy-6-methyl-octanoyl]-3,5-dihydroxy-6-methyl-octanoic acid bound to a carbohydrate via an ester bond, or wherein the at least one saponin is QS-21 or any one or more of QS-21A, QS-21 A-api, QS-21 A-xyl, QS-21B, QS-21 B-api, QS-21 B-xyl, QS-7-xyl, QS-7-api, QS-17-api, QS-17-xyl, QS-18, QS1861, protonated QS1861 (QS1862), Quil-A.

An embodiment is the conjugate of the invention, wherein the cell-surface molecule targeting molecule comprises or consists of a ligand or a proteinaceous ligand or a proteinaceous binding molecule for binding to the cell-surface molecule.

An embodiment is the conjugate of the invention, wherein the cell-surface molecule targeting molecule comprises or consists of a non-proteinaceous ligand and/or a proteinaceous ligand for binding to a cell-surface molecule such as EGF or a cytokine, and/or comprises or consists of an immunoglobulin, at least one binding domain of an immunoglobulin and/or at least one binding fragment of an immunoglobulin, such as an antibody, an IgG, a molecule comprising or consisting of a Vhh domain or Vh domain, a Fab, an scFv, an Fv, a dAb, an $F(ab)_2$, Fcab fragment, which can bind to the cell-surface molecule.

An embodiment is the conjugate of the invention, wherein the cell-surface molecule targeting molecule can bind to a tumor-cell surface molecule, preferably a tumor-cell receptor such as a tumor-cell specific receptor, more preferably a receptor selected from CD71, CA125, EpCAM(17-1A), CD52, CEA, CD44v6, FAP, EGF-IR, integrin, syndecan-1, vascular integrin alpha-V beta-3, HER2, EGFR, CD20, CD22, Folate receptor 1, CD146, CD56, CD19, CD138, CD27L receptor, PSMA, CanAg, integrin-alphaV, CA6, CD33, mesothelin, Cripto, CD3, CD30, CD239, CD70, CD123, CD352, DLL3, CD25, ephrinA4, MUC1, Trop2, CEACAM5, CEACAM6, HER3, CD74, PTK7, Notch3, FGF2, C4.4A, FLT3, CD38, FGFR3, CD7, PD-L1, CTLA4, CD52, PDGFRA, VEGFR1, VEGFR2, preferably selected from CD71, HER2 and EGFR.

An embodiment is the conjugate of the invention, wherein the tumor-cell receptor is internalized by the tumor cell after binding to the cell-surface molecule targeting molecule of the invention or wherein the tumor-cell receptor is internalized by the tumor cell after binding to the conjugate of the invention, and wherein preferably binding of the cell-surface molecule targeting molecule and binding of the conjugate to the tumor-cell receptor is followed by tumor-cell receptor-mediated internalization, e.g. via endocytosis, of a complex of the conjugate and the tumor-cell receptor.

An embodiment is the conjugate of the invention, wherein the cell-surface molecule targeting molecule is or comprises a monoclonal antibody or at least one cell-surface molecule binding fragment or -domain thereof, and preferably comprises or consists of any one of cetuximab, daratumumab, gemtuzumab, trastuzumab, panitumumab, brentuximab, inotuzumab, moxetumomab, polatuzumab, obinutuzumab, OKT-9 anti-CD71 monoclonal antibody of the IgG type, pertuzumab, rituximab, ofatumumab, Herceptin, alemtuzumab, pinatuzumab, OKT-10 anti-CD38 monoclonal antibody, an antibody of Table A2 or Table A3 or Table A4, preferably cetuximab or trastuzumab or OKT-9, or at least one cell-surface molecule binding fragment or -domain thereof.

An embodiment is the conjugate of the invention, wherein the at least one effector moiety comprises or consists of any one or more of an oligonucleotide, a nucleic acid and a xeno nucleic acid, preferably selected from any one or more of a vector, a gene, a cell suicide inducing transgene, deoxyribonucleic acid (DNA), ribonucleic acid (RNA), anti-sense oligonucleotide (ASO, AON), short interfering RNA (siRNA), microRNA (miRNA), DNA aptamer, RNA aptamer, mRNA, mini-circle DNA, peptide nucleic acid (PNA), phosphoramidate morpholino oligomer (PMO), locked nucleic acid (LNA), bridged nucleic acid (BNA), 2'-deoxy-2'-fluoroarabino nucleic acid (FANA), 2'-O-methoxyethyl-RNA (MOE), 2'-0,4'-aminoethylene bridged nucleic acid, 3'-fluoro hexitol nucleic acid (FHNA), a plasmid, glycol nucleic acid (GNA) and threose nucleic acid (TNA), or a derivative thereof, more preferably a BNA, for example a BNA for silencing HSP27 protein expression.

An embodiment is the conjugate of the invention, wherein the at least one effector moiety comprises or consists of any one or more of an oligonucleotide, a nucleic acid and a xeno nucleic acid, preferably selected from any one or more of a vector, a gene, a cell suicide inducing transgene, deoxyribonucleic acid (DNA), ribonucleic acid (RNA), anti-sense oligonucleotide (ASO, AON), short interfering RNA (siRNA), microRNA (miRNA), DNA aptamer, RNA aptamer, mRNA, mini-circle DNA, peptide nucleic acid (PNA), phosphoramidate morpholino oligomer (PMO), locked nucleic acid (LNA), bridged nucleic acid (BNA), 2'-deoxy-2'-fluoroarabino nucleic acid (FANA), 2'-O-methoxyethyl-RNA (MOE), 2'-0,4'-aminoethylene bridged nucleic acid, 3'-fluoro hexitol nucleic acid (FHNA), a plasmid, glycol nucleic acid (GNA) and threose nucleic acid (TNA), or a derivative thereof, more preferably a BNA, for example a BNA for silencing HSP27 protein expression, wherein the at least one effector moiety are for example two different (antisense) oligonucleotides for silencing two different genes.

An embodiment is the conjugate of the invention, wherein the at least one effector moiety comprises or consists of at least one proteinaceous molecule, preferably selected from any one or more of a peptide, a protein, an enzyme such as urease and Cre-recombinase, a ribosome-inactivating protein, a proteinaceous toxin selected from Table A5 and more preferably selected from any one or more of a viral toxin such as apoptin; a bacterial toxin such as Shiga toxin, Shiga-like toxin, *Pseudomonas aeruginosa* exotoxin (PE) or exotoxin A of PE, full-length or truncated diphtheria toxin (DT), cholera toxin; a fungal toxin such as alpha-sarcin; a plant toxin including ribosome-inactivating proteins and the A chain of type 2 ribosome-inactivating proteins such as dianthin e.g. dianthin-30 or dianthin-32, saporin e.g. saporin-S3 or saporin-S6, bouganin or de-immunized derivative debouganin of bouganin, shiga-like toxin A, pokeweed antiviral protein, ricin, ricin A chain, modeccin, modeccin A chain, abrin, abrin A chain, volkensin, volkensin A chain, viscumin, viscumin A chain; or an animal or human toxin such as frog RNase, or granzyme B or angiogenin from humans, or any fragment or derivative thereof; preferably the protein toxin is dianthin and/or saporin.

An embodiment is the conjugate of the invention, wherein the at least one effector moiety comprises or consists of at least one payload, preferably selected from any one or more of a toxin targeting ribosomes, a toxin targeting elongation factors, a toxin targeting tubulin, a toxin targeting DNA and a toxin targeting RNA, more preferably any one or more of emtansine, pasudotox, maytansinoid derivative DM1, maytansinoid derivative DM4, monomethyl auristatin E (MMAE, vedotin), monomethyl auristatin F (MMAF, mafodotin), a Calicheamicin, N-Acetyl-γ-calicheamicin, a pyrrolobenzodiazepine (PBD) dimer, a benzodiazepine, a CC-1065 analogue, a duocarmycin, Doxorubicin, paclitaxel, docetaxel, cisplatin, cyclophosphamide, etoposide, docetaxel, 5-fluorouracyl (5-FU), mitoxantrone, a tubulysin, an indolinobenzodiazepine, AZ13599185, a cryptophycin, rhizoxin, methotrexate, an anthracycline, a camptothecin analogue, SN-38, DX-8951f, exatecan mesylate, truncated form of *Pseudomonas aeruginosa* exotoxin (PE38), a Duocarmycin derivative, an amanitin, α-amanitin, a spliceostatin, a thailanstatin, ozogamicin, tesirine, Amberstatin269 and soravtansine, or a derivative thereof.

An embodiment is the conjugate of the invention, wherein the at least one effector moiety is covalently bound to the cell-surface molecule targeting molecule, either via at least one linker or bound directly to the cell-surface molecule targeting molecule.

An embodiment is the conjugate of the invention, wherein the at least one effector moiety is covalently bound to the cell-surface molecule targeting molecule, thereby forming any one of antibody-drug conjugates Gemtuzumab ozogamicin, Brentuximab vedotin, Trastuzumab emtansine, Inotuzumab ozogamicin, Moxetumomab pasudotox and Polatuzumab vedotin and an antibody-drug conjugate of Table A2 and Table A3.

An embodiment is the conjugate of the invention, wherein the at least one saponin is covalently bound to the cell-surface molecule targeting molecule preferably an amino-acid residue of the cell-surface molecule targeting molecule, via an aldehyde function in the saponin, and/or to the at least one effector moiety preferably via an amino-acid residue in the at least one effector moiety, via an aldehyde function in the saponin, preferably an aldehyde function in position C-23 in a bisdesmosidic triterpene saponin belonging to the type of a 12,13-dehydrooleanane.

An embodiment is the conjugate of the invention, wherein the aldehyde function in the at least one saponin, preferably the aldehyde function in position C-23 of the at least one saponin, is covalently coupled to linker N-ε-maleimidocaproic acid hydrazide, which linker is covalently coupled via a thio-ether bond to a sulfhydryl group in the cell-surface molecule targeting molecule and/or in the at least one effector moiety, such as a sulfhydryl group of a cysteine.

An embodiment is the conjugate of the invention, wherein the at least one saponin is a bisdesmosidic triterpene saponin belonging to the type of a 12,13-dehydrooleanane, with an aldehyde function in position C-23 and comprising a glucuronic acid function in a carbohydrate substituent at the C-3beta-OH group of the saponin, wherein the saponin is covalently bound to an amino-acid residue of the cell-surface molecule targeting molecule and/or to the at least one effector moiety via said glucuronic acid function and preferably via an amino-acid residue in the at least one effector moiety.

An embodiment is the conjugate of the invention, wherein the glucuronic acid function in the carbohydrate substituent at the C-3beta-OH group of the at least one saponin is covalently coupled to linker 1-[Bis(dimethylamino)methylene]-1H-1,2,3-triazolo[4,5-b]pyridinium 3-oxid hexafluorophosphate, which linker is covalently coupled via an amide bond to an amine group in the cell-surface molecule targeting molecule and/or in the at least one effector moiety, such as an amine group of a lysine or an N-terminus of the cell-surface molecule targeting molecule and/or of the at least one effector moiety.

An embodiment is the conjugate of the invention, wherein the at least one saponin is covalently bound to the cell-surface molecule targeting molecule and/or to the at least one effector moiety either directly or via at least one linker such as a bi-functional linker, for example based on N-ε-maleimidocaproic acid hydrazide and/or based on 1-[Bis(dimethylamino)methylene]-1H-1,2,3-triazolo[4,5-b]pyridinium 3-oxid hexafluorophosphate, or a tri-functional linker, such as the tri-functional linker of Scheme II and Structure B.

An embodiment is the conjugate of the invention, wherein the tri-functional linker comprises a second chemical group with at least one saponin covalently bound thereto, a third chemical group for covalent binding to the cell-surface molecule targeting molecule and a first chemical group for covalent binding to the at least one effector moiety, preferably the tri-functional linker is the trifunctional linker of Scheme II and Structure B.

An embodiment is the conjugate of the invention, wherein the at least one saponin is covalently bound to the cell-surface molecule targeting molecule and to the at least one effector moiety via at least one linker comprising a tri-functional linker to which tri-functional linker both the cell-surface molecule targeting molecule and the at least one effector moiety are bound, preferably the tri-functional linker is the trifunctional linker of Scheme II and Structure B.

An embodiment is the conjugate of the invention, wherein the at least one linker comprises at least one cleavable linker, wherein optionally said cleavable linker is subject to cleavage under acidic, reductive, enzymatic or light-induced conditions, and preferably the cleavable linker comprises a cleavable bond selected from a hydrazone bond or a hydrazide bond subject to cleavage under acidic conditions, and/or a bond susceptible to proteolysis, for example proteolysis by Cathepsin B, and/or a bond susceptible for cleavage under reductive conditions such as a disulphide bond.

An embodiment is the conjugate of the invention, wherein the at least one linker comprises at least one cleavable linker, wherein said cleavable linker is subject to cleavage in vivo under acidic conditions as present in endosomes and/or in lysosomes of mammalian cells, preferably of human cells, preferably at pH 4.0-6.5, and more preferably at pH≤5.5.

An embodiment is the conjugate of the invention, wherein the at least one saponin is covalently bound to a lysine side chain, forming an amide bond, and/or to a cysteine side chain, forming a thio-ether linkage or a disulphide bond, wherein the lysine and/or cysteine is/are comprised by the cell-surface molecule targeting molecule and/or is/are comprised by the at least one effector moiety, and wherein the at least one saponin is either directly bound to the lysine and/or cysteine, or is bound via at least one linker optionally comprising a cleavable linker and/or a tri-functional linker such as the tri-functional linker of Scheme II and Structure B.

An embodiment is the conjugate of the invention, wherein the linker is based on N-ε-maleimidocaproic acid hydrazide and/or based on 1-[Bis(dimethylamino)methylene]-1H-1,2,3-triazolo[4,5-b]pyridinium 3-oxid hexafluorophosphate, a tri-functional linker such as the tri-functional linker of Scheme II and Structure B, a cleavable linker, and/or involves any one or more of a disulphide bond, a thio-ether bond, an amide bond, a hydrazide bond.

An embodiment is the conjugate of the invention, wherein the at least one saponin is covalently bound to the cell-surface molecule targeting molecule and/or to the at least one effector moiety via at least one linker, wherein the linker is or comprises a scaffold comprising a polymeric or oligomeric structure and further comprising at least one fourth chemical group for covalently coupling of the scaffold to the cell-surface molecule targeting molecule and/or to the at least one effector moiety.

An embodiment is the conjugate of the invention, wherein the at least one saponin is covalently bound to the polymeric or oligomeric structure of the scaffold via a cleavable bond and/or via a non-cleavable bond.

An embodiment is the conjugate of the invention, wherein the cleavable bond is subject to cleavage under any of acidic conditions, reductive conditions, enzymatic conditions and light-induced conditions, and preferably the cleavable bond comprises a hydrazone bond or a hydrazide bond subject to cleavage under acidic conditions, and/or a bond susceptible to proteolysis, for example proteolysis by Cathepsin B, and/or a bond susceptible for cleavage under reductive conditions such as a disulphide bond.

An embodiment is the conjugate of the invention, wherein the cleavable bond is subject to cleavage in vivo under acidic conditions as present in endosomes and/or in lysosomes of mammalian cells, preferably of human cells, preferably at pH 4.0-6.5, and more preferably at pH 5.5.

An embodiment is the conjugate of the invention, wherein the at least one saponin is covalently bound to the polymeric or oligomeric structure of the scaffold via any one or more of an imine bond, a hydrazone bond, a hydrazide bond, an oxime bond, a 1,3-dioxolane bond, a disulphide bond, a thio-ether bond, an amide bond, a peptide bond or an ester bond, preferably via at least one linker.

An embodiment is the conjugate of the invention, wherein the at least one saponin is covalently bound to the polymeric or oligomeric structure of the scaffold via any one or more of an imine bond, a hydrazone bond and a hydrazide bond, which bond is preferably cleavable according to the invention, wherein preferably the at least one saponin is covalently bound to the polymeric or oligomeric structure of the scaffold via the aldehyde function in position C-23 of the at least one saponin.

An embodiment is the conjugate of the invention, wherein the aldehyde function in position C-23 of the at least one saponin is covalently coupled to linker N-ε-maleimidocaproic acid hydrazide, which linker is covalently coupled via a thio-ether bond to a sulfhydryl group in the polymeric or oligomeric structure of the scaffold, such as a sulfhydryl group of a cysteine.

An embodiment is the conjugate of the invention, wherein the at least one saponin is covalently bound to the polymeric or oligomeric structure of the scaffold via an amide bond, wherein preferably the at least one saponin is covalently bound to the polymeric or oligomeric structure of the scaffold via the glucuronic acid function in the carbohydrate substituent at the C-3beta-OH group of the at least one saponin, when present.

An embodiment is the conjugate of the invention, wherein the glucuronic acid function in the carbohydrate substituent at the C-3beta-OH group of the at least one saponin is covalently coupled to linker 1-[Bis(dimethylamino)methylene]-1H-1,2,3-triazolo[4,5-b]pyridinium 3-oxid hexafluorophosphate, which linker is covalently coupled via an amide bond to an amine group in the polymeric or oligomeric structure of the scaffold, such as an amine group of a lysine or an N-terminus of the polymeric or oligomeric structure of the scaffold.

An embodiment is the conjugate of the invention, wherein the at least one saponin is covalently bound to the polymeric or oligomeric structure of the scaffold, involving in the covalent bond the aldehyde function in position C-23 of the at least one saponin, when present, and/or involving in the covalent bond the glucuronic acid function in the carbohydrate substituent at the C-3beta-OH group of the at least one saponin, when present.

An embodiment is the conjugate of the invention, wherein the at least one fourth chemical group of the scaffold, for covalently coupling of the scaffold to the cell-surface molecule targeting molecule and/or to the at least one effector moiety, is a click chemistry group, preferably selected from any one or more of a tetrazine, an azide, an alkene or an alkyne, or a cyclic derivative of these groups, preferably an azide group.

An embodiment is the conjugate of the invention, wherein the polymeric or oligomeric structure of the scaffold comprises a linear, branched and/or cyclic polymer, oligomer, dendrimer, dendron, dendronized polymer, dendronized oligomer, a DNA, a polypeptide, poly-lysine, a poly-ethylene glycol, or an assembly of these polymeric or oligomeric structures which assembly is preferably built up by covalent cross-linking.

An embodiment is the conjugate of the invention, wherein the at least one saponin is a defined number of saponins or a defined range of saponins, preferably 1-128 saponins or at least 2, 3, 4, 5, 6, 8, 10, 16, 32, 64 or 128 saponins, or any number of saponins therein between, such as 7, 9, 12 saponins.

An embodiment is the conjugate of the invention, wherein the conjugate comprises more than one saponin, preferably 2, 3, 4, 5, 6, 8, 10, 16, 32, 64 or 1-100 saponins, or any number of saponins therein between, such as 7, 9, 12 saponins, covalently bound directly to an amino-acid residue of the cell-surface molecule targeting molecule and/or to the at least one effector moiety and preferably via an amino-acid residue in the at least one effector moiety, preferably to a cysteine and/or to a lysine, and/or covalently bound via at least one linker and/or via at least one cleavable linker and/or via at least one polymeric or oligomeric scaffold, preferably 1-8 of such scaffolds or 2-4 of such scaffolds, wherein 1-32 saponins, preferably 2, 3, 4, 5, 6, 8, 10, 16 or 32 saponins, or any number of saponins therein between, such as 7, 9, 12 saponins, are covalently bound to the at least one scaffold.

An embodiment is the conjugate of the invention, wherein the at least one saponin is covalently bound to the cell-surface molecule targeting molecule and to the at least one effector moiety via a tri-functional linker, the tri-functional linker comprising a second chemical group with at least one saponin covalently bound thereto either directly or via a linker such as a cleavable linker and/or via the scaffold comprising a polymeric or oligomeric structure and a fourth chemical group according to the invention for covalently coupling of the scaffold to the tri-functional linker, the tri-functional linker further comprising a third chemical group for covalent binding to the cell-surface molecule targeting molecule and comprising a first chemical group for covalent binding to the at least one effector moiety, wherein the cell-surface molecule targeting molecule is bound to the third chemical group and/or the at least one effector moiety is bound to the first chemical group, preferably the trifunctional linker is the trifunctional linker of Scheme II and Structure B.

An aspect of the invention relates to a pharmaceutical composition comprising the conjugate of the invention and optionally a pharmaceutically acceptable excipient and/or a pharmaceutically acceptable diluent.

An aspect of the invention relates to a conjugate of the invention or relates to the pharmaceutical composition of the invention, for use as a medicament.

An aspect of the invention relates to a conjugate of the invention or relates to the pharmaceutical composition of the invention, for use in the treatment or prevention of a cancer or an autoimmune disease.

An aspect of the invention relates to any of the following ADCs and AOCs, and their semi-finished conjugates, comprising the cell-surface molecule targeting molecule of the invention and either comprising at least one effector moiety of the invention or comprising at least one saponin of the invention, or both:

Anti-EGFR antibody—saponin;
Anti-EGFR antibody—triterpenoid saponin and/or a bisdesmosidic triterpene saponin belonging to the type of a 12,13-dehydrooleanane with an aldehyde function in position C-23 and optionally comprising a glucuronic acid function in a carbohydrate substituent at the C-3beta-OH group of the saponin;
Anti-EGFR antibody—SO1861;
Anti-EGFR antibody—GE1741;
Anti-EGFR antibody—SA1641;
Anti-EGFR antibody—Quil-A;
Anti-EGFR antibody—QS-21;
Anti-EGFR antibody—saponins in water soluble saponin fraction of *Quillaja saponaria;*
Cetuximab—saponin;
Cetuximab—triterpenoid saponin and/or a bisdesmosidic triterpene saponin belonging to the type of a 12,13-dehydrooleanane with an aldehyde function in position C-23 and optionally comprising a glucuronic acid function in a carbohydrate substituent at the C-3beta-OH group of the saponin;
Cetuximab—SO1861;
Cetuximab—GE1741;
Cetuximab—SA1641;
Cetuximab—Quil-A;
Cetuximab—QS-21;
Cetuximab—saponins in water soluble saponin fraction of *Quillaja saponaria;*
Anti-HER2 antibody—saponin;
Anti-HER2 antibody—triterpenoid saponin and/or a bisdesmosidic triterpene saponin belonging to the type of a 12,13-dehydrooleanane with an aldehyde function in position C-23 and optionally comprising a glucuronic acid function in a carbohydrate substituent at the C-3beta-OH group of the saponin;
Anti-HER2 antibody—SO1861;
Anti-HER2 antibody—GE1741;
Anti-HER2 antibody—SA1641;
Anti-HER2 antibody—Quil-A;
Anti-HER2 antibody—QS-21;
Anti-HER2 antibody—saponins in water soluble saponin fraction of *Quillaja saponaria;*
Trastuzumab—saponin;
Trastuzumab—triterpenoid saponin and/or a bisdesmosidic triterpene saponin belonging to the type of a 12,13-dehydrooleanane with an aldehyde function in position C-23 and optionally comprising a glucuronic acid function in a carbohydrate substituent at the C-3beta-OH group of the saponin;
Trastuzumab—SO1861;
Trastuzumab—GE1741;
Trastuzumab—SA1641;
Trastuzumab—Quil-A;
Trastuzumab—QS-21;
Trastuzumab—saponins in water soluble saponin fraction of *Quillaja saponaria;*
Anti-CD71 antibody—saponin;
Anti-CD71 antibody—triterpenoid saponin and/or a bisdesmosidic triterpene saponin belonging to the type of a 12,13-dehydrooleanane with an aldehyde function in position C-23 and optionally comprising a glucuronic acid function in a carbohydrate substituent at the C-3beta-OH group of the saponin;
Anti-CD71 antibody—SO1861;
Anti-CD71 antibody—GE1741;
Anti-CD71 antibody—SA1641;
Anti-CD71 antibody—Quil-A;
Anti-CD71 antibody—QS-21;
Anti-CD71 antibody—saponins in water soluble saponin fraction of *Quillaja saponaria;*
OKT-9—saponin;
OKT-9—triterpenoid saponin and/or a bisdesmosidic triterpene saponin belonging to the type of a 12,13-dehydrooleanane with an aldehyde function in position C-23 and optionally comprising a glucuronic acid function in a carbohydrate substituent at the C-3beta-OH group of the saponin;
OKT-9—SO1861;
OKT-9—GE1741;
OKT-9—SA1641;
OKT-9—Quil-A;
OKT-9—QS-21;
OKT-9—saponins in water soluble saponin fraction of *Quillaja saponaria;*
Anti-EGFR antibody—oligonucleotide;
Anti-EGFR antibody—antisense oligonucleotide;
Anti-EGFR antibody—siRNA;
Anti-EGFR antibody—antisense BNA;
Anti-EGFR antibody—antisense BNA(HSP27);
Anti-EGFR antibody—proteinaceous toxin;
Anti-EGFR antibody—ribosome inactivating protein;
Anti-EGFR antibody—dianthin;
Anti-EGFR antibody—saporin;
Cetuximab—oligonucleotide;
Cetuximab—antisense oligonucleotide;
Cetuximab—siRNA;
Cetuximab—antisense BNA;
Cetuximab—antisense BNA(HSP27);
Cetuximab—proteinaceous toxin;
Cetuximab—ribosome inactivating protein;
Cetuximab—dianthin;
Cetuximab—saporin;
Anti-HER2 antibody—oligonucleotide;
Anti-HER2 antibody—antisense oligonucleotide;
Anti-HER2 antibody—siRNA;
Anti-HER2 antibody—antisense BNA;
Anti-HER2 antibody—antisense BNA(HSP27);
Anti-HER2 antibody—proteinaceous toxin;
Anti-HER2 antibody—ribosome inactivating protein;
Anti-HER2 antibody—dianthin;
Anti-HER2 antibody—saporin;
Trastuzumab—oligonucleotide;
Trastuzumab—antisense oligonucleotide;
Trastuzumab—siRNA;

Trastuzumab—antisense BNA;
Trastuzumab—antisense BNA(HSP27);
Trastuzumab—proteinaceous toxin;
Trastuzumab—ribosome inactivating protein;
Trastuzumab—dianthin;
Trastuzumab—saporin;
Anti-CD71 antibody—oligonucleotide;
Anti-CD71 antibody—antisense oligonucleotide;
Anti-CD71 antibody—siRNA;
Anti-CD71 antibody—antisense BNA;
Anti-CD71 antibody—antisense BNA(HSP27);
Anti-CD71 antibody—proteinaceous toxin;
Anti-CD71 antibody—ribosome inactivating protein;
Anti-CD71 antibody—dianthin;
Anti-CD71 antibody—saporin;
OKT-9—oligonucleotide;
OKT-9—antisense oligonucleotide;
OKT-9—siRNA;
OKT-9—antisense BNA;
OKT-9—antisense BNA(HSP27);
OKT-9—proteinaceous toxin;
OKT-9—ribosome inactivating protein;
OKT-9—dianthin;
OKT-9—saporin;

Anti-EGFR antibody (-oligonucleotide)(-saponin), wherein the oligonucleotide is any one or more of antisense oligonucleotide, siRNA, antisense BNA, and antisense BNA(HSP27), and wherein the saponin is any one or more of a triterpenoid saponin and/or a bisdesmosidic triterpene saponin belonging to the type of a 12,13-dehydrooleanane with an aldehyde function in position C-23 and optionally comprising a glucuronic acid function in a carbohydrate substituent at the C-3beta-OH group of the saponin, SO1861, GE1741, SA1641, Quil-A, QS-21, and saponins in water soluble saponin fraction of *Quillaja saponaria*, wherein the anti-EGFR antibody preferably is cetuximab;

Anti-EGFR antibody (-proteinaceous toxin)(-saponin), wherein the proteinaceous toxin is any one or more of a ribosome inactivating protein, dianthin and saporin, and wherein the saponin is any one or more of a triterpenoid saponin and/or a bisdesmosidic triterpene saponin belonging to the type of a 12,13-dehydrooleanane with an aldehyde function in position C-23 and optionally comprising a glucuronic acid function in a carbohydrate substituent at the C-3beta-OH group of the saponin, SO1861, GE1741, SA1641, Quil-A, QS-21, and saponins in water soluble saponin fraction of *Quillaja saponaria*, wherein the anti-EGFR antibody preferably is cetuximab;

Anti-HER2 antibody (-oligonucleotide)(-saponin), wherein the oligonucleotide is any one or more of antisense oligonucleotide, siRNA, antisense BNA, and antisense BNA(HSP27), and wherein the saponin is any one or more of a triterpenoid saponin and/or a bisdesmosidic triterpene saponin belonging to the type of a 12,13-dehydrooleanane with an aldehyde function in position C-23 and optionally comprising a glucuronic acid function in a carbohydrate substituent at the C-3beta-OH group of the saponin, SO1861, GE1741, SA1641, Quil-A, QS-21, and saponins in water soluble saponin fraction of *Quillaja saponaria*, wherein the anti-HER2 antibody preferably is trastuzumab;

Anti-HER2 antibody (-proteinaceous toxin)(-saponin), wherein the proteinaceous toxin is any one or more of a ribosome inactivating protein, dianthin and saporin, and wherein the saponin is any one or more of a triterpenoid saponin and/or a bisdesmosidic triterpene saponin belonging to the type of a 12,13-dehydrooleanane with an aldehyde function in position C-23 and optionally comprising a glucuronic acid function in a carbohydrate substituent at the C-3beta-OH group of the saponin, SO1861, GE1741, SA1641, Quil-A, QS-21, and saponins in water soluble saponin fraction of *Quillaja saponaria*, wherein the anti-HER2 antibody preferably is trastuzumab;

Anti-CD71 antibody (-oligonucleotide)(-saponin), wherein the oligonucleotide is any one or more of antisense oligonucleotide, siRNA, antisense BNA, and antisense BNA(HSP27), and wherein the saponin is any one or more of a triterpenoid saponin and/or a bisdesmosidic triterpene saponin belonging to the type of a 12,13-dehydrooleanane with an aldehyde function in position C-23 and optionally comprising a glucuronic acid function in a carbohydrate substituent at the C-3beta-OH group of the saponin, SO1861, GE1741, SA1641, Quil-A, QS-21, and saponins in water soluble saponin fraction of *Quillaja saponaria*, wherein the anti-CD71 antibody preferably is OKT-9; and Anti-CD71 antibody (-proteinaceous toxin)(-saponin), wherein the proteinaceous toxin is any one or more of a ribosome inactivating protein, dianthin and saporin, and wherein the saponin is any one or more of a triterpenoid saponin and/or a bisdesmosidic triterpene saponin belonging to the type of a 12,13-dehydrooleanane with an aldehyde function in position C-23 and optionally comprising a glucuronic acid function in a carbohydrate substituent at the C-3beta-OH group of the saponin, SO1861, GE1741, SA1641, Quil-A, QS-21, and saponins in water soluble saponin fraction of *Quillaja saponaria*, wherein the anti-CD71 antibody preferably is OKT-9.

An embodiment is the semi-finished conjugate of the invention or the conjugate of the invention, wherein the cell-surface molecule targeting molecule is selected from cetuximab, trastuzumab, OKT-9, and/or wherein the effector moiety is selected from dianthin, saporin and antisense BNA(HSP27), and/or wherein the saponin is selected from SO1861, GE1741, SA1641, Quil-A, QS-21, and saponins in water soluble saponin fraction of *Quillaja saponaria.*

An embodiment is the conjugate according to the invention, wherein the cell-surface molecule targeting molecule is selected from cetuximab, trastuzumab, OKT-9, and/or wherein the effector moiety is selected from dianthin, saporin and antisense BNA(HSP27), and/or wherein the saponin is selected from SO1861, GE1741, SA1641, Quil-A, QS-21, and saponins in water soluble saponin fraction of *Quillaja saponaria.*

An aspect of the invention relates to an ADC or an AOCs or a semi-finished ADC conjugate or a semi-finished AOC conjugate comprising the cell-surface molecule targeting molecule of the invention and comprising at least one effector moiety of the invention and/or comprising at least one saponin of the invention, of Structure C:

$$A(\text{-}S)b(\text{-}E)c \qquad \text{Structure C,}$$

wherein A is the cell-surface molecule targeting molecule;
S is the saponin;
E is the effector moiety;
b=0-64, preferably 0, 1, 2, 3, 4, 8, 16, 32, 64 or any whole number or fraction therein between;

c=0-8, preferably 0, 1, 2, 3, 4, 6, 8 or any whole number or fraction therein between, wherein S is coupled to A and/or E, E is coupled to A and/or S, preferably S is coupled to A and E is coupled to A.

An embodiment is the Structure C of the invention, wherein A is an anti-EGFR antibody such as cetuximab, an anti-HER2 antibody such as trastuzumab, an anti-CD71 antibody such as OKT-9, and/or wherein S is any one or more of a saponin, a triterpenoid saponin and/or a bisdesmosidic triterpene saponin belonging to the type of a 12,13-dehydrooleanane with an aldehyde function in position C-23 and optionally comprising a glucuronic acid function in a carbohydrate substituent at the C-3beta-OH group of the saponin, SO1861, GE1741, SA1641, Quil-A, QS-21, and saponins in water soluble saponin fraction of *Quillaja saponaria*, and/or wherein E is any one or more of an oligonucleotide, an antisense oligonucleotide, an siRNA, an antisense BNA, and an antisense BNA(HSP27), and/or any one or more of a proteinaceous toxin, a ribosome inactivating protein, dianthin and saporin.

An embodiment is the Structure C of the invention, the conjugate of the invention or the semi-finished conjugate of the invention, wherein the saponin, if present, and/or the effector moiety, if present, is covalently coupled via at least one linker, such as a cleavable linker, and/or via at least one oligomeric or polymeric scaffold, such as a linker based on N-ε-maleimidocaproic acid hydrazide (EMCH) succinimidyl 3-(2-pyridyldithio)propionate or 3-(2-Pyridyldithio) propionic acid N-hydroxysuccinimide ester (SPDP), and 1-[Bis(dimethylamino)methylene]-1H-1,2,3-triazolo[4,5-b] pyridinium 3-oxid hexafluorophosphate (HATU), and such as a scaffold based on a Dendron such as a G4-Dendron or a tri-functional linker such as the tri-functional linker of Scheme II, and/or wherein at least a lysine side chain and/or a cysteine side chain of the cell-surface molecule targeting molecule, preferably a monoclonal antibody or fragments or domains thereof, is involved in the covalent bond with the saponin and/or the effector moiety and/or the linker and/or the cleavable linker and/or the scaffold, wherein preferably the saponin and/or the effector moiety is covalently linked to the cell-surface molecule targeting molecule, preferably an antibody, wherein the covalent link comprises or consists of an amide bond, a hydrazone bond, a disulphide bond.

An aspect of the invention relates to the use of any of the aforementioned conjugates, ADCs, AOCs, semi-finished ADCs, semi-finished AOCs, as a medicament.

An aspect of the invention relates to the use of any of the aforementioned conjugates, ADCs, AOCs, semi-finished ADCs, semi-finished AOCs, for use in the treatment or prophylaxis of a cancer or an auto-immune disease.

Definitions

The term "linker" has its regular scientific meaning, and here refers to a chemical moiety or a linear stretch of amino-acid residues complexed through peptide bonds, which attaches a molecule or an atom to another molecule, e.g. to a ligand or to an effector molecule or to a scaffold. Typically, the linker comprises a chain of atoms linked by chemical bonds. Any linker molecule or linker technology known in the art can be used in the present disclosure. Where indicated, the linker is a linker for covalently binding of molecules through a chemical group on such a molecule suitable for forming a covalent linkage or bond with the linker. The linker may be a non-cleavable linker, e.g., the linker is stable in physiological conditions. The linker may be a cleavable linker, e.g. a linker that is cleavable, in the presence of an enzyme or at a particular pH range or value, or under physiological conditions such as intracellular conditions in the endosomes such as the late endosomes and the lysosomes of mammalian cells such as human cells. Exemplary linkers that can be used in the context of the present disclosure includes, but is not limited to, N-ε-maleimidocaproic acid hydrazide (EMCH), succinimidyl 3-(2-pyridyldithio)propionate or 3-(2-Pyridyldithio)propionic acid N-hydroxysuccinimide ester (SPDP), and 1-[Bis(dimethylamino)methylene]-1H-1,2,3-triazolo[4,5-b]pyridinium 3-oxid hexafluorophosphate (HATU).

The term "tri-functional linker" has its regular scientific meaning, and here refers to a linker which attaches three molecules via a chemical group on each of the three molecules. The skilled person is able to design such tri-functional linkers, based on the present disclosure and the common general knowledge. Such tri-functional linker can exhibit, for instance, a maleimido group that can be used for conjugation to targeting ligands that exhibit thiol groups to perform a thiol-ene reaction. In addition, the tri-functional linker could exhibit a dibenzocyclooctyne (DBCO) group to perform the so-called strain-promoted alkyne-azide cycloaddition (SPAAC, click chemistry) with an azido bearing saponin. Finally, the tri-functional linker could obtain a third functional group such as a trans-cyclooctene (TCO) group to perform the so-called inverse electron demand Diels-Alder (IEDDA) reaction with a tetrazine (Tz) bearing effector molecule. The skilled person will appreciate that the chemical groups of the tri-functional linker can be all three the same, or different, or the linker may comprise two of the same chemical groups for linking a molecule to the tri-functional linker. The formed bonds between the tri-functional linker can be covalent or non-covalent, and covalent bonds are preferred. The formed bonds between the tri-functional linker and the one or two or three bound molecules via respective chemical groups, can be cleavable (labile) bonds, such as cleavable under acidic conditions inside cells such as endosomes and lysosomes of mammalian cells such as human cells, or can be non-cleavable bonds. Of course, the tri-functional linker may encompass one or two chemical groups for forming covalent bonds while the further two or one chemical group(s), respectively, are/is for forming a non-covalent bond. Of course, the tri-functional linker may encompass one or two chemical groups for forming cleavable bonds while the further two or one chemical group(s), respectively, are/is for forming a non-cleavable bond.

The term "cleavable", such as used in the term "cleavable linker" or "cleavable bond" has its regular scientific meaning, and here refers to being subject to cleavage under acidic conditions, reductive conditions, enzymatic conditions or light-induced conditions. For example, a cleavable linker may be subject to cleavage under acidic conditions, preferably said cleavable linker is subject to cleavage in vivo under acidic conditions as present in endosomes and/or lysosomes of mammalian cells, preferably human cells, preferably at pH 4.0-6.5, and more preferably at pH 5.5. As another example, a cleavable linker may be subject to cleavage by an enzyme, e.g. by cathepsin. Furthermore, an example of a covalent bond cleavable under reductive conditions is a disulphide bond.

The terms "oligomer" and "polymer" in the context of an oligomeric or polymeric scaffold has its regular scientific meaning. A polymer here refers to a substance which has a molecular structure built up chiefly or completely from a large number of equal or similar units bonded together; an oligomer here refers to a polymer whose molecules consist of relatively few repeating units. For example, a structure comprising 5-10 or less equal or similar units, may be called an oligomeric structure, whereas a structure comprising 10-50 monomeric units or more may be called a polymeric structure, whereas a structure of 10 monomeric units may be called either oligomeric or polymeric.

The term "binding site" has its regular scientific meaning, and here refers to a region or an epitope on a molecule, e.g. a protein, DNA or RNA, to which another molecule can bind.

The term "scaffold" has its regular scientific meaning, and here refers to an oligomeric or polymeric template or a carrier or a base (base molecule or base structure), to which one or more molecules, e.g. ligand molecule, saponin of the invention, glycoside, effector molecule, can be covalently bound, either directly, or via a linker, such as a cleavable linker. A scaffold may have a structurally ordered formation such as a polymer, oligomer, dendrimer, dendronized polymer, or dendronized oligomer or have an assembled polymeric structure such as a hydrogel, microgel, nanogel, stabilized polymeric micelle or liposome, but excludes structures that are composed of non-covalent assemblies of monomers such as cholesterol/phospholipid mixtures. A scaffold may comprise a polymeric or oligomeric structure, such as poly- or oligo(amines), e.g., polyethylenimine and poly(amidoamine); or structures such as polyethylene glycol, poly- or oligo(esters), such as poly(lactids), poly (lactams), polylactide-co-glycolide copolymers; or poly (dextrin), poly- or oligosaccharides, such as cyclodextrin or polydextrose; or structures such as natural and/or artificial poly- or oligoamino acids such as poly-lysine or a peptide or a protein, DNA oligo- or polymers, stabilized RNA polymers or PNA (peptide nucleic acid) polymers. Preferably, the polymeric or oligomeric structures are biocompatible, wherein biocompatible means that the polymeric or oligomeric structure does not show substantial acute or chronic toxicity in organisms and can be either excreted as it is or fully degraded to excretable and/or physiological compounds by the body's metabolism.

The term "ligand" has its regular scientific meaning, and here refers to any molecule or molecules which may selectively bind to a target cell-surface molecule or target cell-surface receptor expressed at target cells, e.g. target cancer cells or target auto-immune cells. The ligand may bind to an epitope comprised by receptors or other antigens on the target cells. Preferably, the cell-binding ligands are antibodies.

The term "antibody" as used herein is used in the broadest sense, which may refer to an immunoglobulin (Ig) defined as a protein belonging to the class IgG, IgM, IgE, IgA, or IgD (or any subclass thereof), or a functional binding fragment or binding domain of an immunoglobulin. In the context of the present invention, a "binding fragment" or a "binding domain" of an immunoglobulin is defined as antigen-binding fragment or -domain or other derivative of a parental immunoglobulin that essentially maintains the antigen binding activity of such parental immunoglobulin. Functional fragments and functional domains are antibodies in the sense of the present invention even if their affinity to the antigen is lower than that of the parental immunoglobulin. "Functional fragments and -domains" in accordance with the invention include, but are not limited to, F(ab')2 fragments, Fab' fragments, Fab fragments, scFv, dsFv, single-domain antibody (sdAb), monovalent IgG, scFv-Fc, reduced IgG (rIgG), minibody, diabodies, triabodies, tetrabodies, Fc fusion proteins, nanobodies, variable V domains such as VHH, Vh, and other types of antigen recognizing immunoglobulin fragments and domains. The fragments and domains may be engineered to minimize or completely remove the intermolecular disulphide interactions that occur between the CH1 and CL domains. Functional fragment and -domains offer the advantage of greater tumor penetration because of their smaller size. In addition, the functional fragment or -domain can be more evenly distributed throughout the tumor mass as compared to whole immunoglobulin.

The antibodies (immunoglobulins) of the present invention may be bi- or multifunctional. For example, a bifunctional antibody has one arm having a specificity for one receptor or antigen, while the other arm recognizes a different receptor or antigen. Alternatively, each arm of the bifunctional antibody may have specificity for a different epitope of the same receptor or antigen of the target cell.

The antibodies (immunoglobulins) of the present invention may be, but are not limited to, polyclonal antibodies, monoclonal antibodies, human antibodies, humanized antibodies, chimeric antibodies, resurfaced antibodies, anti-idiotypic antibodies, mouse antibodies, rat antibodies, rat/mouse hybrid antibodies, llama antibodies, llama heavy-chain only antibodies, heavy-chain only antibodies, and veterinary antibodies. Preferably, the antibody (immunoglobulin) of the present invention is a monoclonal antibody. The resurfaced, chimeric, humanized and fully human antibodies are also more preferred because they are less likely to cause immunogenicity in humans. The antibodies of the ADC of the present invention preferably specifically binds to an antigen expressed on the surface of a cancer cell, an autoimmune cell, a diseased cell, an aberrant cell, while leaving any healthy cell essentially unaltered (e.g. by not binding to such normal cell, or by binding to a lesser extent in number and/or affinity to such healthy cell).

Specific antibodies that can be used for the ADCs of the present invention include, but are not limited to, anti-HER2 monoclonal antibody such as trastuzumab and pertuzumab, anti-CD20 monoclonal antibody such as rituximab, ofatumumab, tositumomab and ibritumomab, anti-CA125 monoclonal antibody such as oregovomab, anti-EpCAM (17-1A) monoclonal antibody such as edrecolomab, anti-EGFR monoclonal antibody such as cetuximab, panitumumab and nimotuzumab, anti-CD30 monoclonal antibody such brentuximab, anti-CD33 monoclonal antibody such as gemtuzumab and huMy9-6, anti-vascular integrin alpha-v beta-3 monoclonal antibody such as etaracizumab, anti-CD52 monoclonal antibody such as alemtuzumab, anti-CD22 monoclonal antibody such as epratuzumab, anti-CEA monoclonal antibody such as labetuzumab, anti-CD44v6 monoclonal antibody such as bivatuzumab, anti-FAP monoclonal antibody such as sibrotuzumab, anti-CD19 monoclonal antibody such as huB4, anti-CanAg monoclonal antibody such as huC242, anti-CD56 monoclonal antibody such huN901, anti-CD38 monoclonal antibody such as daratumumab, anti-CA6 monoclonal antibody such as DS6, anti-IGF-IR monoclonal antibody such as cixutumumab and 3B7, anti-integrin monoclonal antibody such as CNTO 95, and anti-syndecan-1 monoclonal antibody such as B-B4. An embodiment is the protein-toxin conjugate of Stemline: ELZONRIS™ (tagraxofusp, SL-401)—ELZONRIS is a novel targeted therapy directed to the interleukin-3 (IL-3) receptor-α (CD123), a target present on a wide range of malignancies.

Any other molecules than antibodies that bind to a cell receptor or antigen of a target cell can also be used as the cell-binding ligand for the ligand-drug conjugates of the present invention and the ligands provided with covalently bound saponin according to the invention. These ligands include, but are not limited to, proteins, polypeptides, peptides, small molecules. Examples of these non-antibody ligands are interferons (e.g. IFN-α, IFN-β, and IFN-γ), transferrins, lectins, epidermal growth factors (EGF) and EGF-like domains, gastrin-releasing peptides (GRP), platelet-derived growth factors (PDGF), transforming growth factors (TGF), vaccinia growth factor (VGF), insulin and insulin-like growth factors (IGF, e.g. IGF-1 and IGF-2), other suitable hormones such as thyrotropin releasing hormones (TRH), melanocyte-stimulating hormones (MSH), steroid hormones (e.g. estrogen and androgen), somatostatin, lymphokines (e.g. IL-2, IL-3, IL-4, and IL-6), colony-stimulating factors (CSF, e.g. G-CSF, M-CSF and GM-CSF), bombesin, gastrin, Arg-Gly-Asp or RGD, aptamers (e.g. AS-1411, GBI-10, RNA aptamers against HIV glycoprotein), small molecules (e.g. folate, anisamide phenylboronic acid), vitamins (e.g., vitamin D), carbohydrates (e.g. hyaluronic acid, galactose).

An "effector molecule" or "effector moiety" or "payload" has its regular scientific meaning and in the context of this invention is any substance that affects the metabolism of a cell by interaction with an intracellular effector molecule target, wherein this effector molecule target is any molecule or structure inside cells excluding the lumen of compartments and vesicles of the endocytic and recycling pathway but including the membranes of these compartments and vesicles. Said structures inside cells thus include the nucleus, mitochondria, chloroplasts, endoplasmic reticulum, Golgi apparatus, other transport vesicles, the inner part of the plasma membrane and the cytosol.

The effector molecule or -moiety is a pharmaceutically active substance, such as a toxin such as a proteinaceous toxin, a drug, a polypeptide or a polynucleotide. A pharmaceutically active substance in this invention is an effector molecule or -moiety that is used to achieve a beneficial outcome in an organism, preferably a vertebrate, more preferably a mammal such as non-human subjects or a human being/subject. Benefits include diagnosis, prognosis, treatment, cure and prevention (prophylaxis) of diseases and/or symptoms and/or health problems. The pharmaceutically active substance may also lead to undesired and sometimes even harmful side effects (adverse events such as observed during clinical trials). In this case, pros and cons must be weighed to decide whether the pharmaceutically active substance is suitable in the particular case. If the effect of the pharmaceutically active substance inside a cell is predominantly beneficial for the organism as a whole, the cell is called a target cell. If the effect inside a cell is predominantly harmful for the organism as a whole, the cell is called an off-target cell. In artificial systems such as cell cultures and bioreactors, target cells and off-target cells depend on the purpose and are defined by the user. Examples of effector molecules and -moieties are a drug, a toxin, a polypeptide (such as an enzyme), a polynucleotide (including polypeptides and polynucleotides that comprise non-natural amino acids or nucleic acids), and any combination thereof.

An effector molecule or effector moiety that is a drug may include, but not limited to, anti-cancer agents, anti-inflammatory agents, and anti-infective (e.g., anti-fungal, antibacterial, anti-parasitic, antiviral) agents. Preferably, the drug molecule of the present invention is an anti-cancer agent or an anti-auto-immune agent. Suitable anti-cancer agents include, but are not limited to, alkylating agents, antimetabolites, spindle poison plant alkaloids, cytotoxic/antitumor antibiotics, topoisomerase inhibitors, photosensitizers, and kinase inhibitors. Also included in the definition of "anti-cancer agent" are: e.g. (i) anti-hormonal agents that act to regulate or inhibit hormone action on tumors such as anti-estrogens and selective estrogen receptor modulators; (ii) aromatase inhibitors that inhibit the enzyme aromatase, which regulates estrogen production in the adrenal glands; (iii) anti-androgens; (iv) protein kinase inhibitors; (v) lipid kinase inhibitors; (vi) antisense oligonucleotides, particularly those which inhibit expression of genes in signaling pathways implicated in aberrant cell proliferation; (vii) ribozymes such as VEGF expression inhibitors and HER2 expression inhibitors; (viii) vaccines such as gene therapy vaccines; topoisomerase 1 inhibitors; (ix) anti-angiogenic agents; and pharmaceutically acceptable salts, acids, solvates and derivatives of any of the above.

An effector molecule or -moiety that is a toxin may include, but is not limited to, proteinaceous toxins (e.g. bacterial-derived toxins, and plant-derived toxins), toxins targeting tubulin filaments, toxins targeting DNA, toxins targeting RNA. Examples of proteinaceous toxins are saporin, dianthin, ricin, modeccin, abrin, volkensin, viscumin, shiga toxin, shiga-like toxin, *Pseudomonas* exotoxin (PE, also known as exotoxin A), diphtheria toxin (DT), and cholera toxin. Examples of tubulin filaments-targeting toxins are maytansinoids (e.g. DM1 and DM4), auristatins (e.g. Monomethyl auristatin E (MMAE) and Monomethyl auristatin F (MMAF)), toxoids, tubulysins, cryptophycins, rhizoxin. Examples of DNA-targeting toxins are calicheamicins: N-Acetyl-γ-calicheamicin, CC-1065 analogs, duocarmycins, doxorubicin, methotrexate, benzodiazepines, camptothecin analogues, and anthracyclines. Examples of DNA-targeting toxins are amanitins, spliceostatins, and thailanstatins. A toxin, as used in this invention, is defined as a pharmaceutically active substance that is able to kill or inactivate a cell. Preferably, a targeted toxin is a toxin that is only, or at least predominantly, toxic for target cells but not for off-target cells. The net effect of the targeted toxin is preferably beneficial for the organism as a whole.

An effector molecule or -moiety that is a polypeptide may be, e.g., a polypeptide that recover a lost function, such as for instance enzyme replacement, gene regulating functions, or a toxin. Examples of polypeptides as effector molecules are, e.g., Cas9; toxins (e.g. saporin, dianthin, gelonin, (de) bouganin, agrostin, ricin (toxin A chain); pokeweed antiviral protein, apoptin, diphtheria toxin, *Pseudomonas* exotoxin) metabolic enzymes (e.g. argininosuccinate lyase, argininosuccinate synthetase), enzymes of the coagulation cascade, repairing enzymes; enzymes for cell signaling; cell cycle regulation factors; gene regulating factors (transcription factors such as NF-κB or gene repressors such as methionine repressor).

An effector molecule or an effector moiety that is a polynucleotide may, e.g., be a polynucleotide that comprises coding information, such as a gene or an open reading frame encoding a protein. It may also comprise regulatory information, e.g. promotor or regulatory element binding regions, or sequences coding for micro RNAs. Such polynucleotide may comprise natural and artificial nucleic acids. Artificial nucleic acids include, e.g. peptide nucleic acid (PNA), Morpholino and locked nucleic acid (LNA), as well as glycol nucleic acid (GNA) and threose nucleic acid (TNA). Each of these is distinguished from naturally occurring DNA or RNA by changes to the backbone of the molecule. Examples of nucleotides as effector molecules are, but not limited to, e.g., DNA: single stranded DNA (e.g. DNA for adenine phosphoribosyltransferase); linear double stranded DNA (e.g. clotting factor IX gene); circular double stranded DNA (e.g. plasmids); RNA: mRNA (e.g. TAL effector molecule nucleases), tRNA, rRNA, siRNA, miRNA, anti-sense RNA; anti-sense oligonucleotides (ASOs, AONs e.g. PNA, PMO, LNA and BNA).

The term "proteinaceous", used in e.g. "proteinaceous molecule" and "proteinaceous toxin", are molecules and toxins comprising at least a string of amino acid residues that can be obtained as an expression product from a single mRNA. Such a molecule or toxin may further comprise any post-translational modifications, a carbohydrate such as an N- or O-linked carbohydrate, disulphide bonds, phosphorylations, sulphatations, etc., as a result of any post-translational modification, and/or may further comprise any other modification such as those resulting from chemical modifications (e.g., linking of effector moieties, saponin, scaffolds, ligands, etc., either directly to e.g. an amino-acid side chain, or via at least one linker (covalently) bound to the molecule for chemically modifying the proteinaceous molecule, and chemically bound (covalently) to the proteinaceous molecule). The term "proteinaceous" also encompasses and includes assemblies of such molecules, e.g. homodimers, heterotrimers, heterohexamers or complex assemblies such as ribosomes.

The terms "specific" and "specifically", in the context of for example "specific binding" and "receptor or molecular target specifically present or expressed at the surface of a tumor cell" and the like, have their normal scientific meaning known in the art, and here refer to e.g. a binding interaction of a first molecule with a second molecule which occurs with a higher affinity relative to any putative binding of the first molecule to a further molecule different from the second molecule, or e.g. to the expression or expression to a higher extent when e.g. the number of receptors or molecular targets is considered, of a cell-surface receptor or molecular target on the surface of a first type of cell such as a tumor cell, autoimmune cell, diseased cell, aberrant cell, relative to the extent of expression of the same receptor or molecular target at a second type of cell such as a healthy cell, etc., wherein expression at the second type of cell can be fully absent or very low, relative to any extent of expression on the tumor cell, etc. Furthermore, the term "specific", for example in "specific binding", has its normal scientific meaning known in the art, and here has the meaning of indicating a molecule that can have an interaction with another molecule with higher binding affinity than background interactions between molecules. Similarly, the term "specificity" refers to an interaction, for example, between two molecules or between a cell and a molecule, which has higher binding affinity than background interactions between molecules. Binding molecules such as immunoglobulins bind via their binding site such as immunoglobulin variable regions of the immunoglobulin, to binding sites on molecules, such as epitopes, cell-surface receptors, etc., with a higher binding affinity than background interactions between molecules. In the context of the invention, background interactions are typically interactions with an affinity lower than a $K_D$ of 10E-4 M. Similarly, "specific binding domains" are domains that preferentially bind to binding sites on molecules, such as epitopes, cell-surface receptors, etc., with a higher binding affinity than background interactions between molecules. In the context of the invention, "background interactions" are typically interactions with an affinity lower than a $K_D$ of 10E-4 M. Preferably, specific binding domains bind with an affinity higher than a $K_D$ of about 10E-5 M.

The term "binding" is defined as interactions between molecules that can be distinguished from background interactions.

Throughout the specification, the term "fragment" refers to an amino acid sequence which is part of a protein domain or which builds up an intact protein domain. Binding fragments according to the invention must have binding specificity for the respective target such as a cell-surface receptor, e.g. on the surface of a diseased cell such as a tumor cell.

The term "ADC" or "antibody-drug conjugate" has its regular scientific meaning known to the skilled person, and here refers to a class of biopharmaceutical drugs designed as a targeted therapy for treating e.g. cancer. Unlike chemotherapy, ADCs are intended to target and kill tumor cells while sparing healthy cells. ADCs are composed of an antibody linked to a biologically active cytotoxic (anticancer) payload or drug. ADCs combine the targeting capabilities of monoclonal antibodies with the cancer-killing ability of cytotoxic drugs. They are designed with the intention to discriminate between healthy cells and diseased tissue such as tumor cells in a tumor.

The term "Saponinum album" has its normal meaning and here refers to a mixture of saponins produced by Merck KGaA (Darmstadt, Germany) containing saponins from *Gypsophila paniculata* and *Gypsophila arostii*, containing SA1657 and mainly SA1641.

The term "Quillajasaponin" has its normal meaning and here refers to the saponin fraction of *Quillaja saponaria* and thus the source for all other QS saponins, mainly containing QS-18 and QS-21.

"QS-21" or "QS21" has its regular scientific meaning and here refers to a mixture of QS-21 A-apio (~63%), QS-21 A-xylo (~32%), QS-21 B-apio (~3.3%), and QS-21 B-xylo (~1.7%).

Similarly, "QS-21A" has its regular scientific meaning and here refers to a mixture of QS-21 A-apio (~65%) and QS-21 A-xylo (~35%).

Similarly, "QS-21 B" has its regular scientific meaning and here refers to a mixture of QS-21 B-apio (~65%) and QS-21 B-xylo (~35%).

The term "Quil-A" refers to a commercially available semi-purified extract from *Quillaja saponaria* and contains variable quantities of more than 50 distinct saponins, many of which incorporate the triterpene-trisaccharide substructure Gal-(1→2)-[Xyl-(1→3)]-GlcA- at the C-3beta-OH group found in QS-7, QS-17, QS18, and QS-21. The saponins found in Quil-A are listed in van Setten (1995), Table 2 [Dirk C. van Setten, Gerrit van de Werken, Gijsbert Zomer and Gideon F. A. Kersten, *Glycosyl Compositions and Structural Characteristics of the Potential Immuno-adjuvant Active Saponins in the Quillaja saponaria Molina Extract Quil A, RAPID COMMUNICATIONS IN MASS SPECTROMETRY, VOL.* 9,660-666 (1995)]. Quil-A and also Quillajasaponin are fractions of saponins from *Quillaja saponaria* and both contain a large variety of different saponins with largely overlapping content. The two fractions differ in their specific composition as the two fractions are gained by different purification procedures.

The term "QS1861" and the term "QS1862" refer to QS-7 and QS-7 api. QS1861 has a molecular mass of 1861 Dalton, QS1862 has a molecular mass of 1862 Dalton. QS1862 is described in Fleck et al. (2019) in Table 1, row no. 28 [Juliane Deise Fleck, Andresa Heemann Betti, Francini Pereira da Silva, Eduardo Artur Troian, Cristina Olivaro, Fernando Ferreira and Simone Gasparin Verza, *Saponins from Quillaja saponaria and Quillaja brasiliensis: Particular Chemical Characteristics and Biological Activities, Mol-*

*ecules* 2019, 24, 171; doi:10.3390/molecules24010171]. The described structure is the api-variant QS1862 of QS-7. The molecular mass is 1862 Dalton as this mass is the formal mass including proton at the glucuronic acid. At neutral pH, the molecule is deprotonated. When measuring in mass spectrometry in negative ion mode, the measured mass is 1861 Dalton.

The terms first, second, third and the like in the description and in the claims, are used for distinguishing between similar elements and not necessarily for describing a sequential or chronological order. The terms are interchangeable under appropriate circumstances. The embodiments of the invention can operate in other sequences than described or illustrated herein.

Furthermore, the various embodiments, although referred to as "preferred" or "e.g." or "for example" or "in particular" are to be construed as exemplary manners in which the invention may be implemented rather than as limiting the scope of the invention.

The term "comprising", used in the claims, should not be interpreted as being restricted to the elements or steps listed thereafter; it does not exclude other elements or steps. It needs to be interpreted as specifying the presence of the stated features, integers, steps or components as referred to, but does not preclude the presence or addition of one or more other features, integers, steps or components, or groups thereof. Thus, the scope of the expression "a pharmaceutical composition comprising A and B" should not be limited to a pharmaceutical composition consisting only of components A and B, rather with respect to the present invention, the only enumerated components of the pharmaceutical composition are A and B, and further the claim should be interpreted as including equivalents of those components. Similarly, the scope of the expression "a method comprising step A and step B" should not be limited to a method consisting only of steps A and B, rather with respect to the present invention, the only enumerated steps of the method are A and B, and further the claim should be interpreted as including equivalents of those steps.

In addition, reference to a feature by the indefinite article "a" or "an" does not exclude the possibility that more than one of the features such as for example a component, excipient, saponin, etc. are present, unless the context clearly requires that there is one and only one of the features. The indefinite article "a" or "an" thus usually means "at least one".

Figure 12:
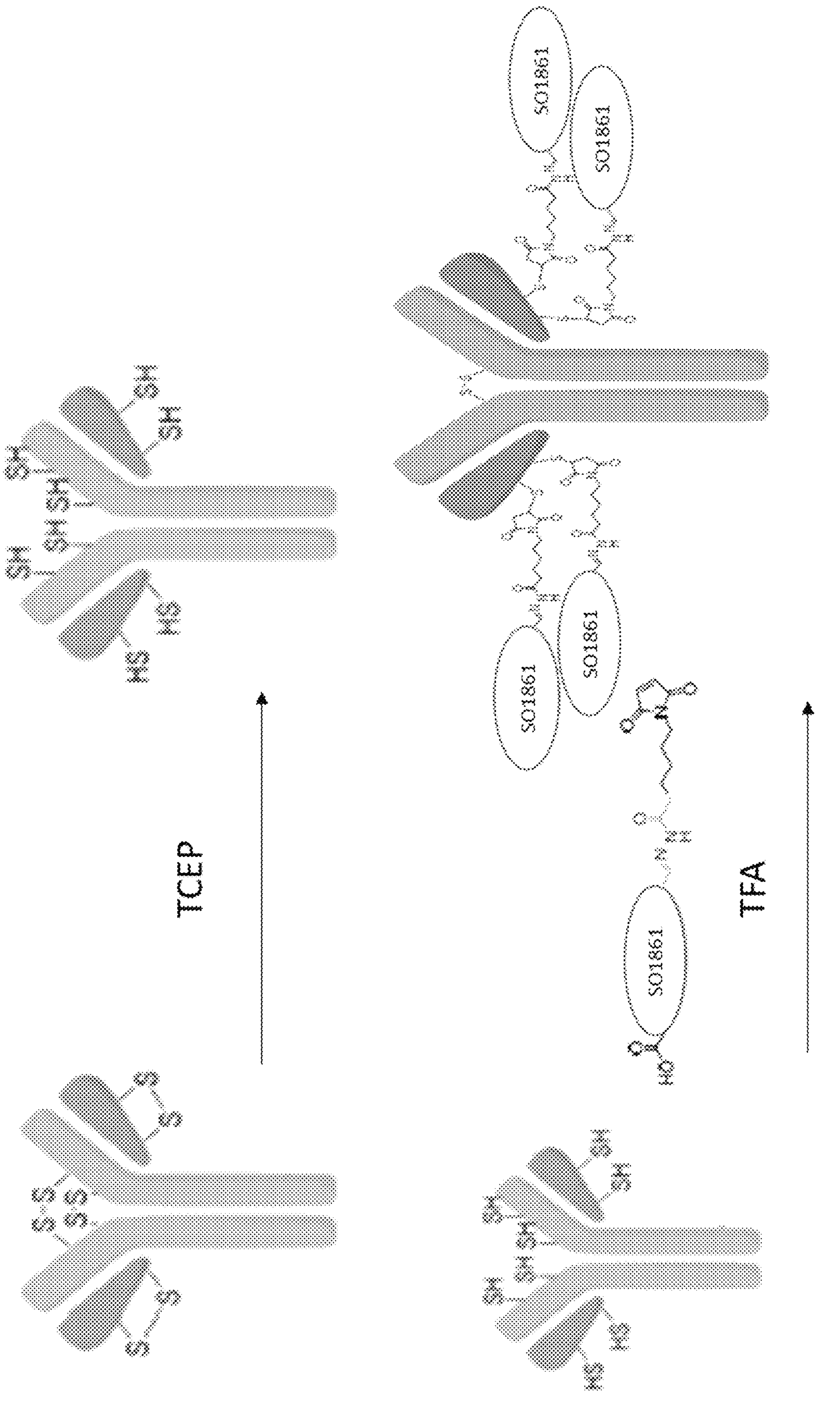

FIG. 12. Antibody-SO1861 conjugation procedure. Shown is the coupling reaction of the linking of four moieties of a plant-derived saponin SO1861 to the four cysteines in the light chain of an antibody. First, the disulphide bonds in the IgG are disrupted under influence of exposure to TCEP (Tris(2-carboxyethyl)phosphine); second, the saponin SO1861 comprising a chemical linker bound to it, is added together with trifluoro acetic acid, and four saponin moieties are linked to the IgG. For producing cleavable 'ready to conjugate' saponins the aldehyde group of SO1861 was reacted with an EMCH (ε-maleimidocaproic acid hydrazide) linker. The hydrazide group of EMCH forms an acid cleavable hydrazone bond with the aldehyde of SO1861. At the same time the EMCH linker presents a maleimide group that is thiol (sulfhydryl group) reactive and thus can be conjugated to thiols of the IgG, i.e. the ligand moiety. Herewith, an endosomal escape enhancing conjugate of the invention is provided, and/or a first binding molecule of the invention is provided.

Figure 13:
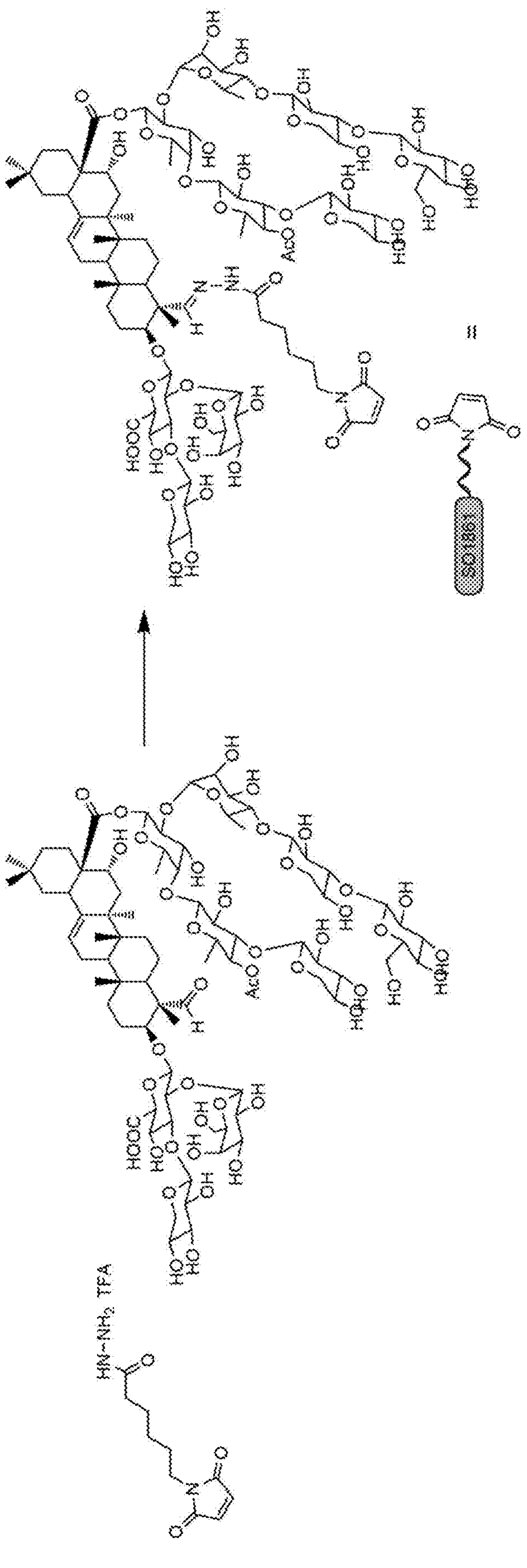

FIG. 13. SO1861-EMCH synthesis

Figure 14:
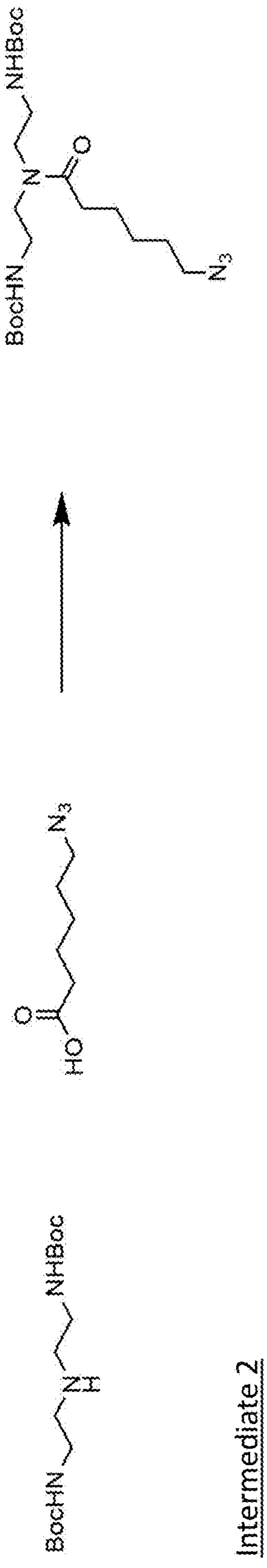
Figure 14:
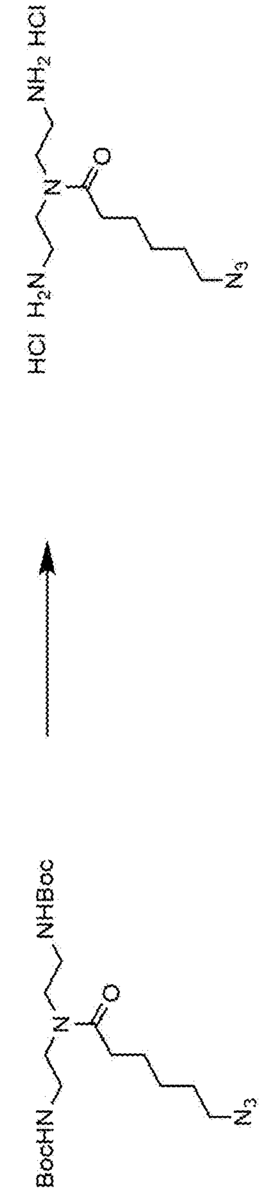
Figure 14:
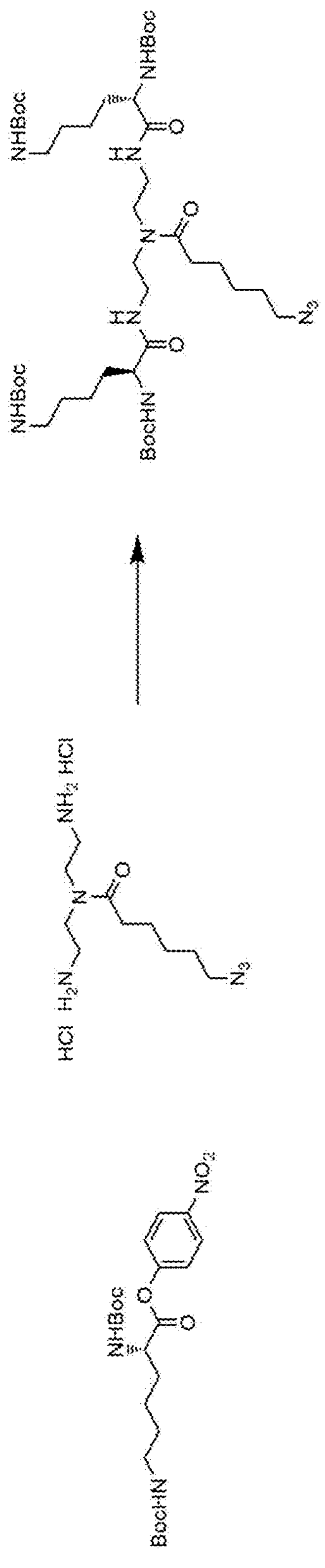
Figure 14:
Figure 14:
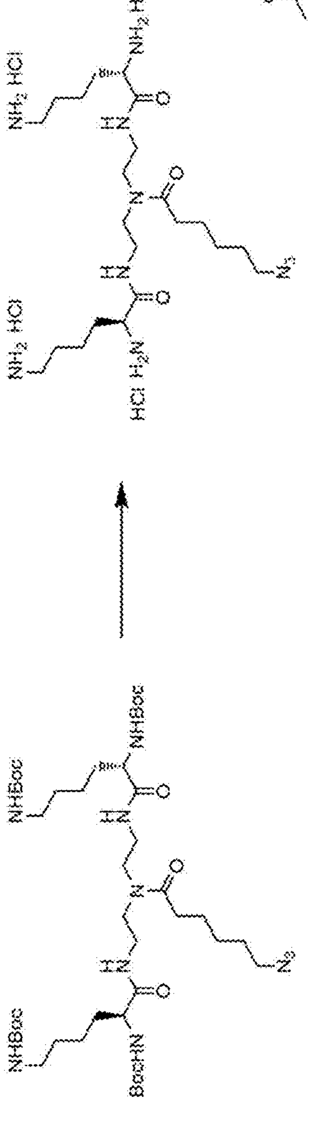
Figure 14:
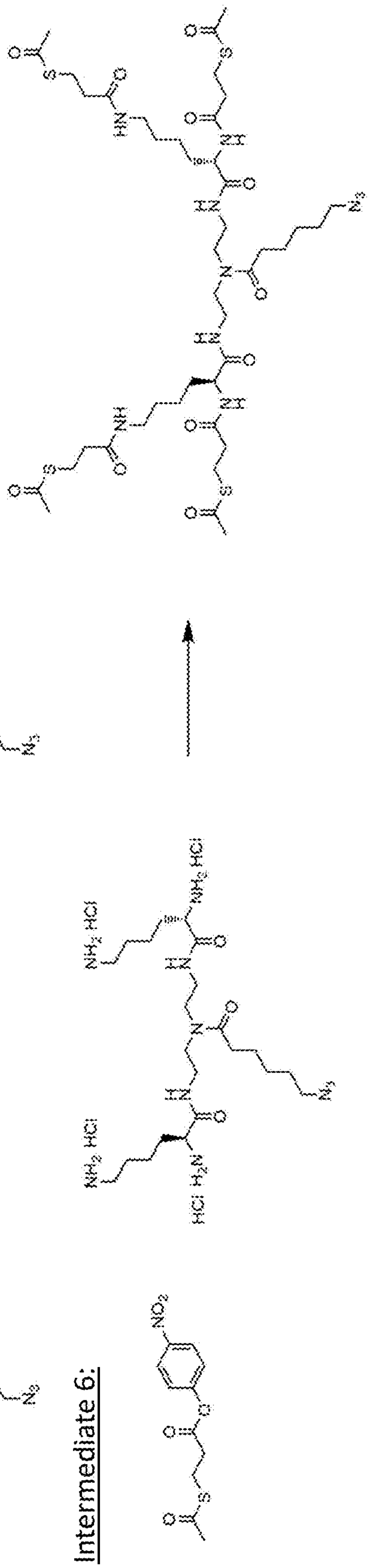
Figure 14:
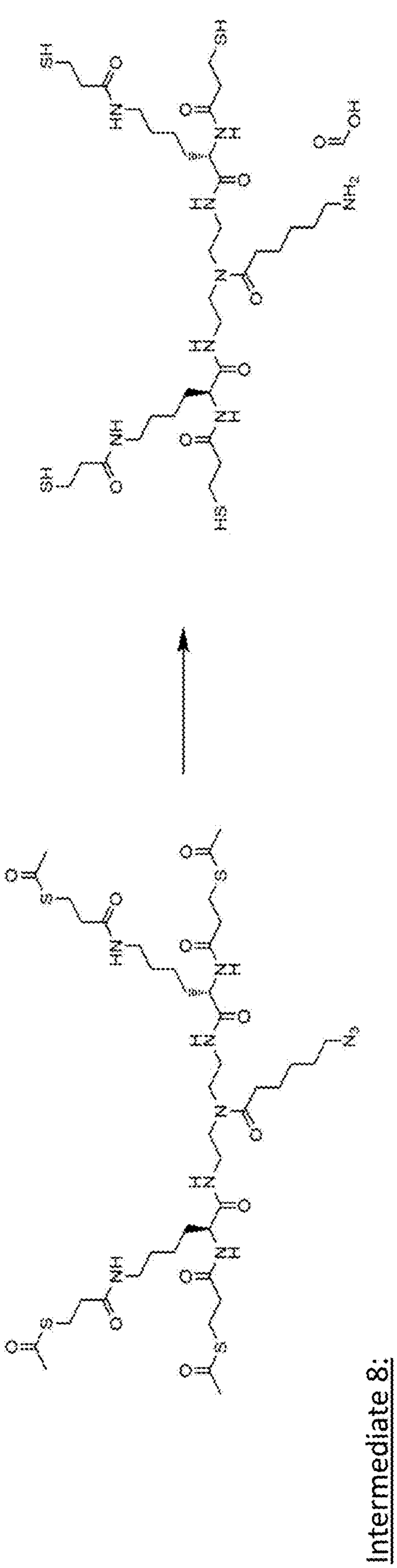
Figure 14:
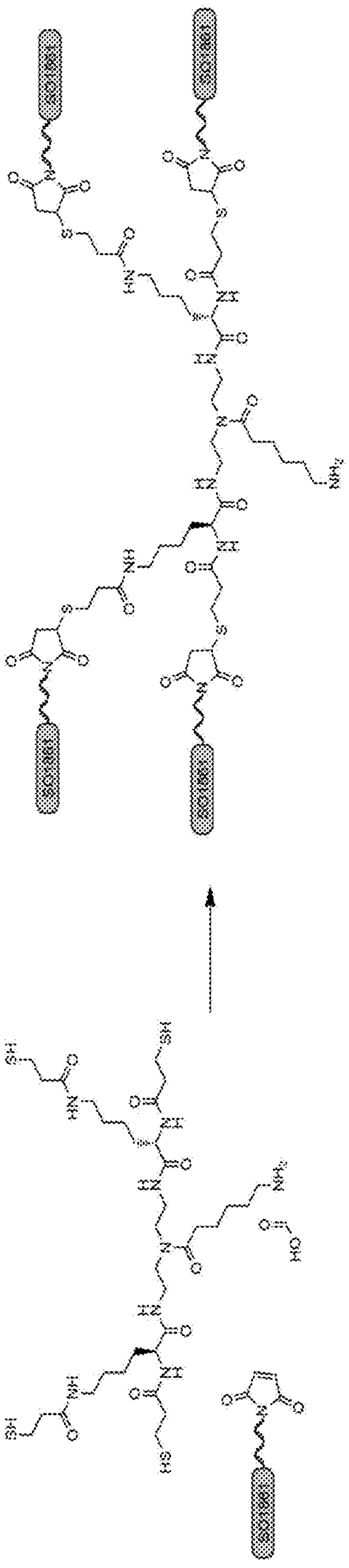
Figure 14:
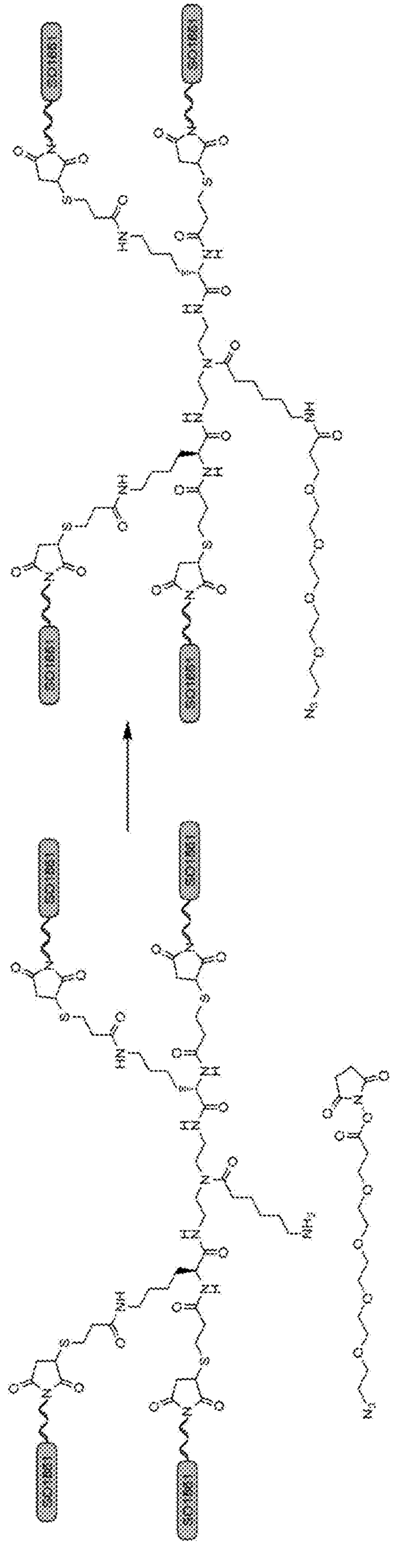
Figure 14:
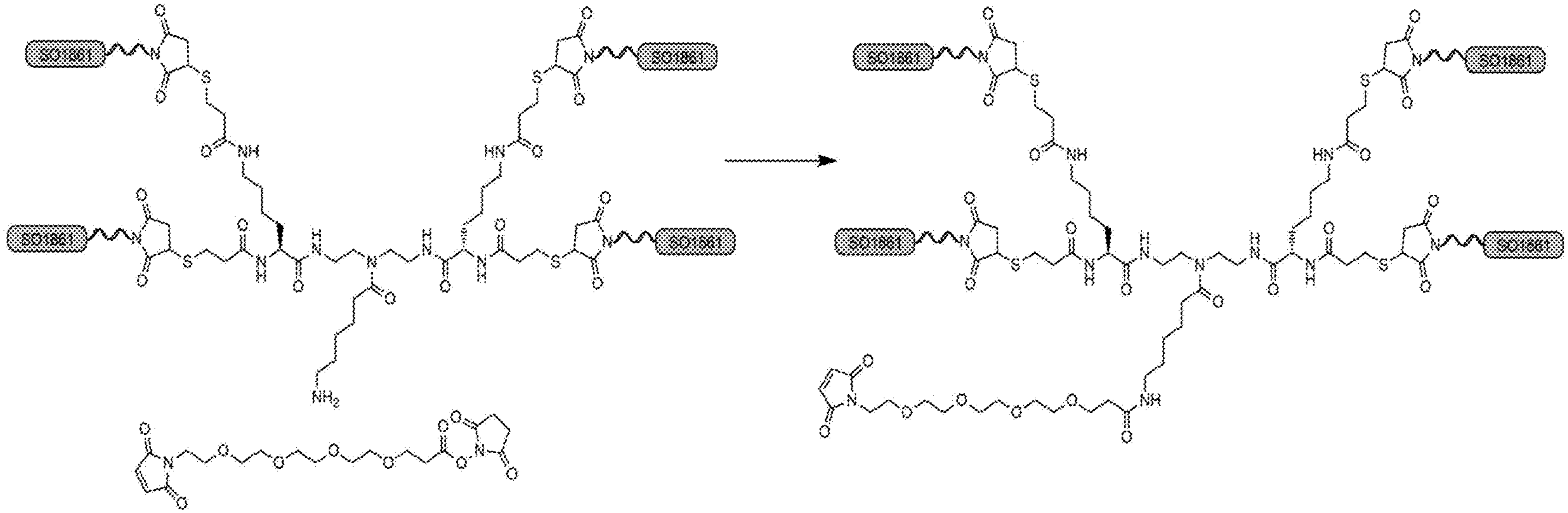
Figure 14:
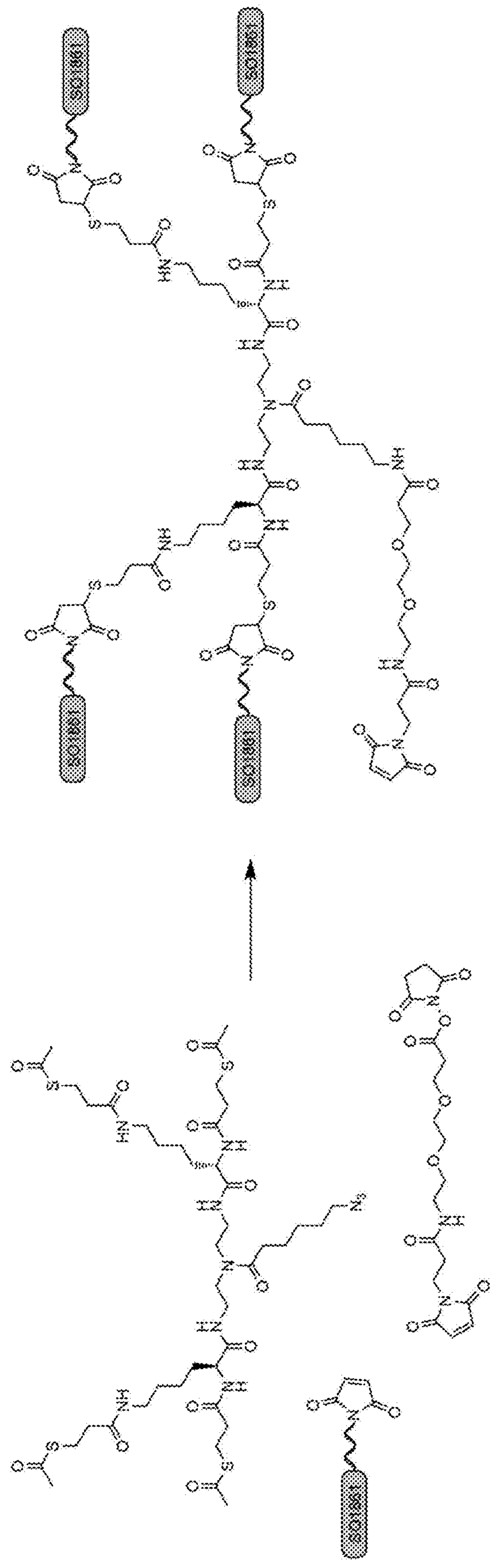

FIG. 14 Dendron-(-L-SO1861)$^4$ synthesis

Figure 15:
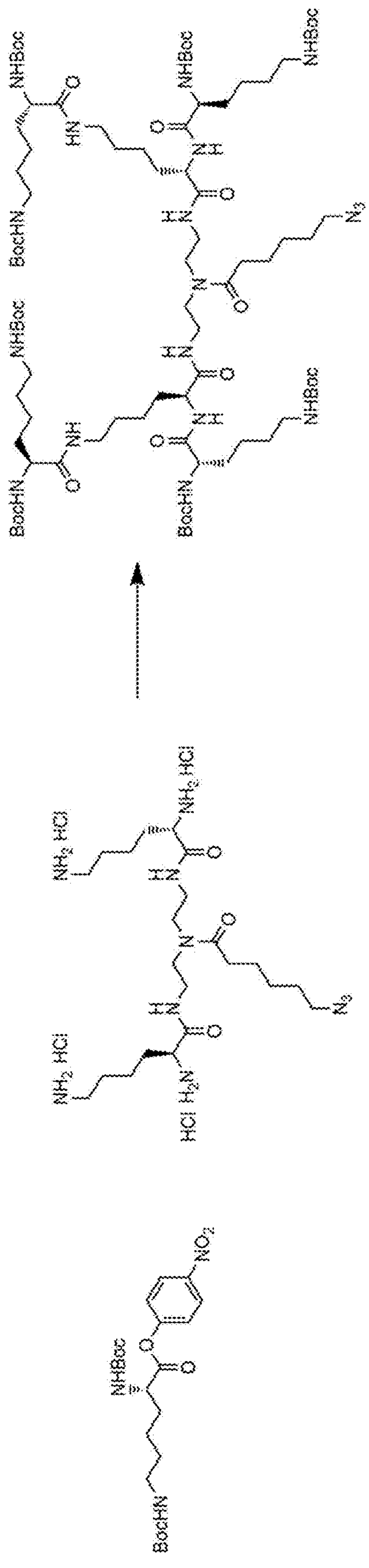
Figure 15:
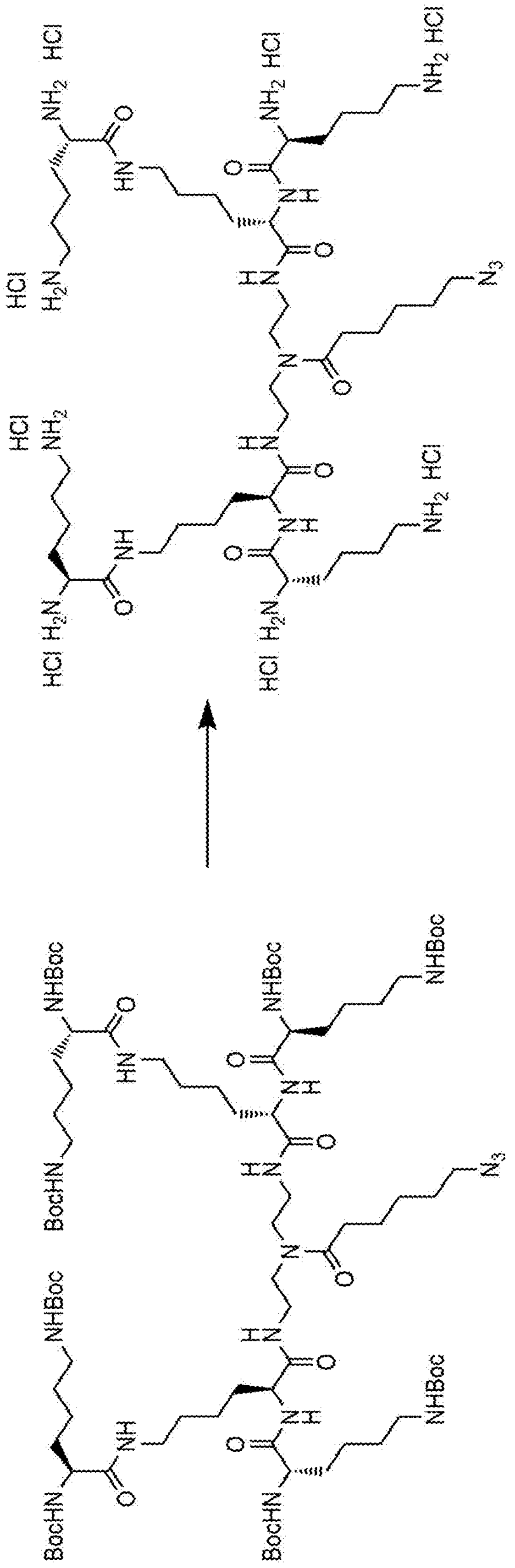
Figure 15:
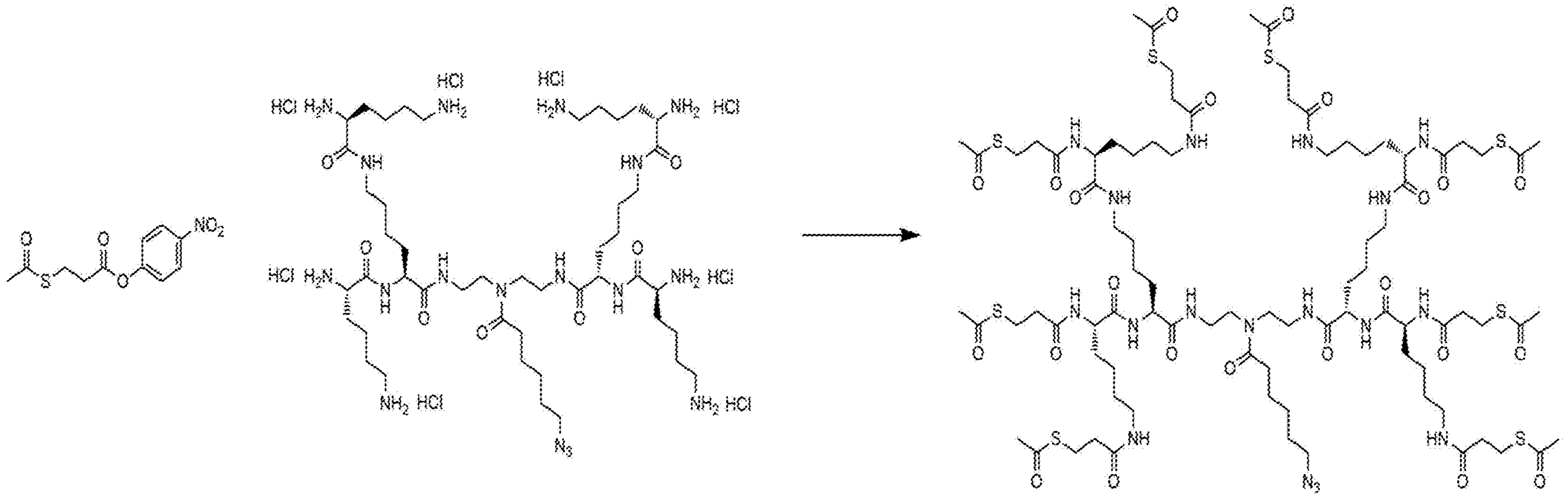
Figure 15:
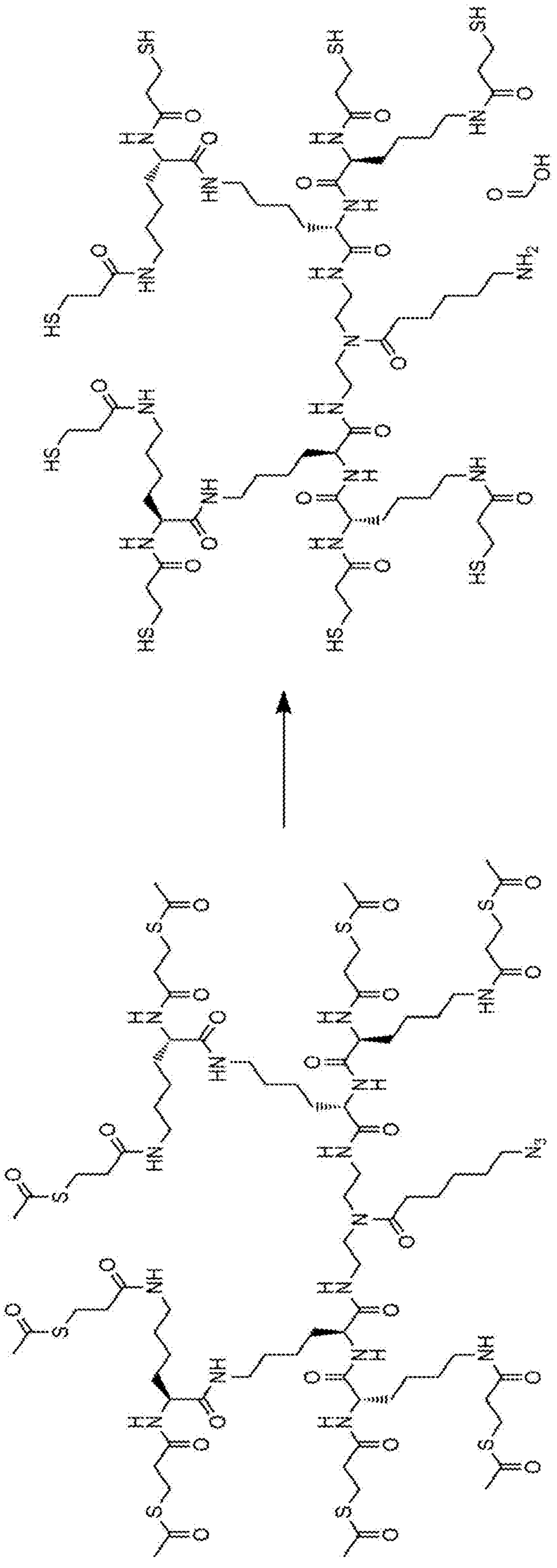
Figure 15:
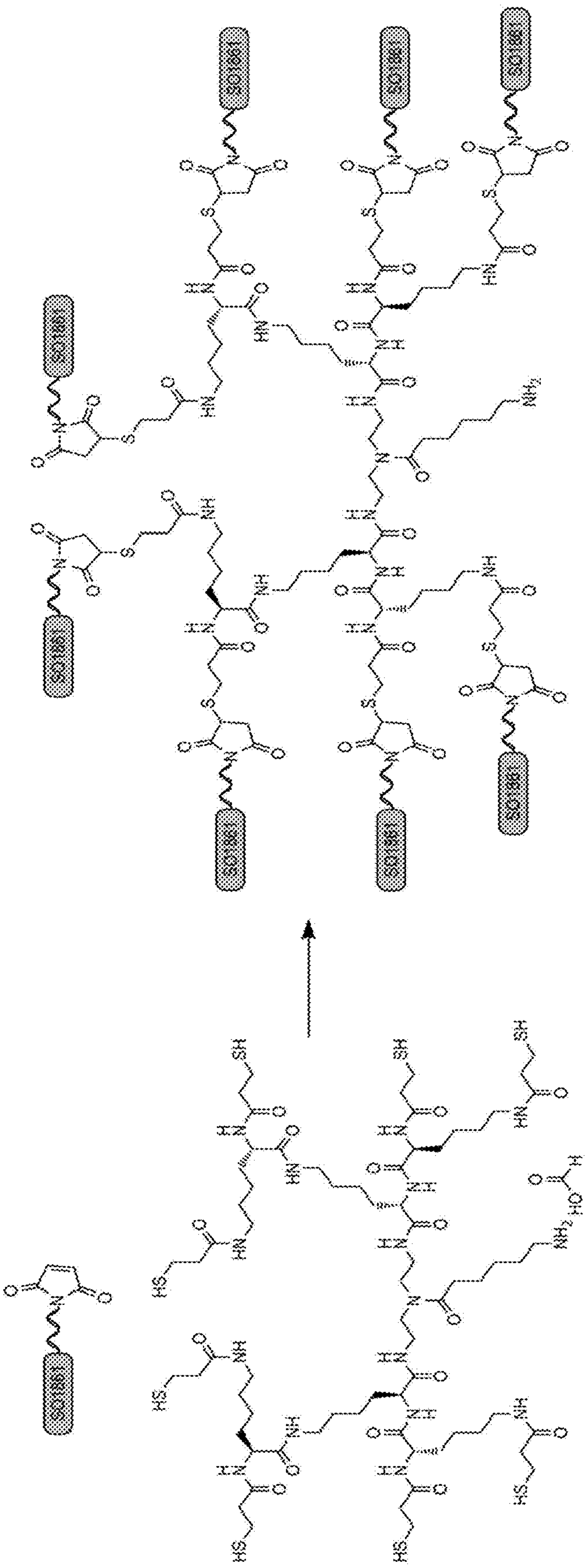

FIG. 15. Dendron-(-L-SO1861)$^8$ synthesis

Figure 16:
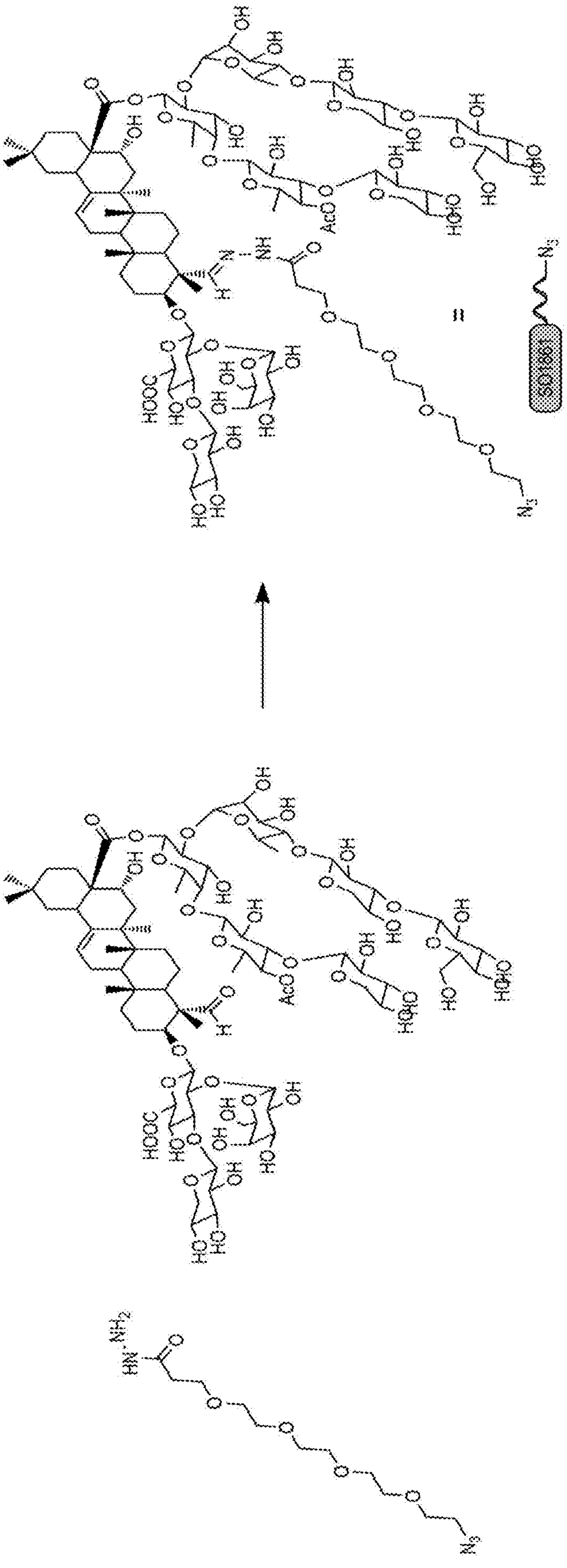
Figure 16:
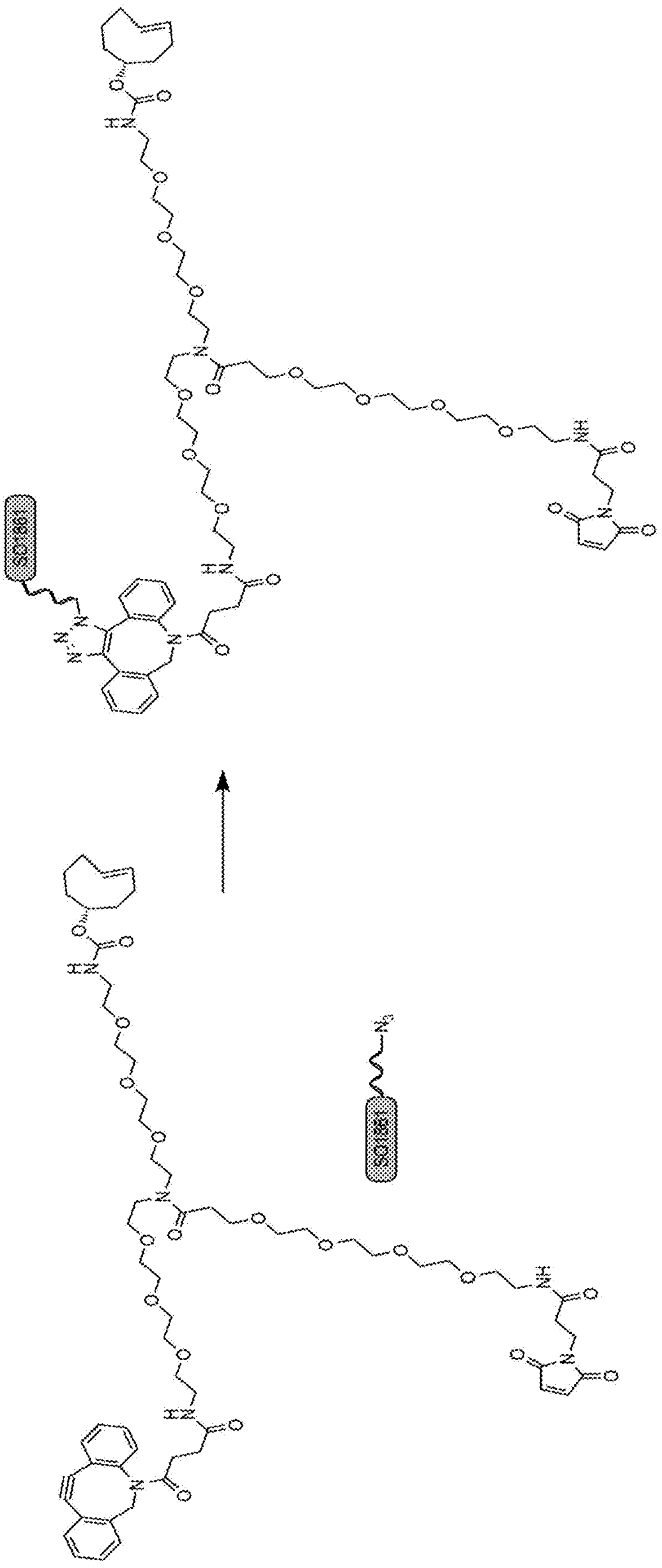
Figure 16:
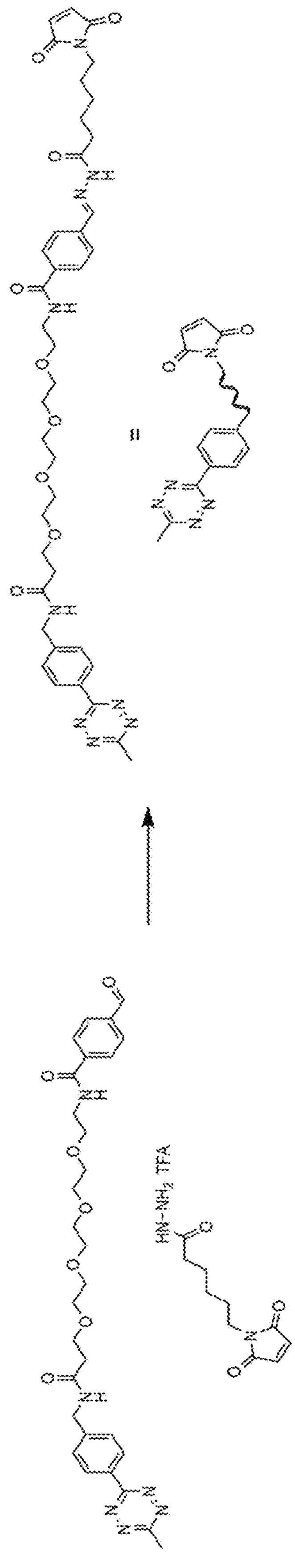
Figure 16:
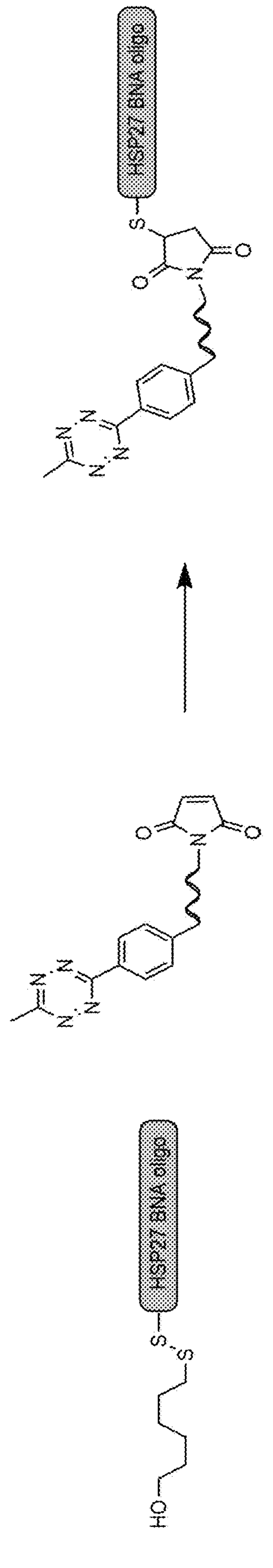
Figure 16:
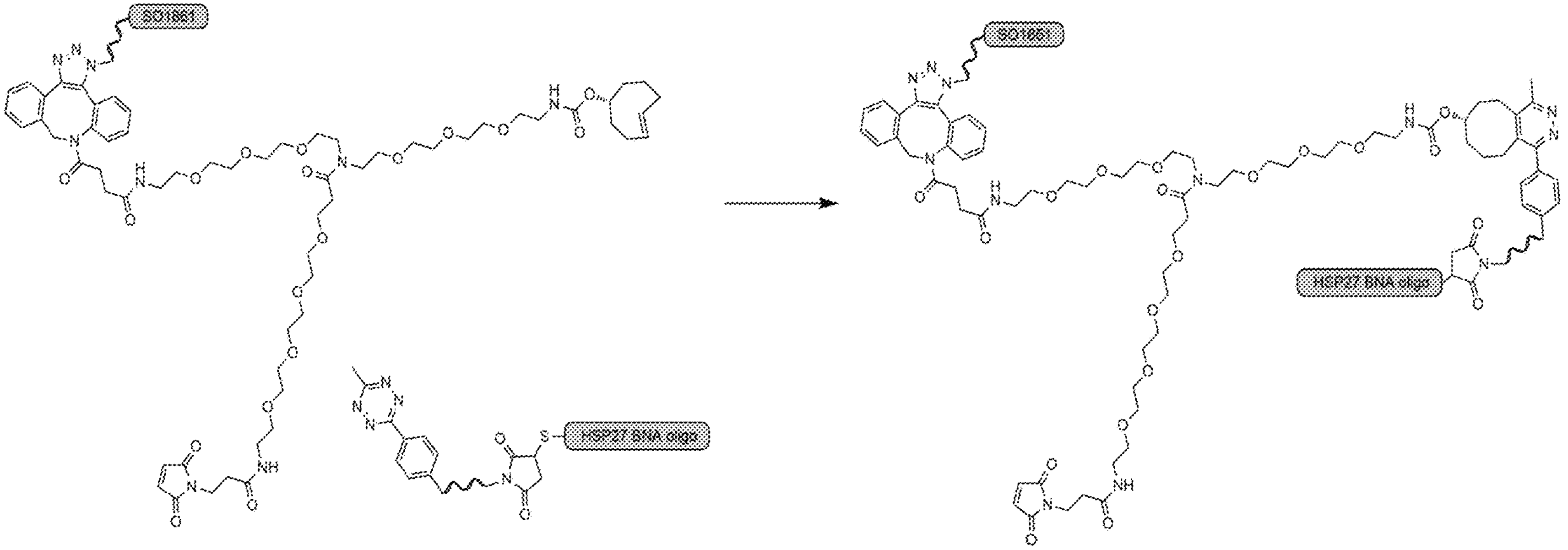

FIG. 16. SO181-L-trifunctional linker-L-HSP27BNA synthesis

Figure 17:
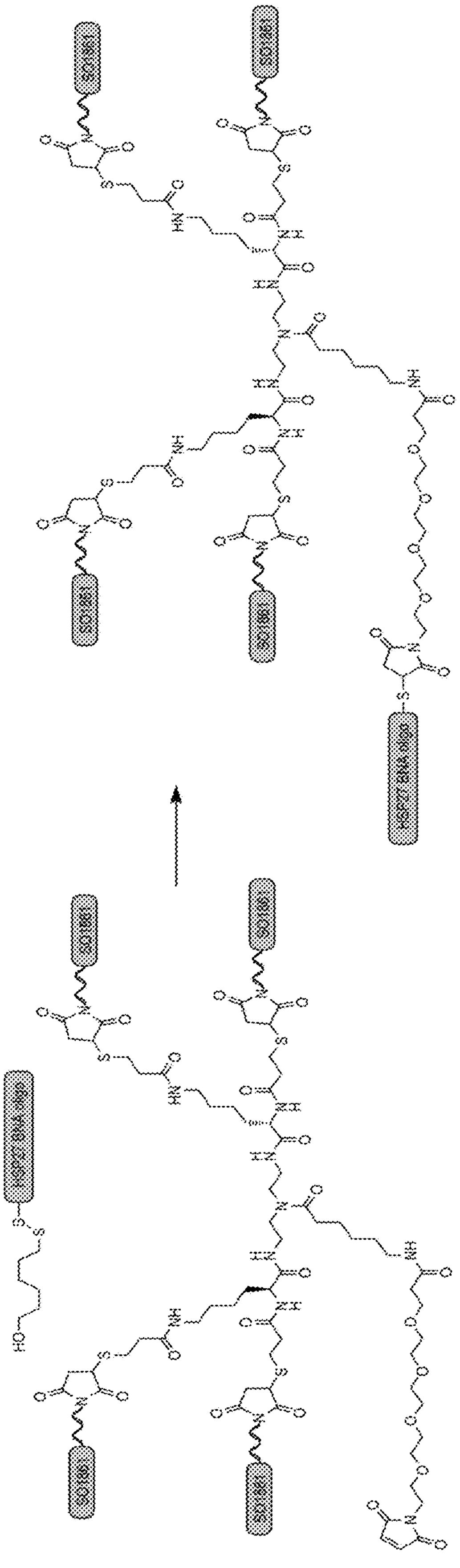

FIG. 17. HSP27BNA-dendron-(-L-SO1861)$^4$ synthesis

Figure 18:
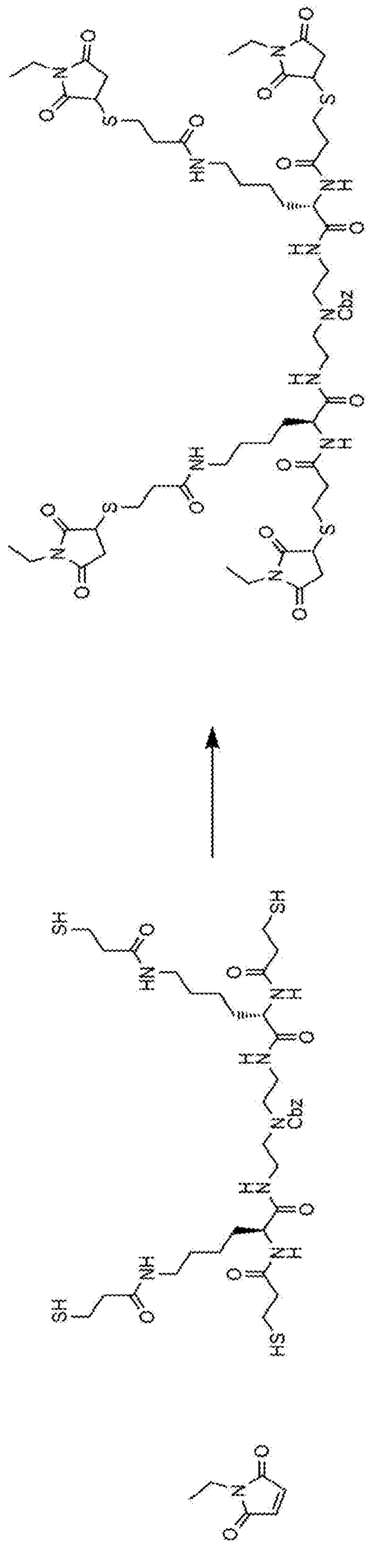

FIG. 18. Dendron(NEM)$^4$ synthesis

Figure 19:
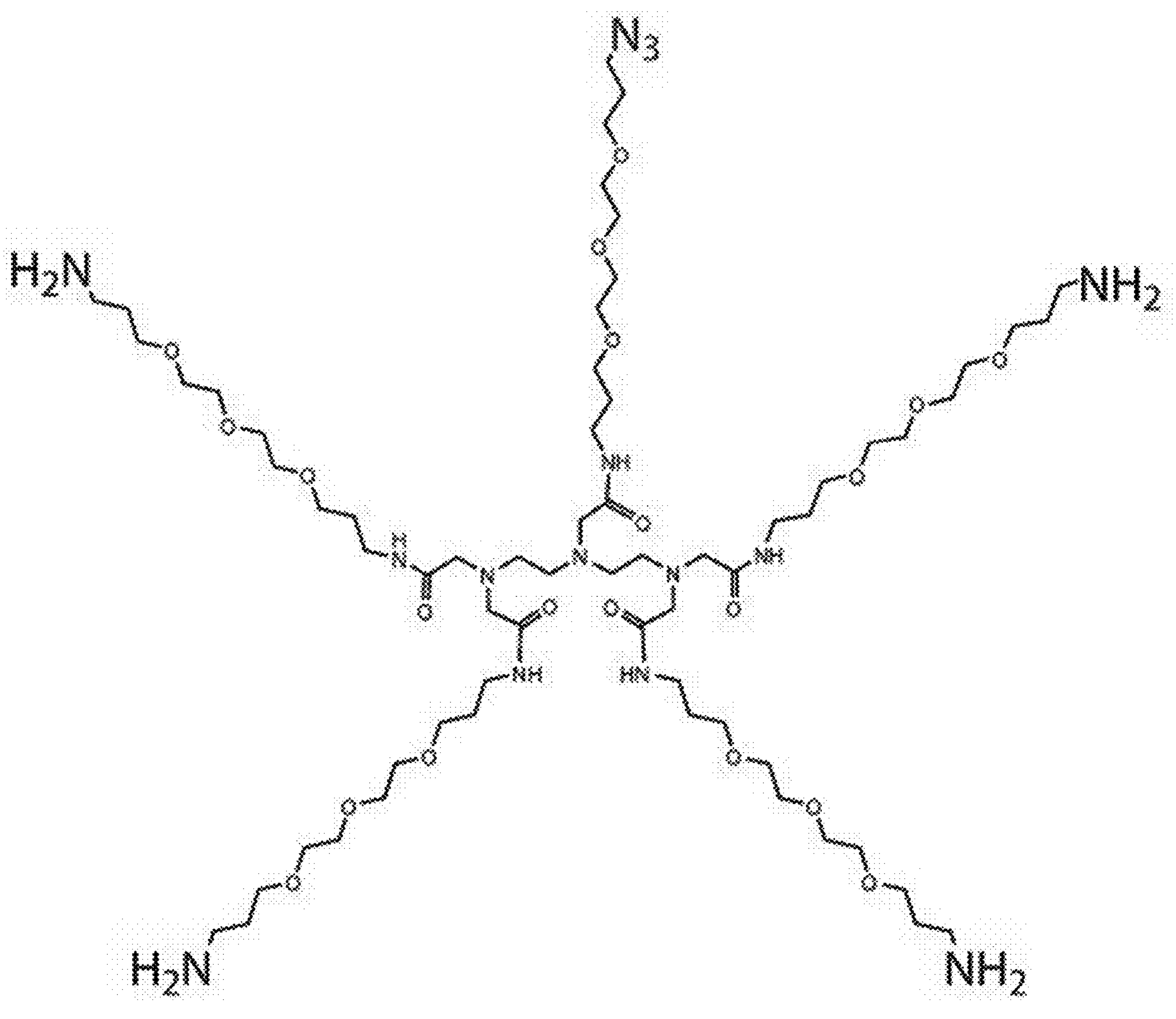

FIG. 19: Scaffold precursor with four amino groups for saponin linkage and an azide group for click chemistry.

Figure 20:
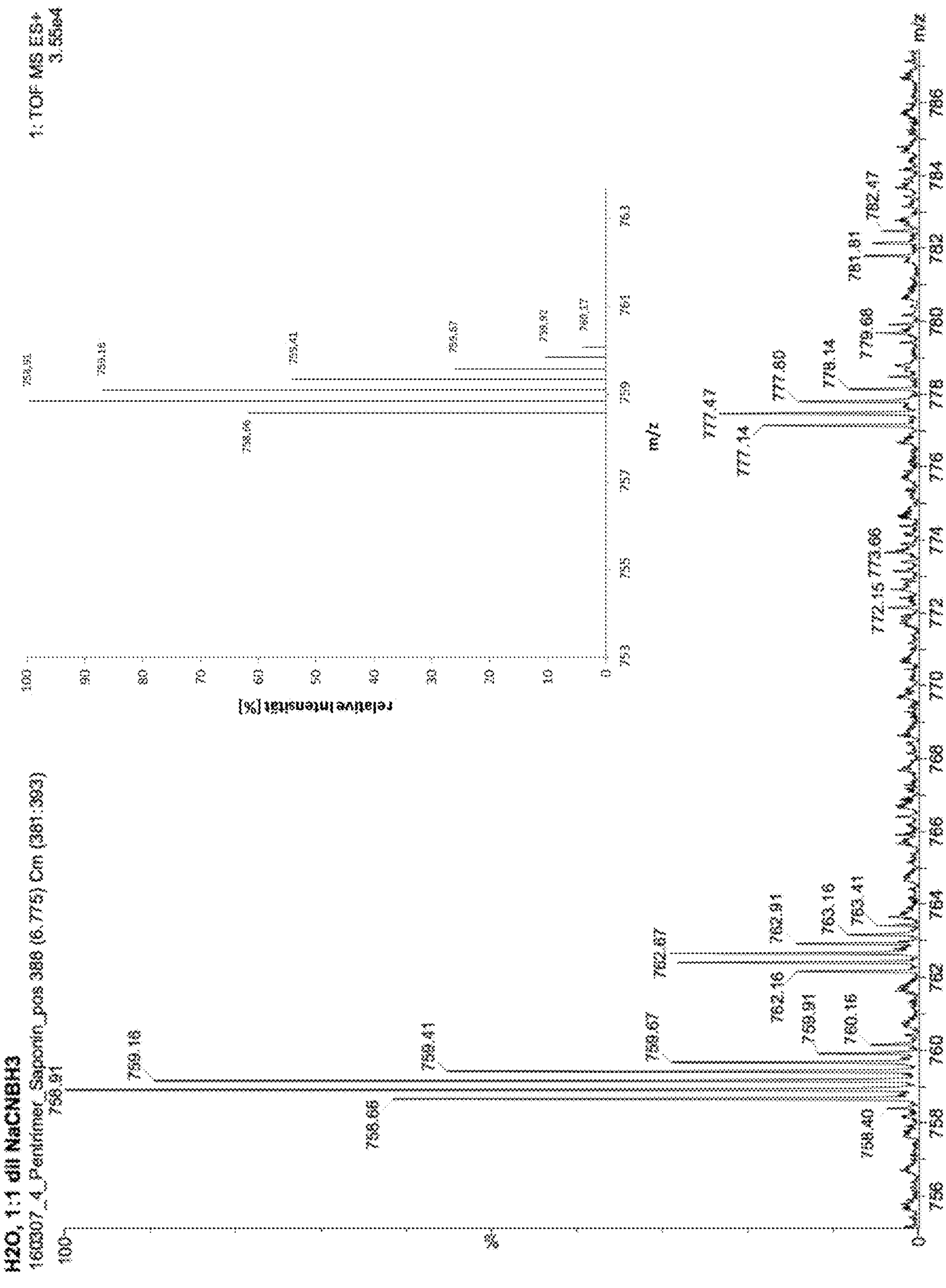

FIG. 20: Evidence for the coupling of saponins to the model scaffold. The inset shows the theoretically expected peeks and intensity distribution for coupled saponins. The experimental data obtained by LC-MS/ESI-MS show almost exactly the same peaks at m/z 758-760 Da proving successful saponin coupling.

Figure 21:
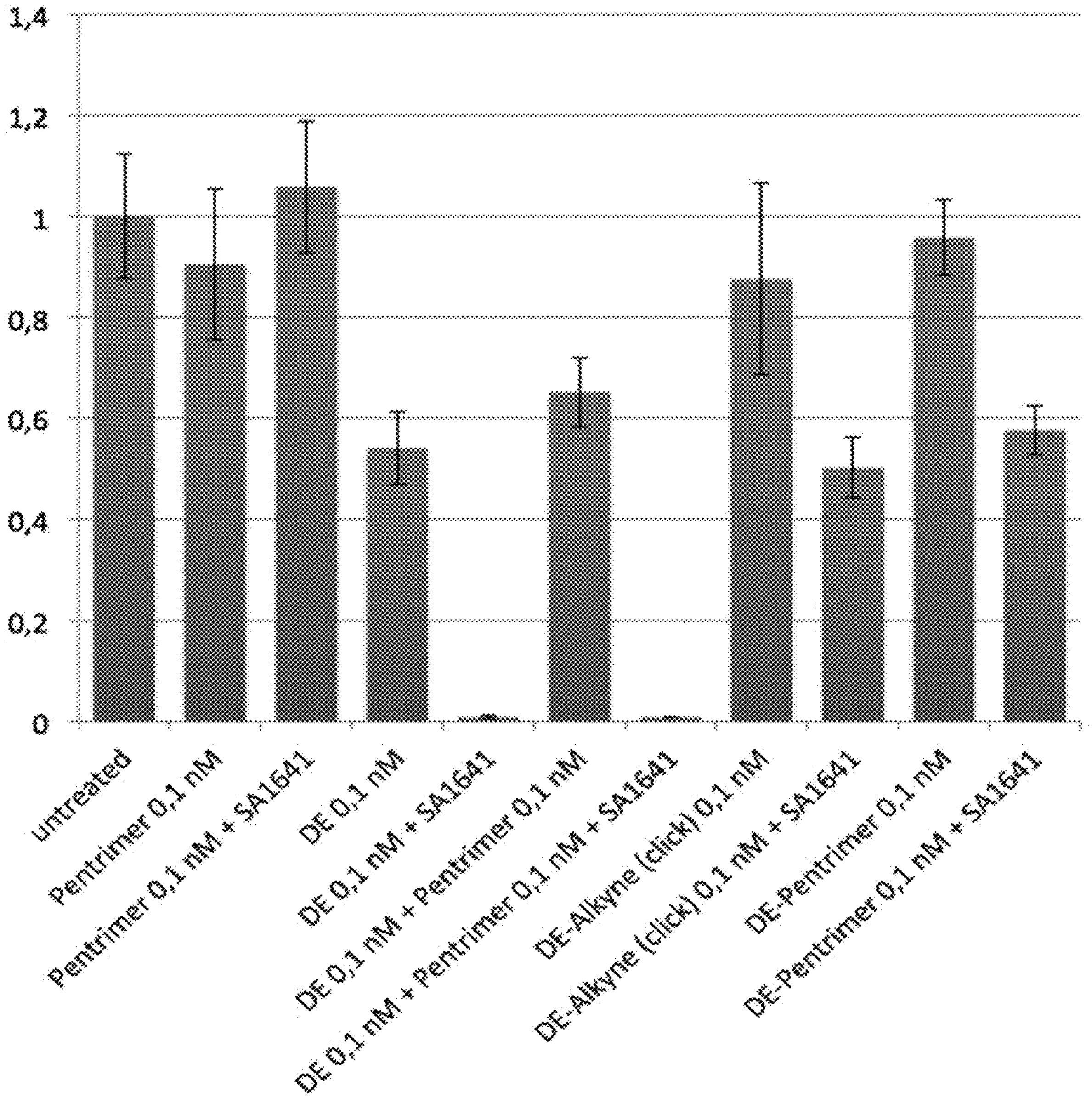

FIG. 21: Cytotoxicity assays using the targeted toxin dianthin-Epidermal Growth Factor (dianthin-EGF). Untreated cells were normalized to 1. The polymeric structure (Pentrimer) has no influence on cell viability neither in the presence nor in the absence of Dianthin-EGF and saponin (SA1641) indicating no intrinsic cytotoxicity of the polymeric structure. The clickable targeted toxin (Dianthin-EGF-Alkyne) has a markedly reduced activity, which is a result of the toxin modification but does not have any relation to the scaffold. The functionalized polymeric structure has the same activity as the unclicked targeted toxin, indicating that the functionalization of the scaffold does not impair effector molecule activity. The effect of saponins is identical in the presence and absence of the polymeric structure showing that the polymeric structure does not impair the efficacy of the saponins in the two-component system.

Figure 22:
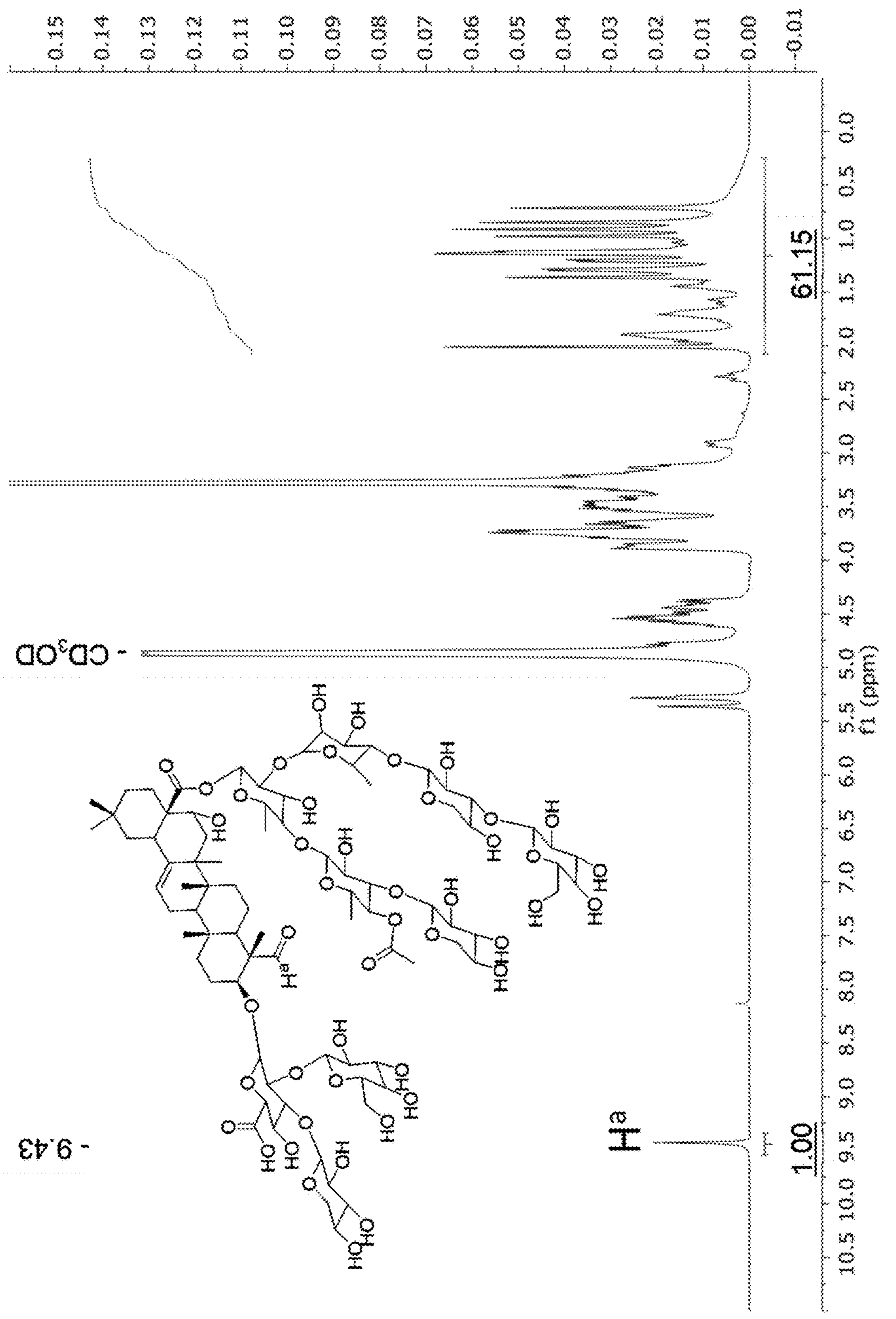
Figure 22:
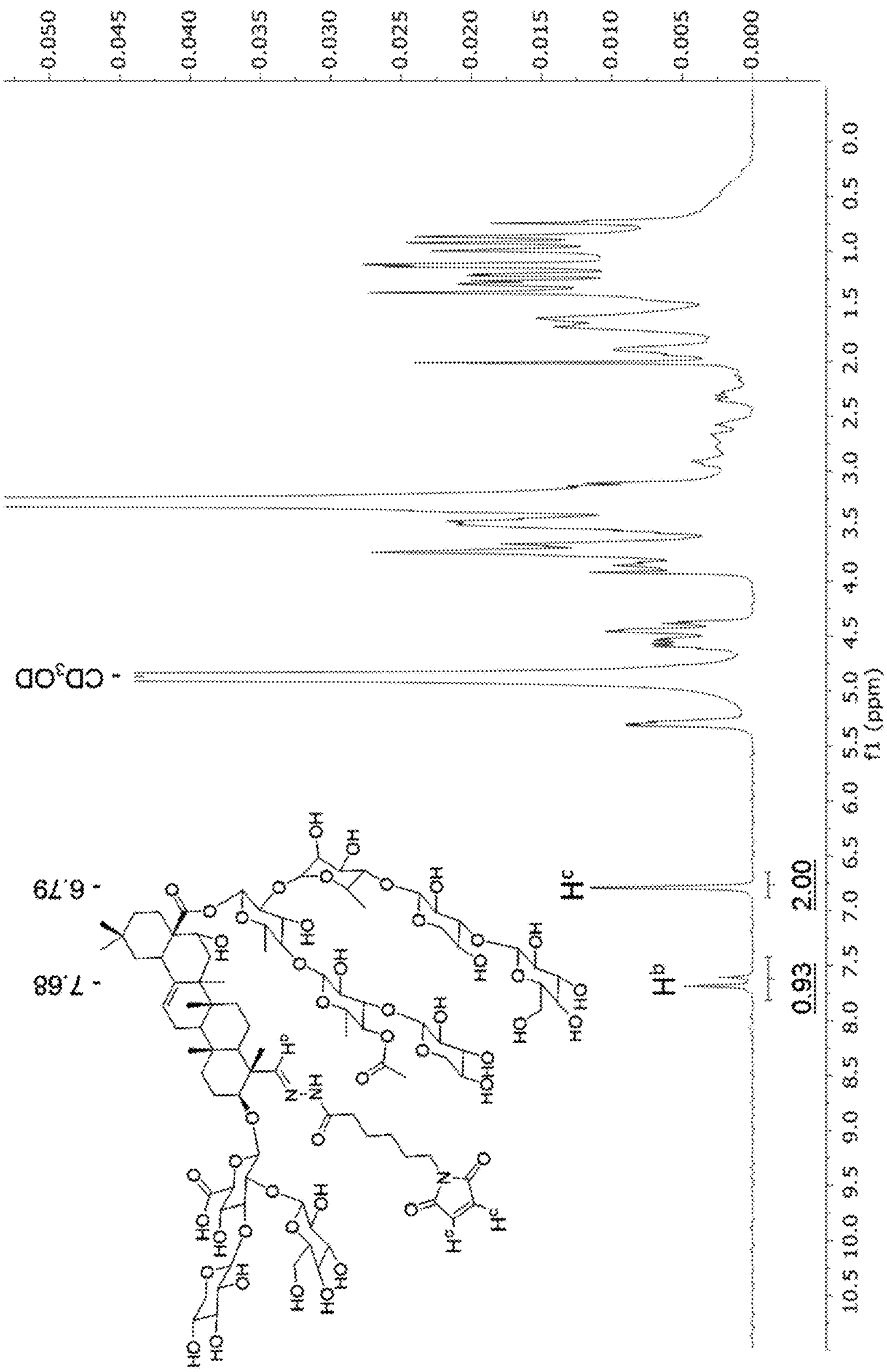

FIG. 22: H-NMR spectrum of (A) SO1861 and (B) SO1861-EMCH (EMCH=N-ε-maleimidocaproic acid hydrazide). (A) The peak at 9.43 ppm ($H^a$) corresponds to the aldehyde proton of SO1861. (B) The peak at 6.79 ppm (H°) corresponds to the maleimide protons of SO1861-EMCH, while the peak at 7.68 ppm ($H^b$) corresponds to the hydrazone proton. The absence of the signal at 9.43 ppm indicates a quantitative conversion of the aldehyde group.

Figure 23:
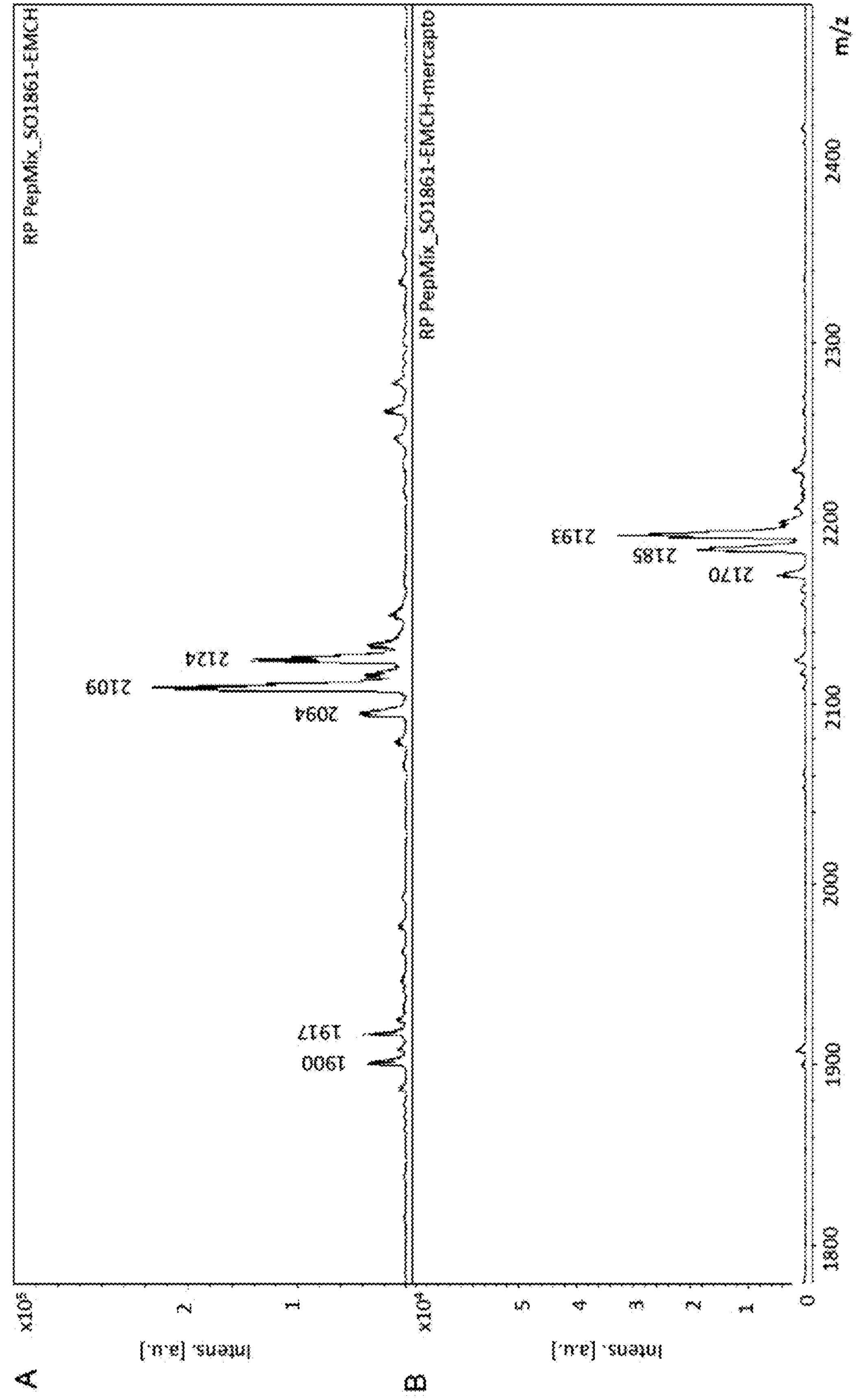

FIG. 23: (A) MALDI-TOF-MS spectrum of SO1861-EMCH and (B) SO1861-EMCH-mercaptoethanol. (A) RP mode: m/z 2124 Da ($[M+K]^+$, saponin-EMCH), m/z 2109 Da ($[M+K]^+$, SO1861-EMCH), m/z 2094 Da ($[M+Na]^+$, SO1861-EMCH). (B) RP mode: m/z 2193 Da ($[M+K]^+$, saponin-EMCH-mercaptoethanol), m/z 2185 Da ($[M+K]^+$, SO1861-EMCH-mercaptoethanol), m/z 2170 Da ($[M+Na]^+$, SO1861-EMCH-mercaptoethanol).

Figure 24:
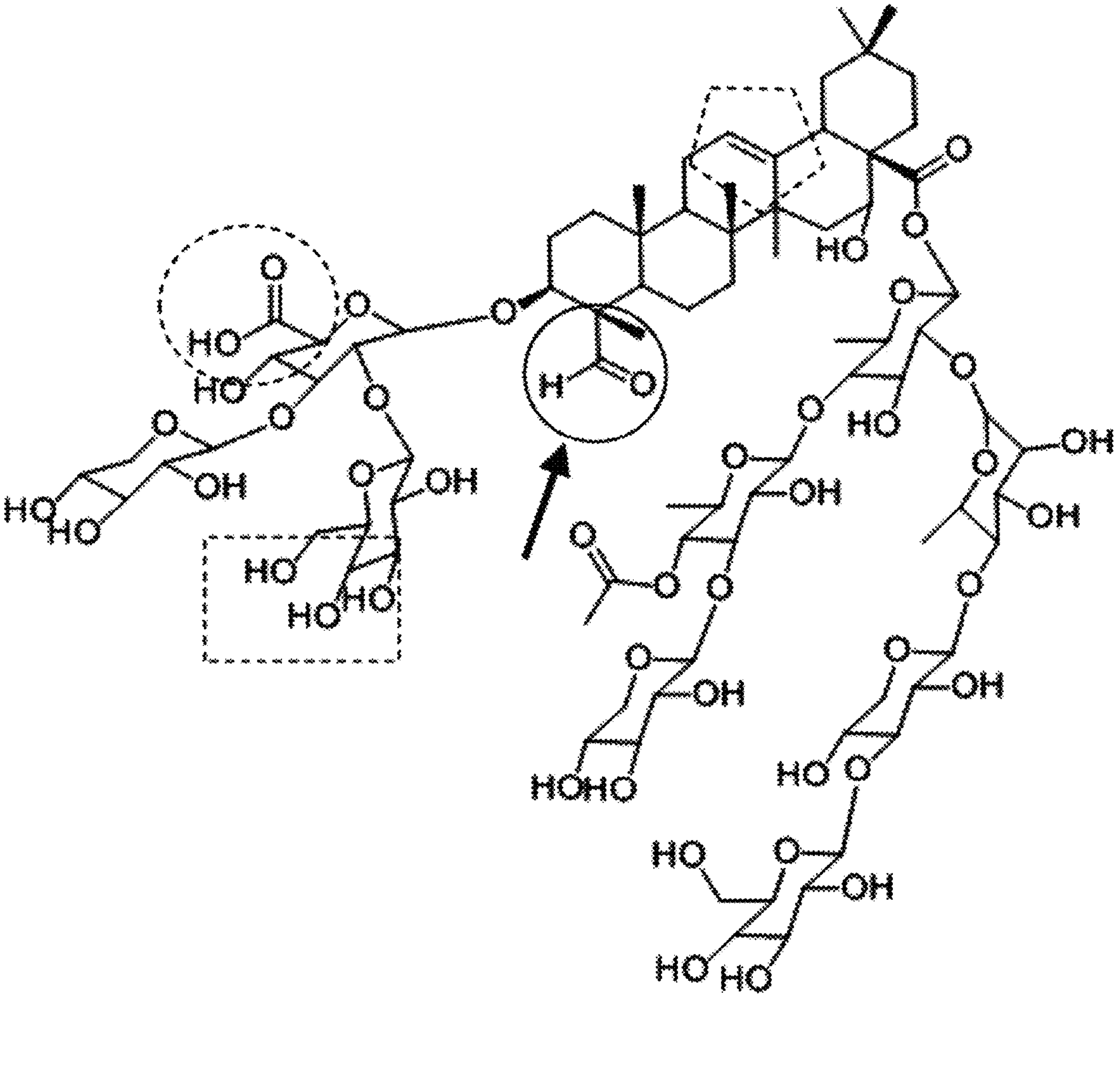

FIG. 24: SO1861 structure with highlighted chemical groups for conjugation of endosomal escape enhancing saponins to a polymeric structure. Highlighted groups are aldehyde (black circle), carboxylic acid (dashed circle), alkene (dashed pentagon), and alcohol (dashed box). The aldehyde group (arrow) is most suitable group for chemoselective and reversible conjugation reactions.

Figure 25:
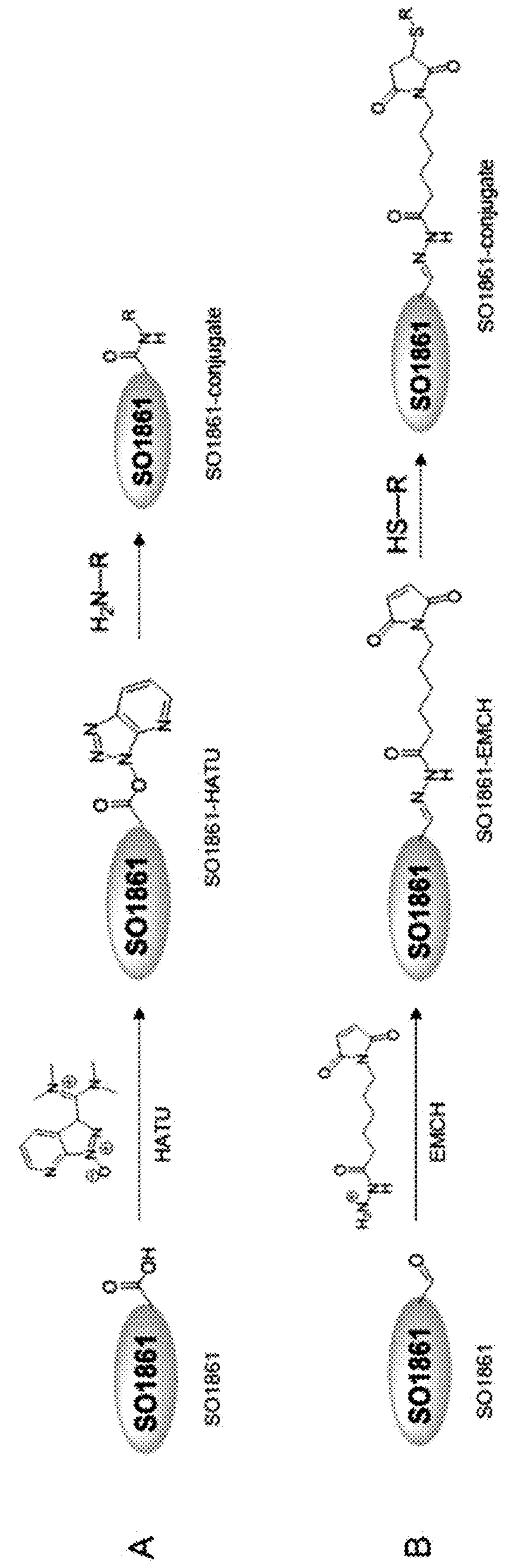

FIG. 25: Strategy for producing (A) stable and (B) cleavable 'ready-to conjugate' endosomal escape enhancer saponins.

Figure 26:
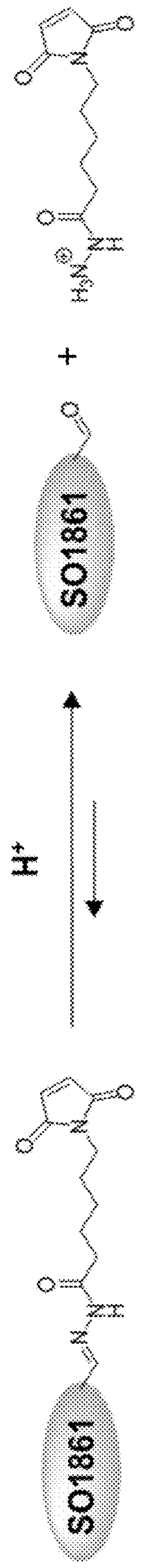

FIG. 26: Hydrolysis of the hydrazone bond of SO1861-EMCH under acidic conditions.

Figure 27:
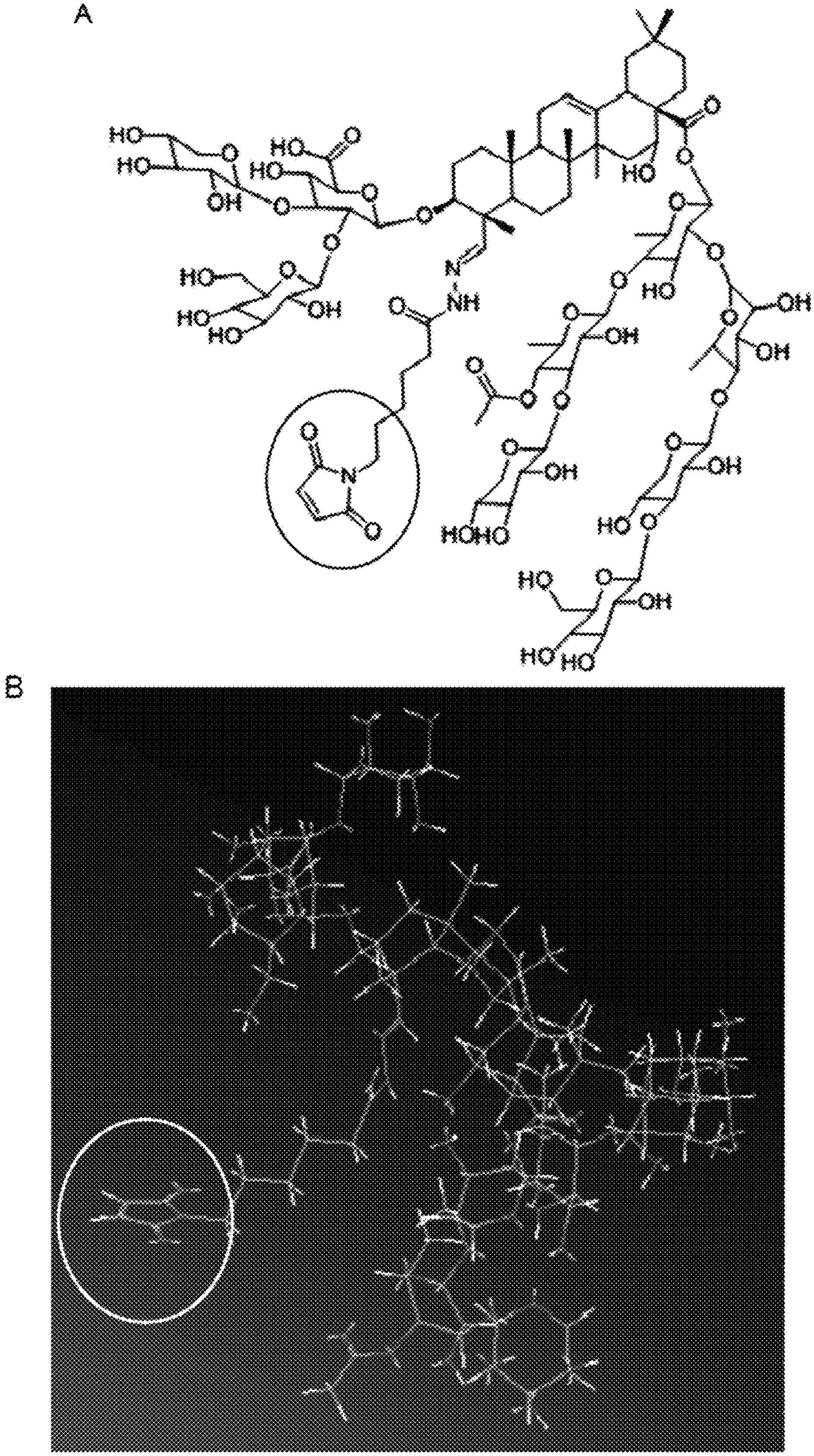

FIG. 27: SO1861-EMCH structure. (A) Standard molecular structure, and (B) 3D model. Maleimide group is marked with a circle.

Figure 28:
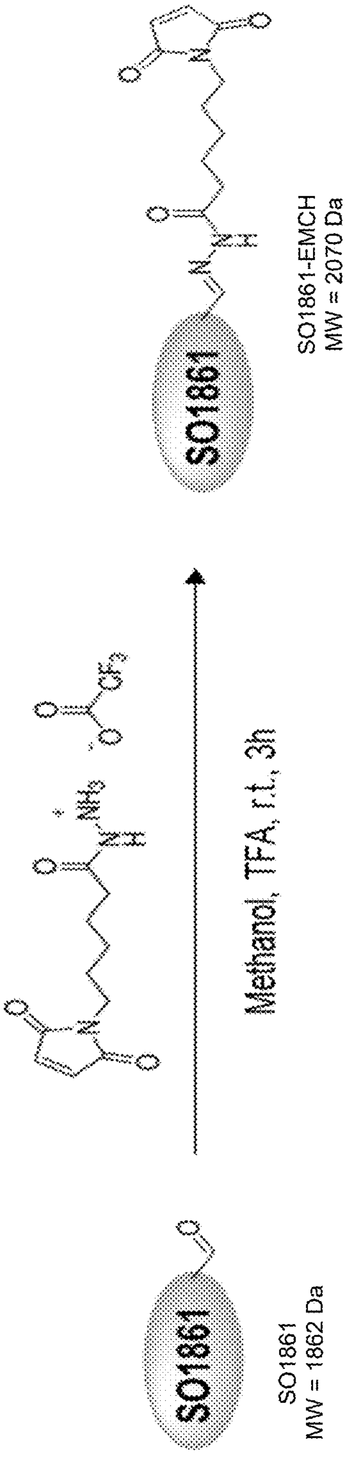
Figure 28:
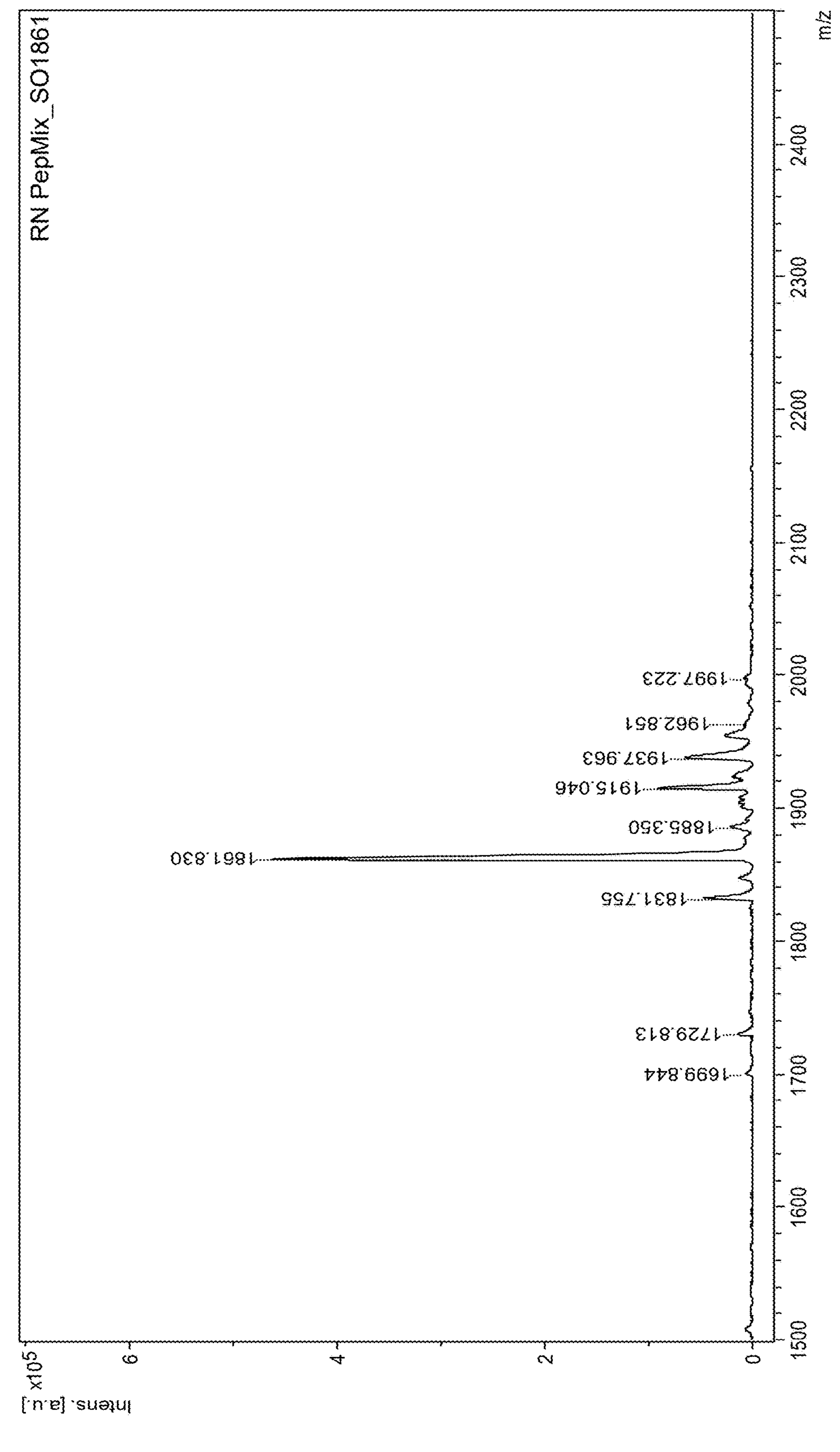
Figure 28:
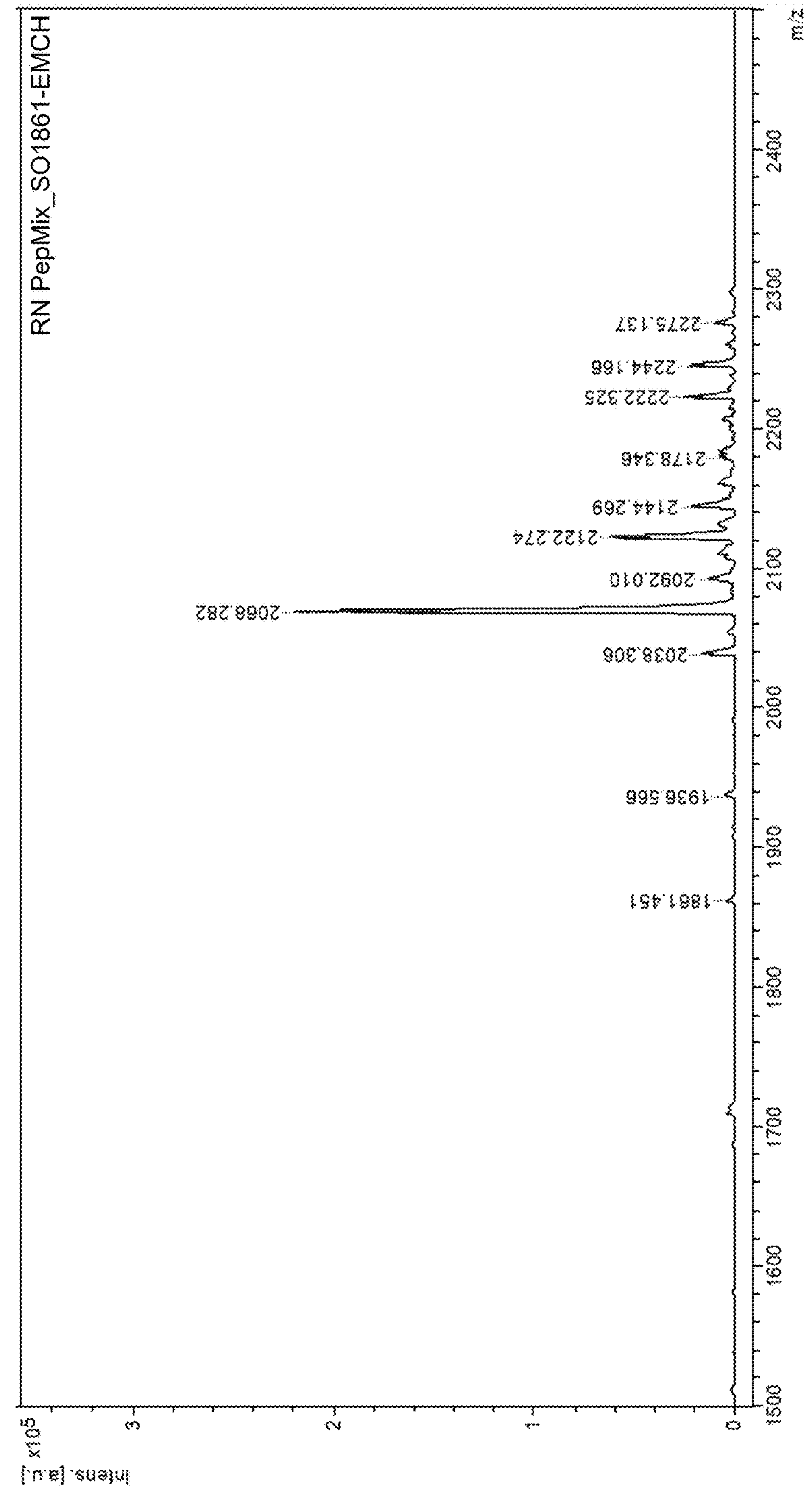

FIG. 28: (A) SO1861-EMCH synthesis scheme. (B) MALDI-TOF-MS spectra of SO1861 (m/z 1861 Da) and (C) SO1861-EMCH (m/z 2068 Da) in negative reflector mode. TFA: trifluoroacetic acid, r.t: room temperature, h: hours, and MW: molecular weight.

Figure 29:
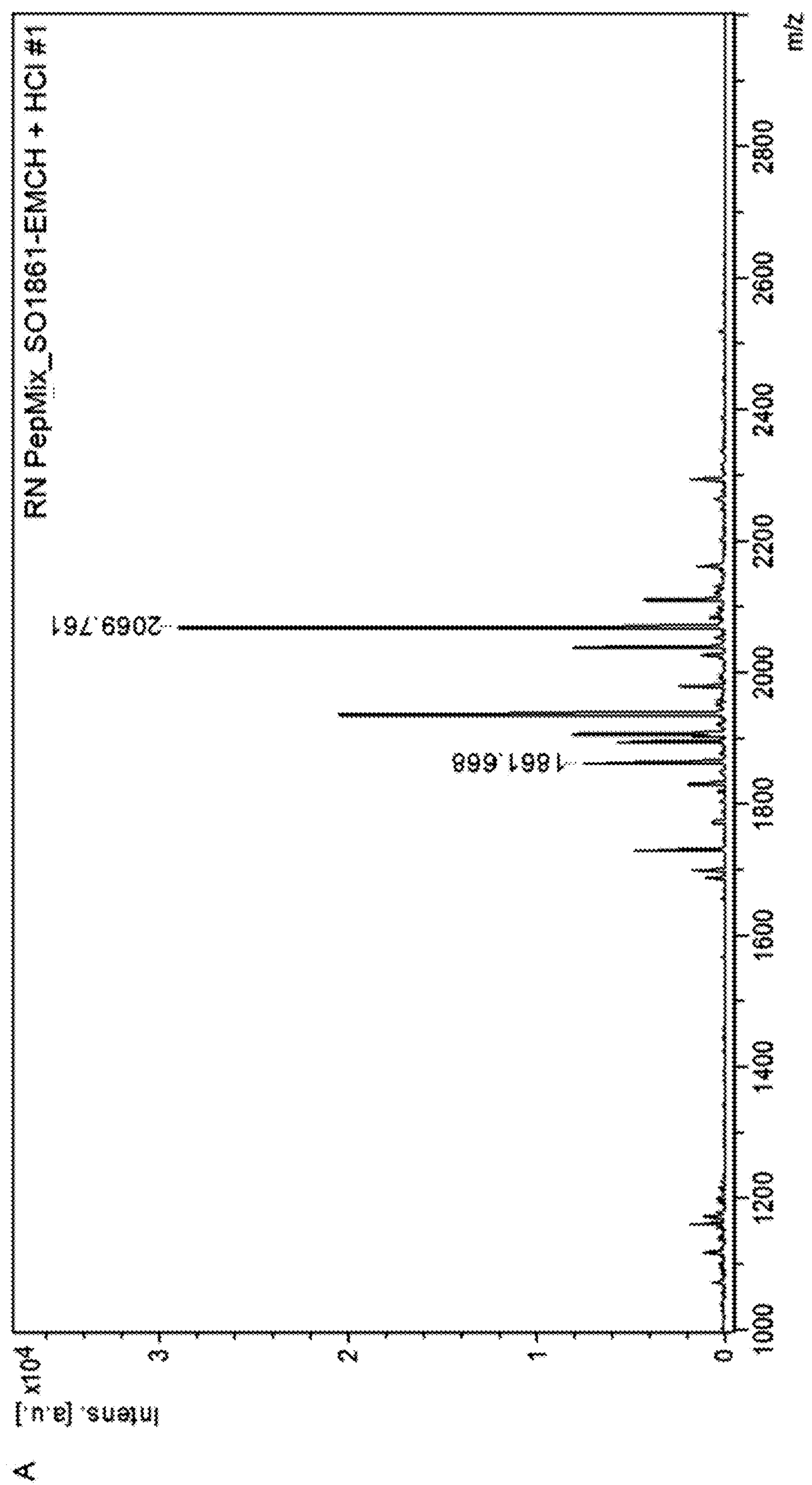
Figure 29:
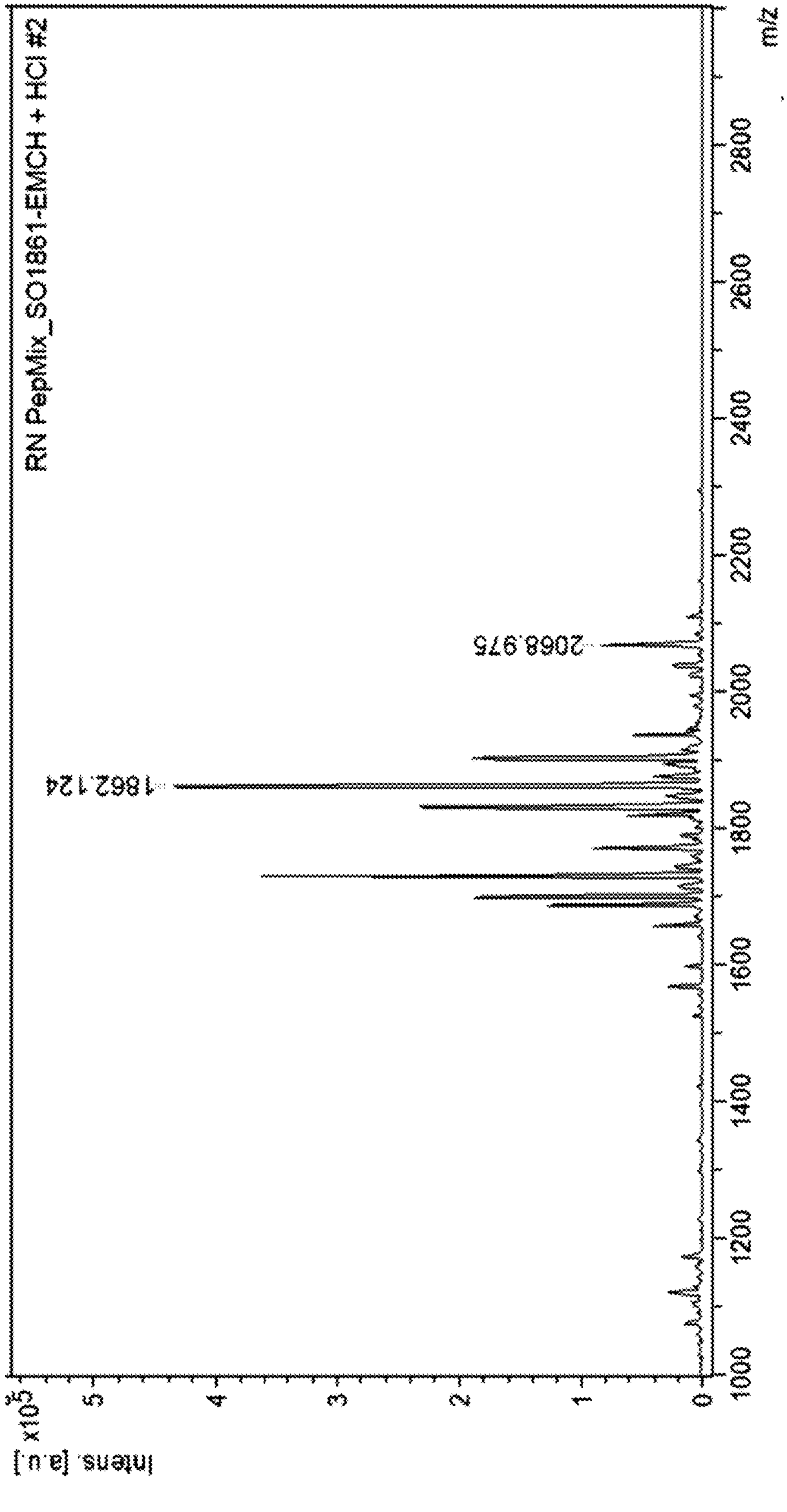

FIG. 29: MALDI-TOF-MS spectra of SO1861-EMCH (A) before and (B) after hydrolysis in HCl solution at pH 3.

Figure 30:
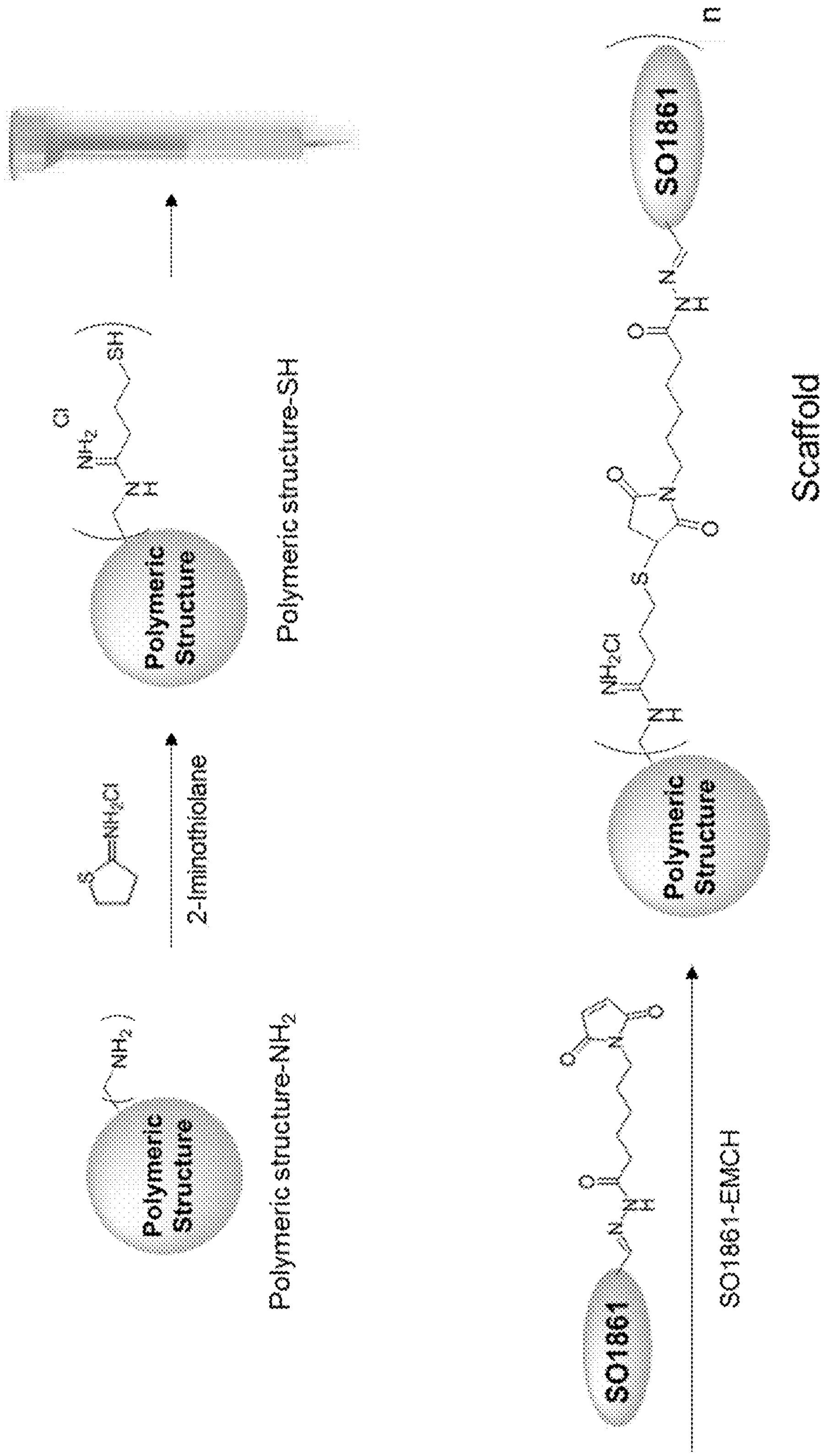

FIG. 30: Reaction scheme of SO1861-EMCH conjugation to any amine-bearing polymeric structure.

Figure 31:
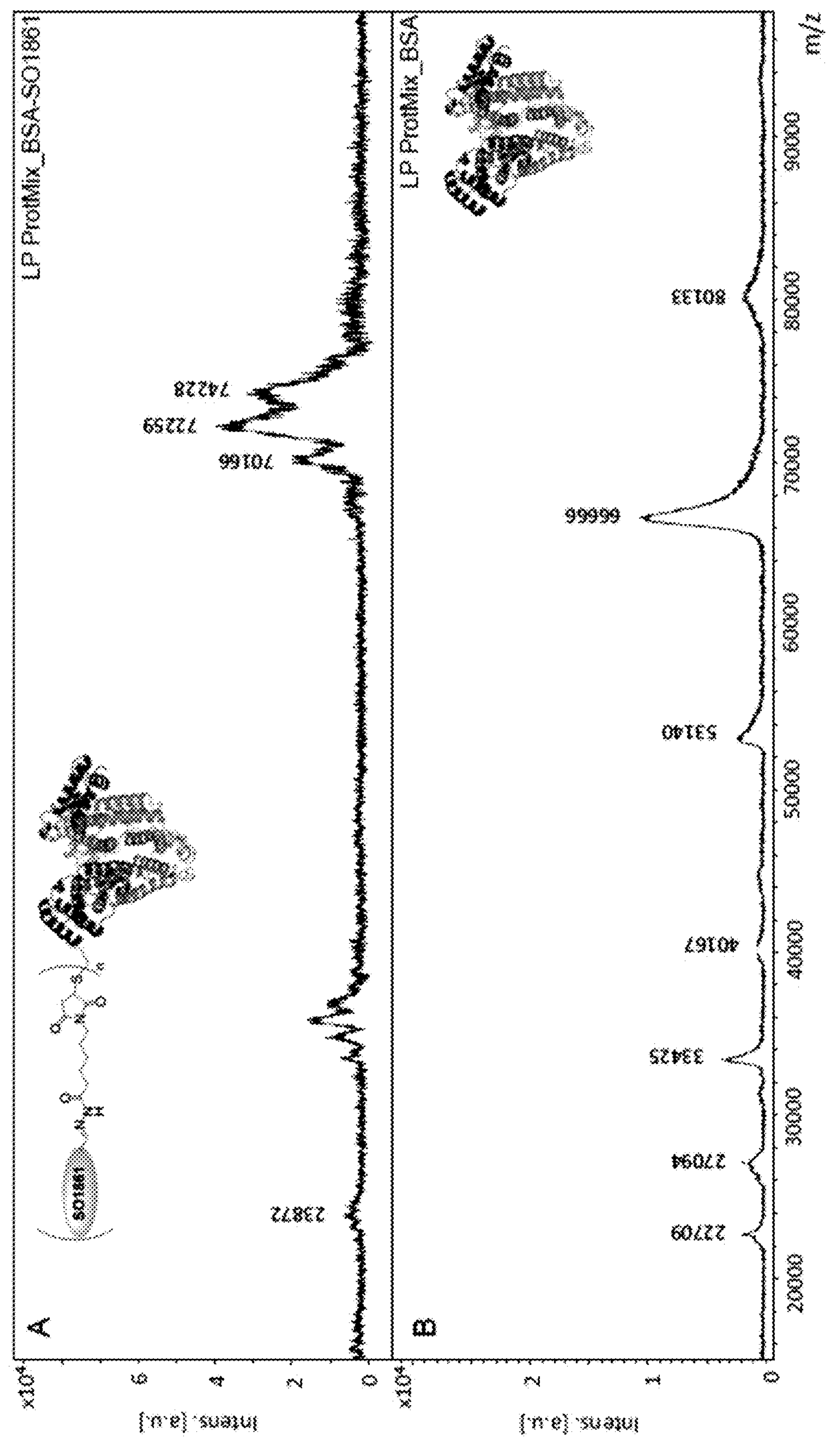

FIG. 31: MALDI-TOF-MS spectra of (A) BSA-SO1861 (m/z 70.0 kDa, 72.1 kDa, 74.2 kDa), and (B) BSA (m/z 66.6 kDa).

Figure 32:
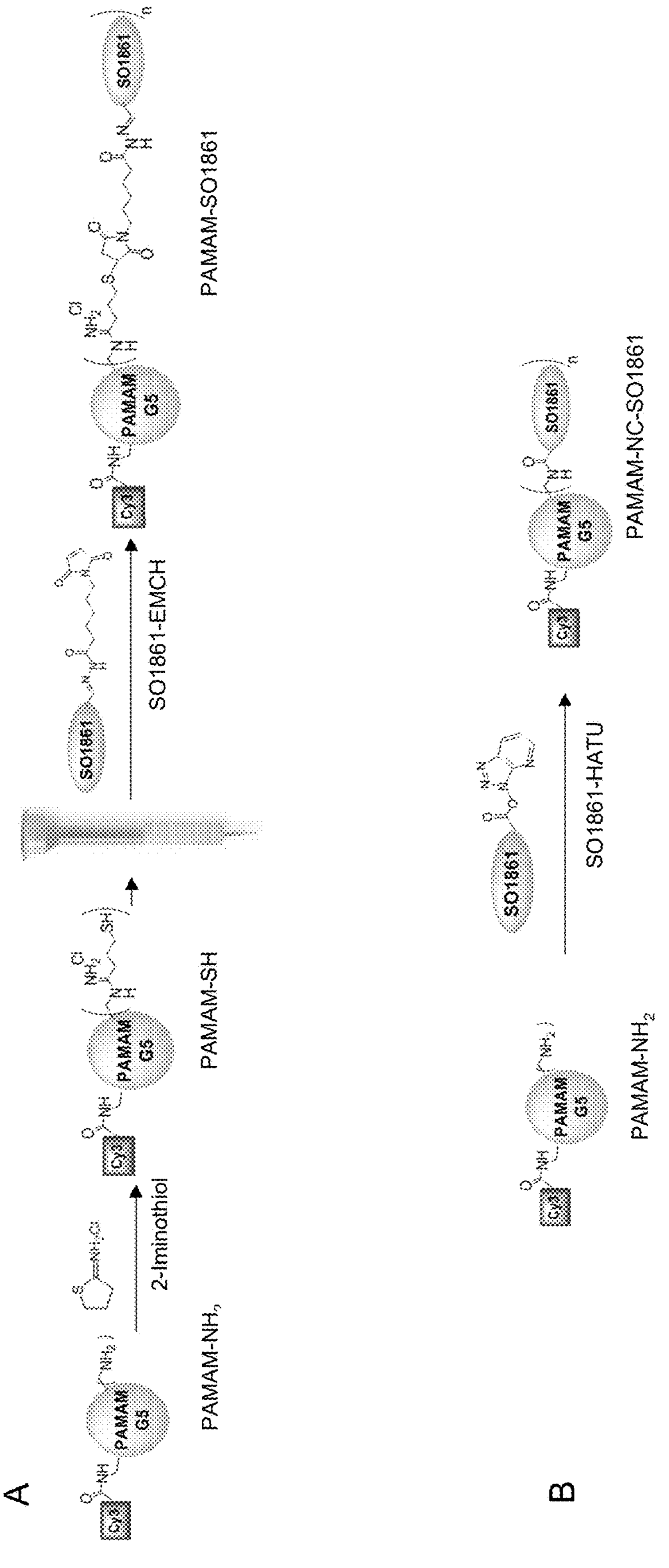

FIG. 32: Reaction scheme of (A) SO1861-EMCH and (B) SO1861-HATU (HATU=1-[Bis(dimethylamino)methylene]-1H-1,2,3-triazolo[4,5-b]pyridinium 3-oxid hexafluorophosphate) conjugation to a cyanine 3 dye labeled polyamidoamine (PAMAM) G5 dendrimer.

Figure 33:
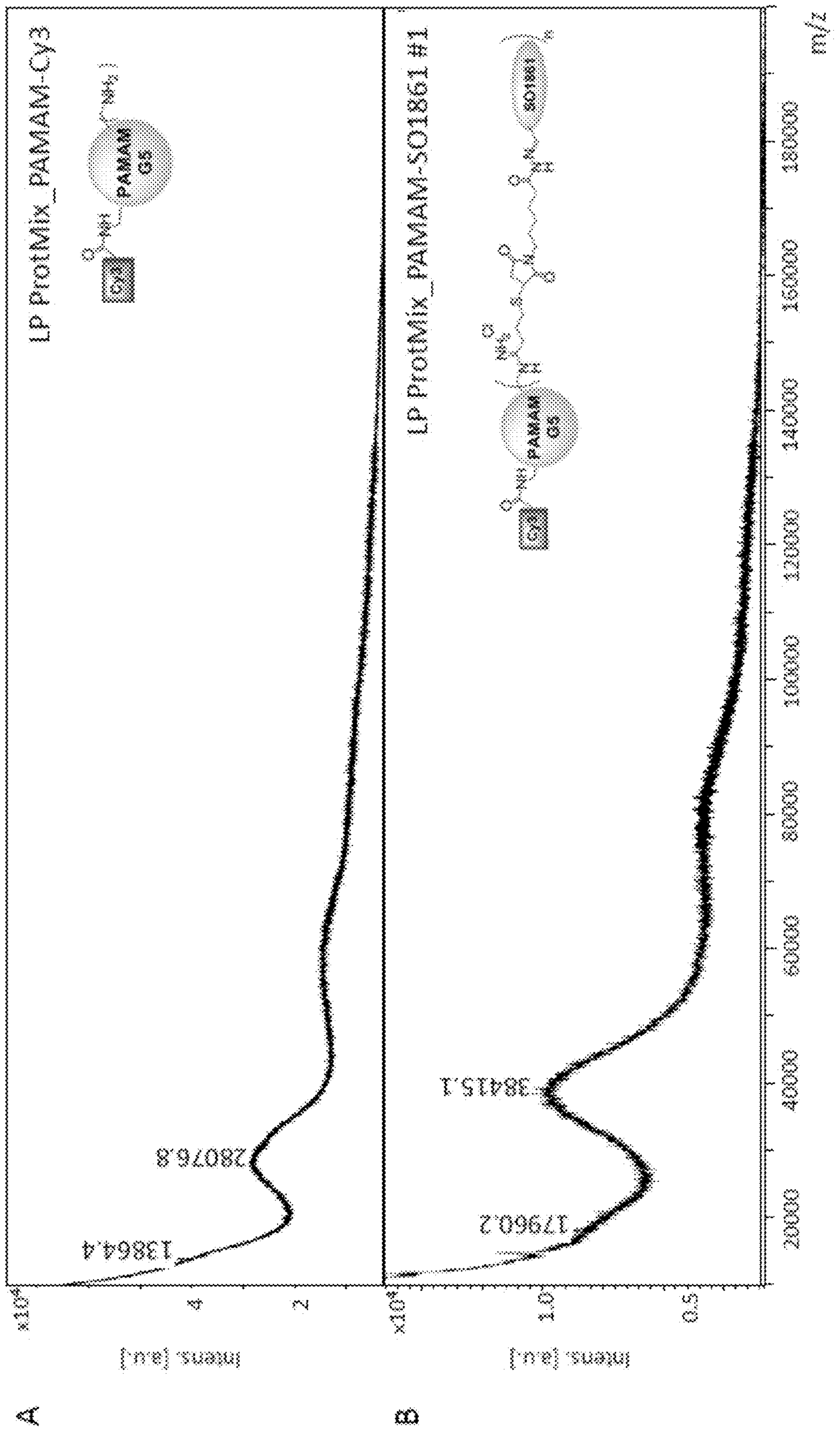
Figure 33:
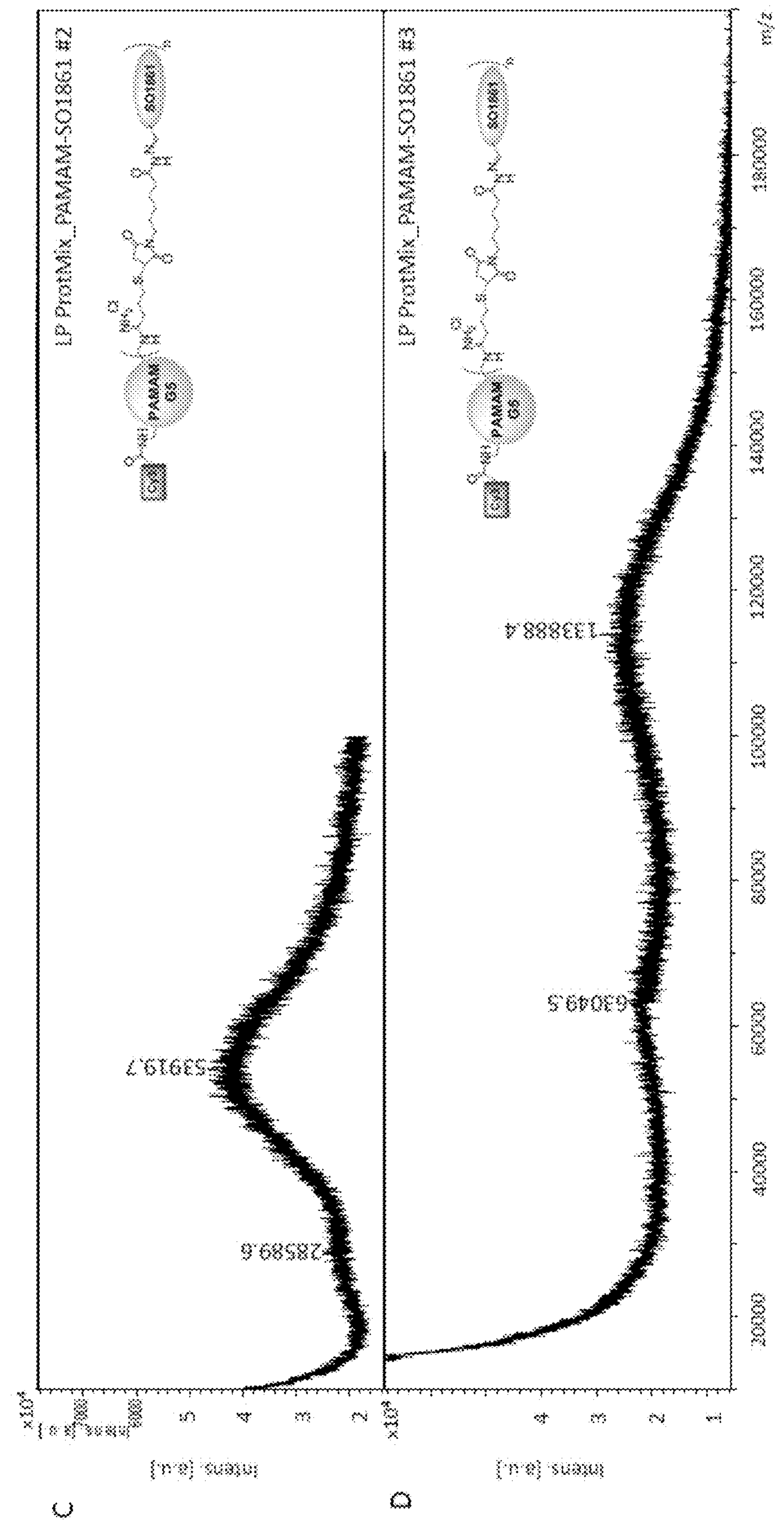

FIG. 33: MALDI-TOF-MS spectra of (A) Cy3-PAMAM, (B-D) Cy3-PAMAM-SO1861 with increasing SO1861-EMCH feed equivalents from (B) up to bottom (D). (B) corresponds to Cy3-PAMAM-SO1861 with 5 SO1861 attached per PAMAM, (C) corresponds to Cy3-PAMAM-SO1861 with 13 SO1861 attached per PAMAM, and (D) corresponds to Cy3-PAMAM-SO1861 with 51 SO1861 attached per PAMAM.

Figure 34:
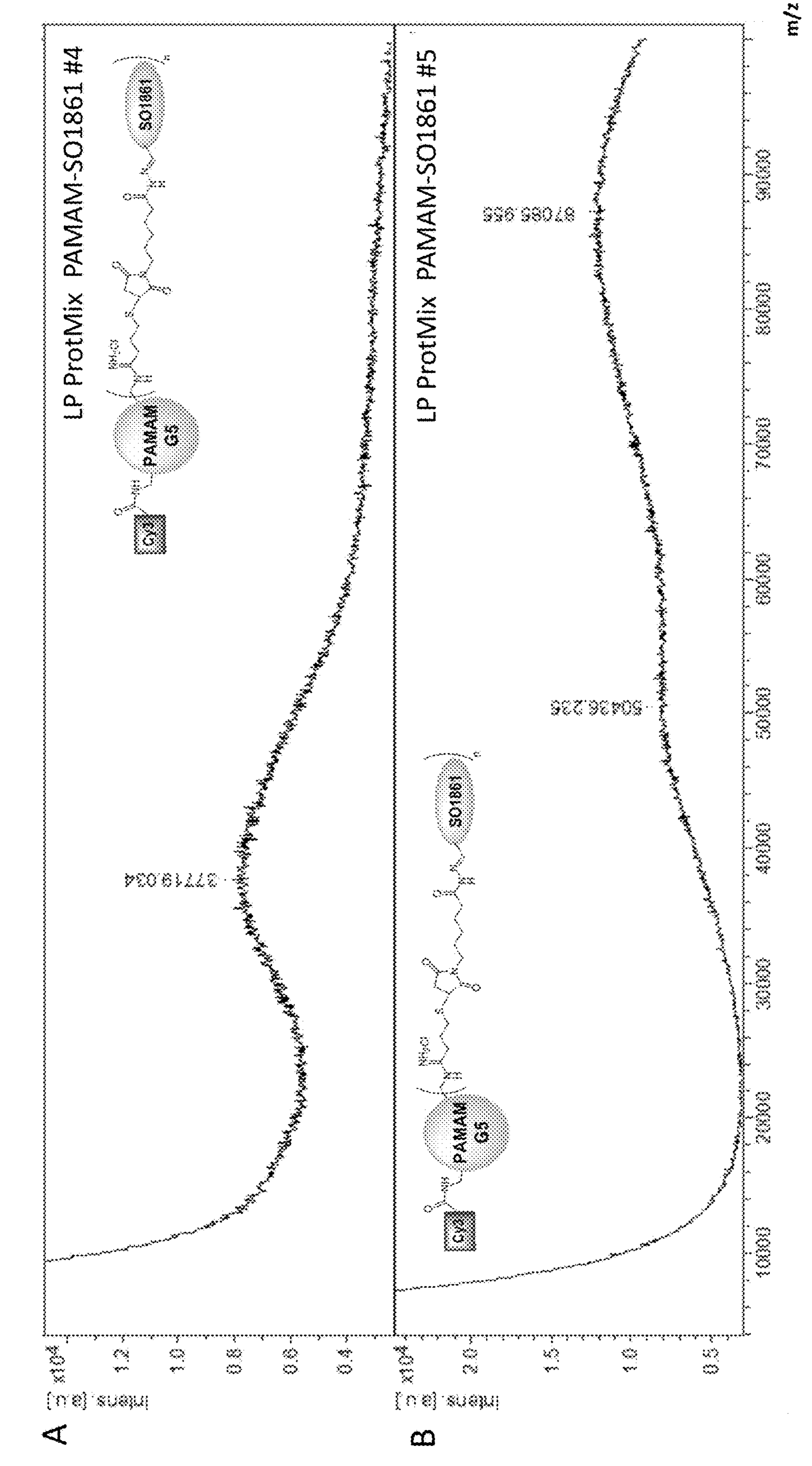

FIG. 34: MALDI-TOF-MS spectra of (A) Cy3-PAMAM-SO1861 with 5 equivalents feed SO1861-EMCH and (B) Cy3-PAMAM-SO1861 with 30 equivalents feed SO1861-EMCH.

Figure 35:
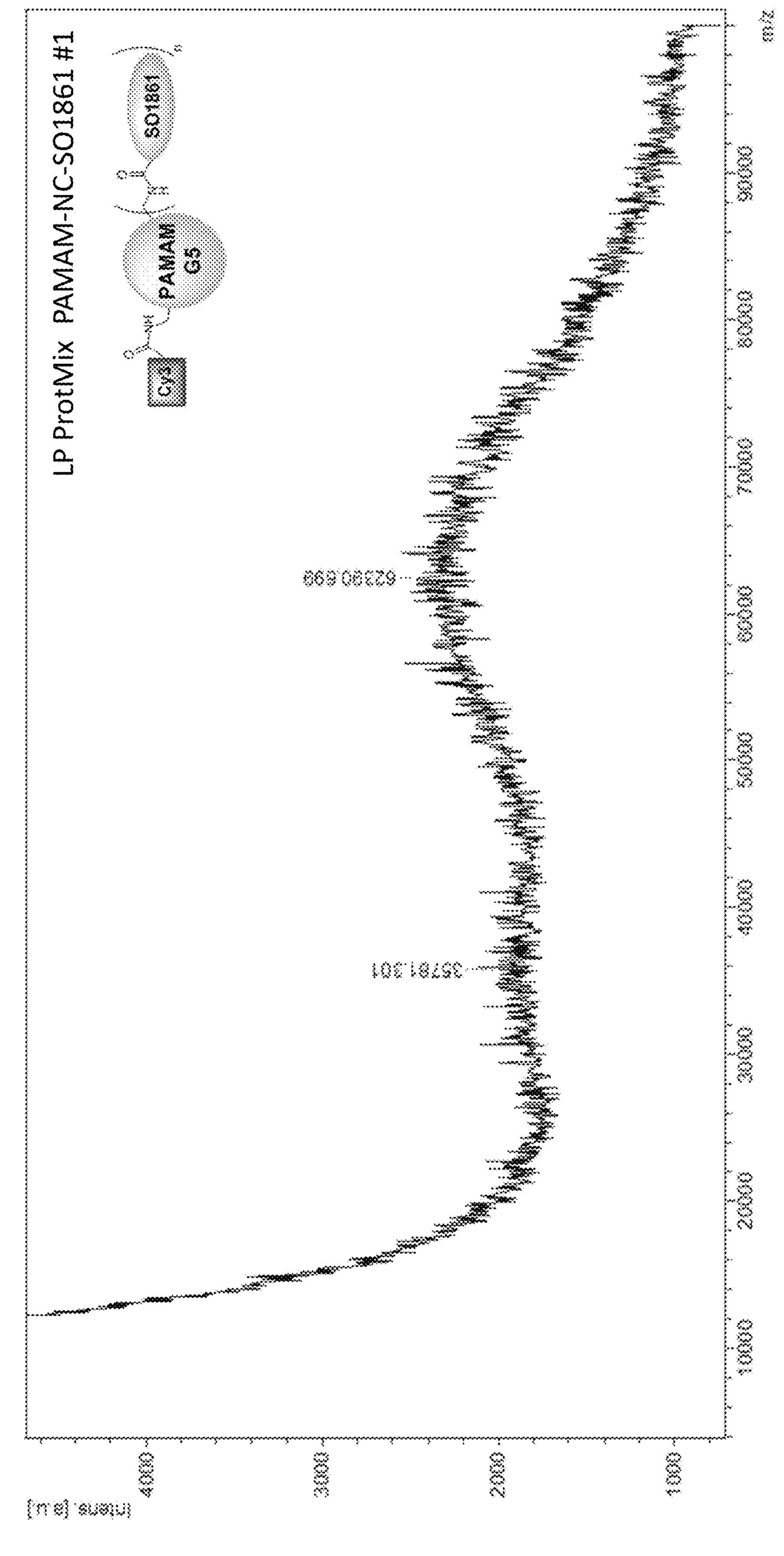

FIG. 35: MALDI-TOF-MS spectra of Cy3-PAMAM-NC-SO1861 (NC=stable bond ("non-cleavable").

Figure 36:
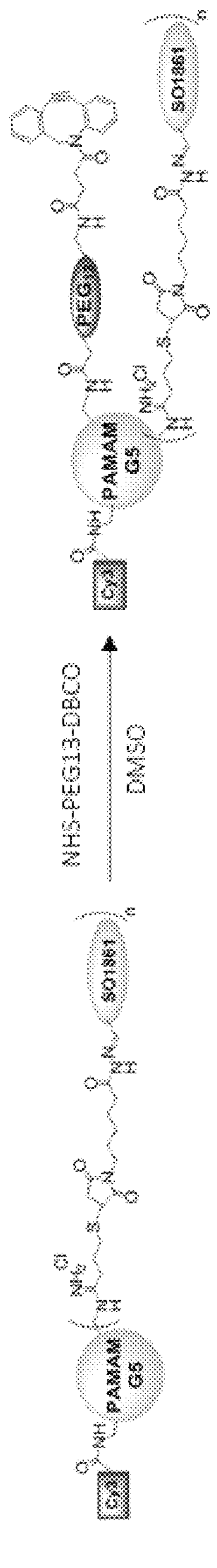
Figure 36:
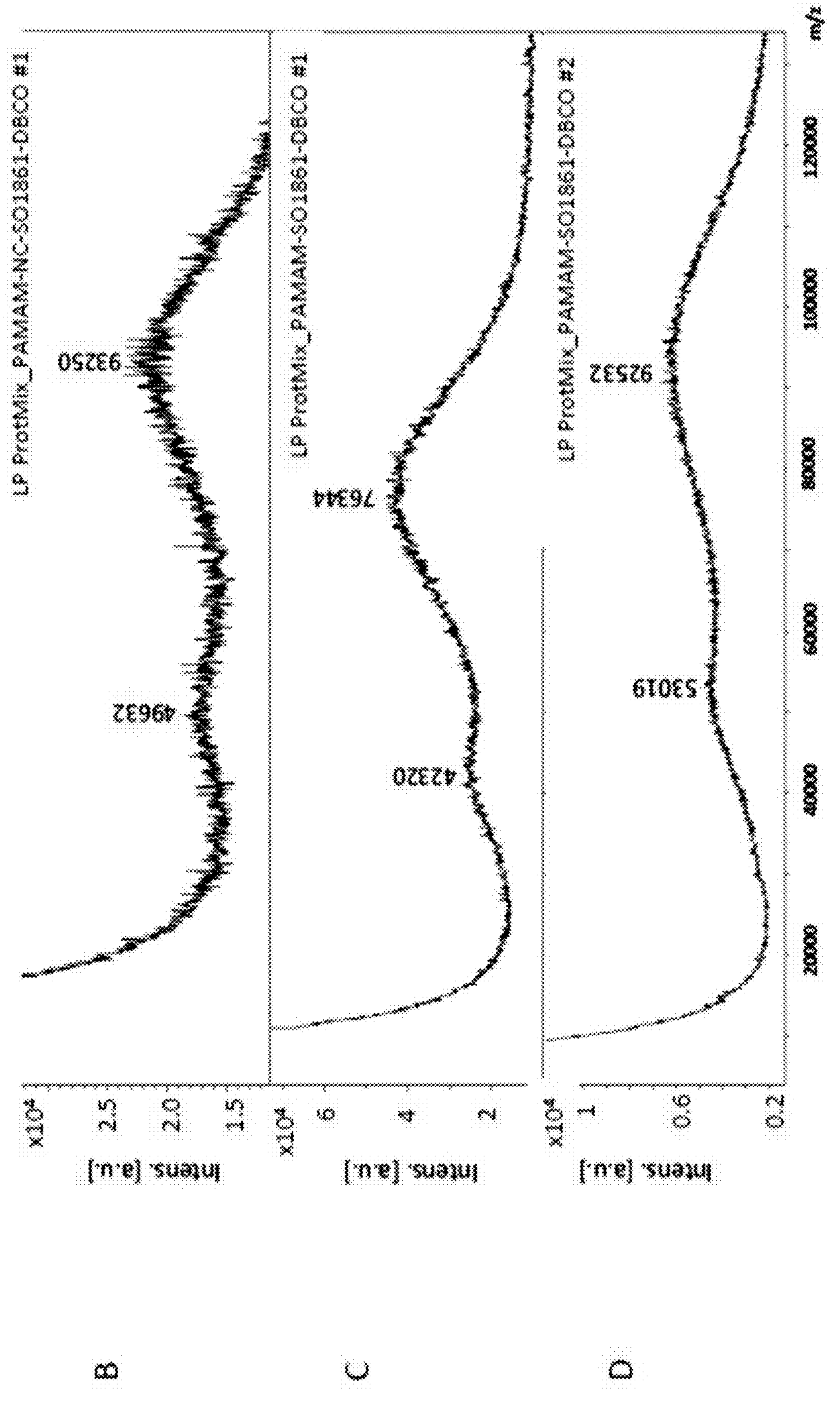

FIG. 36: (A) Reaction scheme and MALDI-TOF-MS spectra of (B) Cy3-PAMAM-NC-SO1861-Dibenzocyclooctyne (DBCO), (C) Cy3-PAMAM-$(SO1861)_5$-DBCO, and (D) Cy3-PAMAM-$(SO1861)_{27}$-DBCO.

Figure 37:
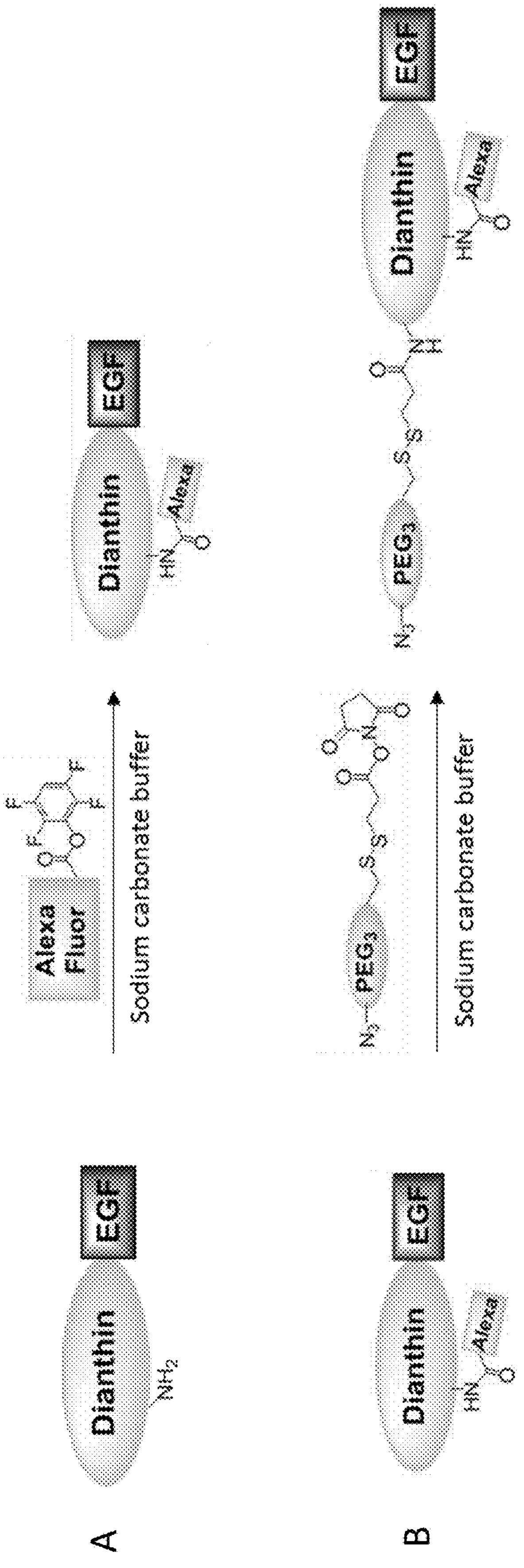
Figure 37:
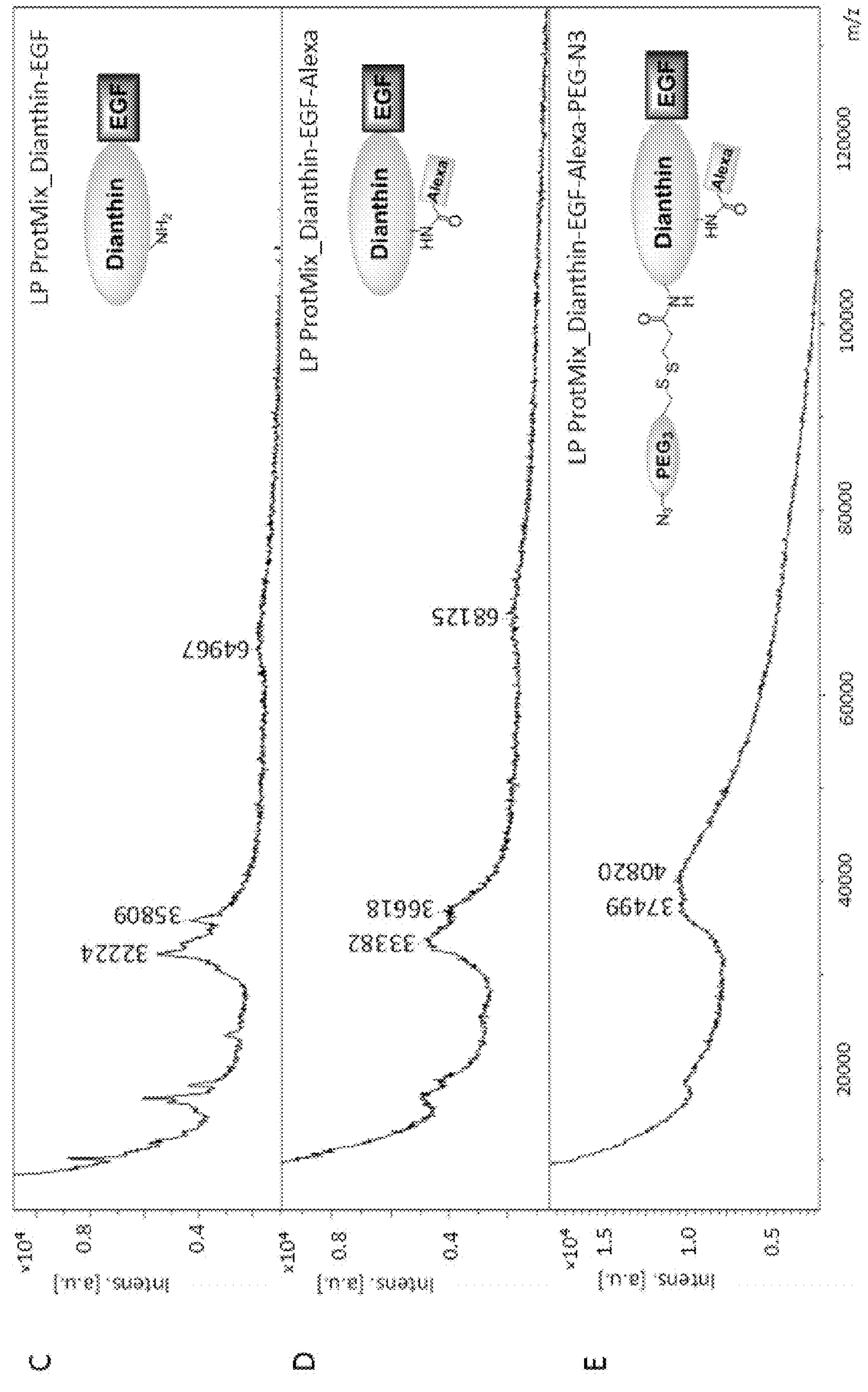

FIG. 37: Reaction scheme of (A) dianthin-EGF-Alexa488 and (B) dianthin-EGF-Alexa488-SS-PEG-$N_3$. MALDI-TOF-MS spectra of (C) dianthin-EGF, (D) dianthin-EGF-Alexa488, and (E) dianthin-EGF-Alexa488-SS-PEG-$N_3$; Alexa488: Alexa Fluor 488 dye.

Figure 38:
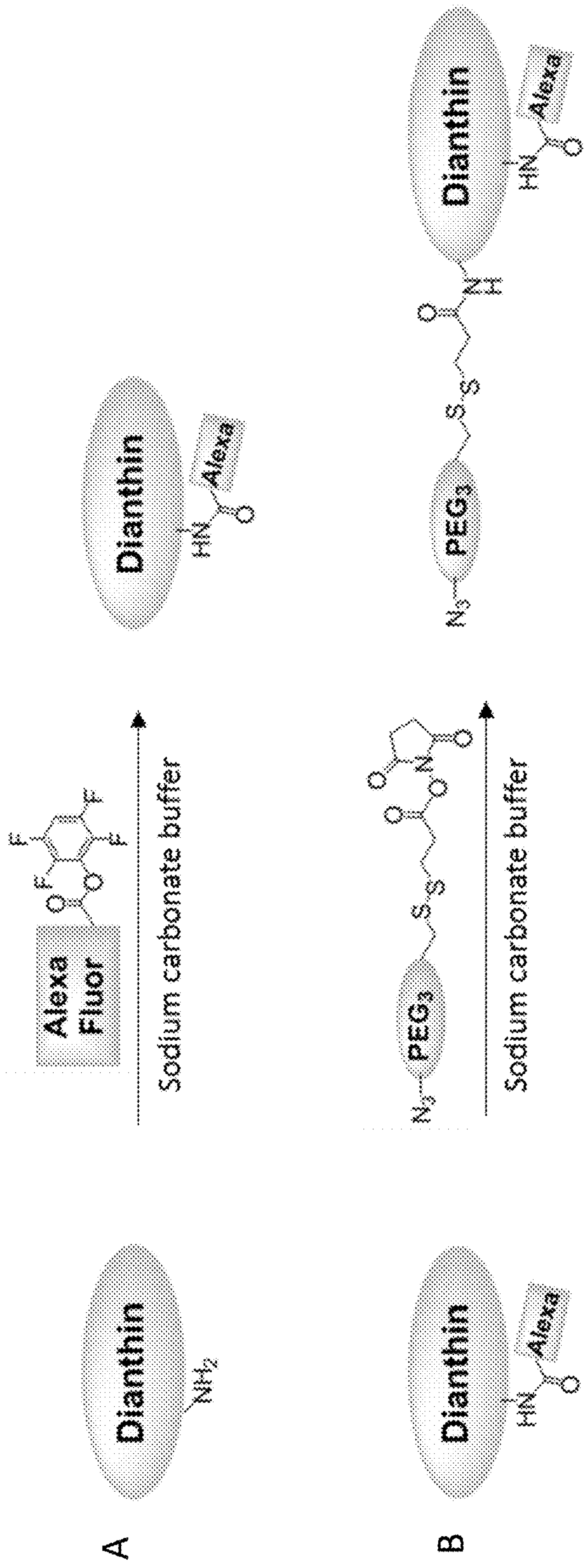
Figure 38:
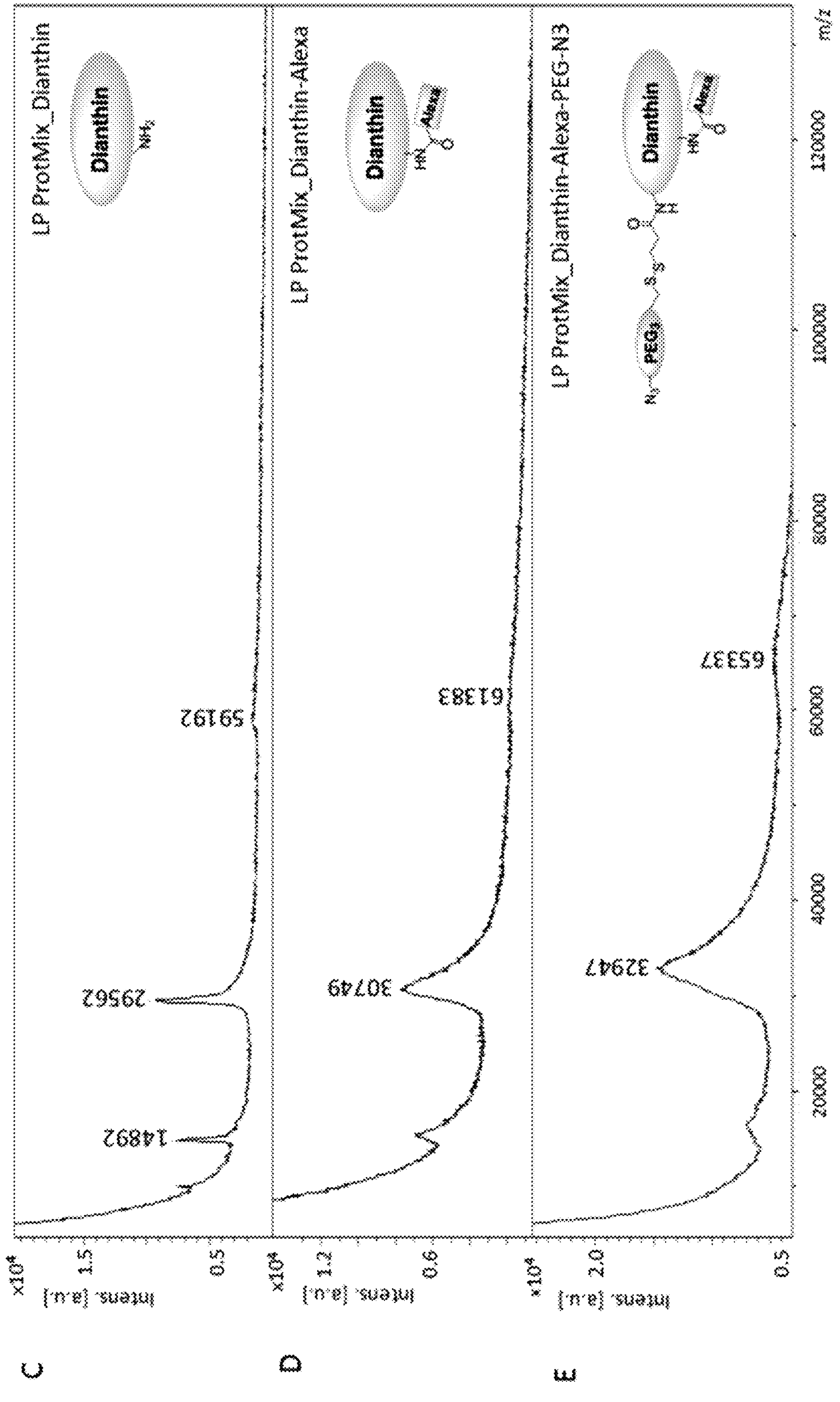

FIG. 38: Reaction scheme of (A) dianthin-Alexa488 and (B) dianthin-Alexa488-SS-PEG-$N_3$. MALDI-TOF-MS spectra of (C) dianthin, (D) dianthin-Alexa488, and (E) dianthin-Alexa488-SS-PEG-$N_3$; Alexa488: Alexa Fluor 488 dye.

Figure 39:
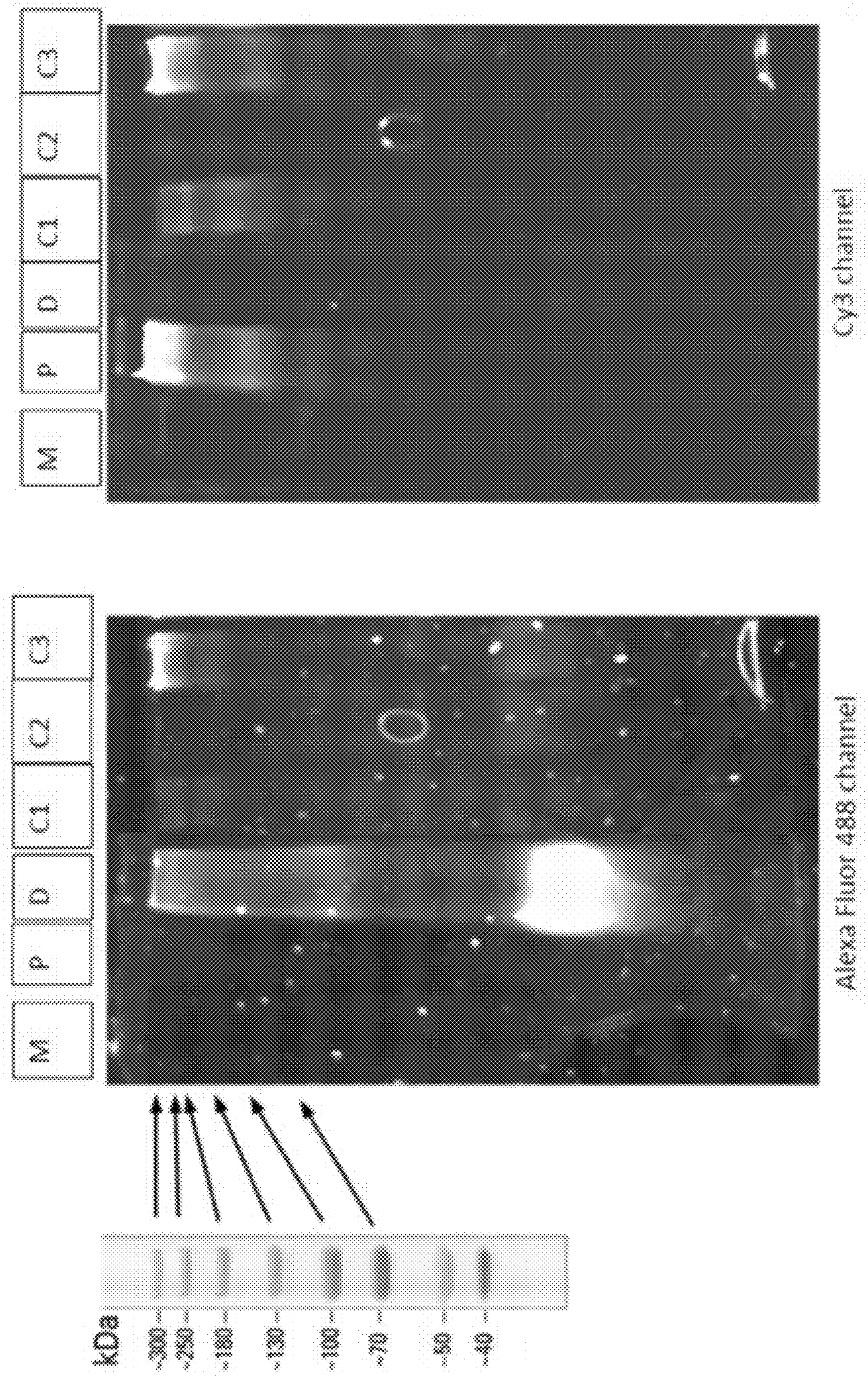

FIG. 39: Fluorescence images of SDS-PAGE gel performed on a VersaDoc imaging system. M=marker, P=Cy3-PAMAM-$(SO1861)_{27}$-DBCO, D=dianthin-EGF-Alexa488-SS-PEG-$N_3$, C1=Cy3-PAMAM-$(SO1861)_5$-Dianthin-EGF-Alexa488, C2=Cy3-PAMAM-NC-SO1861-Dianthin-EGF-Alexa488, and C3=Cy3-PAMAM-$(SO1861)_{27}$-Dianthin-EGF-Alexa488.

Figure 40:
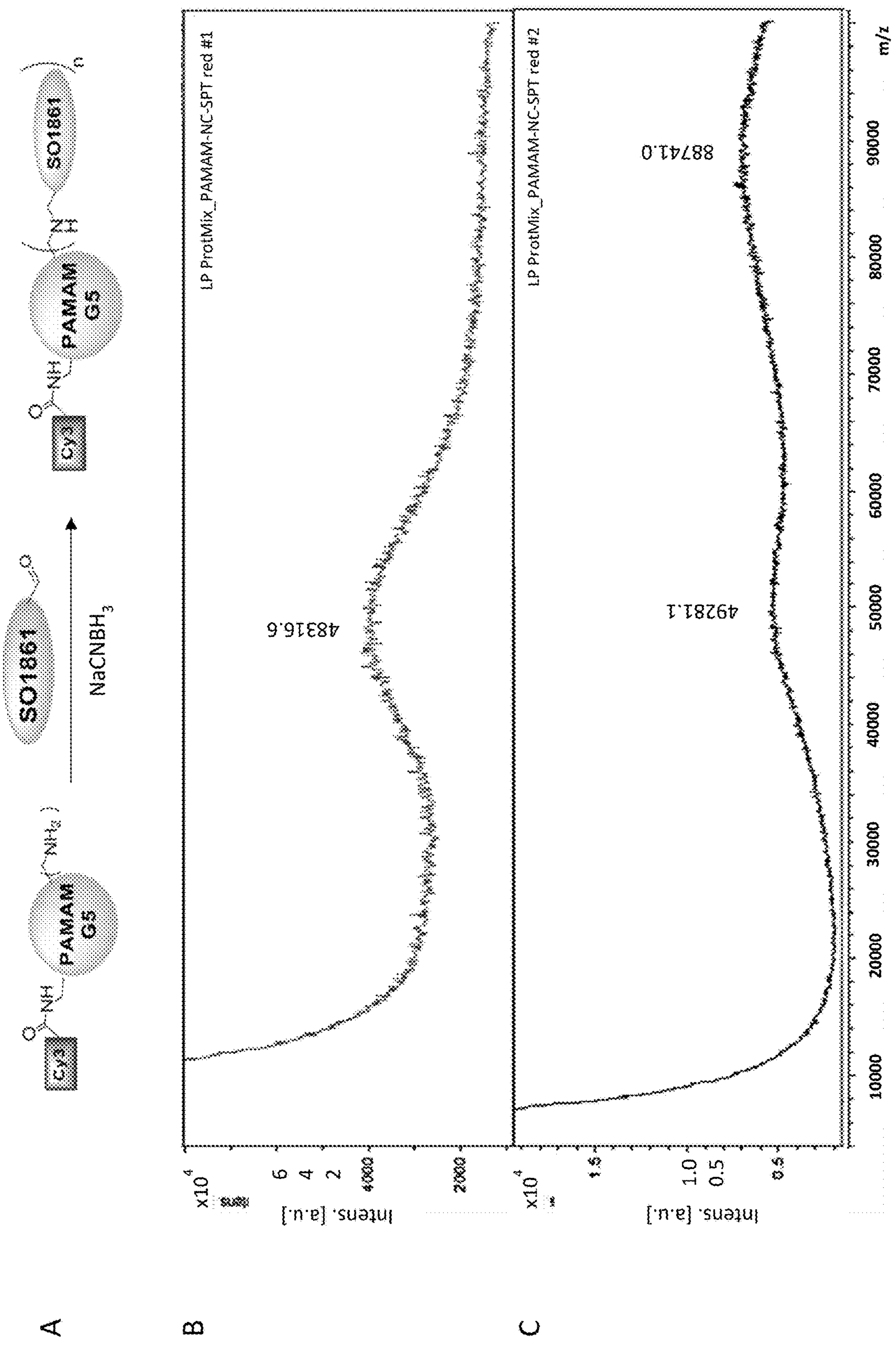

FIG. 40: (A) Synthesis scheme of Cy3-PAMAM-NC-SO1861 via reductive amination. (B, and C) Respective MALDI-TOF-MS spectra.

Figure 41:
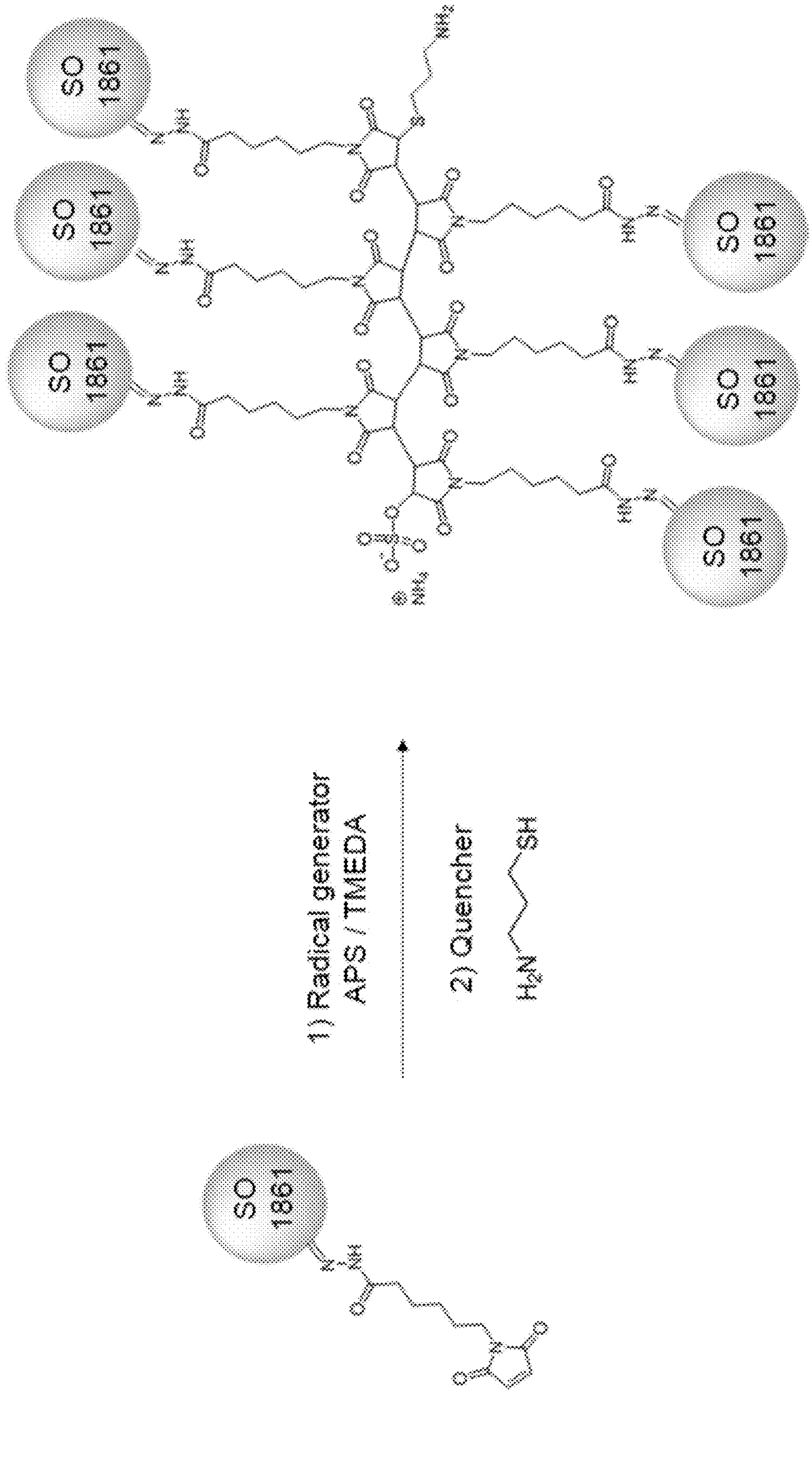

FIG. 41: Reaction scheme for the generation of poly (SO1861) using SO1861-EMCH as monomer, the APS/TMEDA system as polymerization initiator, and aminopropanethiol as radical quencher.

Figure 42:
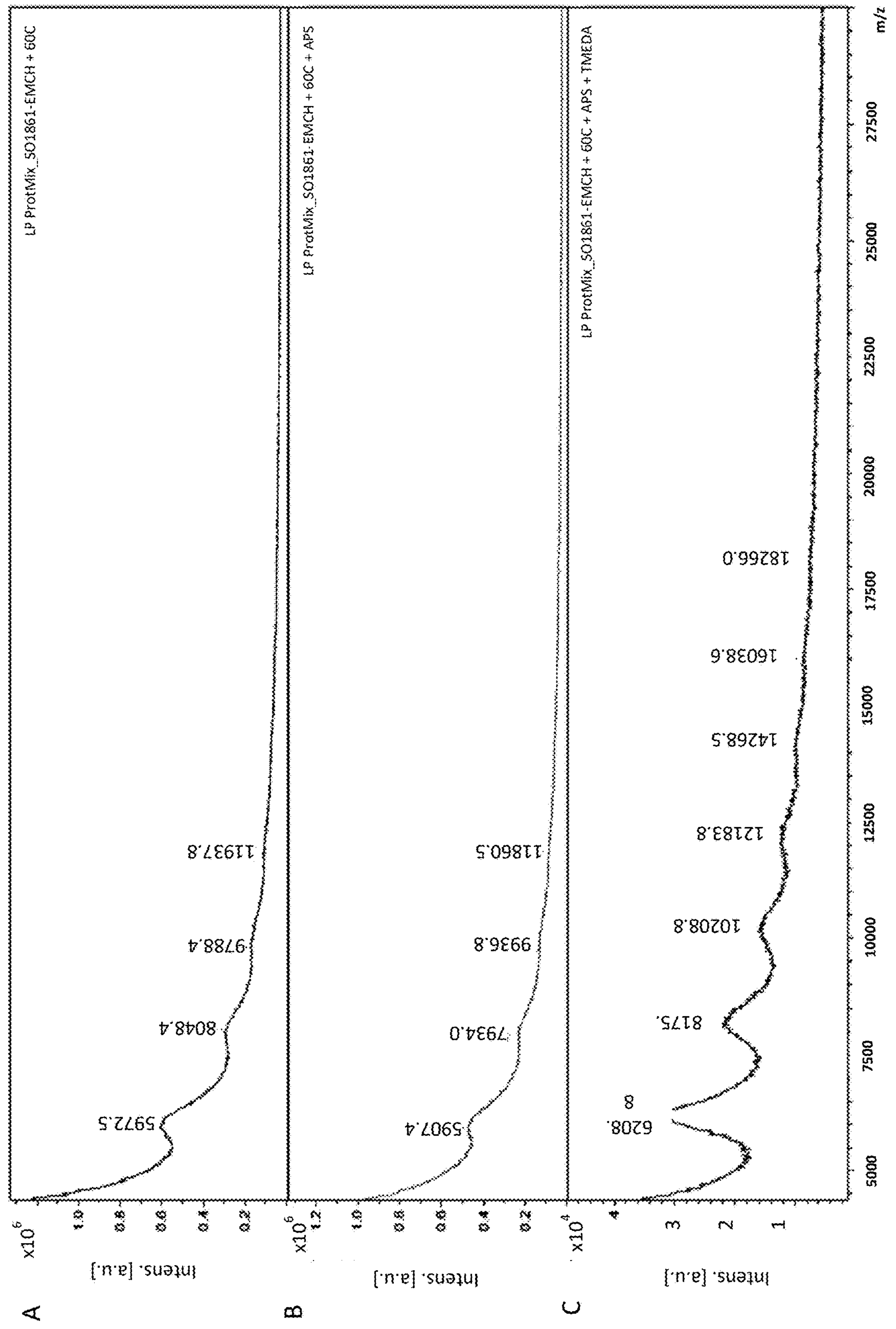

FIG. 42: MALDI-TOF-MS spectra of poly(SO1861) reaction batches. (A) SO1861-EMCH at 60° C., (B) SO1861-EMCH+11-3 equivalents APS at 60° C., (C) SO1861-EMCH+11-3 equivalents APS/TMEDA at 60° C.

Figure 43:
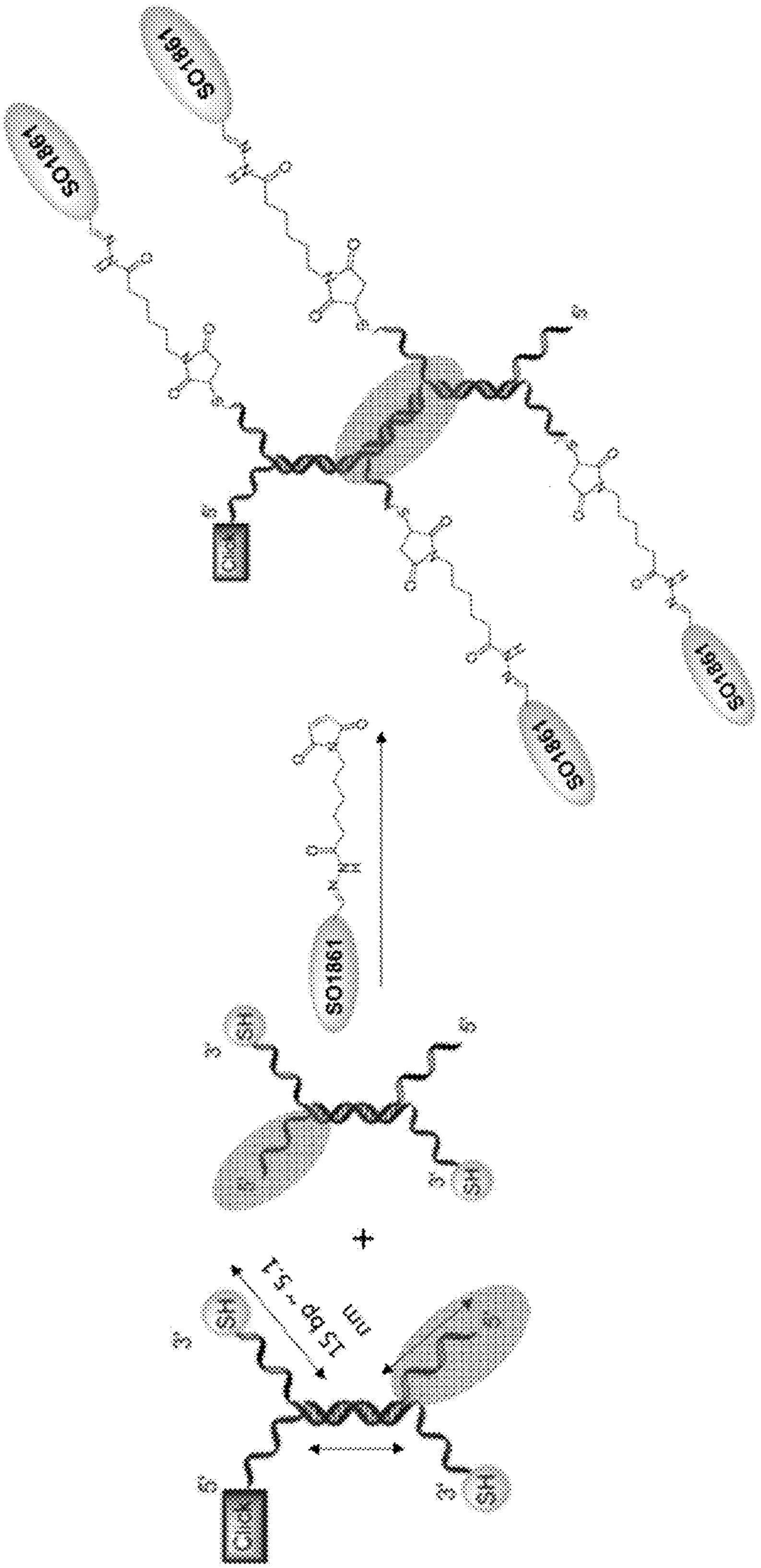

FIG. 43: DNA approach. Usage of the principle of DNA-origami to generate a DNA based scaffold that is able to conjugate and release glycoside molecules. In addition, one of the DNA strands obtains a click chemistry moiety that can be used for conjugation to a targeted toxin to form a functionalized scaffold. bp: base pair.

Figure 44:
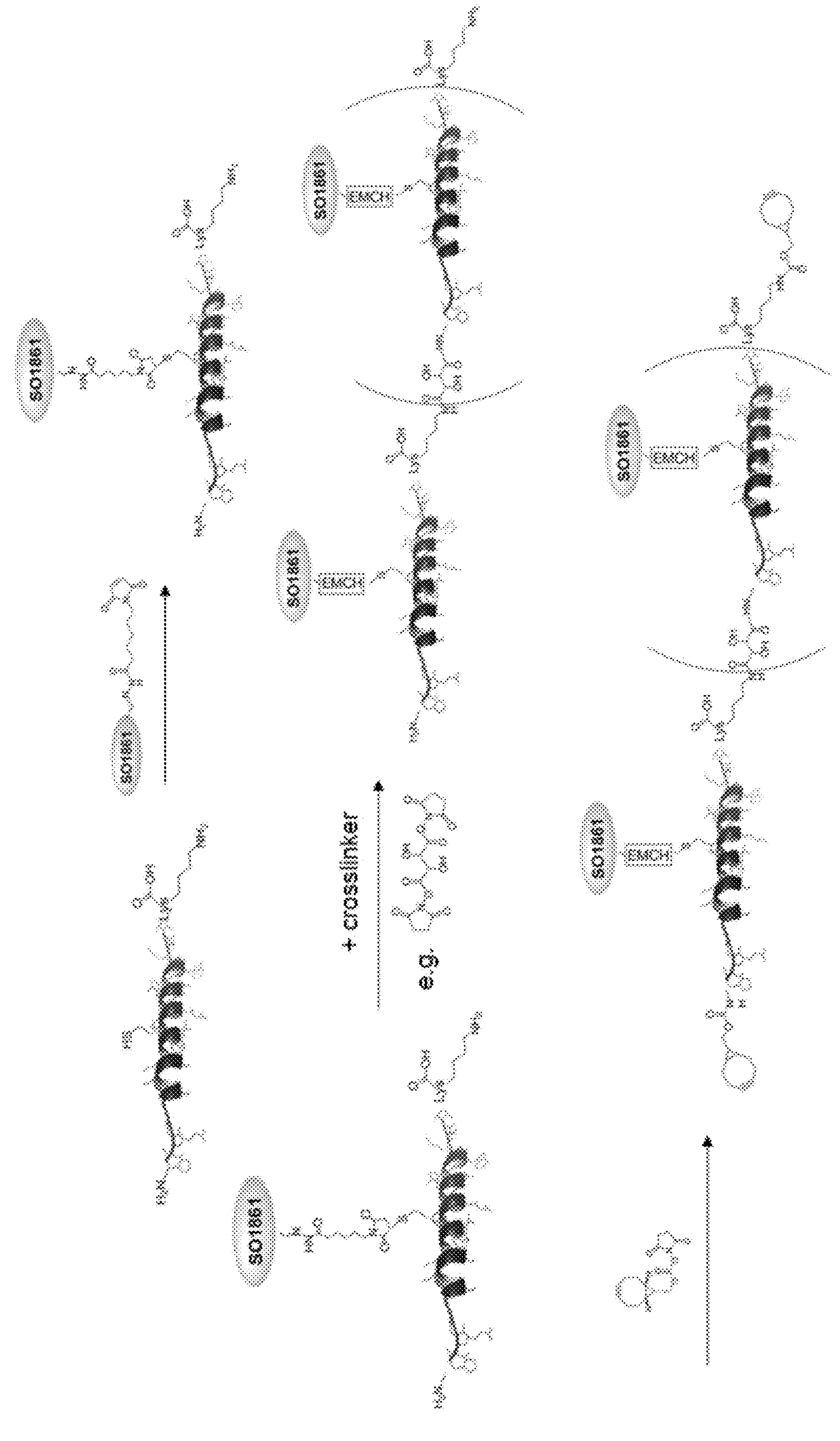

FIG. 44: Poly(peptide-SO1861) approach. Usage of a peptide sequence that can conjugate and release glycoside molecules and which can react with itself to form a poly (peptide-SO1861) construct.

The poly(peptide) chain endings can be further modified with click chemistry moieties (e.g., BCN-NHS linker) that can be used for conjugation to a toxin.

Figure 45:
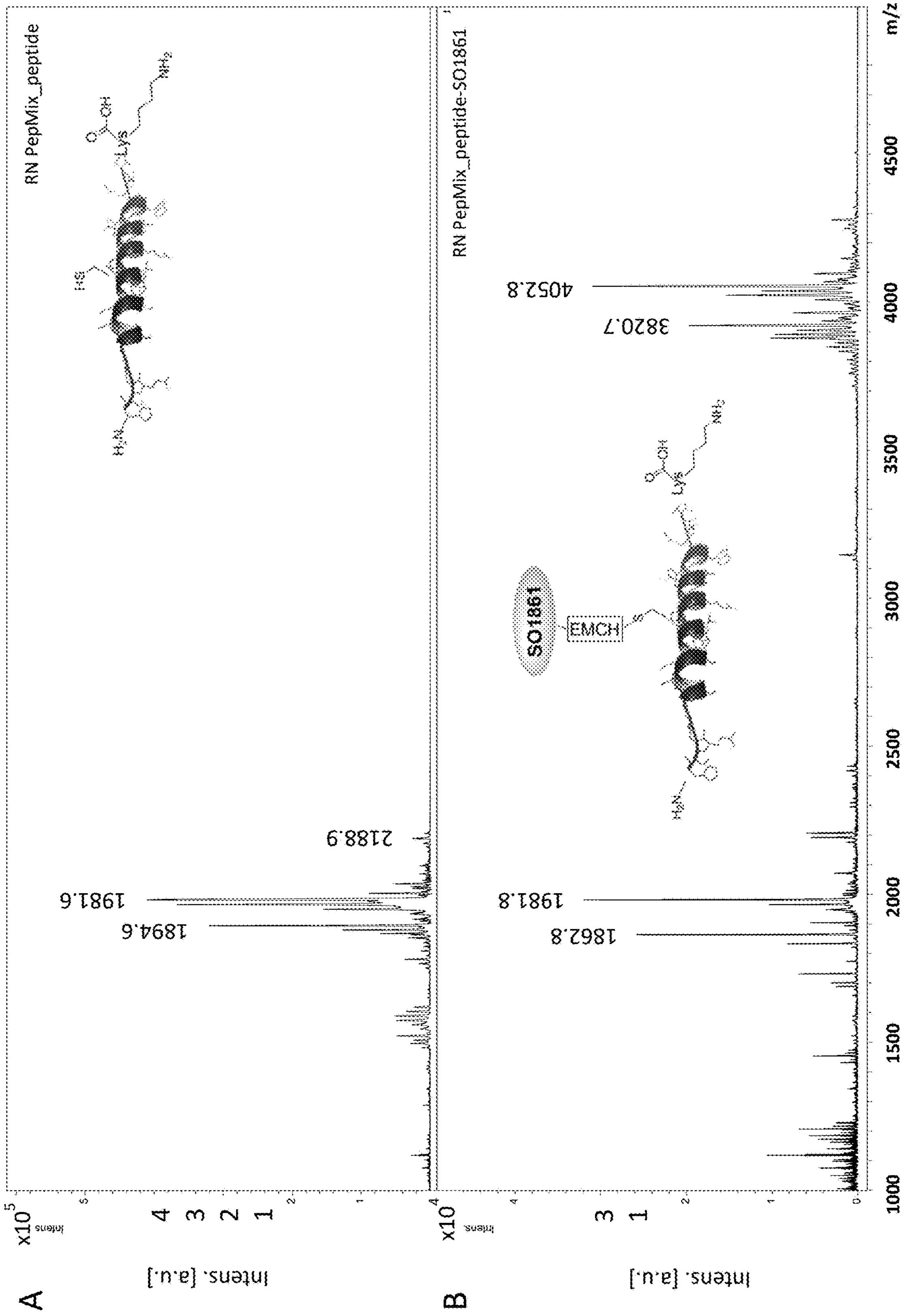

FIG. 45. MALDI-TOF-MS spectra of (A) native peptide, (B) peptide-SO1861 conjugate.

Figure 46:
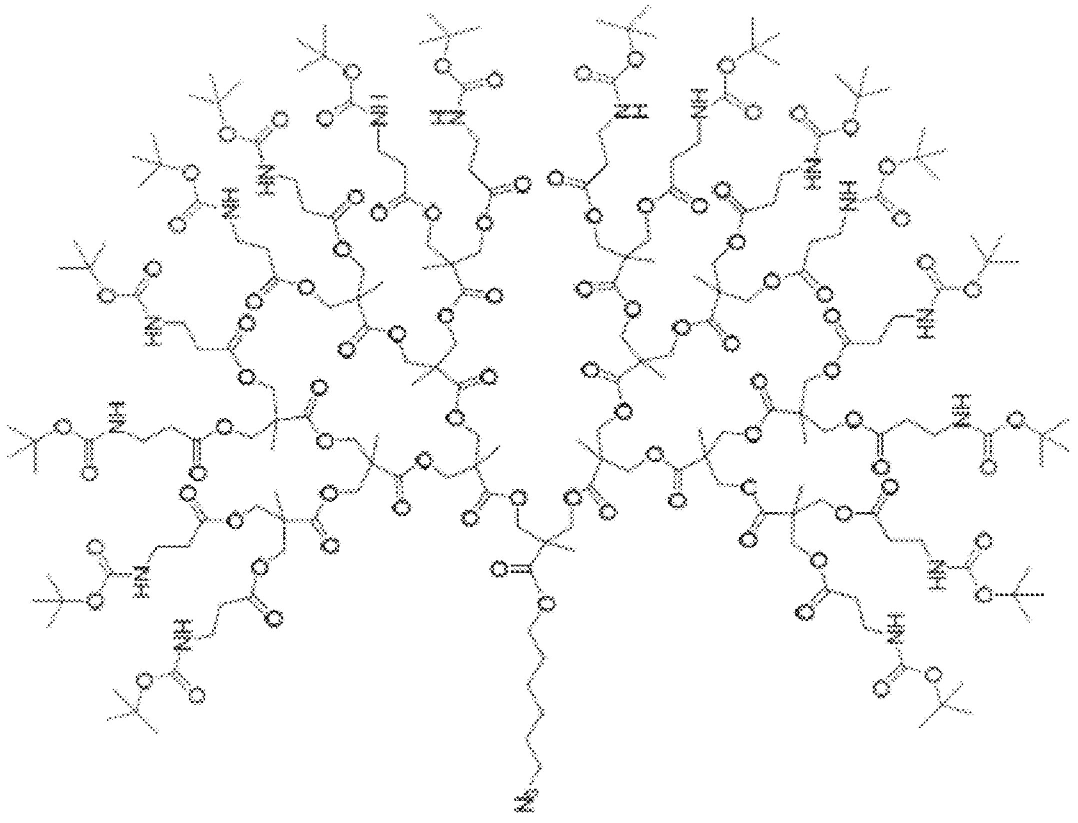
Figure 46:
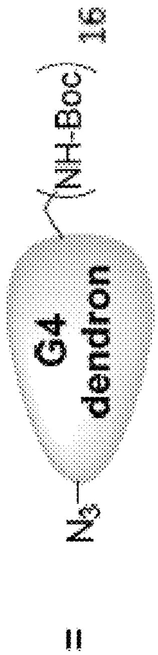

FIG. 46. Molecular structure of G4-dendron with protected amino groups.

Figure 47:
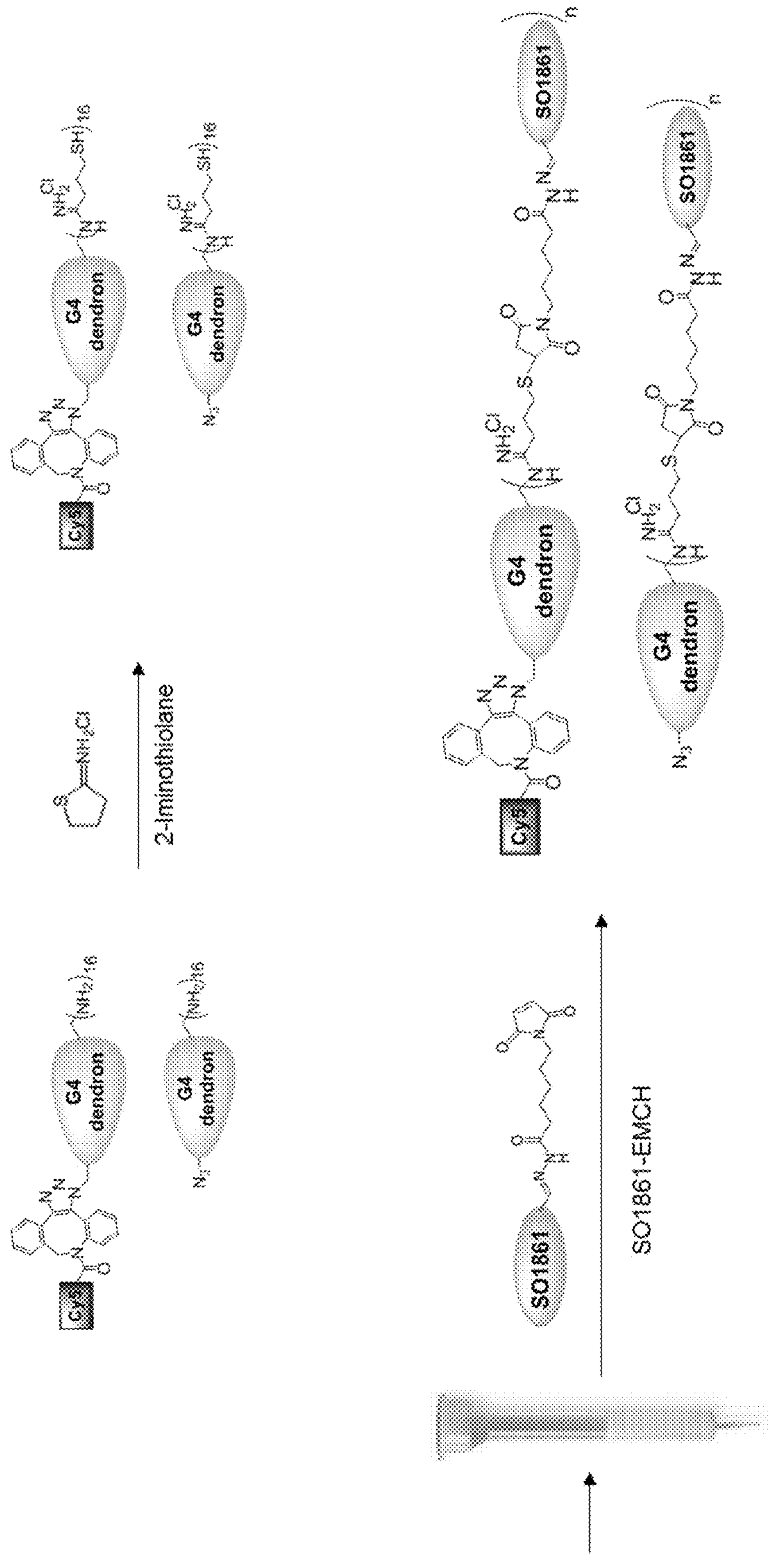

FIG. 47. Synthesis scheme for the generation of dendron based scaffolds and functional scaffolds.

Figure 48:
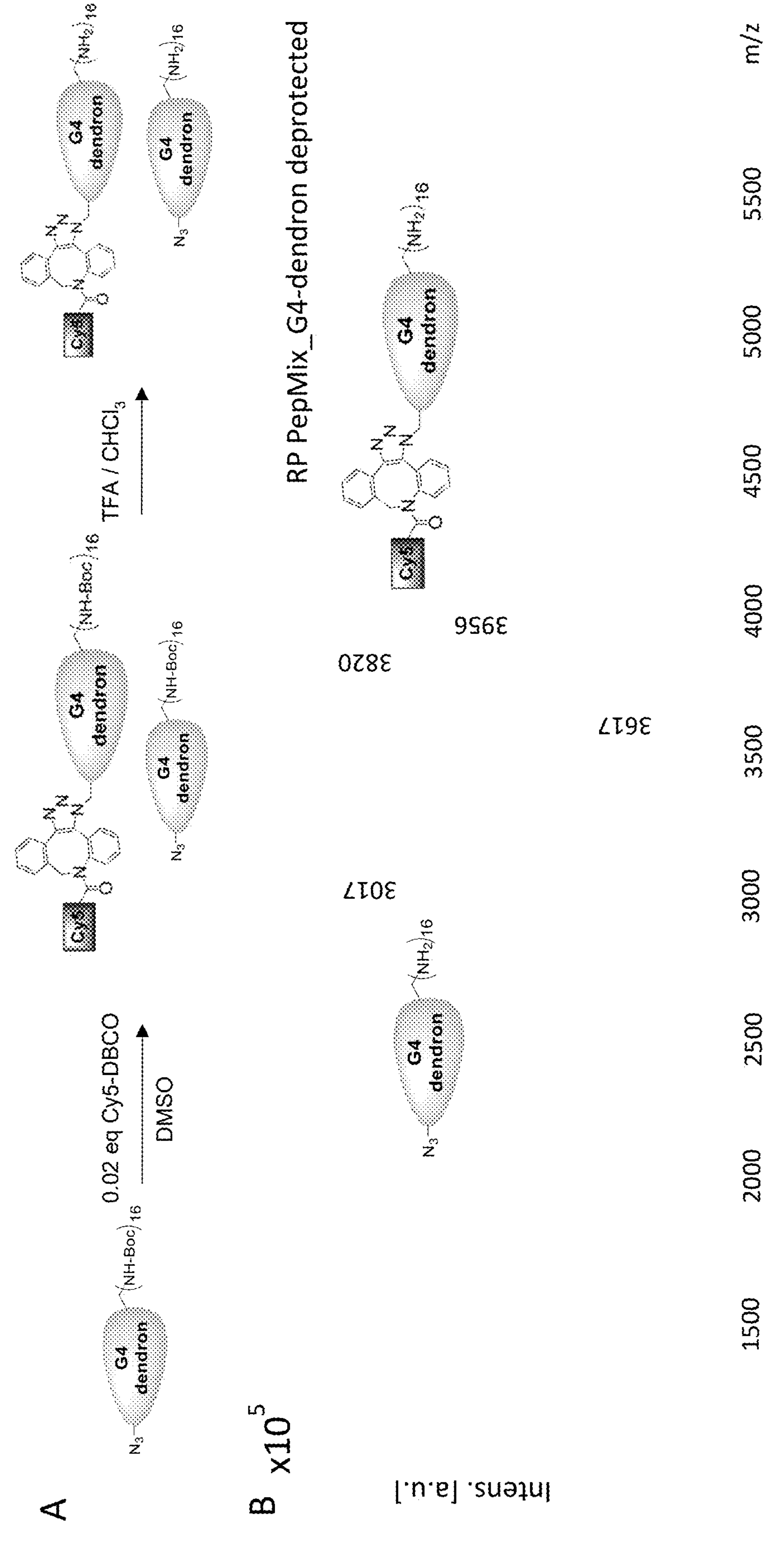

FIG. 48. (A) Reaction scheme for partial dye labeling and deprotection of the G4-dendron. (B) MALDI-TOF-MS spectrum of deprotected and partially dye labeled G4-dendron.

Figure 49:
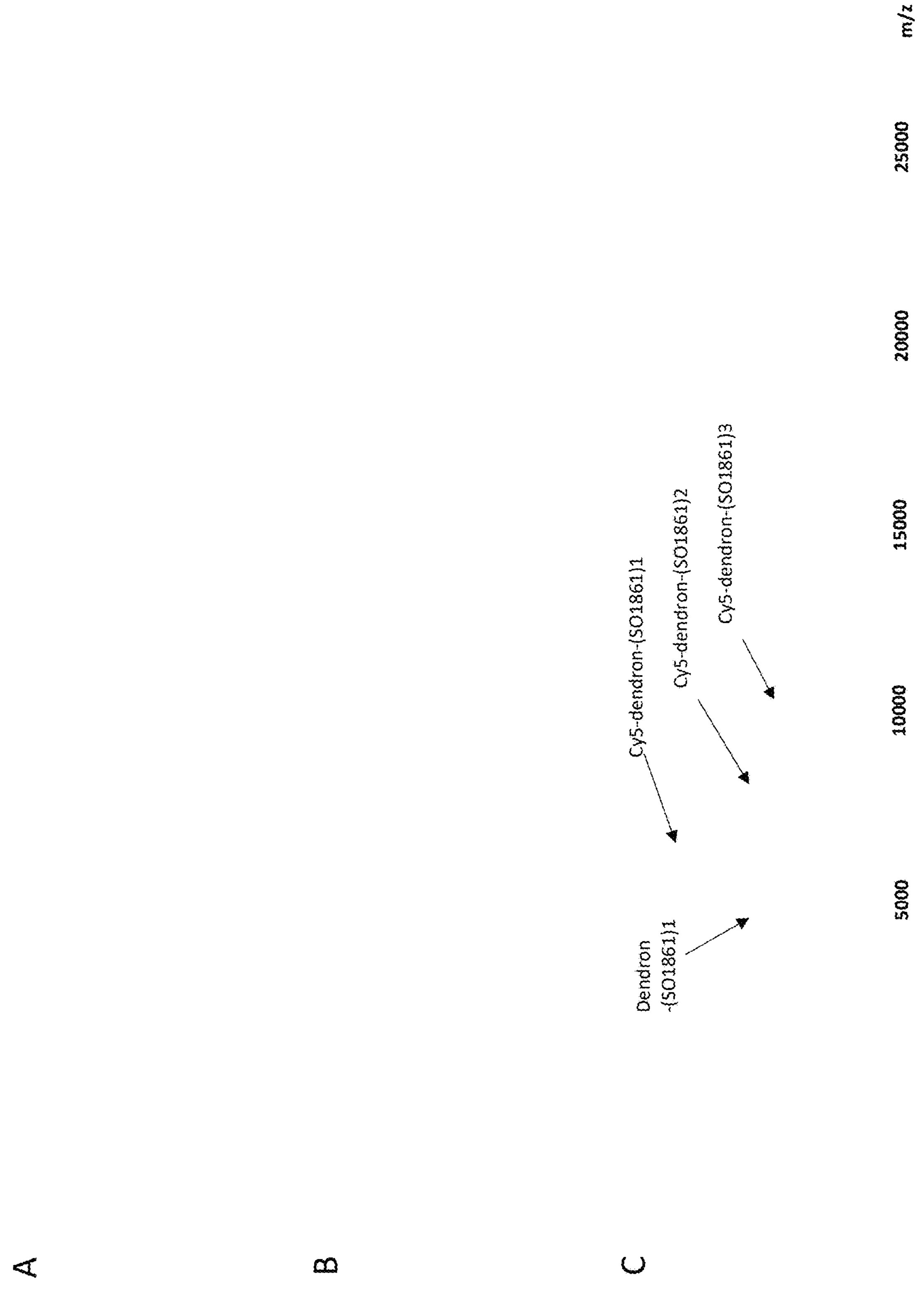

FIG. 49. MALDI-TOF-MS spectra of G4-dendron-SO1861 scaffolds with (A) 22 feed equivalents of SO1861-EMCH, (B) 10 feed equivalents of SO1861-EMCH, and (C) 3 feed equivalents of SO1861-EMCH.

Figure 50:
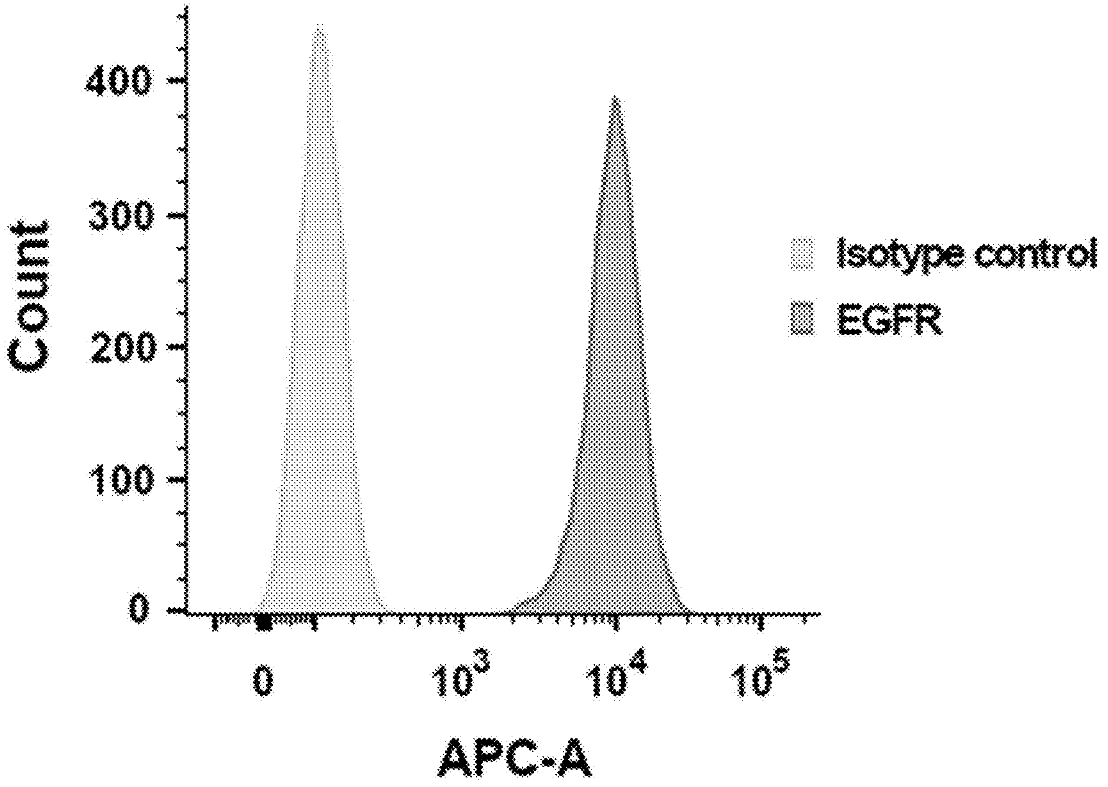
Figure 50:
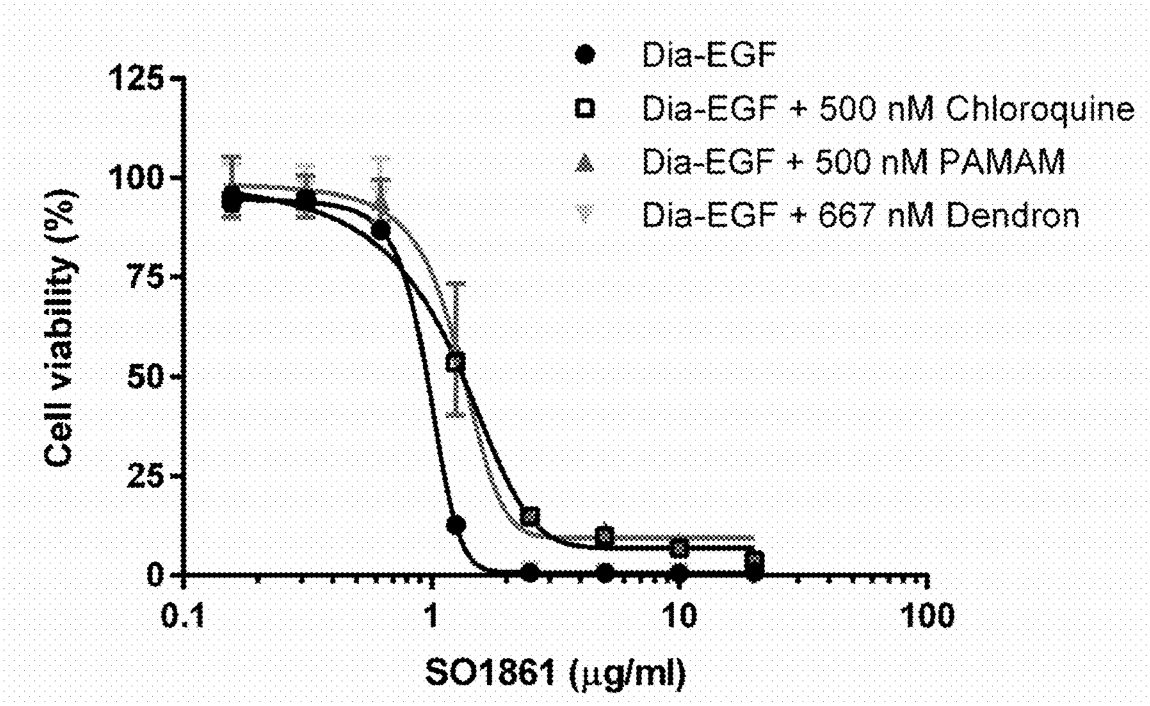
Figure 50:
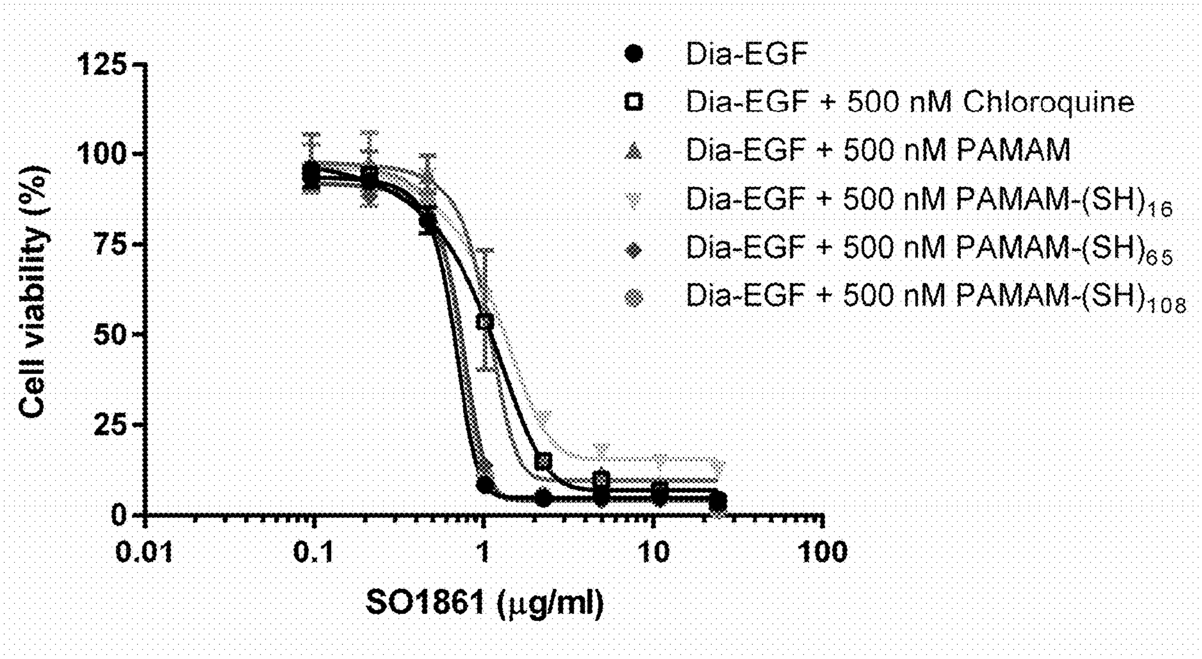
Figure 50:
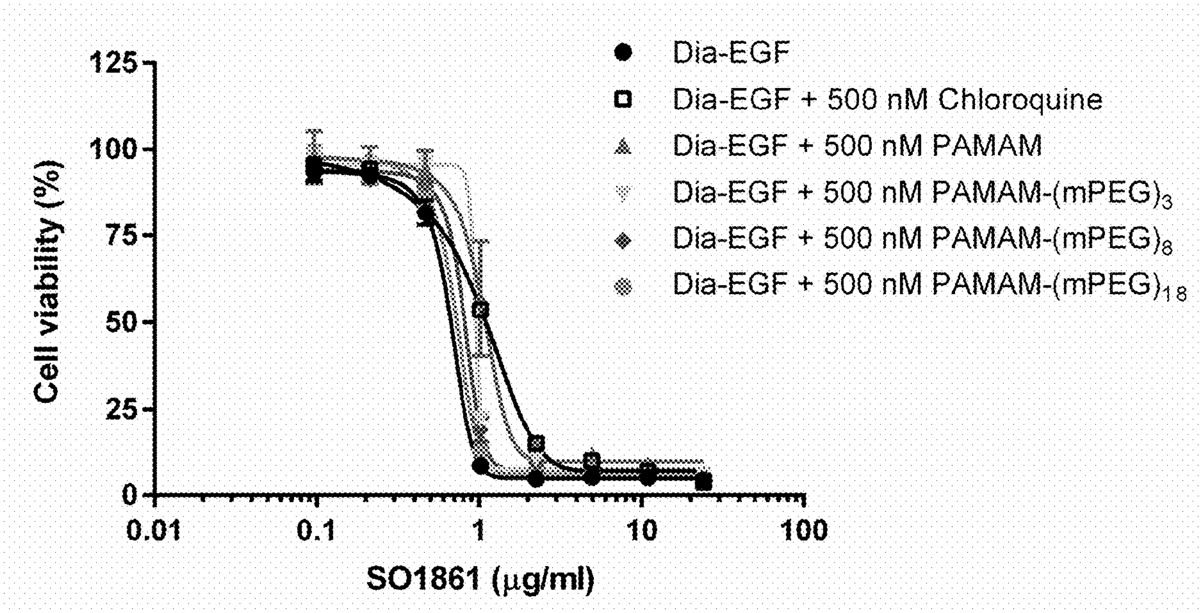

FIG. 50. Cell viability curves of HeLa cells treated with (A) EGFR cell surface expression as determined by FACS analyses of HeLa cells (B, see Table 19), cell viability of HeLa cells treated with SO1861+dianthin-EGF (Dia-EGF), SO1861+dianthin-EGF+500 nM chloroquine, SO1861+dianthin-EGF+500 nM PAMAM, SO1861+dianthin-EGF+667 nM dendron (C) cell viability of HeLa cells treated with SO1861+dianthin-EGF, SO1861+dianthin-EGF+500 nM chloroquine, SO1861+dianthin-EGF+500 nM PAMAM, SO1861+dianthin-EGF+500 nM PAMAM-$(SH)_{16}$, SO1861+dianthin-EGF+500 nM PAMAM-$(SH)_{65}$, SO1861+dianthin-EGF+500 nM PAMAM-$(SH)_{108}$ (D) cell viability of HeLa cells treated with SO1861+dianthin-EGF, SO1861+dianthin-EGF+500 nM chloroquine, SO1861+dianthin-EGF+500 nM PAMAM, SO1861+dianthin-EGF+500 nM PAMAM-$(mPEG)^3$, SO1861+dianthin-EGF+500 nM PAMAM-$(mPEG)^8$, SO1861+dianthin-EGF+500 nM PAMAM-$(mPEG)^{18}$.

Figure 51:
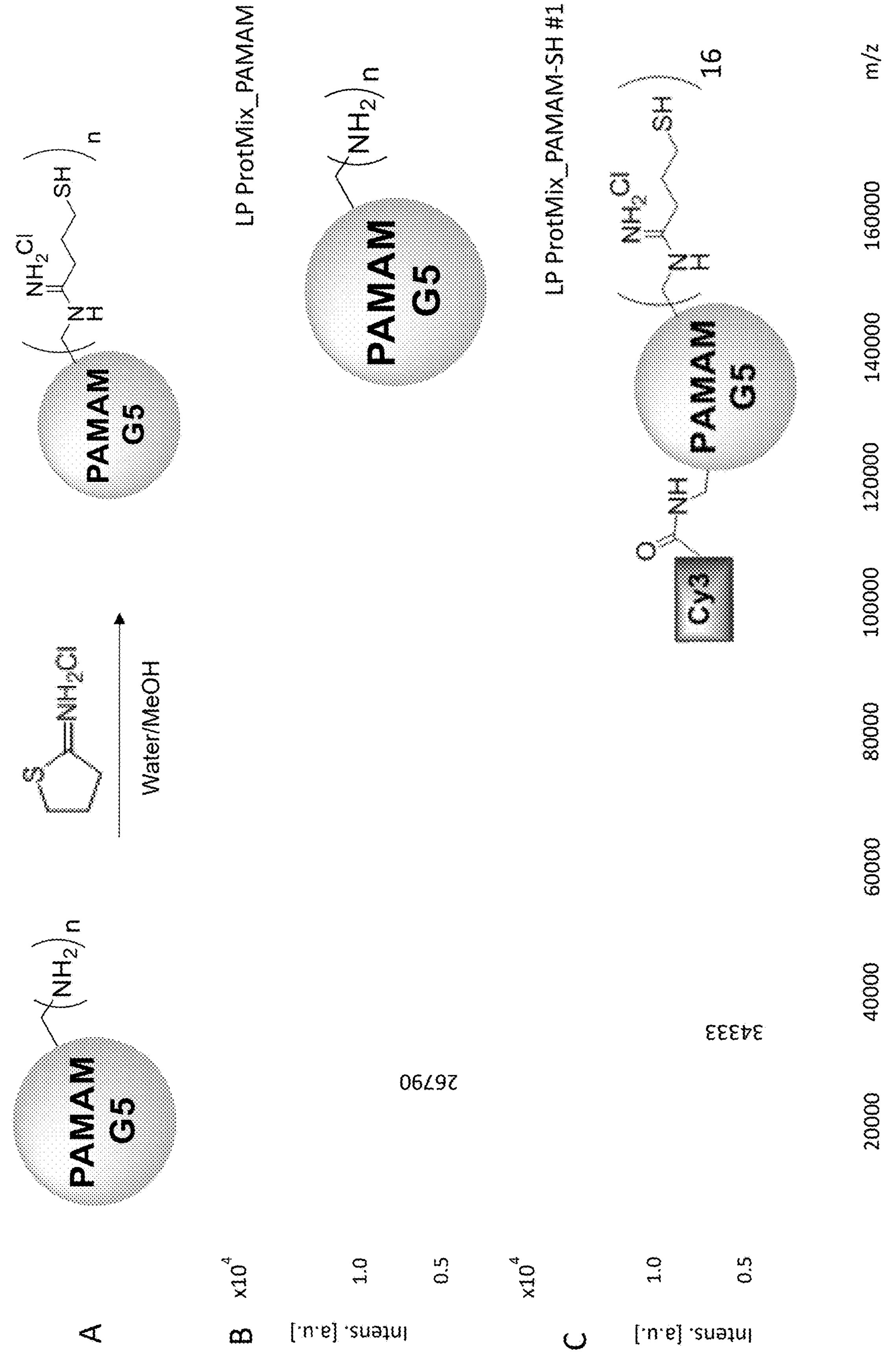
Figure 51:
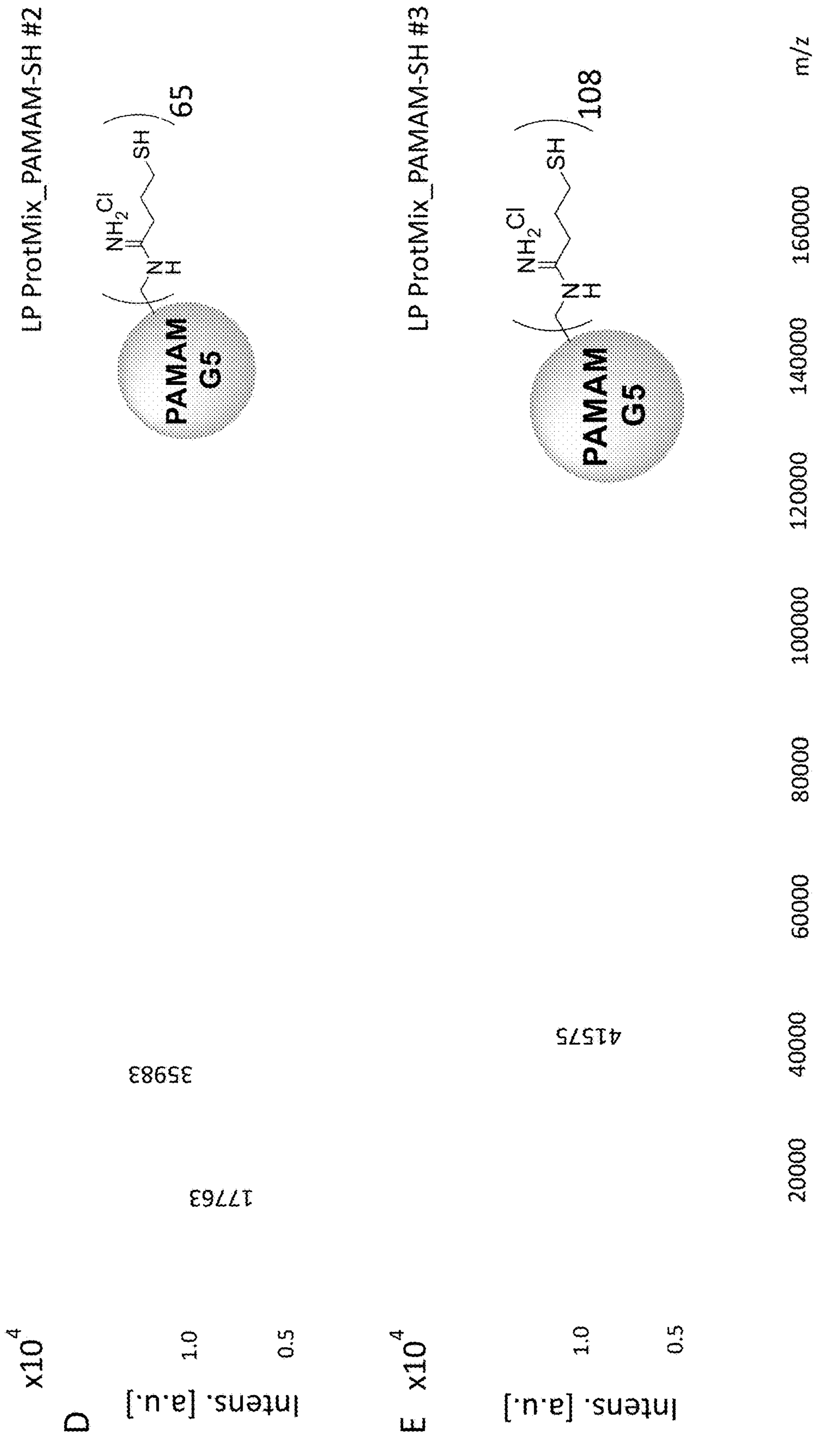

FIG. 51. (A) Reaction scheme of the thiolation of PAMAM using the thiolation reagent 2-iminothiolane. MALDI-TOF-MS spectra of (B) native PAMAM, (C) thiolated PAMAM-$(SH)_{16}$, (D) thiolated PAMAM-$(SH)_{65}$, and (E) thiolated PAMAM-$(SH)_{108}$.

Figure 52:
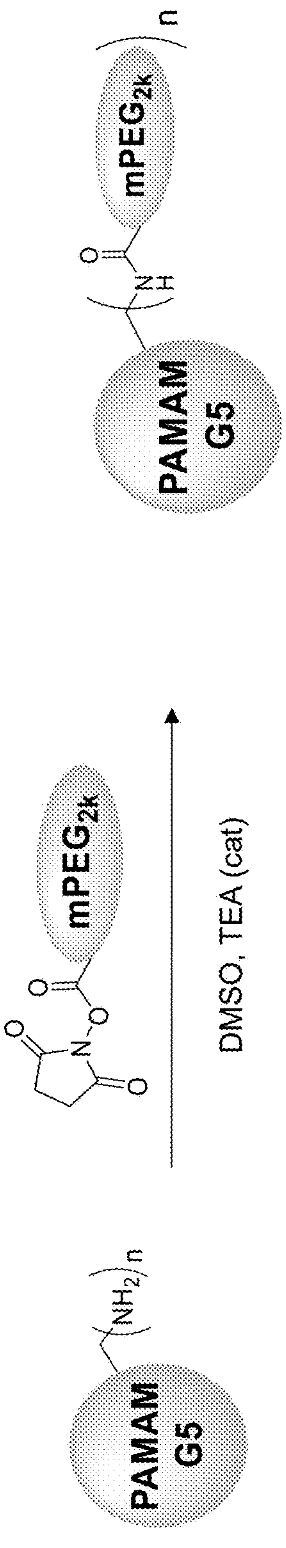
Figure 52:
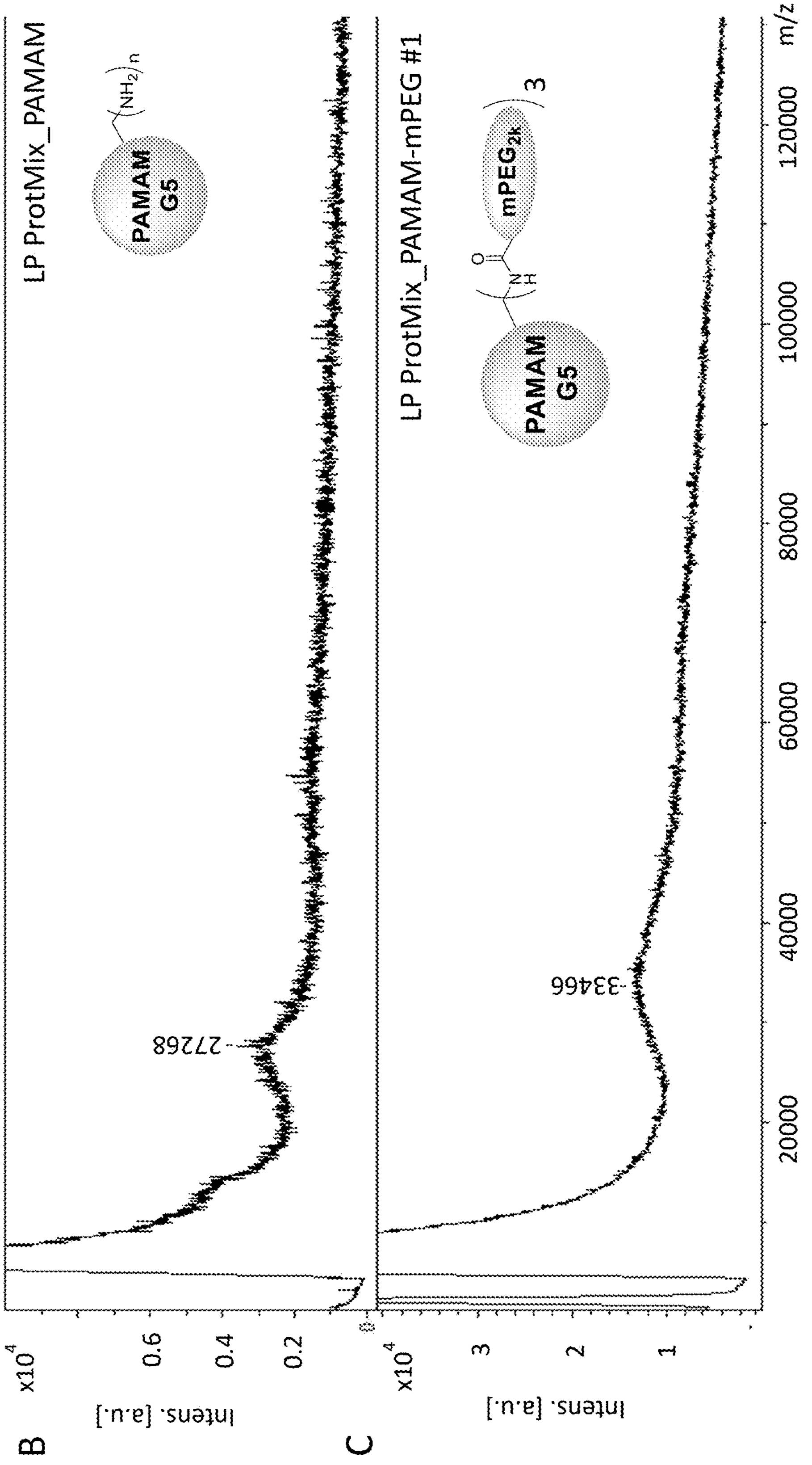
Figure 52:
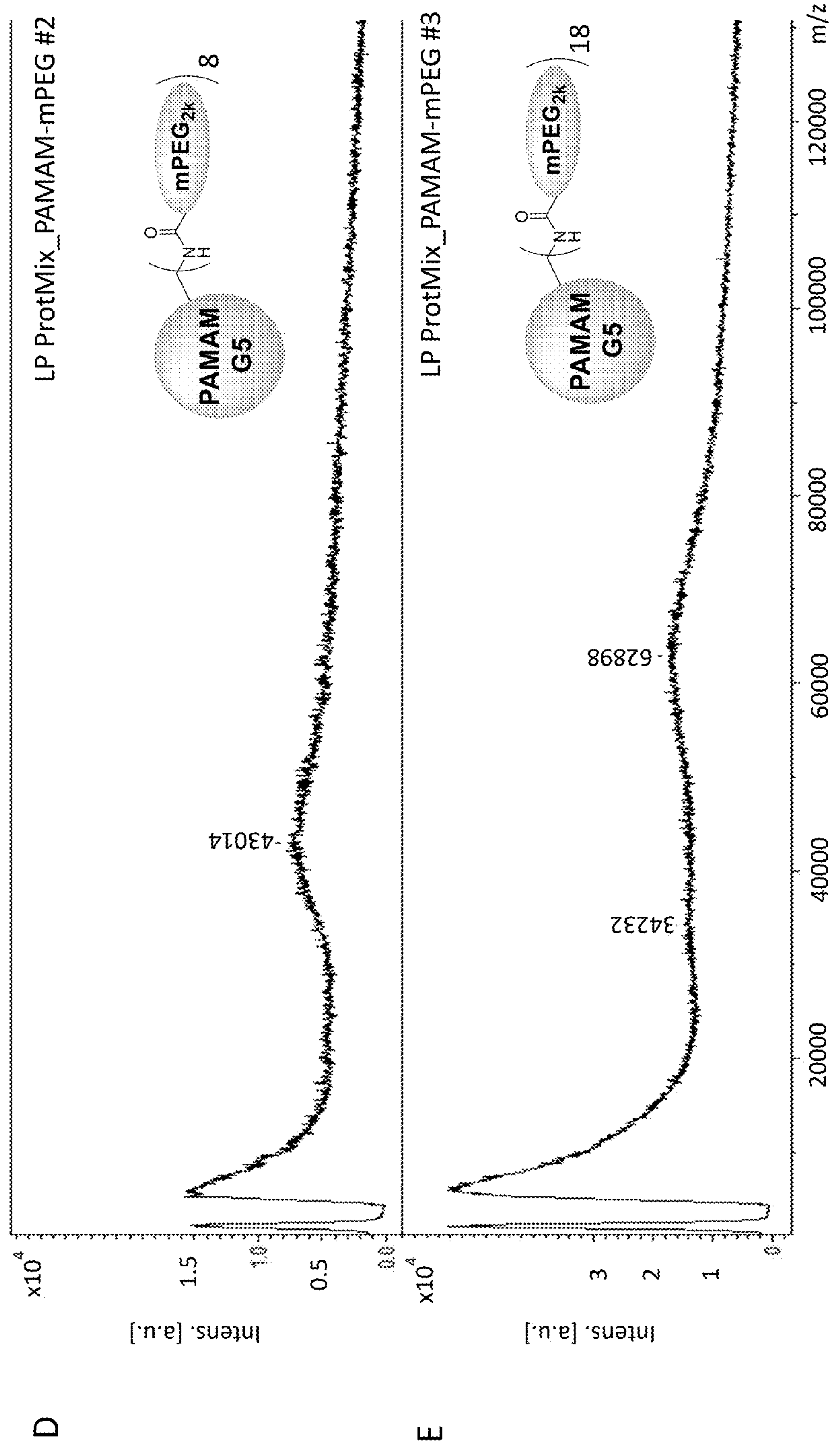

FIG. 52. (A) Reaction scheme of the PEGylation of PAMAM using the PEGylating reagent $mPEG_{2k}$-NHS. MALDI-TOF-MS spectra of (B) native PAMAM, (C) PEGylated PAMAM-$(mPEG_{2k})_3$, (D) PEGylated PAMAM-$(mPEG_{2k})_8$, and (E) PEGylated PAMAM-$(mPEG_{2k})_{18}$.

Figure 53:
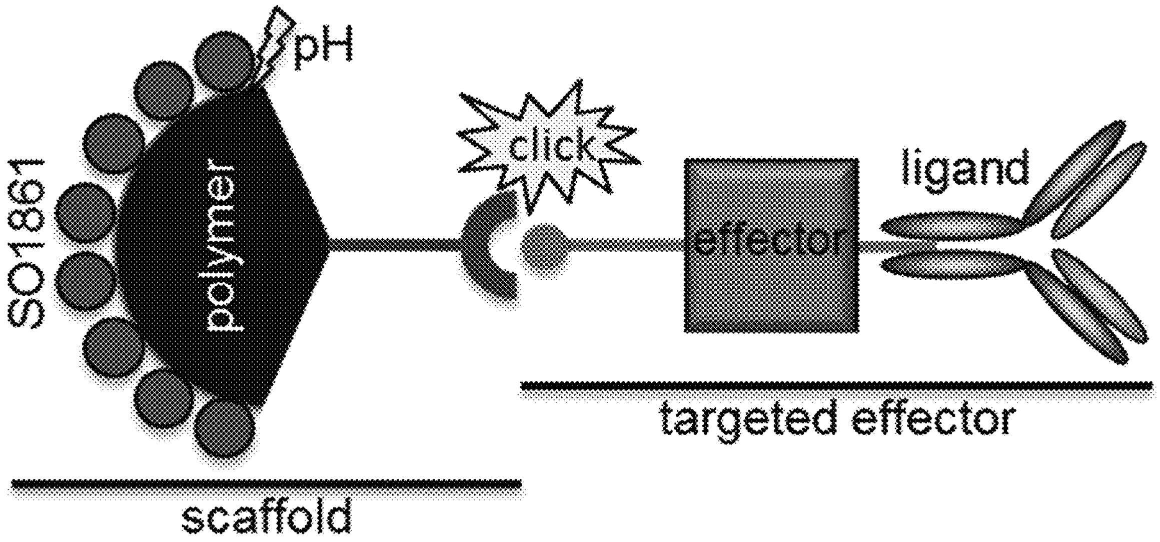

FIG. 53: Basic scaffold with click chemistry function to link any desired effector molecule. The user determines the position of the click chemistry position in the effector molecule and all further properties of the effector molecule, e.g. choice and position of an optional ligand.

Figure 54:
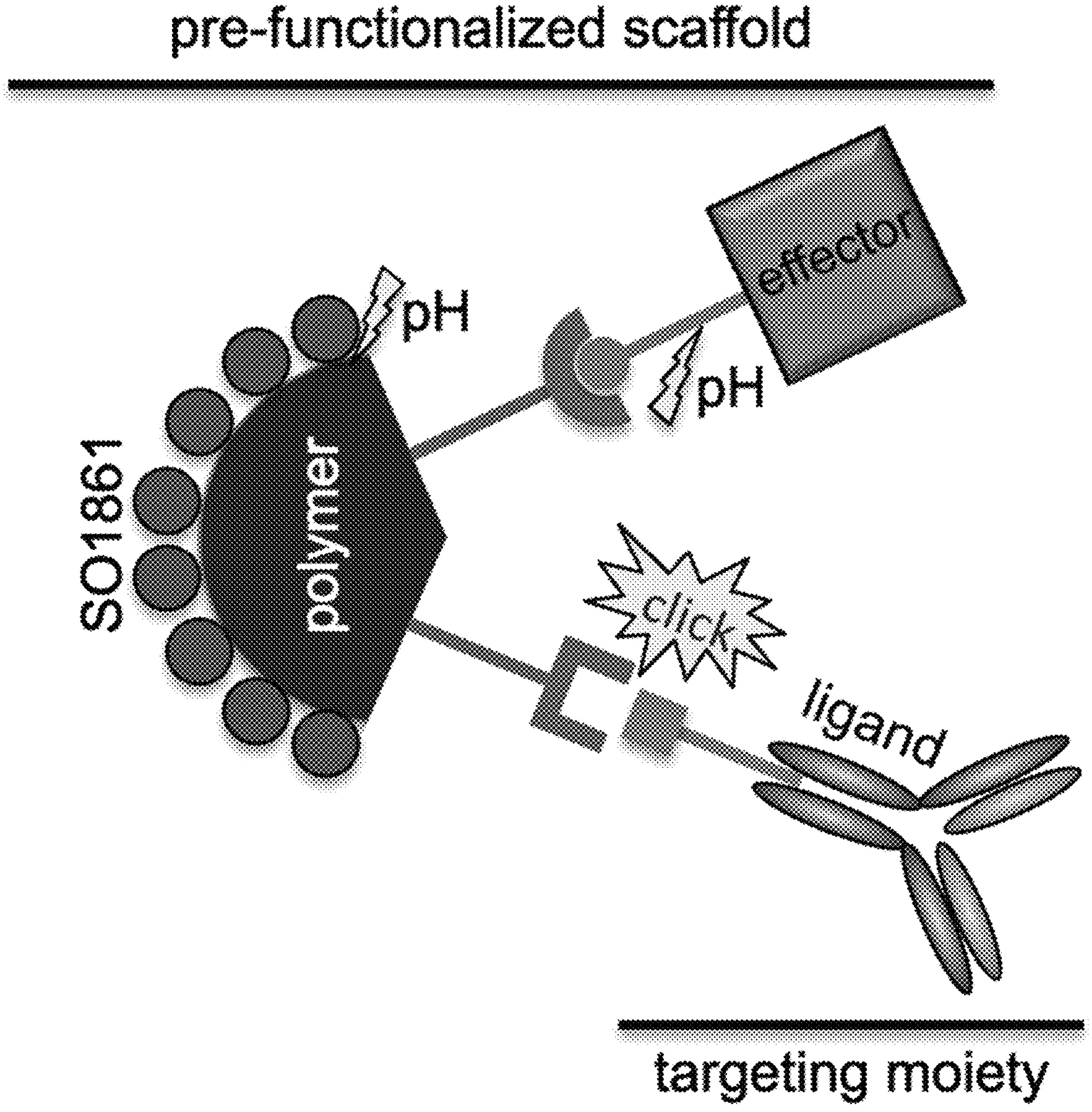

FIG. 54: Functionalized scaffold with pre-bound effector molecule and click chemistry function to link any desired ligand. Optionally, a pH-sensitive linkage can be provided to release the effector molecule from the scaffold after reaching the endosomes.

DETAILED DESCRIPTION

In order for a bioactive molecule to work, the molecule must be able to engage with its target, e.g. in the blood serum, on the outside of the cell surface or inside a cell or an organelle. The active moiety of almost all protein-based targeted toxins, e.g., must enter the cytosol of the target cell to mediate its target modulatory effect. In many constellations the toxin remains ineffective since (1) the targeting moiety is poorly internalized and remains bound to the outside of the cells, (2) is recycled back to the cell surface after internalization or (3) transported to the endolysosomes where it is degraded. Although these fundamental issues are known for decades and more than 500 targeted toxins have been investigated in the past decades, the problems have not been solved yet and only a couple of antibody-targeted protein toxin have been admitted to the market, albeit with warning labels for severe toxicity. Moxetumomab pasudotox-tdfk (LUMOXITI©, AstraZeneca Pharmaceuticals LP), has been approved for relapsed or refractory hairy cell leukemia by the FDA to date. Other of such approved ADCs are Elzonris, Ontak.

To overcome these problems, many strategies have been described including approaches to redirect the toxins to endogenous cellular membrane transport complexes of the biosynthetic pathway in the endoplasmic reticulum and techniques to disrupt or weaken the membrane integrity of endosomes, i.e. the compartments of the endocytic pathway in a cell, and thus facilitating the endosomal escape. This comprises the use of lysosomotropic amines, carboxylic ionophores, calcium channel antagonists, various cell-penetrating peptides of viral, bacterial, plant, animal, human and synthetic origin, other organic molecules and light-induced techniques. Although the efficacy of the targeted toxins was typically augmented in cell culture hundred- or thousand-fold, in exceptional cases more than million-fold, the requirement to co-administer endosomal escape enhancers with other substances harbors new problems including additional side effects, loss of target specificity, difficulties to determine the therapeutic window and cell type-dependent variations.

All strategies, including physicochemical techniques, require enhancer molecules that interact more or less directly with membranes and comprise essentially small chemical molecules, secondary metabolites, peptides and proteins. A common feature of all these substances is that they are per se not target cell-specific and distribute with other kinetics than the targeted toxins. This is one major drawback of the current approaches.

The present invention will be described with respect to particular embodiments but the invention is not limited thereto but only by the claims. The embodiments of the invention described herein can operate in combination and cooperation, unless specified otherwise.

While the invention has been described in terms of several embodiments, it is contemplated that alternatives, modifications, permutations and equivalents thereof will become apparent to one having ordinary skill in the art upon reading the specification and upon study of the drawings and graphs. The invention is not limited in any way to the illustrated embodiments. Changes can be made without departing from the scope which is defined by the appended claims.

An aspect of the invention relates to a conjugate comprising a cell-surface molecule targeting molecule and at least one effector moiety and further comprising at least one covalently bound saponin.

The inventors established that the therapeutic window of a conjugate such as an antibody drug conjugate or an antibody-oligonucleotide conjugate, increases when administered to a tumor-bearing mammal (mouse) to whom the conjugate is administered, wherein said conjugate comprises at least one covalently bound saponin. The conjugate of the invention has at least one glycoside such as a saponin bound thereto, preferably covalently, more preferably via a cleavable linker. The saponin augments the therapeutic efficacy of the effector moiety bound to the cell-surface molecule targeting molecule, likely by enhancing the endosomal escape of the effector moiety into the cytosol where the activity of the effector moiety is desired. This way, already at a lower dose than the conventional dose of the ADC or the AOC, i.e. the conjugate of the invention, therapeutic effect is established under influence of the presence of the conjugate comprising the saponin(s) thereby bringing the saponin(s) near, at and/or inside the targeted cell. The targeted cell is for example a diseased cell such as a tumor cell or an auto-immune cell or a B-cell disease related B-cell, etc. The effector moiety is for example a toxin as part of an ADC or an oligonucleotide such as an antisense BNA as part of an AOC according to the invention.

An embodiment is the conjugate of the invention, wherein the at least one saponin is a triterpenoid saponin and/or a bisdesmosidic triterpene saponin belonging to the type of a 12,13-dehydrooleanane with an aldehyde function in position C-23 and optionally comprising a glucuronic acid function in a carbohydrate substituent at the C-3beta-OH group of the saponin, and/or a saponin isolated from any one or more of a *Gypsophila* species and/or a *Saponaria* species and/or an *Agrostemma* species and/or a *Quillaja* species such as *Quillaja saponaria*.

An embodiment is the conjugate of the invention, wherein the at least one saponin is a single specific saponin or is a mixture of two or more different saponins.

An embodiment is the conjugate of the invention, wherein the at least one saponin has a molecular mass of 3.000 Dalton or less, preferably 2.500 Dalton or less, more preferably 2.300 Dalton or less, most preferably, 2.000 Dalton or less, such as 1.500 Dalton-1.900 Dalton.

An embodiment is the conjugate of the invention, wherein the at least one saponin is one or more of the saponins in Table A1 or Scheme I, SO1861, SA1657, GE1741, SA1641, QS-21, QS-21A, QS-21 A-api, QS-21 A-xyl, QS-21B, QS-21 B-api, QS-21 B-xyl, QS-7-xyl, QS-7-api, QS-17-api, QS-17-xyl, QS1861, QS1862, Quillajasaponin, Saponinum album, QS-18, Quil-A, Gyp1, gypsoside A, AG1, AG2, SO1542, SO1584, SO1658, SO1674, SO1832, or any of their stereomers and/or any combinations thereof, preferably the saponin is SO1861 and/or GE1741 and/or SA1641 and/or QS-21 and/or saponin with a quillaic acid aglycon core, a Gal-(1→2)-[Xyl-(1→3)]-GlcA carbohydrate substituent at the C-3beta-OH group and a Glc-(1→3)-Xyl-(1→4)-Rha-(1→2)-[Xyl-(1→3)-4-OAc-Qui-(1→4)]-Fuc carbohydrate substituent at the C-28-OH group, and/or is 3-O-beta-D-galactopyranosyl-(1→2)-[beta-D-xylopyranosyl-(1→3)]-beta-D-glucuronopyranosyl quillaic acid 28-O-beta-D-glucopyranosyl-(1→3)-beta-D-xylopyranosyl-(1→4)-alpha-L-rhamnopyranosyl-(1→2)-[beta-D-xylopyranosyl-(1→3)-4-OAc-beta-D-quinovopyranosyl-(1→4)]-beta-D-fucopyranoside, more preferably the at least one saponin is SO1861 and/or QS-21.

The inventors disclose here that covalently coupling saponins such as saponins in the water-soluble fraction of *Quillaja saponaria*, QS-21, SA1641, SO1861, Table A1, Scheme I, to the cell-surface molecule targeting molecule such as a proteinaceous molecule, such as via a tri-functional linker, e.g. the tri-functional linker of Scheme II, or via an oligomeric or polymeric structure of a scaffold comprising covalently bound saponins, results in improved cell toxicity exerted by the effector moiety such as a toxin, comprised by the conjugate, under influence of the covalently coupled saponin in the conjugate.

An embodiment is the conjugate of the invention comprising a saponin comprising one or several or all of the indicated structural features of the saponin of Structure A in Scheme I, the saponin of structure A referred to as a saponin with an 'ideal' structure when endosomal escape enhancing activity towards an effector moiety present in the endosome of a cell contacted with conjugate of the invention, and/or a saponin selected from any one or more of the further saponins in Scheme I:

SCHEME I

STRUCTURE A

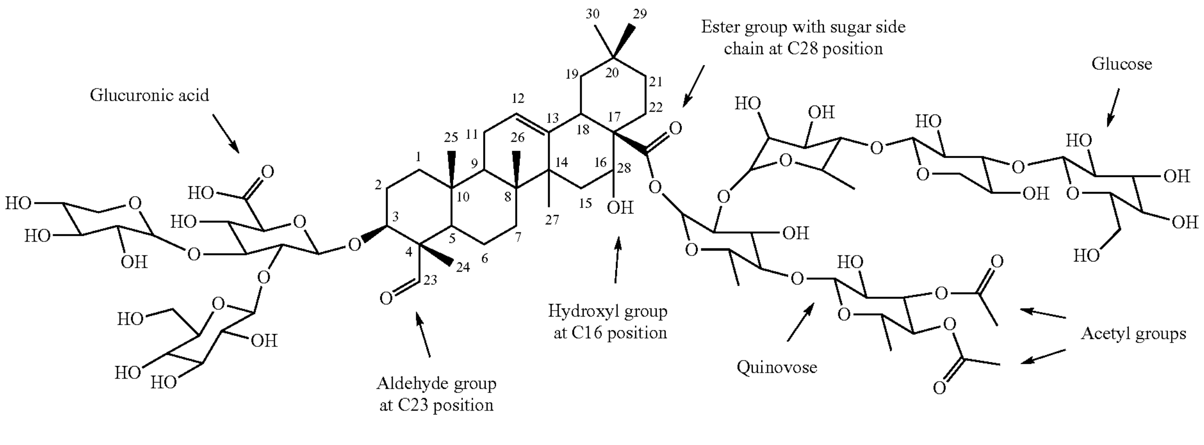

-continued
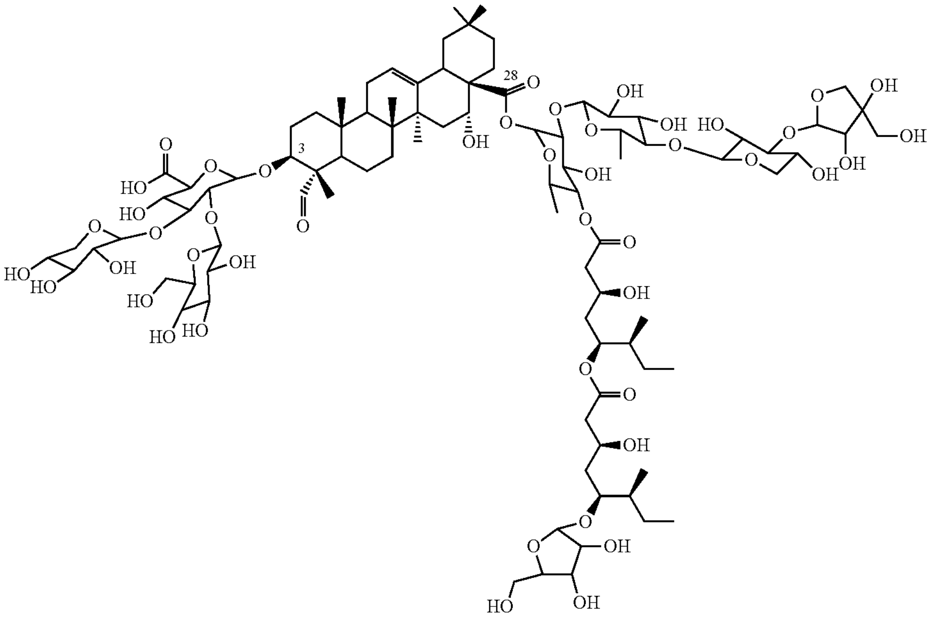
QS-21-A-api
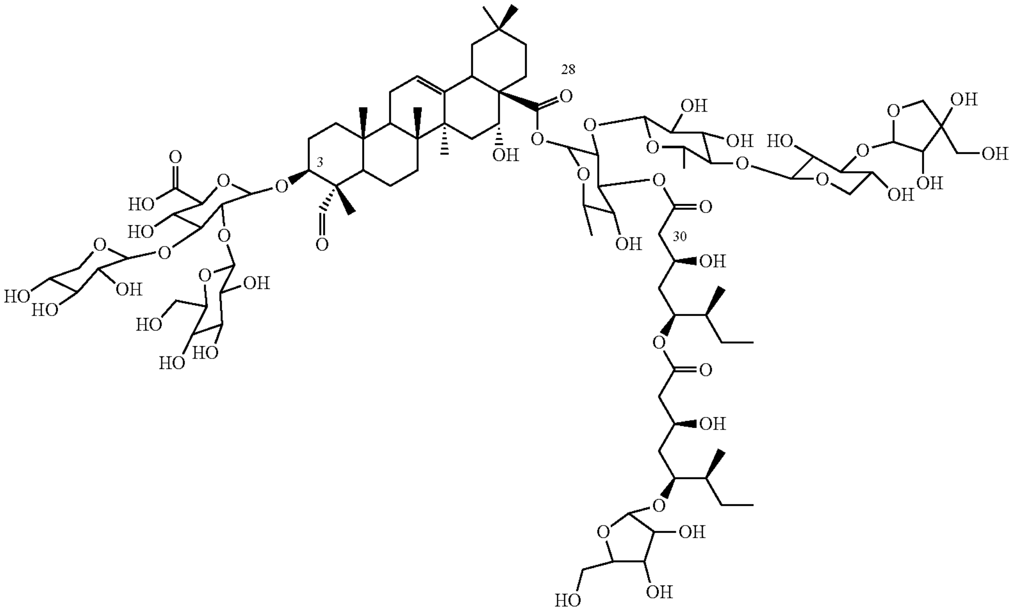
QS-21-B-api

-continued
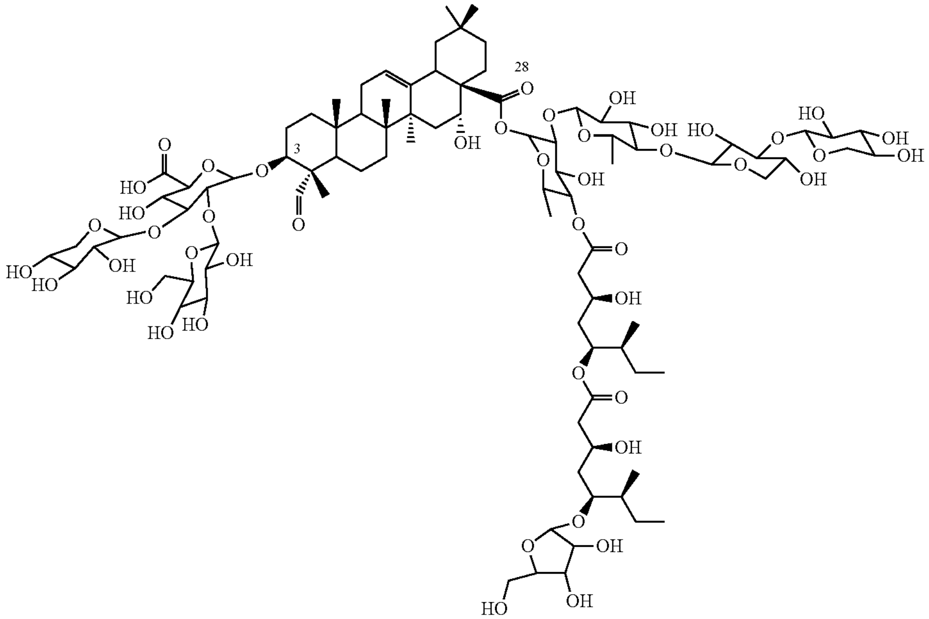
QS-21-A-xyl
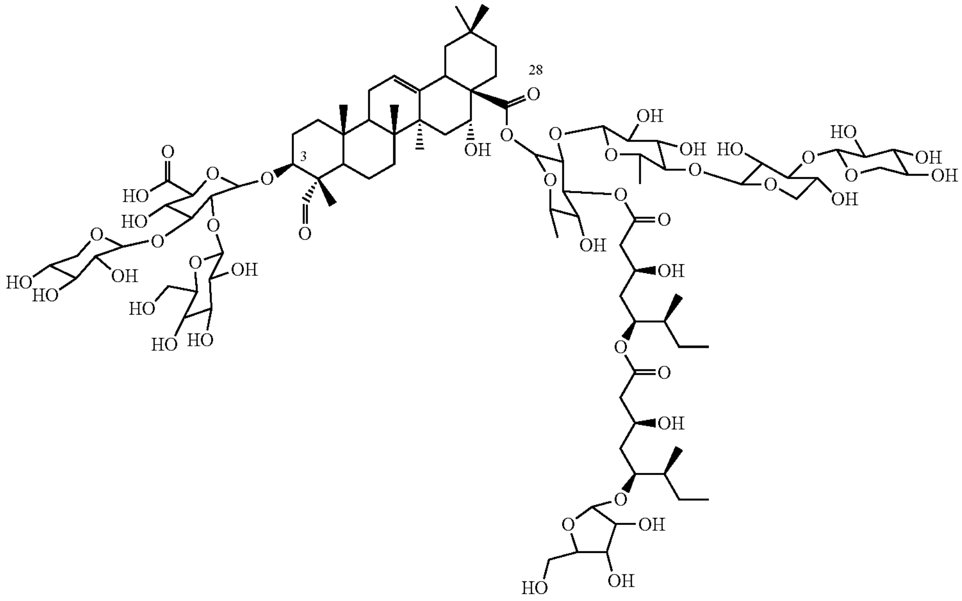
QS-21-B-xyl

-continued
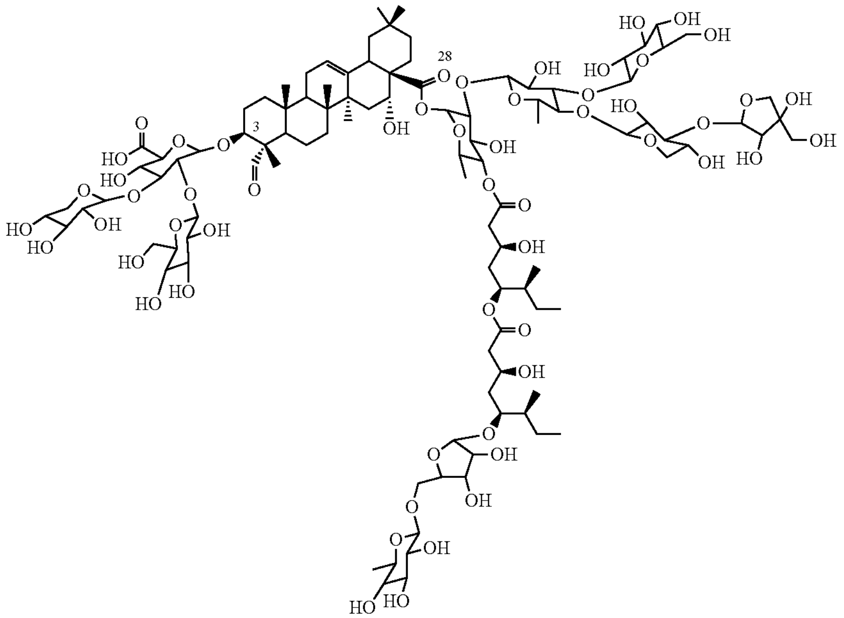
QS-17-api
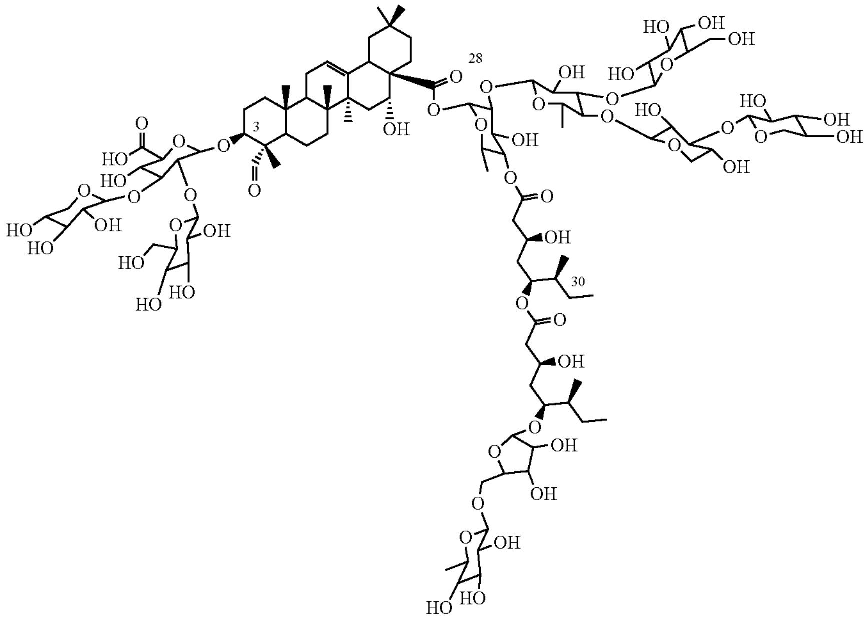
QS-17-xyl

-continued

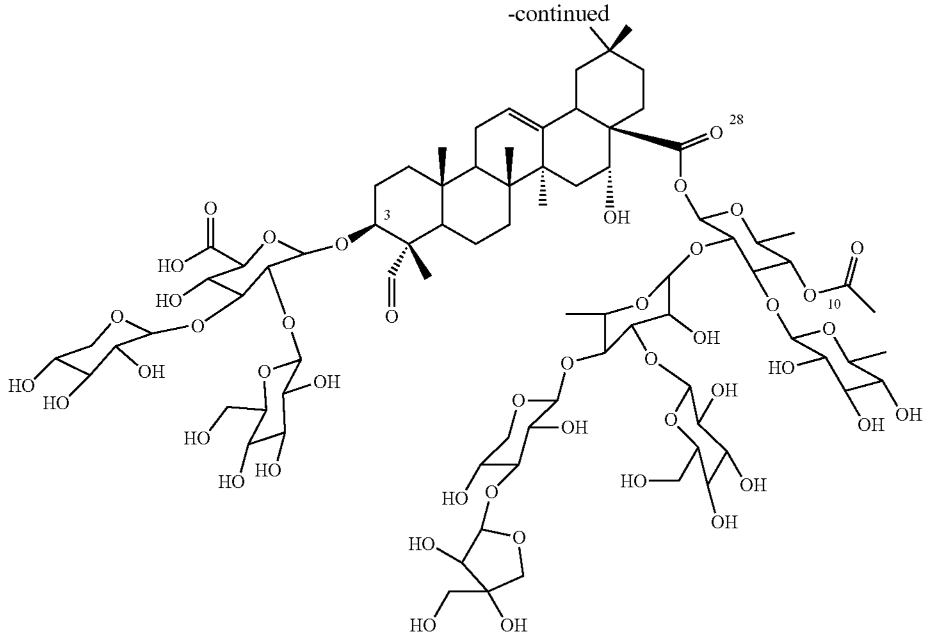

QS-7-api

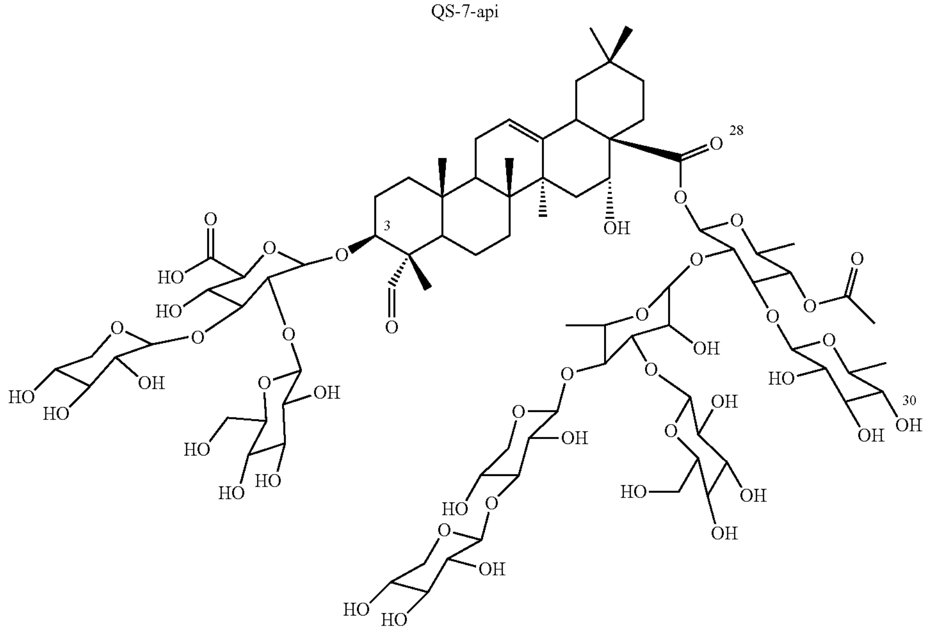

QS-7-xyl

According to the invention, a glycoside, such as a saponin according to the invention, bound to the cell-surface molecule targeting molecule comprised by the conjugate of the invention, which has the 'ideal' structure for the purpose of enhancing endosomal escape of an effector molecule comprised by the conjugate of the invention is a bisdesmosidic saponin according to Structure A of Scheme I, having a molecular mass of at least 1.500 Dalton and comprising an oleanan-type triterpene containing an aldehyde group at the C-23 position and optionally a hydroxyl group at the C-16 position, with a first branched carbohydrate side chain at the C-3 position which first branched carbohydrate side chain optionally contains glucuronic acid, wherein the saponin contains an ester group with a second branched carbohydrate side chain at the C-28 position which second branched carbohydrate chain preferably comprises at least four carbohydrate units, optionally containing at least one acetyl residue such as two acetyl residues and/or optionally comprising deoxy carbohydrates and/or optionally comprising quinovose and/or optionally comprising glucose and/or optionally comprising 4-methoxycinnamic acid and/or optionally comprising 5-O-[5-O-Ara/Api-3,5-dihydroxy-6-methyl-octanoyl]-3,5-dihydroxy-6-methyl-octanoic acid and/or optionally comprising 5-O-[5-O-Rha-(1-2)-Ara/Api-3,5-dihydroxy-6-methyl-octanoyl]-3,5-dihydroxy-6-methyl-octanoic acid bound to a carbohydrate via an ester bond.

SO1861 is different from the "ideal structure" displayed in Scheme I, Structure A, only in having only one acetyl residue at the quinovose and having an additional xylose.

The “ideal structure” of a saponin for enhancing endosomal escape of an effector molecule or effector moiety, is a saponin which preferably has the Structure A of Scheme I, and saponins which display the endosomal escape enhancing activity have one or more of the structural features displayed in Structure A of Scheme I. Without wishing to be bound by any theory, the inventors belief that the Structure A of Scheme I represents an “ideal saponin” (and not a minimum requirement saponin) for endosomal escape enhancing activity, which means that not all of the structures (chemical groups) can or must be present in each saponin with at least sufficient endosomal escape enhancing activity to promote accumulation of the effector moiety in the cytosol, and which means that some saponins might have other structure elements such as acyl chains, and/or for yet other saponins that display endosomal escape enhancing activity, the sugars can be different than the sugars displayed in Scheme I. For example, the QS-21 saponin and some of the saponins in the water soluble fraction of *Quillaja saponaria* (*Quillaja* saponins; Quil-A) differ in the carbohydrate modification at C-28 when the ideal structure of Structure A in Scheme I is considered: presence of an acyl chain in QS-21 for example. In the water soluble fraction of *Quillaja saponaria*, saponins such as QS-7, QS1862, are similar to the ideal Structure A, and are similar to SO1861.

An embodiment is the conjugate of the invention, wherein the at least one saponin is a bisdesmosidic saponin having a molecular mass of at least 1.500 Dalton and comprising an oleanan-type triterpene containing an aldehyde group at the C-23 position and optionally a hydroxyl group at the C-16 position, with a first branched carbohydrate side chain at the C-3 position which first branched carbohydrate side chain optionally contains glucuronic acid, wherein the saponin contains an ester group with a second branched carbohydrate side chain at the C-28 position which second branched carbohydrate chain preferably comprises at least four carbohydrate units, optionally containing at least one acetyl residue such as two acetyl residues and/or optionally comprising deoxy carbohydrates and/or optionally comprising quinovose and/or optionally comprising glucose and/or optionally comprising 4-methoxycinnamic acid and/or optionally comprising 5-O-[5-O-Ara/Api-3,5-dihydroxy-6-methyl-octanoyl]-3,5-dihydroxy-6-methyl-octanoic acid and/or optionally comprising 5-O-[5-O-Rha-(1→2)-Ara/Api-3,5-dihydroxy-6-methyl-octanoyl]-3,5-dihydroxy-6-methyl-octanoic acid bound to a carbohydrate via an ester bond, or wherein the at least one saponin is QS-21 or any one or more of QS-21A, QS-21 A-api, QS-21 A-xyl, QS-21B, QS-21 B-api, QS-21 B-xyl, QS-7-xyl, QS-7-api, QS-17-api, QS-17-xyl, QS-18, QS1861, protonated QS1861 (QS1862), Quil-A.

Table A1 and Scheme I and the above embodiments summarize a series of saponins that have been identified for their endosomal escape enhancing activity when contacted to mammalian cells, in particular human tumor cells, in free form together with a second molecule (e.g. an effector moiety or effector molecule, such as a toxin, an oligonucleotide). Reference is also made to the saponins with such endosomal escape enhancing activity listed in Table 9 and 10 of Boettger (2013) [Stefan Böttger, Untersuchungen zur synergistischen Zytotoxizit§ t zwischen Saponinen und Ribosomen inaktivierenden Proteinen Typ I, *Dissertation zur Erlangung des akademischen Grades des Doktors der Naturwissenschaften* (*Dr. rer. nat.*), *eingereicht im Fachbereich Biologie, Chemie, Pharmazie der Freien Universität Berlin, Tabelle 9, Tabelle* 10, page 67-74]. Indeed, in cell-based bioassays using human tumor cells it was established for the saponins tabulated in Table A1 and those in Scheme I and in the various embodiments of the invention described herein, that under influence of these saponins, when part of the conjugate of the invention, the effector moiety such as a nucleic acid and/or a toxin such as a protein toxin (e.g. one or more of the protein toxins listed in Table A5), comprised by the conjugate, is delivered into the cytosol with increased efficiency and/or efficacy, presumably through intracellular release from the (late) endosomes and lysosomes. That is to say, endosomal and/or lysosomal escape of such effector moieties bound by the conjugate of the invention, e.g. nucleic acids and/or toxins, is less efficient in the absence of the saponin.

Surprisingly, the inventors now demonstrate that a water-soluble saponin fraction from *Quillaja saponaria*, comprising QS-21 and its family members QS-21A, QS-21 A-api, QS-21 A-xyl, QS-21B, QS-21 B-api, QS-21 B-xyl, QS-7-xyl, QS-7-api, QS-17-api, QS-17-xyl, QS1861, QS1862, QS-18 and Quil-A, also exhibits the ability to potentiate a biological effect in vitro of e.g. a nucleic acid bound to a monoclonal antibody or a protein toxin bound to a monoclonal antibody (examples of conjugates of the invention comprising covalently bound oligonucleotide or payload such as a (protein) toxin), when administered to tumor cells of a mammalian species (human) in the form of a covalent conjugate comprising a monoclonal antibody (cell-surface molecule targeting molecule of the invention), together with bound effector moiety and the at least one glycoside such as the QS-21 and its family member saponins encompassed by such QS-21 preparation (e.g. water soluble fraction of *Quillaja saponaria*), comprised by conjugate as a covalent conjugate, wherein the effector molecule and the glycoside, e.g. saponin fraction of *Quillaja saponaria*, QS-21, SO1861, SA1641, GE1741, are covalently bound to for example the cell-surface molecule targeting molecule directly or via a linker or via a polymeric or oligomeric scaffold, either directly or via at least one linker. Without wishing to be bound by any theory, the observed stimulation or potentiation of for example antisense BNA mediated reduction of tumor-cell HSP27 expression (HSP27 gene silencing) in the presence of saponins derived from *Quillaja saponaria* in vitro may (also) relate to activation of the inflammasome in the tumor cell by the saponins, for example resulting in tumor cell pyroptosis. The inventors established that cell-surface molecule targeting molecules of the invention conjugated to for example antisense BNA or dianthin or saporin, exerted any anti-tumor cell activity in vitro at all or improved anti-tumor cell activity when contacted with cells in bio-based cell assays, when the conjugate comprises a saponin such that the saponin(s) is/are targeted to the same (tumor) cells, whereas in the absence of the saponin(s), i.e. conventional ADC format without linked saponin(s), no such activity towards the tumor cell was observed. Presence of covalently coupled saponin in the conjugate of the invention proved to be essential for the efficient exertion of the activity of the effector moiety in the conjugate.

QS-21, and also the water-soluble saponins fraction comprising QS-21 from *Quillaja saponaria* is already for a long time known and previously intensively applied for its immune-potentiating abilities, e.g. as an adjuvant in e.g. sub-unit vaccines. For example, QS-21 is applied in two phase III clinical trials with human patients, who were vaccinated with a sub-unit vaccine mixed with an adjuvant comprising QS-21 (Glaxo-Smith-Kline, MAGRIT trial, DERMA study), wherein the sub-unit was MAGE-A3 protein, which is specifically expressed and presented by tumor cells. The anti-tumor vaccinations, potentiated with QS-21, aimed for extension of disease-free survival of the cancer patients (melanoma; non-small cell lung cancer). In addition, QS-21 has been tested as an adjuvant in clinical trials for developing anti-cancer vaccine treatment, for vaccines for HIV-1 infection, in development of a vaccine against hepatitis B, and for anti-malaria vaccine development using QS-21 comprising adjuvants AS01 and AS02 of Glaxo-Smith-Kline. Previous studies revealed an immune response elicited against MAGE-A3 peptides presented at the cancer cell surface, under influence of the QS-21 saponin comprising adjuvant (AS15; GSK). To the surprise of the inventors, the saponin fraction of *Quillaja saponaria*, and thus likely QS-21 (as part of the water soluble saponin fraction of *Quillaja saponaria*) potentiates the anti-tumor cell activity of e.g. a payload such as a protein toxin (dianthin), bound to the cell-surface molecule targeting molecule (e.g. the ligand EGF) in the conjugate of the invention (e.g. the ligand EGF).

By targeting a single cell-surface molecule with the conjugate of the invention, the delivery of the saponin and the effector moiety bound to the cell-surface molecule targeting molecule in the conjugate of the invention, at and inside the cytosol of the targeted cell, exposing the cell-surface molecule on the cell surface, is improved and more specific, compared to for example contacting the cell with only a regular ADC lacking the saponin of the invention, thus without the presence of the cell-targeted saponin (conjugate of the invention). An aberrant cell selected for targeting by the cell-surface molecule targeting molecule of the conjugate, ideally bears the epitope on the cell-surface molecule to which the cell-surface molecule targeting molecule can bind, to a high extent (i.e. relatively higher expression of the targeted cell-surface molecule on the targeted cell such as for example a tumor cell or an auto-immune cell, than the expression on a non-targeted cell such as for example a healthy cell) and/or expose the epitope in the targeted cell-surface molecule for binding of the cell-surface molecule targeting molecule of the conjugate, specifically, when (neighboring) healthy cells in a patient are considered. Preferably, the cell-surface molecule targeted by the cell-surface molecule targeting molecule of the conjugate of the invention is relatively highly and/or specifically expressed on the targeted (diseased, tumor) cell compared to healthy cells. An embodiment is the conjugate of the invention, wherein the target cell-surface molecule for the cell-surface molecule targeting molecule of the conjugate such as a tumor-cell receptor, is expressed specifically or to a relatively higher extent when compared to expression of the cell-surface molecule on the surface of a healthy (neighboring) cell. Thus, the epitope on the targeted cell-surface molecule is ideally unique to the targeted diseased cells, and is at least specifically present and exposed at the surface of the targeted cells. Binding of the conjugate of the invention to the epitope on the cell-surface molecule on a targeted cell is followed by endocytosis of the complex of the conjugate and the target cell-surface molecule. Since the conjugate only can enter the target cell through binding interaction with a cell-surface molecules specifically expressed to a sufficient extent or uniquely expressed on the targeted cell when compared to healthy cells that should not be targeted, accumulation of a therapeutically active amount of effector moiety and saponin comprised by the conjugate, inside the target cells is only possible and occurring if expression levels of the targeted cell-surface molecule is above a certain minimal expression threshold. At the same time, the fact that the effector moiety bound to the cell-surface molecule targeting molecule of the conjugate is only capable of exerting its intracellular (e.g. cytotoxic or gene silencing) activity in the presence of very same conjugate bearing the covalently bound saponin, also provides a safeguard against negative and undesired side effects of the effector moiety towards e.g. healthy cells and healthy tissue not meant to be targeted and affected by the effector moiety, when compared to exposure of cells to an ADC without the covalently bound saponin(s). That is to say, sufficiently low expression or even absence of exposed cell-surface molecule, to which a conjugate could bind, does ideally not allow entrance into (non-targeted) healthy cells of the conjugate to amounts that would result in endosomal escape of the effector moiety under influence of the saponin comprised by the conjugate. Since the ADC with coupled saponin or the AOC with covalently coupled saponin according to the invention can be used at lower dose compared to when the ADC or AOC without coupled saponin was applied in the therapeutic regimen, entrance of ADC with coupled saponin or entrance of AOC with coupled saponin in healthy cells to low extent already bears a lower risk for occurrence of unwanted side effects when for example the targeting and killing of target diseased cells such as tumor cells and auto-immune cells is considered.

An embodiment is the conjugate of the invention, wherein the cell-surface molecule targeting molecule comprises or consists of a ligand or a proteinaceous ligand or a proteinaceous binding molecule for binding to the cell-surface molecule.

An embodiment is the conjugate of the invention, wherein the cell-surface molecule targeting molecule comprises or consists of a non-proteinaceous ligand and/or a proteinaceous ligand for binding to a cell-surface molecule such as EGF or a cytokine, and/or comprises or consists of an immunoglobulin, at least one binding domain of an immunoglobulin and/or at least one binding fragment of an immunoglobulin, such as an antibody, an IgG, a molecule comprising or consisting of a Vhh domain or Vh domain, a Fab, an scFv, an Fv, a dAb, an $F(ab)_2$, Fcab fragment, which can bind to the cell-surface molecule.

The inventors established that such immunoglobulins, domains thereof, ligands, etc., are particularly suitable for application as the cell-surface molecule targeting molecule of the conjugate comprising the binding site for binding to the target cell surface molecule. For example, antibodies and binding domains of antibodies are suitable for targeting an epitope in a selected cell-surface molecule exposed on the cell surface, resulting in targeting the conjugate and thus the effector moiety and the saponin together to target cells expressing the cell-surface molecule targeted by the cell-surface molecule targeting molecule of the conjugate. Similarly, ligands such as EGF, targeting the EGFR on target cells, are suitable for application as the cell-surface molecule targeting molecule in the conjugate.

Preferred are cell-surface molecule targeting molecules for binding an epitope in a target cell surface molecule, which are specific for the binding of the conjugate to the cell-surface molecule. Cell-surface molecule targeting molecules of the invention based on antibodies or domains or binding fragments thereof for example provide for such desired specificity for a selected epitope on a selected cell-surface molecule of a selected cell for targeting such as a diseased cell, a tumor cell, an auto-immune cell, etc.

Therefore, cell-surface molecule targeting molecules based on antibodies or binding molecules (fragments, domains), such as (human, humanized, chimeric) monoclonal antibodies, are preferred for the conjugates of the invention.

An embodiment is the conjugate of the invention, wherein the cell-surface molecule targeting molecule can bind to a tumor-cell surface molecule, preferably a tumor-cell receptor such as a tumor-cell specific receptor, more preferably a receptor selected from CD71, CA125, EpCAM(17-1A), CD52, CEA, CD44v6, FAP, EGF-IR, integrin, syndecan-1, vascular integrin alpha-V beta-3, HER2, EGFR, CD20, CD22, Folate receptor 1, CD146, CD56, CD19, CD138, CD27L receptor, PSMA, CanAg, integrin-alphaV, CA6, CD33, mesothelin, Cripto, CD3, CD30, CD239, CD70, CD123, CD352, DLL3, CD25, ephrinA4, MUC1, Trop2, CEACAM5, CEACAM6, HER3, CD74, PTK7, Notch3, FGF2, C4.4A, FLT3, CD38, FGFR3, CD7, PD-L1, CTLA4, CD52, PDGFRA, VEGFR1, VEGFR2, preferably selected from CD71, HER2 and EGFR. These receptors are preferred examples of molecules bearing epitopes to which the cell-surface molecule targeting molecule of the conjugate of the invention can bind, which molecules are sufficiently specific or even uniquely expressed at the surface of selected target cells for binding of the conjugate, such that the conjugate binds uniquely, and/or specifically, or at least preferentially and at least to a larger extent to said target cells compared to binding of the conjugate to cells which express and expose the receptor to a lower extent or does not expose the receptor at the cell surface. The target cells are for example aberrant cells, tumor cells, malignant cells, diseased cells, B-cells involved in malignancy, auto-immune cells, etc.

An embodiment is the conjugate of the invention, wherein the tumor-cell receptor is internalized by the tumor cell after binding to the cell-surface molecule targeting molecule of the invention or wherein the tumor-cell receptor is internalized by the tumor cell after binding to the conjugate of the invention, and wherein preferably binding of the cell-surface molecule targeting molecule and binding of the conjugate to the tumor-cell receptor is followed by tumor-cell receptor-mediated internalization, e.g. via endocytosis, of a complex of the conjugate and the tumor-cell receptor.

An embodiment is the conjugate of the invention, wherein the tumor-cell receptor is internalized by the tumor cell upon binding and/or internalization is induced by the binding to the cell-surface molecule targeting molecule of the invention, or wherein the tumor-cell receptor is internalized by the tumor cell after binding to the conjugate of the invention, or internalized upon and/or due to the binding of the conjugate to the tumor cell receptor, and wherein preferably binding of the cell-surface molecule targeting molecule and binding of the conjugate to the tumor-cell receptor induces and/or results in tumor-cell receptor-mediated internalization, e.g. via endocytosis, of a complex of the conjugate and the tumor-cell receptor.

Synchronization is the missing link between a successful delivery strategy for mice and its application in humans. Indeed, the inventors established in a series of in vivo mouse tumor models that separately administering to the mice a dose of free saponin and a dose of e.g. ADC without coupled saponin, did not result in any desired anti-tumor activity such as delayed tumor growth, tumor regression, diminished and slower tumor growth, compared to control animals not treated with the ADC in the presence of free saponin. The free saponin was administered using various routes of administration and using various time points of administering the free saponin compared to the moment of administering the ADC (administering free saponin before, during and after administering the ADC). The ADC tested in in vivo tumor models was cetuximab-dianthin (with free SO1861), or trastuzumab-saporin (with free SO1861). Varying the dose of free saponin did not provide for an efficacious anti-tumor activity. The ADCs referred to were administered at a dose that in itself did not inflict any beneficial anti-tumor effect on the tumor-bearing animals. Surprisingly, the inventors now established that beneficial anti-tumor activity in various in vitro mammalian cell-based bioassays using human tumor cells and/or in various in vivo animal tumor models can be achieved by treating the cells or animals with conjugates according to the invention. The conjugates optionally comprising a scaffold according to the invention (see below). The scaffold for example being a tri-functional linker with a covalently bound saponin (e.g. SO1861, QS-21) via a cleavable or non-cleavable linkage, and/or with a covalently bound effector moiety (e.g. dianthin, gene-silencing antisense BNA (HSP27) via a non-cleavable bond or a cleavable bond, the scaffold linked with a covalently bond to the cell-surface molecule targeting molecule of the conjugate such as a monoclonal antibody such as cetuximab, trastuzumab, OKT-9, or the scaffold being a dendron, such as a dendron, for example G4-dendron, to which for example four moieties can bind such as four saponin molecules, or a dendron for binding for example two saponins and two effector molecules, the dendron comprising a chemical group for (covalent) coupling to the cell-surface molecule targeting molecule of the conjugate such as a ligand or an antibody or fragment or domain thereof. Reference is made to the further embodiments and the Examples section, exemplifying various of these scaffolds according to the invention, showing in vivo and/or in vitro anti-tumor cell activity when cell toxicity exerted by e.g. a proteinaceous toxin is considered or when gene silencing in the tumor cell is considered.

Without wishing to be bound by any theory, in view of the failures observed when treatment of tumor-bearing animals with an ADC together with free saponin is considered, it is preferred to synchronize the presence of both, the at least one saponin, and the effector moiety, preferably a toxin or an oligonucleotide, in compartments or vesicles of the endocytic pathway of the target cell, e.g. a tumor cell or an auto-immune cell. With ADC and free saponin, synchronizing the presence of the molecules in the late endosomes, in order to obtain the synergistic effects in vivo was not beneficially obtainable according to attempts of the inventors. In one aspect, the invention preferably solves at least the following problem with respect to combining the effector moiety and the saponin(s) in a single conjugate molecule: without wishing to be bound by any theory the only reasonable chemical group within, e.g., the saponins that can be used for (covalent), in particular single and cleavable, retainable coupling is required for the endosomal escape activity. Known restrictions are most likely the reason why saponins have not been used in combination with pharmaceutically active substances in clinical investigations other than the application of saponins in vaccination regimes wherein the use of an immune-potentiating adjuvant substance was implied, although the striking endosomal escape enhancer effect of, e.g., saponins listed in Table A1 and Scheme I is known for more than 10 years. For example providing a conjugate of the invention with a covalently bound saponin, for example in the context of a scaffold carrying several saponins, solves these difficulties, at least in part. Surprisingly, the saponins previously applied for their immune-potentiating activity in the vaccination context involving saponins as adjuvant component, are now also suitably for (covalent) coupling to the cell-surface molecule targeting molecule comprised by the conjugate of the invention, for anti-tumor activity in vitro and in vivo.

An embodiment is the conjugate of the invention, wherein the cell-surface molecule targeting molecule is or comprises a monoclonal antibody or at least one cell-surface molecule binding fragment or -domain thereof, and preferably comprises or consists of any one of cetuximab, daratumumab, gemtuzumab, trastuzumab, panitumumab, brentuximab, inotuzumab, moxetumomab, polatuzumab, obinutuzumab, OKT-9 anti-CD71 monoclonal antibody of the IgG type, pertuzumab, rituximab, ofatumumab, Herceptin, alemtuzumab, pinatuzumab, OKT-10 anti-CD38 monoclonal antibody, an antibody of Table A2 or Table A3 or Table A4, preferably cetuximab or trastuzumab or OKT-9, or at least one cell-surface molecule binding fragment or -domain thereof.

As said, by targeting the cell-surface molecule with the cell-surface molecule targeting molecule of the conjugate of the invention, the delivery of the saponin and the effector moiety at and inside the cytosol of the very same targeted cell is improved and more specific. An aberrant cell selected for targeting by the cell-surface molecule targeting molecule of the conjugate ideally bears the cell-surface molecule to a high extent and/or specifically, when (neighboring) healthy cells in a patient are considered. Thus, the epitope on the targeted cell-surface molecule is ideally unique to the targeted diseases cells, and is at least specifically present and exposed at the surface of the targeted cells. Binding of the conjugate is followed by endocytosis of the complexes of the conjugate and the target cell-surface molecule.

Tables A2, A3 and A4 list preferred examples of the cell-surface molecule comprising the epitope for the cell-surface molecule targeting molecule of the conjugate of the invention. When the cell-surface molecule is specifically expressed on the target cell, preferably binding of the conjugate to the cell-surface molecule results in the specific targeting of the conjugate to the desired target cell such as a tumor cell exposing the tumor-cell surface molecule, whereas other cells such as healthy cells, which do not express the cell-surface molecule or do express cell-surface molecule to a lower extent, compared to expression of the cell-surface molecule(s) on the targeted (aberrant) cell, are not targeted by the conjugate or are only targeted to a lower extent.

A pharmaceutically active substance in this invention is an effector moiety that is used to achieve a beneficial outcome in an organism, preferably a vertebrate, more preferably a human being such as a cancer patient or an auto-immune patient. Benefit includes diagnosis, prognosis, treatment, cure and/or prevention of diseases and/or symptoms. The pharmaceutically active substance may also lead to undesired harmful side effects. In this case, pros and cons must be weighed to decide whether the pharmaceutically active substance is suitable in the particular case. If the effect of the pharmaceutically active substance inside a cell is predominantly beneficial for the whole organism, the cell is called a target cell. If the effect inside a cell is predominantly harmful for the whole organism, the cell is called an off-target cell. In artificial systems such as cell cultures and bioreactors, target cells and off-target cells depend on the purpose and are defined by the user.

An effector moiety that is a polypeptide may be, e.g., a polypeptide that recover a lost function, such as for instance enzyme replacement, gene regulating functions, or a toxin.

An embodiment is the conjugate of the invention, wherein the at least one effector moiety comprises or consists of any one or more of an oligonucleotide, a nucleic acid and a xeno nucleic acid, preferably selected from any one or more of a vector, a gene, a cell suicide inducing transgene, deoxyribonucleic acid (DNA), ribonucleic acid (RNA), anti-sense oligonucleotide (ASO, AON), short interfering RNA (siRNA), microRNA (miRNA), DNA aptamer, RNA aptamer, mRNA, mini-circle DNA, peptide nucleic acid (PNA), phosphoramidate morpholino oligomer (PMO), locked nucleic acid (LNA), bridged nucleic acid (BNA), 2'-deoxy-2'-fluoroarabino nucleic acid (FANA), 2'-O-methoxyethyl-RNA (MOE), 2'-0,4'-aminoethylene bridged nucleic acid, 3'-fluoro hexitol nucleic acid (FHNA), a plasmid, glycol nucleic acid (GNA) and threose nucleic acid (TNA), or a derivative thereof, more preferably a BNA, for example a BNA for silencing HSP27 protein expression.

The inventors show that a tumor-cell targeting monoclonal antibody provided with covalently coupled antisense BNA such as BNA(HSP27) and provided with covalently coupled saponin of the invention, that is contacted with tumor cells, both the BNA and the saponin coupled to the antibody (e.g. cetuximab) via a cleavable bond, is capable of silencing HSP27 in vivo in tumors, compared to control and compared to the AOC bearing the BNA only and not the saponin (SO1861, Quil-A). Administering an ADC-saponin conjugate of the invention or an antibody-oligonucleotide conjugate-saponin conjugate of the invention (AOC-saponin), such as an antibody-BNA-saponin conjugate, thus endows the ADC-saponin or AOC-saponin with anti-tumor cell activity not seen with only the ADC or only the AOC, which do not have the covalently saponins bound to the monoclonal antibody, at the same dose. Noteworthy, the AOC and the separate monoclonal antibody with covalently coupled saponin as a combination of two separate conjugates, increase HSP27 expression in tumor cells, when administered to tumor-bearing mice separately in separate groups of mice, compared to a control group (vehicle administered, only). Only administration of the AOC-saponin conjugate of the invention comprising the effector moiety of the invention, displays reduced HSP27 expression when compared to controls. The antisense BNA (HSP27) was BNA with oligo nucleic acid sequence 5'-GGCacagccagtgGCG-3' according to Zhang et al. (2011) [Y Zhang, Z Qu, S Kim, V Shi, B Liao1, P Kraft, R Bandaru, Y Wu, L M Greenberger and I D Horak, *Down-modulation of cancer targets using locked nucleic acid (LNA)-based antisense oligonucleotides without transfection, Gene Therapy* (2011) 18, 326-333]. Noteworthy, to the best of the knowledge of the inventors, BNA is designed for application as a free nucleic acid. The inventors are now the first to demonstrate that the antisense BNA can be covalently coupled through a (non-)cleavable linker with a ligand or an antibody, in a way that gene-silencing activity is retained in vitro and more importantly in vivo in the tumor cells of a tumor-bearing animal. This approach of providing BNA based AOCs opens new ways to administer targeted BNA to human (cancer) patients in need thereof.

An embodiment is the conjugate of the invention, wherein the at least one effector moiety comprises or consists of at least one proteinaceous molecule, preferably selected from any one or more of a peptide, a protein, an enzyme such as urease and Cre-recombinase, a ribosome-inactivating protein, a proteinaceous toxin selected from Table A5 and more preferably selected from any one or more of a viral toxin such as apoptin; a bacterial toxin such as Shiga toxin, Shiga-like toxin, *Pseudomonas aeruginosa* exotoxin (PE) or exotoxin A of PE, full-length or truncated diphtheria toxin (DT), cholera toxin; a fungal toxin such as alpha-sarcin; a plant toxin including ribosome-inactivating proteins and the A chain of type 2 ribosome-inactivating proteins such as dianthin e.g. dianthin-30 or dianthin-32, saporin e.g.

saporin-S3 or saporin-S6, bouganin or de-immunized derivative debouganin of bouganin, shiga-like toxin A, pokeweed antiviral protein, ricin, ricin A chain, modeccin, modeccin A chain, abrin, abrin A chain, volkensin, volkensin A chain, viscumin, viscumin A chain; or an animal or human toxin such as frog RNase, or granzyme B or angiogenin from humans, or any fragment or derivative thereof; preferably the protein toxin is dianthin and/or saporin.

An embodiment is the conjugate of the invention, wherein the at least one effector moiety comprises or consists of at least one payload, preferably selected from any one or more of a toxin targeting ribosomes, a toxin targeting elongation factors, a toxin targeting tubulin, a toxin targeting DNA and a toxin targeting RNA, more preferably any one or more of emtansine, pasudotox, maytansinoid derivative DM1, maytansinoid derivative DM4, monomethyl auristatin E (MMAE, vedotin), monomethyl auristatin F (MMAF, mafodotin), a Calicheamicin, N-Acetyl-γ-calicheamicin, a pyrrolobenzodiazepine (PBD) dimer, a benzodiazepine, a CC-1065 analogue, a duocarmycin, Doxorubicin, paclitaxel, docetaxel, cisplatin, cyclophosphamide, etoposide, docetaxel, 5-fluorouracyl (5-FU), mitoxantrone, a tubulysin, an indolinobenzodiazepine, AZ13599185, a cryptophycin, rhizoxin, methotrexate, an anthracycline, a camptothecin analogue, SN-38, DX-8951f, exatecan mesylate, truncated form of *Pseudomonas aeruginosa* exotoxin (PE38), a Duocarmycin derivative, an amanitin, α-amanitin, a spliceostatin, a thailanstatin, ozogamicin, tesirine, Amberstatin269 and soravtansine, or a derivative thereof.

An effector moiety useful in the present invention preferably relies on late endosomal escape for exerting its effect. Some effectors, such as, e.g., a *Pseudomonas* exotoxin, are rerouted to other organelles prior to the "late endosomal stage" and, thus, would normally not benefit from coupling to the second proteinaceous molecule according to the present invention. However, such toxin may be adapted for use with the present invention, e.g., by deleting the signal peptide responsible rerouting. In particular toxins that are highly toxic and would require only one molecule to escape the endosomes to kill a cell maybe modified to be less potent. It is preferred to use a toxin that kills a cell if at least 2, more preferably at least 5, more preferably at least 10, more preferably at least 20, more preferably at least 50, most preferably at least 100 toxin molecules escape the endosome. It is further preferred that a conjugate of the invention comprises a covalently conjugated functionalized scaffold, i.e. a scaffold such as an oligomeric or polymeric scaffold or a tri-functional linker, comprising covalently bound effector moietie(s) for targeting the scaffold comprising the bound effector moietie(s) at a target cell such as a tumor cell or an auto-immune cell. Further, in order to reduce off-target toxicity, cell membrane non-permeable small molecule toxins are preferred effector molecules over cell membrane permeable toxins.

The term "ligand" as used in this invention has its ordinary meaning and preferably means a molecule or structure that is able to bind another molecule or structure on the cell surface of a target cell, wherein said molecule or structure on the cell surface can be endocytosed and is preferably absent or less prominent on off-target cells. Preferably, said molecule or structure on the cell surface is constitutively endocytosed. More preferably a conjugate or more specifically a cell-surface molecule targeting molecule, in this invention induces endocytosis of said molecule or structure on the cell surface of target cells after binding to said molecule or structure. This is for instance the case for Epidermal Growth Factor Receptor (EGFR), HER2 and CD71 present on the surface of a variety of cancer cells. Examples of molecules or structures on the cell surface of target cells that are constitutively endocytosed, are for instance Claudin-1 or major histocompatibility complex class II glycoproteins. A cell-surface molecule targeting molecule can, e.g., be an antibody, a growth factor or a cytokine. Combining in a conjugate of the invention a toxin with a cell-surface molecule targeting molecule and with at least one saponin of the invention is one possibility to create a targeted toxin. A toxin that is only toxic in a target cell because it interferes with processes that occur in target cells only can also be seen as a targeted toxin (as in off-target cells it cannot exert its toxic action, e.g. apoptin). Preferably, a targeted toxin is a toxin that is combined with a cell-surface molecule targeting molecule such as e.g. a monoclonal antibody in order to be active in target cells and not in off-target cells (as it is only bound to and endocytosed by target cells). In a conjugate of the invention comprising a functionalized scaffold comprising e.g. the effector moiety and/or the saponin(s), the cell-surface molecule targeting molecule such as the monoclonal antibody guides the effector moiety and/or the saponin(s) via the scaffold to the target cells. After internalization, the at least one glycoside, preferably a saponin comprised by the conjugate of the invention, mediates the endosomal escape of the effector moiety. The saponin is typically a saponin listed in Table A1 and Scheme I, and preferably the saponin is SO1861 and/or QS-21, and/or SA1641 and/or GE1741.

Preferably, the effector moiety comprised by the conjugate of the invention, which effect is enhanced by the saponins comprised by the conjugate, detaches from the conjugate, e.g. detaches from an antibody present in the conjugate as the cell-surface molecule targeting molecule, when endocytosed. This can be achieved by a cleavable bond that breaks, e.g. under acidic, reductive, enzymatic or light-induced conditions.

An embodiment is the conjugate of the invention, wherein the at least one effector moiety is covalently bound to the cell-surface molecule targeting molecule, either via at least one linker or bound directly to the cell-surface molecule targeting molecule.

An embodiment is the conjugate of the invention, wherein the at least one effector moiety is covalently bound to the cell-surface molecule targeting molecule, thereby forming any one of antibody-drug conjugates Gemtuzumab ozogamicin, Brentuximab vedotin, Trastuzumab emtansine, Inotuzumab ozogamicin, Moxetumomab pasudotox and Polatuzumab vedotin and an antibody-drug conjugate of Table A2 and Table A3.

An embodiment is the conjugate of the invention, wherein the at least one saponin is covalently bound to the cell-surface molecule targeting molecule preferably an amino-acid residue of the cell-surface molecule targeting molecule, via an aldehyde function in the saponin, and/or to the at least one effector moiety preferably via an amino-acid residue in the at least one effector moiety, via an aldehyde function in the saponin, preferably an aldehyde function in position C-23 in a bisdesmosidic triterpene saponin belonging to the type of a 12,13-dehydrooleanane.

An embodiment is the conjugate of the invention, wherein the aldehyde function in the at least one saponin, preferably the aldehyde function in position C-23 of the at least one saponin, is covalently coupled to linker N-ε-maleimidocaproic acid hydrazide, which linker is covalently coupled via a thio-ether bond to a sulfhydryl group in the cell-surface molecule targeting molecule and/or in the at least one effector moiety, such as a sulfhydryl group of a cysteine.

An embodiment is the conjugate of the invention, wherein the at least one saponin is a bisdesmosidic triterpene saponin belonging to the type of a 12,13-dehydrooleanane, with an aldehyde function in position C-23 and comprising a glucuronic acid function in a carbohydrate substituent at the C-3beta-OH group of the saponin, wherein the saponin is covalently bound to an amino-acid residue of the cell-surface molecule targeting molecule and/or to the at least one effector moiety via said glucuronic acid function and preferably via an amino-acid residue in the at least one effector moiety.

An embodiment is the conjugate of the invention, wherein the glucuronic acid function in the carbohydrate substituent at the C-3beta-OH group of the at least one saponin is covalently coupled to linker 1-[Bis(dimethylamino)methylene]-1H-1,2,3-triazolo[4,5-b]pyridinium 3-oxid hexafluorophosphate, which linker is covalently coupled via an amide bond to an amine group in the cell-surface molecule targeting molecule and/or in the at least one effector moiety, such as an amine group of a lysine or an N-terminus of the cell-surface molecule targeting molecule and/or of the at least one effector moiety.

An embodiment is the conjugate of the invention, wherein the at least one saponin is covalently bound to the cell-surface molecule targeting molecule and/or to the at least one effector moiety either directly or via at least one linker such as a bi-functional linker, for example based on N-ε-maleimidocaproic acid hydrazide and/or based on 1-[Bis(dimethylamino)methylene]-1H-1,2,3-triazolo[4,5-b]pyridinium 3-oxid hexafluorophosphate, or a tri-functional linker, such as the tri-functional linker of Scheme II and Structure B.

An embodiment is the conjugate of the invention, wherein the tri-functional linker comprises a second chemical group with at least one saponin covalently bound thereto, a third chemical group for covalent binding to the cell-surface molecule targeting molecule and a first chemical group for covalent binding to the at least one effector moiety, preferably the tri-functional linker is the trifunctional linker of Scheme II and Structure B.

An embodiment is the conjugate of the invention, wherein the at least one saponin is covalently bound to the cell-surface molecule targeting molecule and to the at least one effector moiety via at least one linker comprising a tri-functional linker to which tri-functional linker both the cell-surface molecule targeting molecule and the at least one effector moiety are bound, preferably the tri-functional linker is the trifunctional linker of Scheme II and Structure B.

An embodiment is the tri-functional linker of the invention such as the tri-functional linker of Scheme II and Structure B and/or FIG. 16 of the invention.

An embodiment is the use of the tri-functional linker according to the invention such as the tri-functional linker of Scheme II and Structure B, for the manufacture of a conjugate, such as an ADC or an AOC, preferably a conjugate comprising at least one saponin of the invention, ADC-saponin conjugate and/or AOC-saponin conjugate according to the invention.

An embodiment is the semi-finished product comprising the tri-functional linker of the invention, wherein at least one saponin according to the invention is covalently bound to the tri-functional linker and/or wherein at least one effector moiety according to the invention is covalently bound to the tri-functional linker, either directly or via at least one linker and/or via at least one oligomeric or polymeric scaffold of the invention, wherein the linker is preferably a cleavable linker according to the invention, the effector moiety of the invention being preferably a toxin such as a protein toxin selected from dianthin, saporin, and/or the saponin of the invention being preferably any one or more of Quil-A, QS-21, QS-7, QS1861, SO1861, SA1641, GE1741 and the water-soluble saponin fraction of *Quillaja saponaria*.

An embodiment is the conjugate of the invention, wherein the at least one linker comprises at least one cleavable linker, wherein optionally said cleavable linker is subject to cleavage under acidic, reductive, enzymatic or light-induced conditions, and preferably the cleavable linker comprises a cleavable bond selected from a hydrazone bond or a hydrazide bond subject to cleavage under acidic conditions, and/or a bond susceptible to proteolysis, for example proteolysis by Cathepsin B, and/or a bond susceptible for cleavage under reductive conditions such as a disulphide bond.

An embodiment is the conjugate of the invention, wherein the at least one linker comprises at least one cleavable linker, wherein said cleavable linker is subject to cleavage in vivo under acidic conditions as present in endosomes and/or in lysosomes of mammalian cells, preferably of human cells, preferably at pH 4.0-6.5, and more preferably at pH≤5.5.

An embodiment is the conjugate of the invention, wherein the at least one saponin is covalently bound to a lysine side chain, forming an amide bond, and/or to a cysteine side chain, forming a thio-ether linkage or a disulphide bond, wherein the lysine and/or cysteine is/are comprised by the cell-surface molecule targeting molecule and/or is/are comprised by the at least one effector moiety, and wherein the at least one saponin is either directly bound to the lysine and/or cysteine, or is bound via at least one linker optionally comprising a cleavable linker and/or a tri-functional linker such as the tri-functional linker of Scheme II and Structure B.

An embodiment is the conjugate of the invention, wherein the linker is based on N-ε-maleimidocaproic acid hydrazide and/or based on 1-[Bis(dimethylamino)methylene]-1H-1,2,3-triazolo[4,5-b]pyridinium 3-oxid hexafluorophosphate, a tri-functional linker such as the tri-functional linker of Scheme II and Structure B, a cleavable linker, and/or involves any one or more of a disulphide bond, a thio-ether bond, an amide bond, a hydrazide bond.

An embodiment is the conjugate of the invention, wherein the at least one saponin is covalently bound to the cell-surface molecule targeting molecule and/or to the at least one effector moiety via at least one linker, wherein the linker is or comprises a scaffold comprising a polymeric or oligomeric structure and further comprising at least one fourth chemical group for covalently coupling of the scaffold to the cell-surface molecule targeting molecule and/or to the at least one effector moiety.

An embodiment is the conjugate of the invention, wherein the at least one saponin is covalently bound to the polymeric or oligomeric structure of the scaffold via a cleavable bond and/or via a non-cleavable bond.

An embodiment is the conjugate of the invention, wherein the cleavable bond is subject to cleavage under any of acidic conditions, reductive conditions, enzymatic conditions and light-induced conditions, and preferably the cleavable bond comprises a hydrazone bond or a hydrazide bond subject to cleavage under acidic conditions, and/or a bond susceptible to proteolysis, for example proteolysis by Cathepsin B, and/or a bond susceptible for cleavage under reductive conditions such as a disulphide bond.

An embodiment is the conjugate of the invention, wherein the cleavable bond is subject to cleavage in vivo under acidic conditions as present in endosomes and/or in lysosomes of mammalian cells, preferably of human cells, preferably at pH 4.0-6.5, and more preferably at pH 5.5.

An embodiment is the conjugate of the invention, wherein the at least one saponin is covalently bound to the polymeric or oligomeric structure of the scaffold via any one or more of an imine bond, a hydrazone bond, a hydrazide bond, an oxime bond, a 1,3-dioxolane bond, a disulphide bond, a thio-ether bond, an amide bond, a peptide bond or an ester bond, preferably via at least one linker.

An embodiment is the conjugate of the invention, wherein the at least one saponin is covalently bound to the polymeric or oligomeric structure of the scaffold via any one or more of an imine bond, a hydrazone bond and a hydrazide bond, which bond is preferably cleavable according to the invention, wherein preferably the at least one saponin is covalently bound to the polymeric or oligomeric structure of the scaffold via the aldehyde function in position C-23 of the at least one saponin.

An embodiment is the conjugate of the invention, wherein the aldehyde function in position C-23 of the at least one saponin is covalently coupled to linker N-ε-maleimidocaproic acid hydrazide, which linker is covalently coupled via a thio-ether bond to a sulfhydryl group in the polymeric or oligomeric structure of the scaffold, such as a sulfhydryl group of a cysteine.

An embodiment is the conjugate of the invention, wherein the at least one saponin is covalently bound to the polymeric or oligomeric structure of the scaffold via an amide bond, wherein preferably the at least one saponin is covalently bound to the polymeric or oligomeric structure of the scaffold via the glucuronic acid function in the carbohydrate substituent at the C-3beta-OH group of the at least one saponin, when present.

An embodiment is the conjugate of the invention, wherein the glucuronic acid function in the carbohydrate substituent at the C-3beta-OH group of the at least one saponin is covalently coupled to linker 1-[Bis(dimethylamino)methylene]-1H-1,2,3-triazolo[4,5-b]pyridinium 3-oxid hexafluorophosphate, which linker is covalently coupled via an amide bond to an amine group in the polymeric or oligomeric structure of the scaffold, such as an amine group of a lysine or an N-terminus of the polymeric or oligomeric structure of the scaffold.

An embodiment is the conjugate of the invention, wherein the at least one saponin is covalently bound to the polymeric or oligomeric structure of the scaffold, involving in the covalent bond the aldehyde function in position C-23 of the at least one saponin, when present, and/or involving in the covalent bond the glucuronic acid function in the carbohydrate substituent at the C-3beta-OH group of the at least one saponin, when present.

An embodiment is the conjugate of the invention, wherein the at least one fourth chemical group of the scaffold, for covalently coupling of the scaffold to the cell-surface molecule targeting molecule and/or to the at least one effector moiety, is a click chemistry group, preferably selected from any one or more of a tetrazine, an azide, an alkene or an alkyne, or a cyclic derivative of these groups, preferably an azide group.

An embodiment is the conjugate of the invention, wherein the polymeric or oligomeric structure of the scaffold comprises a linear, branched and/or cyclic polymer, oligomer, dendrimer, dendron, dendronized polymer, dendronized oligomer, a DNA, a polypeptide, poly-lysine, a poly-ethylene glycol, or an assembly of these polymeric or oligomeric structures which assembly is preferably built up by covalent cross-linking.

An embodiment is the conjugate of the invention, wherein the at least one saponin is a defined number of saponins or a defined range of saponins, preferably 1-128 saponins or at least 2, 3, 4, 5, 6, 8, 10, 16, 32, 64 or 128 saponins, or any number of saponins therein between, such as 7, 9, 12 saponins.

An embodiment is the conjugate of the invention, wherein the conjugate comprises more than one saponin, preferably 2, 3, 4, 5, 6, 8, 10, 16, 32, 64 or 1-100 saponins, or any number of saponins therein between, such as 7, 9, 12 saponins, covalently bound directly to an amino-acid residue of the cell-surface molecule targeting molecule and/or to the at least one effector moiety and preferably via an amino-acid residue in the at least one effector moiety, preferably to a cysteine and/or to a lysine, and/or covalently bound via at least one linker and/or via at least one cleavable linker and/or via at least one polymeric or oligomeric scaffold, preferably 1-8 of such scaffolds or 2-4 of such scaffolds, wherein 1-32 saponins, preferably 2, 3, 4, 5, 6, 8, 10, 16 or 32 saponins, or any number of saponins therein between, such as 7, 9, 12 saponins, are covalently bound to the at least one scaffold.

An embodiment is the conjugate of the invention, wherein the at least one saponin is covalently bound to the cell-surface molecule targeting molecule and to the at least one effector moiety via a tri-functional linker, the tri-functional linker comprising a second chemical group with at least one saponin covalently bound thereto either directly or via a linker such as a cleavable linker and/or via the scaffold comprising a polymeric or oligomeric structure and a fourth chemical group according to the invention for covalently coupling of the scaffold to the tri-functional linker, the tri-functional linker further comprising a third chemical group for covalent binding to the cell-surface molecule targeting molecule and comprising a first chemical group for covalent binding to the at least one effector moiety, wherein the cell-surface molecule targeting molecule is bound to the third chemical group and/or the at least one effector moiety is bound to the first chemical group, preferably the trifunctional linker is the trifunctional linker of Scheme II and Structure B.

Figure 2:
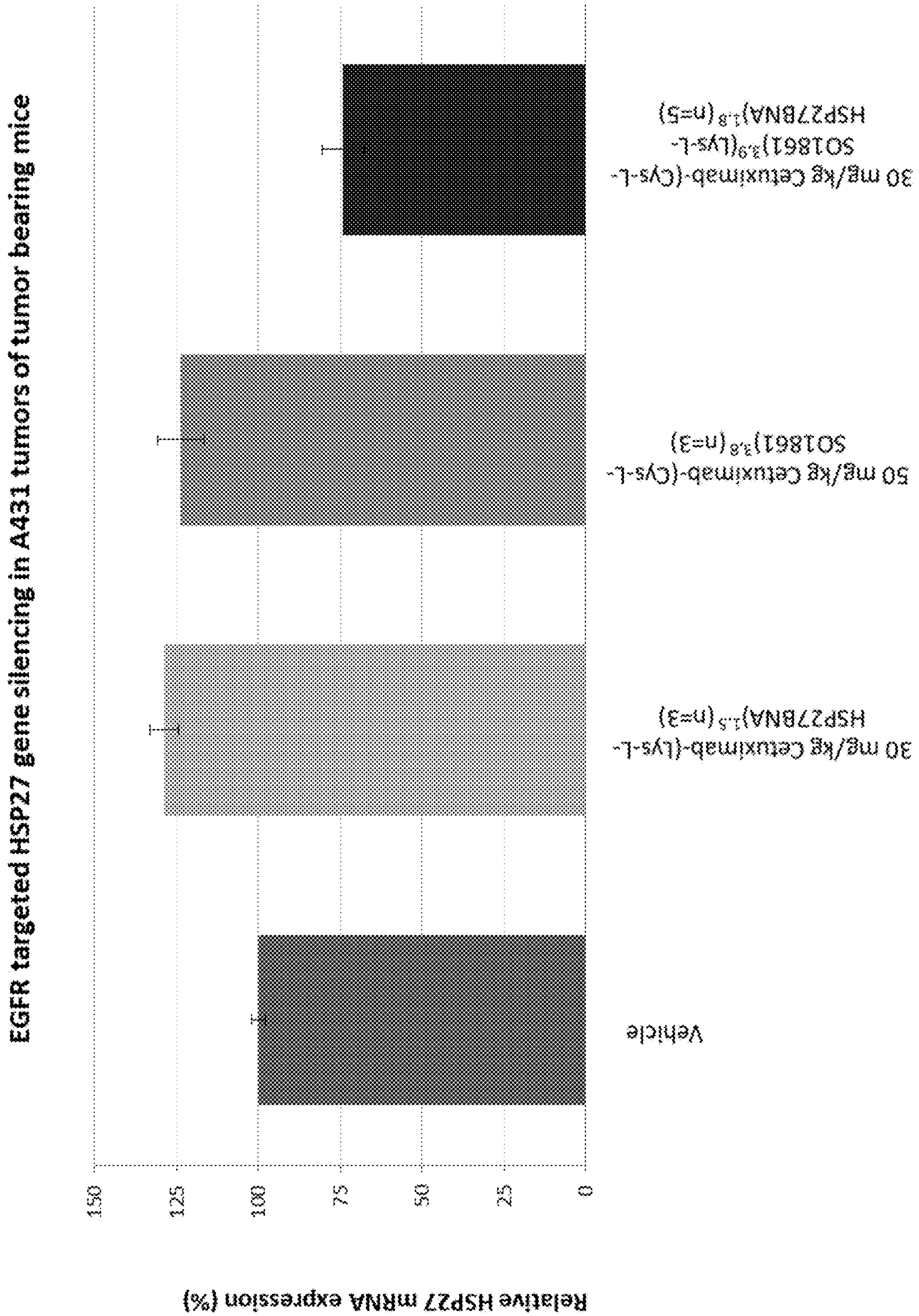
FIG. 2. Tumor targeted antisense BNA oligo nucleotide delivery and gene silencing in tumor bearing mice. 30 mg/kg cetuximab-(Cys-L-SO1861)$^{3,9}$(Lys-L-HSP27BNA)$^{1,8}$ in A431 tumor bearing mice reveals induced efficient tumor targeted gene silencing, compared to the controls.
Figure 3:
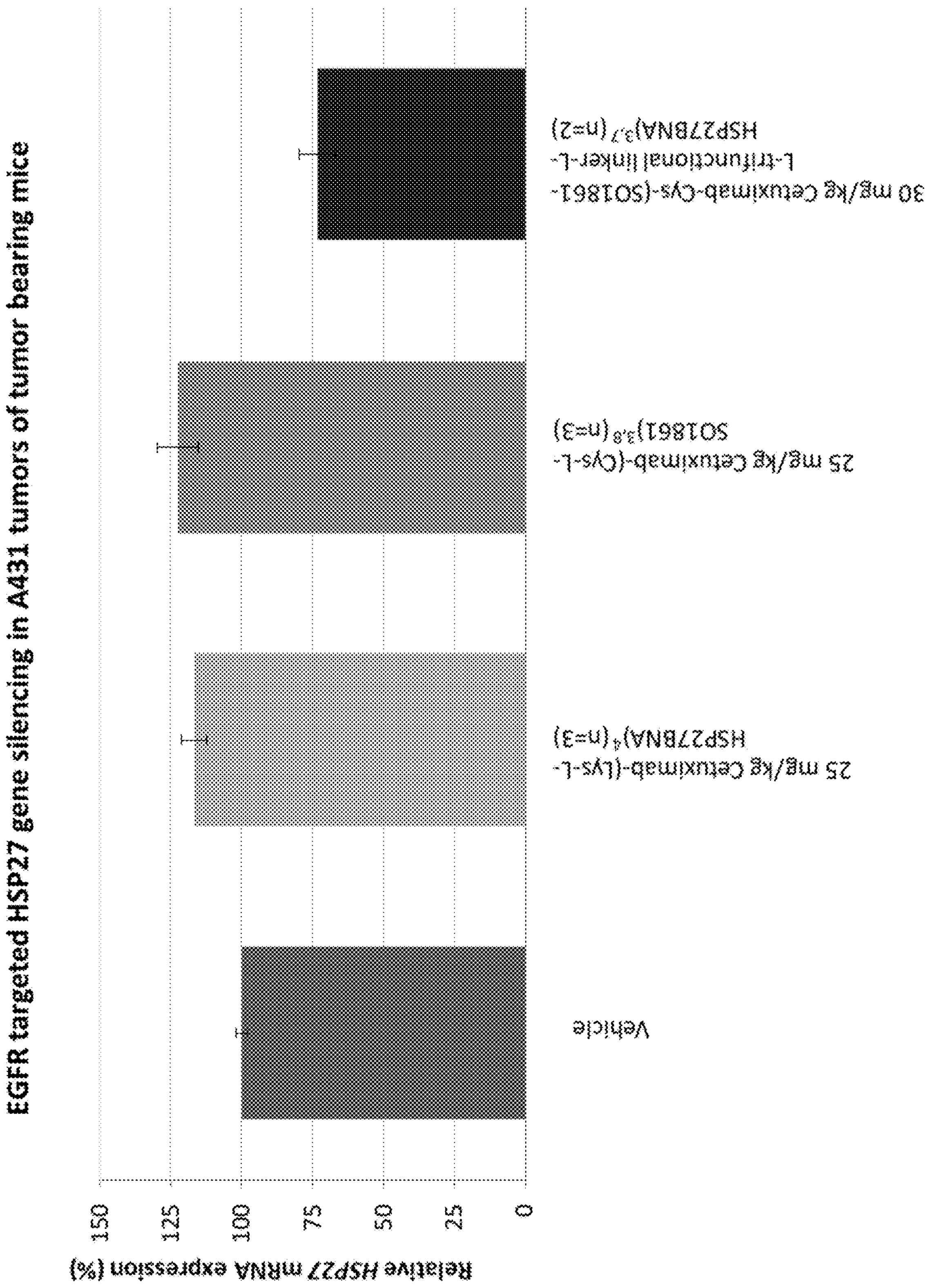
FIG. 3. Tumor targeted antisense BNA oligo nucleotide delivery and gene silencing in tumor bearing mice. 30 mg/kg cetuximab-Cys-(SO1861-L-trifunctional linker-L-HSP27BNA)$^{3,7}$ in A431 tumor bearing mice reveals induced efficient tumor targeted gene silencing, compared to the controls.

According to the invention, typically the saponin is a saponin listed in Table A1, Scheme I. It has been proven beneficial for the activity of the saponin, e.g. the endosomal escape enhancing activity inside cells when the entry into the cell and the accumulation inside the cytosol of an effector moiety covalently coupled to the cell-surface molecule targeting molecule of the conjugate of the invention, is considered, when the saponin is covalently coupled to the cell-surface molecule targeting molecule (directly or indirectly via first binding to the effector moiety, the effector moiety being directly coupled to the cell-surface molecule targeting molecule) involving a hydrazone bond, and/or a hydrazide bond, and/or a disulphide bond. Such bond types readily cleave under the acidic conditions inside (late) endosomes and lysosomes of mammalian cells, e.g. human cells, and/or under the reductive conditions. Alternatively, the inventors also demonstrate that covalent coupling of saponin to the cell-surface molecule targeting molecule via a bond that is not readily cleavable under the physiological conditions inside cells, e.g. (late) endosomes, lysosomes, cytosol, is also beneficial to the potentiating activity of the saponin on the biological effect of e.g. an effector moiety such as a nucleic acid (e.g. BNA silencing HSP27) and a proteinaceous toxin such as saporin. An example of such a bond is an amide bond, for coupling a saponin to a lysine side chain, either directly or via a (cleavable) linker and/or via an oligomeric or polymeric scaffold. Throughout the application, including the claims, the term 'cleavable linker', 'cleavable bond', etc., is also referred to as 'labile linker' ('L') and 'labile bond', for example in the context of cleavage of such a bond or linker in the (late) endosome and/or lysosome when a conjugate of the invention, e.g. a conjugate optionally comprising a scaffold with saponins coupled to the cell-surface molecule targeting molecule through a linker and/or via the scaffold via hydrazone bonds or disulphide bonds, is referred to. For example, FIG. 2 and FIG. 3 show the in vivo HSP27 gene silencing in human tumors in mice. The tumor-bearing mice were treated with a conjugate of the invention consisting of monoclonal antibody with saponin bound thereto via a labile linker (hydrazone bond) and with antisense BNA for silencing the HSP27 gene in the tumor cells, covalently coupled to the monoclonal antibody via a disulphide bond, according to the invention. That is to say, without wishing to be bound by any theory, the hydrazone bond and the disulphide bond are cleaved in the (late) endosomes and/or lysosomes of the targeted tumor cells that express the epitope on the targeted cell-surface molecule, here the EGFR, at the cell surface, once the conjugate of the invention is internalized by e.g. endocytosis. Cleavage of the bonds likely contributes to the endosomal escape enhancing activity of the saponin when the entry of the BNA from the endosome and/or lysosome into the cytosol is considered, although such cleavage is not a necessity for observing the gene silencing effect of the cetuximab-SO1861-BNA conjugate of the invention.

The skilled person will appreciate that a tri-functional linker is a scaffold of the invention suitable for covalently coupling one, two or three saponin moieties. For the tri-functional linker covalent coupling of one or two saponin moieties is preferred. The second and/or third binding site is for example suitable for covalent coupling a proteinaceous ligand such as the cell-surface molecule targeting molecule. Typical proteinaceous ligands are EGF for targeting (tumor) cells expressing EGFR at the cell surface, and cytokines for targeting tumor cells or autoimmune cells. Moreover, the second or third binding site of the tri-functional linker is suitable for covalent coupling of an immunoglobulin such as a monoclonal antibody, i.e. the cell-surface molecule targeting molecule for binding to a cell surface molecule such as a tumor cell surface molecule, preferably a tumor-cell specific molecule, more preferably a tumor cell receptor that is specifically (over-)expressed at the surface of the tumor cell. Similarly, the immunoglobulin, or any fragment(s) and/or domain(s) thereof which encompass the binding specificity of the immunoglobulin, is suitable for binding to a cell surface molecule such as a receptor, expressed at the surface of an autoimmune cell. Thus, in an embodiment, the conjugate of the invention comprises the tri-functional linker, said linker comprises or consists of a covalently bound saponin, e.g. QS-21, SO1861, and the covalently bound cell-surface molecule targeting molecule such as a cell targeting moiety such as a ligand or an antibody for (specific) binding to a tumor cell, an auto-immune cell, a diseased cell, an aberrant cell, a non-healthy cell, a B-cell disease.

An embodiment is the conjugate of the invention, comprising the oligomeric tri-functional linker as the scaffold core structure, according to Scheme II:

SCHEME II

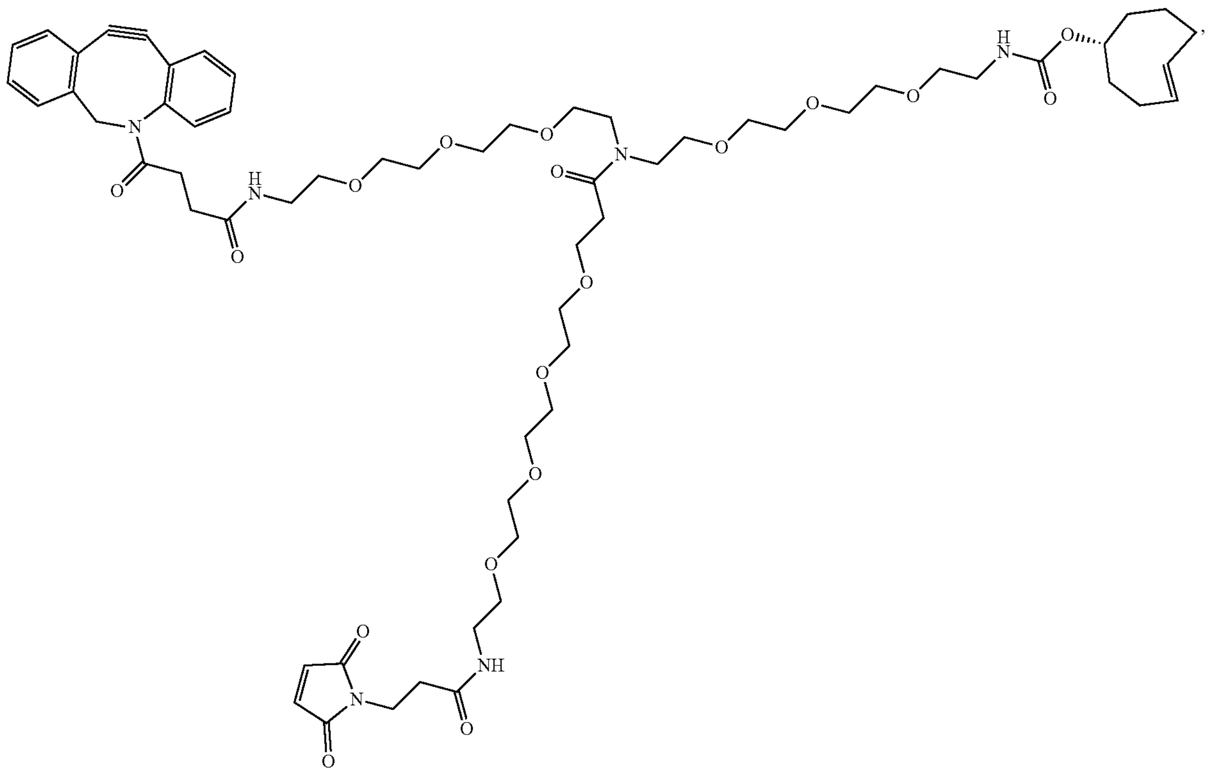
, wherein the saponin and the effector moiety are covalently bound to the tri-functional linker scaffold via labile, cleavable hydrazone linkers (acid sensitive) and/or via a maleimide comprising bond, whereas the binding of the scaffold to the cell-surface molecule targeting molecule such as an antibody is established via labile, cleavable hydrazone linkers (acid sensitive) and/or via a maleimide comprising bond with cysteines in the binding site, such as 1, 2, 3 or 4 cysteines, therewith forming Structure B:

Structure B

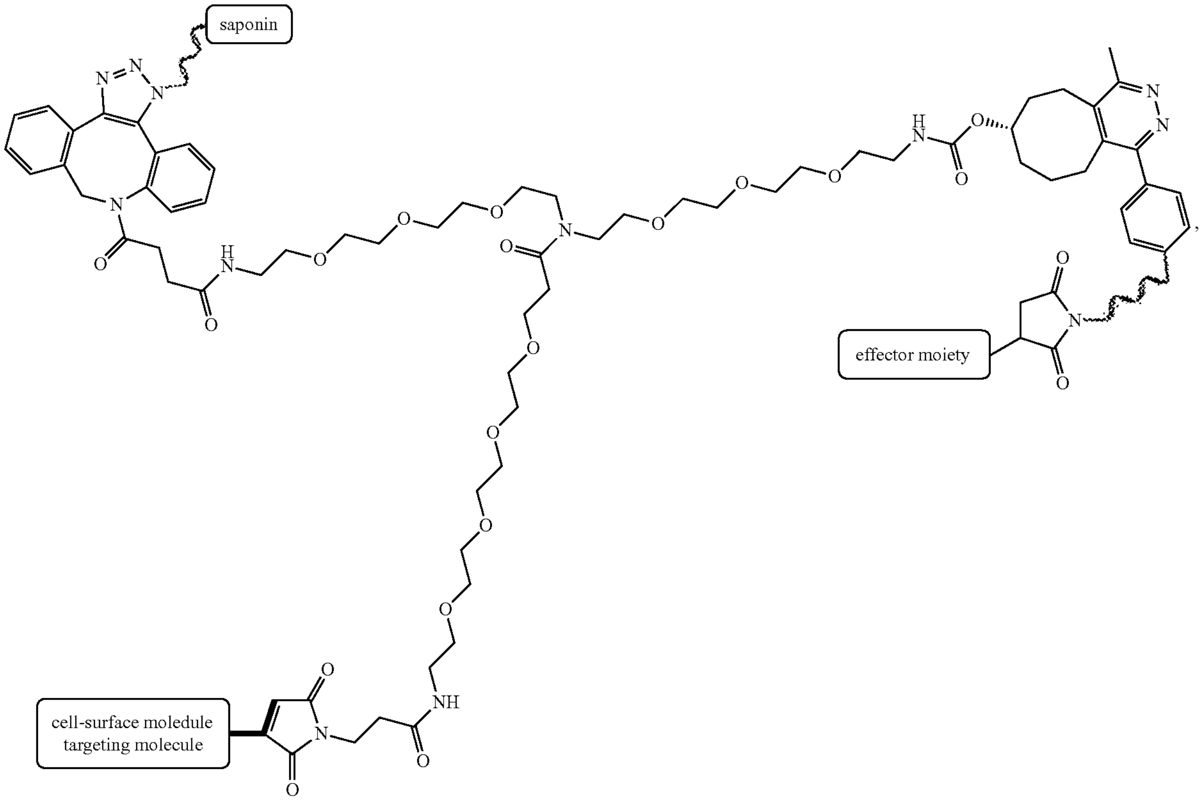

such that 1-4 scaffolds are covalently bound to a single cell-surface molecule targeting molecule, e.g. an antibody such as a monoclonal antibody.

An embodiment is the conjugate of the invention wherein the linkage between saponin and the cell-surface molecule targeting molecule preferably occurs via an acid-labile bond that is stable at pH 7.4 and, preferably releases the saponin below pH 6.5, more preferably between pH 6.5 and 5.0. This is, e.g., realized via an imine formed by an amino group of a linker linking the saponin and the cell-surface molecule targeting molecule and the aldehyde group of the saponin. Other chemical bonds that fulfill the pH-condition can also be used for aldehyde coupling, e.g. particular hydrazones or acetals, requiring hydrazides and hydroxyl groups as the functional group of the linker, respectively. If the bond is a cleavable bond, a saponin is preferably attached to the polymeric or oligomeric structure of a scaffold via an aldehyde function or via one of the carboxyl groups in saponin, more preferably through the aldehyde function, preferably an aldehyde function in position 23. Alternatively, a saponin is preferably attached to the cell-surface molecule targeting molecule via the polymeric or oligomeric structure of the scaffold via a linker that connects the polymeric or oligomeric structure of the scaffold either via the aldehyde function or via the carboxylic acid function of the saponin.

An embodiment is the conjugate of the invention, wherein the at least one saponin is bound to the cell-surface molecule targeting molecule via a stable bond. In a more preferred embodiment, the stable bond between the saponin and the cell-surface molecule targeting molecule preferably occurs via an amide coupling or amine formation. This is, e.g., realized via carbodiimide mediated amide bond formation by an amino group of a polymeric or oligomeric scaffold structure linking the saponin and the cell-surface molecule targeting molecule together, and the activated glucuronic acid group of the saponin. Chemical bonds that fulfill the stable bond definition can also be used for aldehyde coupling, e.g. particular amines derived after reductive amination, requiring primary amino groups as the functional group of a polymeric or oligomeric structure of a scaffold or a linker. If the bond is a stable bond, the saponin is preferably attached to a linker or a scaffold via one of the carboxyl groups of the saponin, the linker or scaffold further linked to the cell-surface molecule targeting molecule.

An embodiment is the conjugate of the invention wherein the saponin is coupled to the cell-surface molecule targeting molecule via a scaffold according to the invention, wherein the chemical group for covalently coupling of the scaffold to the binding site is a click chemistry group.

An embodiment is the conjugate of the invention wherein the saponin is coupled to the cell-surface molecule targeting molecule via a scaffold according to the invention, wherein the click chemistry group is a tetrazine, an azide, an alkene or an alkyne, or a cyclic derivative of any of these groups, preferably an azide. A click chemistry group is a functional chemical group suitable for click chemistry, which is defined as a reaction that is modular, wide in scope, gives very high yields, generates only inoffensive byproducts, offers high selectivity, and high tolerance over different functional groups, and is stereospecific. The required process characteristics include simple reaction conditions, readily available starting materials and reagents, the use of no solvent or a solvent that is benign (such as water) or easily removed, and simple product isolation. The click chemistry group for coupling the saponin to the cell-surface molecule targeting molecule in the conjugate of the invention optionally via a scaffold or a linker, is preferably a tetrazine, azide, alkene, or alkyne, or reactive derivates of them such as methyltetrazine or maleimide (alkene), more preferably an alkyne, or a cyclic derivative of these groups, such as cyclooctyne (e.g. aza-dibenzocyclooctyne, difluorocyclooctyne, bicyclo [6.1.0]non-4-yne, dibenzocyclooctyne).

A conjugate according to the invention thus comprises at least one saponin. With "at least one" in this context is meant that the conjugate comprises one saponin molecule but may also comprise a couple (e.g. two, three or four) of saponins or a multitude (e.g. 10, 20 or 100) of saponins. Depending on the application, the conjugate may comprise a covalently bound scaffold with covalently bound saponins, wherein the scaffold may be designed such that it comprises a defined number of saponins. Preferably, a conjugate according to the invention comprises a defined number or range of saponins, rather than a random number. This is especially advantageous for drug development in relation to marketing authorization. A defined number in this respect means that a conjugate preferably comprises a previously defined number of saponins. This is, e.g., achieved by designing a scaffold comprising a polymeric structure with a certain number of possible moieties for the saponin(s) to attach. Under ideal circumstances, all of these moieties are coupled to a saponin and the scaffold than comprises the prior defined number of saponins. It is envisaged to offer a standard set of scaffolds, comprising, e.g., two, four, eight, sixteen, thirty-two, sixty-four, etc., saponins so that the optimal number can be easily tested by the user according to his needs. An embodiment is the conjugate of the invention comprising the scaffold of the invention, wherein the saponin is present in a defined range as, e.g., under non-ideal circumstances, not all moieties present in a polymeric structure bind a saponin. Such ranges may for instance be 2-4 saponin molecules per scaffold, 3-6 saponin molecules per scaffold, 4-8 saponin molecules per scaffold, 6-8 saponin molecules per scaffold, 6-12 saponin molecules per scaffold and so on. In such case, a conjugate comprising a scaffold according to the invention thus comprises 2, 3 or 4 saponins if the range is defined as 2-4.

The scaffold is fundamentally independent of the type of saponin covalently bound to the scaffold, the scaffold subsequently (in sequential order) covalently coupled to the conjugate. Thus, the conjugate comprising the scaffold is the basis product for a new platform technology. Since the at least one covalently bound saponin mediates intracellular delivery of the effector moiety bound to the cell-surface molecule targeting molecule comprised by the conjugate of the invention, the scaffold technology according to the invention is the first system known that mediates controlled intracellular effector moiety delivery by saponins. The scaffold provides an optimized and functionally active unit that can be linked to the saponin(s) and to the cell-surface molecule targeting molecule comprised by the conjugate, e.g. a ligand, an antibody, etc., at a single and defined position.

An embodiment is the conjugate comprising a scaffold according to the invention, wherein the number of monomers of the polymeric or oligomeric structure is an exactly defined number or range. Preferably, the polymeric or oligomeric structure comprises structures such as poly(amines), e.g., polyethylenimine and poly(amidoamine), or structures such as polyethylene glycol, poly(esters), such as poly(lactides), poly(lactams), polylactide-co-glycolide copolymers, poly(dextrin), or a peptide or a protein, or structures such as natural and/or artificial polyamino acids, e.g. poly-lysine, DNA polymers, stabilized RNA polymers or PNA (peptide nucleic acid) polymers, either appearing as linear, branched or cyclic polymer, oligomer, dendrimer, dendron, dendronized polymer, dendronized oligomer or assemblies of these structures, either sheer or mixed. Preferably, the polymeric or oligomeric structures are biocompatible, wherein biocompatible means that the polymeric or oligomeric structure does not show substantial acute or chronic toxicity in organisms and can be either excreted as it is or fully degraded to excretable and/or physiological compounds by the body's metabolism. Assemblies can be built up by covalent cross-linking or non-covalent bonds and/or attraction. They can therefore also form nanogels, microgels, or hydrogels, or they can be attached to carriers such as inorganic nanoparticles, colloids, liposomes, micelles or particle-like structures comprising cholesterol and/or phospholipids. Said polymeric or oligomeric structures preferably bear an exactly defined number or range of coupling moieties for the coupling of glycoside molecules (and/or effector molecules and/or carrier molecules such as a ligand, monoclonal antibody or a fragment thereof). Preferably at least 50%, more preferably at least 75%, more preferably at least 85%, more preferably at least 90%, more preferably at least 95%, more preferably at least 98%, more preferably at least 99%, most preferably 100% of the exactly defined number or range of coupling moieties in the polymeric or oligomeric structure is occupied by a glycoside molecule in a scaffold according to the invention.

Preferably, a dendron is a branched, clearly defined tree-like polymer with a single chemically addressable group at the origin of the tree, called the focal point. A dendrimer is a connection of two or more dendrons at their focal point. A dendronized polymer is a connection of the focal point of one or more dendrons to a polymer. In a preferred embodiment, a scaffold according to the invention is provided, wherein the polymeric or oligomeric structure comprises a linear, branched or cyclic polymer, oligomer, dendrimer, dendron, dendronized polymer, dendronized oligomer or assemblies of these structures, either sheer or mixed, wherein assemblies can be built up by covalent cross-linking or non-covalent attraction and can form nanogels, microgels, or hydrogels, and wherein, preferably, the polymer is a derivative of a poly(amine), e.g., polyethylenimine and poly(amidoamine), and structures such as polyethylene glycol, poly(esters), such as poly(lactids), poly(lactams), polylactide-co-glycolide copolymers, and poly(dextrin), and structures such as natural and/or artificial polyamino acids such as poly-lysine, or a peptide or a protein or DNA polymers, stabilized RNA polymers or PNA (peptide nucleic acid) polymers. Preferably, the polymeric or oligomeric structures are biocompatible.

An embodiment is the conjugate of the invention for use according to the invention, wherein the conjugate comprises more than one covalently bound saponin, preferably 2, 3, 4, 5, 6, 8, 10, 16, 32, 64, 128 or 1-100 saponins, or any number of saponins therein between, such as 7, 9, 12 saponins, or any.

An embodiment is the conjugate of the invention, wherein the at least one saponin is covalently bound to the polymeric or oligomeric structure of the oligomeric or polymeric scaffold via at least one cleavable linker according to the invention.

An embodiment is the conjugate of the invention, wherein the chemical group of the oligomeric or polymeric scaffold, for covalently coupling of the oligomeric or polymeric scaffold to the amino-acid residue of the cell-surface molecule targeting molecule in the conjugate, is a click chemistry group, preferably selected from a tetrazine, an azide, an alkene or an alkyne, or a cyclic derivative of these groups, more preferably said chemical group is an azide.

An embodiment is the conjugate of the invention, wherein the polymeric or oligomeric structure of the oligomeric or polymeric scaffold comprises a linear, branched and/or cyclic polymer, oligomer, dendrimer, dendron, dendronized polymer, dendronized oligomer, a DNA, a polypeptide, poly-lysine, a poly-ethylene glycol, or an assembly of these polymeric or oligomeric structures which assembly is preferably built up by covalent cross-linking.

The inventors established that covalent coupling, preferably via cleavable bonds or linkers, of the saponin to the cell-surface molecule targeting molecule in the conjugate of the invention, according to any of the embodiments here above, provides efficient and cell-targeted potentiation of the activity of an effector moiety comprised by said conjugate. Coupling saponin to a cysteine side chain or a lysine side chain of the cell-surface molecule targeting molecule in the conjugate such as a monoclonal antibody, directly or via a linker, proved to be a beneficial way of specific and efficient delivery of effector-moiety potentiating activity inside the target cell, when also the effector moiety is delivered in the same target cell by using the very same cell-surface molecule targeting molecule to which also the saponin(s) is/are covalently bound.

To explain the invention in more detail, the process of cellular uptake of substances (although the inventors do not wish to be bound by any theory) and the used terminology in this invention is described. The uptake of extracellular substances into a cell by vesicle budding is called endocytosis. Said vesicle budding can be characterized by (1) receptor-dependent ligand uptake mediated by the cytosolic protein clathrin, (2) lipid-raft uptake mediated by the cholesterol-binding protein caveolin, (3) unspecific fluid uptake (pinocytosis), or (4) unspecific particle uptake (phagocytosis). All types of endocytosis run into the following cellular processes of vesicle transport and substance sorting called the endocytic pathways. The endocytic pathways are complex and not fully understood. Without wishing to be bound by any theory, organelles may be formed de novo and mature into the next organelle along the endocytic pathway. It is, however, now hypothesized that the endocytic pathways involve stable compartments that are connected by vesicular traffic. A compartment is a complex, multifunctional membrane organelle that is specialized for a particular set of essential functions for the cell. Vesicles are considered to be transient organelles, simpler in composition, and are defined as membrane-enclosed containers that form de novo by budding from a preexisting compartment. In contrast to compartments, vesicles can undergo maturation, which is a physiologically irreversible series of biochemical changes. Early endosomes and late endosomes represent stable compartments in the endocytic pathway while primary endocytic vesicles, phagosomes, multivesicular bodies (also called endosome carrier vesicles), secretory granules, and even lysosomes represent vesicles. The endocytic vesicle, which arises at the plasma membrane, most prominently from clathrin-coated pits, first fuses with the early endosome, which is a major sorting compartment of approximately pH 6.5. A large part of the cargo and membranes internalized are recycled back to the plasma membrane through recycling vesicles (recycling pathway). Components that should be degraded are transported to the acidic late endosome (pH lower than 6) via multivesicular bodies. Lysosomes are vesicles that can store mature lysosomal enzymes and deliver them to a late endosomal compartment when needed. The resulting organelle is called the hybrid organelle or endolysosome. Lysosomes bud off the hybrid organelle in a process referred to as lysosome reformation. Late endosomes, lysosomes, and hybrid organelles are extremely dynamic organelles, and distinction between them is often difficult. Degradation of an endocytosed molecule occurs inside an endolysosome or lysosome. Endosomal escape is the active or passive release of a substance from the inner lumen of any kind of compartment or vesicle from the endocytic pathway, preferably from clathrin-mediated endocytosis, or recycling pathway into the cytosol. Endosomal escape thus includes but is not limited to release from endosomes, endolysosomes or lysosomes, including their intermediate and hybrid organelles.

Unless specifically indicated otherwise and in particular when relating to the endosomal escape mechanism of the glycoside molecule such as the saponin of the invention, whenever the word "endosome" or "endosomal escape" is used herein, it also includes the endolysosome and lysosome, and escape from the endolysosome and lysosome, respectively. After entering the cytosol, said substance might move to other cell units such as the nucleus.

In formal terms, a glycoside is any molecule in which a sugar group is bound through its anomeric carbon to another group via a glycosidic bond. Glycoside molecules, such as saponins, in the context of the invention are such molecules that are further able to enhance the effect of an effector moiety, without wishing to be bound by any theory, in particular by facilitating the endosomal escape of the effector moiety. Without wishing to be bound by any theory, the glycoside molecules (saponins, such as those listed in Table A1) interact with the membranes of compartments and vesicles of the endocytic and recycling pathway and make them leaky for said effector moieties resulting in augmented endosomal escape. With the term "the scaffold is able to augment endosomal escape of the effector moiety" is meant that the at least one saponin (glycoside molecule), which is coupled via a linker or directly to the cell-surface molecule targeting molecule or via the polymeric or oligomeric structure of the scaffold, is able to enhance endosomal escape of an effector moiety when both molecules are within an endosome, e.g. a late endosome, optionally and preferably after the at least one glycoside such as a saponin is released from the conjugate such as from a linker or polymeric or oligomeric structure comprised by said conjugate, e.g., by cleavage of a cleavable bond between the at least one glycoside (saponin) and the conjugate (for example via a polymeric or oligomeric structure of a scaffold and/or via a linker). Even though a bond between the at least one glycoside such as a saponin according to the invention and the cell-surface molecule targeting molecule of the conjugate of the invention, optionally via a linker or a scaffold, may be a "stable bond", that does not mean that such bond cannot be cleaved in the endosomes by, e.g., enzymes. For instance, the glycoside or saponin, optionally together with a linker or a part of the oligomeric or polymeric structure of a scaffold, may be cleaved off from the remaining linker fragment or oligomeric or polymeric structure. It could, for instance be that a protease cuts a (proteinaceous) linker or proteinaceous polymeric structure, e.g., albumin, thereby releasing the at least one glycoside, saponin. It is, however, preferred that the glycoside molecule (preferably saponin) is released in an active form, preferably in the original form that it had before it was (prepared to be) coupled to the cell-surface molecule targeting molecule of the conjugate optionally via a linker and/or an oligomeric or polymeric scaffold; thus the glycoside (saponin) has its natural structure after such cleavage or the glycoside (saponin) has (part of) a chemical group or linker bound thereto, after such cleavage, while glycoside biological activity (saponin biological activity), e.g. endosomal/lysosomal escape enhancing activity towards an effector moiety present in the same endosome or lysosome, is maintained or restored upon said cleavage of the bond between the glycoside (saponin) and the cell-surface molecule targeting molecule, e.g. an antibody, optionally comprising a linker and/or a scaffold of the invention. With regard to the present invention the term "stable" with respect to bonds between e.g. saponins and amino-acid residues of the cell-surface molecule targeting molecule in the conjugate, a linker, a polymeric or oligomeric structures (of the scaffold), ligands, (monoclonal) immunoglobulins or binding domains or -fragments thereof, and/or effectors (effector moieties, effector molecules), is meant that the bond is not readily broken or at least not designed to be readily broken by, e.g., pH differences, salt concentrations, or UV-light, reductive conditions. With regard to the present invention the term "cleavable" with respect to bonds between e.g. saponins and the cell-surface molecule targeting molecule, linkers, amino-acid residues, polymeric or oligomeric structures of the scaffold, ligands, antibodies and/or effectors, is meant that the bond is designed to be readily broken by, e.g., pH differences, salt concentrations, under reductive conditions, and the like. The skilled person is well aware of such cleavable bonds and how to prepare them.

Before the present invention one of the major hurdles of introducing ADCs and AOCs on the market was the small therapeutic window: a therapeutically effective dose of an ADC or an AOC is accompanied with (unacceptable) side effects, hampering development and implication in treatment of patients with the ADCs. By the application of the conjugate of the invention, such as ADC-saponin conjugate and AOC-saponin conjugate, it has now become possible to guide one or multiple glycoside molecules (saponin(s)) to a (target) cell, together with the ADC carrying a payload or together with a (monoclonal) antibody conjugated with an oligonucleotide such as a BNA according to the invention. In particular, it was previously not possible to specifically guide an effector moiety of an ADC or AOC or any other conjugate of a payload and a (proteinaceous) cell-surface molecule targeting molecule, and a (predefined, controllable) particular number or range of glycoside molecules (saponins) per effector moiety at the same time to the cytosol of cells, such as via the endocytic pathway of a cell.

A solution provided for by the invention comprises the covalent binding of at least one saponin to the cell-surface molecule targeting molecule of the conjugate of the invention. A further solution provided for by the invention comprises (first) polymerizing the glycoside molecules (saponins) using an oligomeric or polymeric scaffold, and providing the cell-surface molecule targeting molecule comprised by the conjugate of the invention with a cluster of covalently bound saponins, enabling re-monomerization of the one or more saponins at the intracellular site where the mode of action of the saponin is desired, e.g. after endocytosis. "Polymerizes" in this context means the reversible and/or irreversible multiple conjugation of saponin molecules to the first proteinaceous molecule, either via linker, or directly or via a polymeric or oligomeric structure to form a scaffold or the reversible and/or irreversible multiple conjugation of (modified) saponins thereby forming a polymeric or oligomeric structure to form a scaffold. "Re-monomerization" in this context means the cleavage of the saponins from the conjugate, from the linker linking the saponin(s) to the cell-surface molecule targeting molecule of the conjugate or from the scaffold, for example after endocytosis, and regaining the (native) chemical state of the unbound saponins, which unbound saponins may or may not comprise additional chemical groups such as a chemical group for linking the saponin to a linker, an amino-acid residue of the conjugate or to the scaffold, and/or a (chemical) linker bound to a chemical group of the saponin such as an aldehyde group or carboxylic acid group. Due to the complex chemistry of the saponins for example the 'polymerization' of saponins at a scaffold or other linking linker and their 're-monomerization' at a desired location such as intracellularly e.g. after endocytosis, was a challenging task. In particular, the chemical reactions used for providing the linkers and the scaffold comprising covalently linked glycosides for covalent binding to the conjugate, e.g. triterpenoid saponins (polymerization of the glycosides), normally occur in water-free organic solvents, but saponins and for example biocompatible polymers applied as a scaffold for bearing bound saponins, are water-soluble molecules. The chemical properties of the unmodified saponin further prohibited polymerization by itself and, one other possible solution, to bind multiple saponins (directly) to the effector molecule was estimated not to be very promising, as an effector molecule (drug, toxin, polypeptide or polynucleotide) does typically not provide sufficient binding sites and because the coupling product would become quite heterogeneous and/or coupling biologically active molecules such as a saponin and e.g. a peptide, a toxin, a nucleic acid together bears the risk for influencing and hampering the activity of one or even both molecules bound together in such saponin-comprising conjugate. Further, there was a considerable risk that the effector moiety comprised by the conjugate of the invention loses its function when a saponin is coupled to the e.g. ADC or antibody-oligonucleotide conjugate (AOC). Embodiments of the present invention solves at least one of these drawbacks.

An effector molecule, or effector moiety, in the context of this invention is any substance that affects the metabolism of a cell by interaction with an intracellular effector molecule target, wherein this effector molecule target is any molecule or structure inside cells excluding the lumen of compartments and vesicles of the endocytic and recycling pathway but including the membranes of these compartments and vesicles. Said structures inside cells thus include the nucleus, mitochondria, chloroplasts, endoplasmic reticulum, Golgi apparatus, other transport vesicles, the inner part of the plasma membrane and the cytosol. Cytosolic delivery of an effector moiety in the context of the invention preferably means that the effector moiety is able to escape the endosome (and/or lysosome), which, as defined previously, also includes escaping the endolysosome and the lysosome, and is preferably able to reach the effector moiety target as described herein. The invention also encompasses a new type of molecule, referred to as scaffold that serves to bring both an effector moiety and at least one glycoside molecule such as a saponin of the invention in an endosome at the same time in a pre-defined ratio, when the effector moiety is comprised by the conjugate of the invention and the saponin is comprised by the conjugate. Within the context of the present invention, the polymeric or oligomeric structure of the scaffold is a structurally ordered formation such as a polymer, oligomer, dendrimer, dendronized polymer, or dendronized oligomer or it is an assembled polymeric structure such as a hydrogel, microgel, nanogel, stabilized polymeric micelle or liposome, but excludes structures that are composed of non-covalent assemblies of monomers such as cholesterol/phospholipid mixtures. The terms "polymer, oligomer, dendrimer, dendronized polymer, or dendronized oligomer" have their ordinary meaning. In particular a polymer is a substance which has a molecular structure built up chiefly or completely from a large number of equal or similar units bonded together and an oligomer is a polymer whose molecules consist of relatively few repeating units. There is no consensus about one specific cut-off for "many" and "a few" as used in the above definition of polymer and oligomer, respectively. However, as the scaffold may comprise a polymeric or an oligomeric structure, or both, the full range of numbers of similar units bonded together applies to such structure. i.e. from 2 monomeric units to 100 monomeric units, 1000 monomeric units, and more. A structure comprising 5 or less, for instance maybe called an oligomeric structure, whereas a structure comprising 50 monomeric units maybe called a polymeric structure. A structure of 10 monomeric units maybe called either oligomeric or polymeric. A scaffold as defined herein, further comprises at least one glycoside molecule such as a saponin of the invention. A scaffold preferably includes a polymeric or oligomeric structure such as poly- or oligo(amines), e.g., polyethylenimine and poly(amidoamine), and biocompatible structures such as polyethylene glycol, poly- or oligo (esters), such as poly(lactids), poly(lactams), polylactide-co-glycolide copolymers, and poly(dextrin), poly- or oligosaccharides, such as cyclodextrin or polydextrose, and poly- or oligoamino acids, such as poly-lysine or a peptide or a protein, or DNA oligo- or polymers. An assembled polymeric structure as defined herein comprises at least one scaffold and, optionally, other individual polymeric or oligomeric structures. Other individual polymeric or oligomeric structures of said assembly may be (a) scaffolds (thus comprising at least one glycoside molecule such as a saponin of the invention), (b) functionalized scaffolds (thus comprising at least one glycoside molecule such as a saponin, and at least one effector moiety, (c) polymeric or oligomeric structures without a glycoside molecule such as a saponin of the invention (See Table A1 for example), but with at least one effector moiety. A functionalized assembled polymeric structure is an assembled polymeric structure that contains (a) at least one functionalized scaffold or (b) at least one scaffold and at least one polymeric structure comprising at least one effector moiety, etc. bound to the cell-surface molecule targeting molecule of the conjugate of the invention. Polymeric or oligomeric structures within an assembled polymeric structure that do not comprise any of the above mentioned molecules (i.e. no glycosides such as saponins, no effector moieties) are in particular added as structural components of the assembled structures, which help to build up or to stabilize the assembled structure ("glue-like"). Without wishing to be bound by any theory, the acidic environment seems to be a prerequisite for the synergistic action between glycoside (saponin) and effector moiety.

Whether or not a conjugate of the invention comprising saponins, either or not further comprising one or more (cleavable) linkers and/or optionally a scaffold, is able to disturb the acidic environment and inhibit the endosomal escape function of the at least one glycoside (saponin) can be easily determined with an assay as described in Example 12 and as known in the art. The inhibition is described as "fold amount increases of glycoside necessary to induced 50% cell killing". It is preferred that the scaffold does not lead to an increase that is at least the increase in glycoside molecules (saponins) necessary to obtain 50% cell killing observed when using Chloroquine as a positive control. Alternatively, and preferably, the conjugate comprising saponins, either or not further comprising one or more (cleavable) linkers and/or optionally a scaffold does not lead to an at least 4-fold increase of glycoside molecules to induce 50% cell killing, more preferably does not lead to an at least 2-fold increase. The fold increase is to be measured in assay, essentially as described in Example 12, wherein Chloroquine, as a positive control, induces a 2-fold increase in glycoside amount, preferably saponin amount wherein the saponin is any one or more of the saponins of the invention (see Table A1, Scheme I, previous embodiments) to observe 50% cell killing.

With the term "improving or enhancing an effect of an effector moiety" is meant that the glycoside molecule, preferably a saponin of the invention, increases the functional efficacy of that effector moiety (e.g. the therapeutic index of a toxin or a drug or an oligonucleotide such as a BNA; the metabolic efficacy of a modifier in biotechnological processes; the transfection efficacy of genes in cell culture research experiments), preferably by enabling or improving its target engagement. Acceleration, prolongation, or enhancement of antigen-specific immune responses are preferably not included. Therapeutic efficacy includes but is not limited to a stronger therapeutic effect, preferably with lower dosing and/or with less side effects. "Improving an effect of an effector moiety" can also mean that an effector moiety, which could not be used because of lack of effect (and was e.g. not known as being an effector moiety), becomes effective when used in combination with the present invention. Any other effect, which is beneficial or desired and can be attributed to the combination of effector moiety and the saponin, as provided by the invention is considered to be "an improved effect". In an embodiment, the scaffold comprising bound saponin(s) and comprised by the conjugate of the invention enhances an effect of the effector moiety comprised by said conjugate which effect is intended and/or desired. In case of a conjugate comprising saponin bound to a proteinaceous scaffold, the proteinaceous polymeric structure of the scaffold as such may have, for instance, an effect on colloid osmotic pressure in the blood stream. If such effect is not the intended or desired effect of such a functionalized scaffold comprised by the conjugate, the proteinaceous structure of the scaffold is not an effector moiety as defined in the invention. Or, for instance in case of a DNA- or RNA-based scaffold carrying bound saponins and comprised by the conjugate, parts of that DNA or RNA may have an (unintended) function, e.g., by interfering with expression. If such interference is not the intended or desired effect of the ultimate functionalized scaffold, the DNA- or RNA polymeric structure of the scaffold is not the effector moiety as defined in the invention.

A number of preferred features can be formulated for endosomal escape enhancers comprised by the conjugate of the invention, i.e. a glycoside or saponin, preferably a saponin according to the invention: (1) they are preferably not toxic and do not invoke an immune response, (2) they preferably do not mediate the cytosolic uptake of the effector moiety into off-target cells, (3) their presence at the site of action is preferably synchronized with the presence of the effector moiety, (4) they are preferably biodegradable or excretable, and (5) they preferably do not substantially interfere with biological processes of the organism unrelated to the biological activity of the effector molecule with which the endosomal escape enhancer is combined with, e.g. interact with hormones. Examples of glycoside molecules such as saponins of the invention that fulfill the before mentioned criteria, at least to some extent, are bisdesmosidic triterpenes, preferably bisdesmosidic triterpene saponins, such as SO1861, SA1641, QS-21, GE1741, and the saponins in Table A1, Scheme I.

An embodiment is the conjugate of the invention such as the antibody-drug conjugate or antibody-oligonucleotide conjugate or ligand-drug conjugate of the invention, wherein the antibody can bind to any one of CD71, CA125, EpCAM (17-1A), CD52, CEA, CD44v6, FAP, EGF-IR, integrin, syndecan-1, vascular integrin alpha-V beta-3, HER2, EGFR, CD20, CD22, Folate receptor 1, CD146, CD56, CD19, CD138, CD27L receptor, PSMA, CanAg, integrin-alphaV, CA6, CD33, mesothelin, Cripto, CD3, CD30, CD239, CD70, CD123, CD352, DLL3, CD25, ephrinA4, MUC1, Trop2, CEACAM5, CEACAM6, HER3, CD74, PTK7, Notch3, FGF2, C4.4A, FLT3, CD38, FGFR3, CD7, PD-L1, CTLA4, CD52, PDGFRA, VEGFR1, VEGFR2, preferably CD71, HER2, EGFR, and/or is or comprises any one of cetuximab, daratumumab, gemtuzumab, trastuzumab, panitumumab, brentuximab, inotuzumab, moxetumomab, polatuzumab, obinutuzumab, OKT-9 anti-CD71 monoclonal antibody of the IgG type, pertuzumab, rituximab, ofatumumab, Herceptin, alemtuzumab, pinatuzumab, OKT-10 anti-CD38 monoclonal antibody, an antibody of Table A2 or Table A3 or Table A4, preferably cetuximab or trastuzumab or OKT-9, or at least one tumor-cell receptor binding-fragment thereof and/or at least one tumor-cell receptor binding-domain thereof, and/or wherein the antibody-drug conjugate comprises any one of Gemtuzumab ozogamicin, Brentuximab vedotin, Trastuzumab emtansine, Inotuzumab ozogamicin, Moxetumomab pasudotox and Polatuzumab vedotin and an antibody-drug conjugate of Table A2 and Table A3, or wherein the ligand-drug conjugate comprises at least one ligand for binding to a cell-surface molecule such as EGF or a cytokine.

As said before, the at least one saponin that is comprised by the conjugate according to the invention increases the efficacy of at least current and new effector moieties as defined in this invention. Potential side-effects will be decreased due to lowering of dosing of the effector moiety comprised by the conjugate, without lowering the efficacy. Therefore, the invention provides a conjugate according to the invention for use in medicine or for use as a medicament. Thus, an aspect of the invention relates to a conjugate according to the invention, the conjugate comprising at least a saponin and at least one effector moiety, for use as a medicament. Also provided is the use of a conjugate according to the invention for manufacturing a medicament. Especially cancer medicines, and in particular the classical chemotherapy medicaments, are notorious for their side effects. Because of targeting and synchronization in time and place of both the pharmaceutically active substance comprised by the conjugate and the saponin comprised by the very same conjugate molecule, a therapeutic conjugate according to the invention is especially valuable for use as a medicament, in particular for use in a method of treating cancer. The invention thus provides a therapeutic conjugate according to the invention for use in a method of treating cancer. The invention also provides a therapeutic conjugate according to the invention for use in a method of treating acquired or hereditary disorders, in particular monogenic deficiency disorders. The therapeutic conjugate thus comprises the at least one saponin and the at least one effector moiety. Thus, an aspect of the invention relates to a therapeutic conjugate according to the invention, wherein the conjugate comprises a covalently bound effector moiety and comprises a covalently bound saponin, for use in a method for the treatment of a cancer or an auto-immune disease.

A further application of the conjugate of the invention in medicine is the substitution of intracellular enzymes in target cells that produce these enzymes in insufficient amount or insufficient functionality. The resulting disease might be hereditary or acquired. In most cases, only symptomatic treatment is possible and for a number of rare diseases, insufficient treatment options lead to a shortened life span of concerned patients. An example for such a disease is phenylketonuria, which is an inborn error of metabolism that results in decreased metabolism of the amino acid phenylalanine. The disease is characterized by mutations in the gene for the hepatic enzyme phenylalanine hydroxylase. Phenylketonuria is not curable to date. The incidence is approximately 1:10,000 with the highest known incidence in Turkey with 1:2,600. A cell-surface molecule targeting molecule comprised by the conjugate of the invention, preferably an antibody, with bound phenylalanine hydroxylase or with a bound polynucleotide that encodes phenylalanine hydroxylase can be used to target liver cells by use of a suitable specific antibody, and to substitute the defect enzyme in hepatocytes. This is one example of use of the therapeutic conjugate of the invention comprising a saponin bound thereto and the enzyme or the oligonucleotide bound thereto according to the invention, for substitution or gene therapy. In a preferred embodiment, a therapeutic conjugate according to the invention for use in a method of gene therapy or substitution therapy is provided.

With the conjugate of the invention it has now become possible to design and manufacture a one-component, non-viral clinically applicable gene delivery technology. For example, the conjugate of the invention allows for development of non-viral based gene delivery technology, which enhances therapeutic efficacy with lower therapeutic dose thereby improving the health of patients. The conjugate of the invention, in particular when comprising a covalently bound cell-surface molecule targeting molecule such as a monoclonal antibody for binding to a (tumor, auto-immune) cell-surface specific molecule, and when bound to an effector moiety such as an oligonucleotide for example a BNA, allows for overcoming a longstanding and major bottleneck in the field of gene delivery, namely efficient, safe and cost-effective transfer of gene therapeutic products across the endosomal membrane into the cytosol/nucleosol. Indeed, gene therapy is one of the most promising treatment options for future advanced therapies in a broad range of diseases. Successful gene delivery requires the recognition of target cells as well as cytosolic and nucleosolic uptake of the gene. One of the major problems in the field of non-viral gene therapy is the inefficient and insufficiently safe delivery of genetic material for therapeutic use in patients.

Thus, when applying the conjugate of the invention, comprising a cell-targeting cell-surface molecule targeting molecule such as a ligand or preferably an antibody (fragment, domain thereof) and comprising an oligonucleotide such as an antisense BNA, the inventors now made it possible to overcome a longstanding and major bottleneck in the field of gene delivery: safe transfer of gene therapeutic products across the endosomal membrane into the cytosol/nucleosol. The conjugate of the invention represents technology designed for allowing targeting of any addressable cell type with all known genetic agents, thereby ensuring better patient therapy not limited to inherited disorders, but also for cancer therapy and therefore of importance for large patient groups. The technology based on the conjugate of the invention may comprise a polymeric or oligomeric scaffold that serves as a carrier for endosomal escape enhancers (EEEs), such as the saponins of Table A1 and Scheme I and any of the embodiments according to the invention, for the cell-surface molecule targeting molecule such as a targeting ligand or (monoclonal) (tumor-cell specific) antibody, and for the effector moiety, here an effector gene such as an LNA or BNA. Use of the conjugate of the invention, e.g. comprising a cell-targeting antibody (fragment) and an oligonucleotide such as a BNA, has potential to bring any kind of biological macromolecules into the cytosol and the nucleus. Development of new targeting ligands and monoclonal (human, humanized) antibodies is under continuous investigation by numerous research groups and companies worldwide. The same for the oligonucleotides that are aimed for delivery in the cytosol of diseases cells such as cancer cells. The conjugate of the invention thus also presents as a molecular interface in which present and future targeting ligands and antibodies and present and future therapeutic oligonucleotides (as well as payloads such as protein toxins) are linked or can be linked to for example an oligomeric or polymeric scaffold module of the invention by click chemistry, allowing for customized drug applications and for future developments in the field of tissue and cell targeting techniques. The conjugate of the invention can comprise antibodies and ligands as the cell-surface molecule targeting molecule. The worldwide market of gene therapeutics is rapidly growing and is covering potential treatments for a wide range of disease areas such as, cancer, cardiovascular diseases, Parkinson's, Alzheimer, HIV and many rare (monogenetic) diseases. The current viral vector-based gene therapeutic technologies have significant challenges, such as safety, manufacturing logistics, and associated high costs. The conjugate of the invention allows for use in a technology platform which represents an alternative for a current viral gene delivery technology. Therefore, the conjugate of the invention is suitable for implementing in approaches for developing non-viral gene treatments for diseases such as cancers, cardiovascular diseases, Parkinson's disease, Alzheimer's disease, HIV infection and many rare (monogenetic) diseases. The conjugate of the invention is suitable for developing novel treatments for transforming the field of antibody-drug conjugates (ADCs) and oligonucleotide-based therapeutics by making non-viral vector based gene therapeutics such as based on targeted antisense BNA. The application of the conjugate of the invention, in particular in a covalent conjugate with an antibody and an oligonucleotide such as a BNA and at least one saponin, is one of the many beneficial approaches made possible due to the present invention. For example, use of the conjugate of the invention now allows for exploitation of the endocytic pathway of mammalian cells. Endocytosis is exploited for the delivery of therapeutics, wherein the conjugate of the invention contributes to improved uptake and endosomal escape of e.g. siRNAs which are comprised by the conjugate. The conjugate of the invention is suitably used together with small molecules that act as delivery enhancers for e.g. payloads, oligonucleotides. Herewith, the conjugate of the invention bearing the covalently coupled oligonucleotide such as a BNA and bearing the covalently coupled cell targeting moiety such as a ligand and preferably an antibody (domain or fragment) and bearing the saponins of the invention, provides a solution for the current problem seen with current endosomal escape enhancers and gene therapeutic product, relating to their application as two components, thus complicating therapeutic approval and clinical applicability, since such a conjugate of the invention is a single-conjugate therapeutic molecule encompassing the saponin, gene product such as a BNA and the (tumor) cell targeting moiety such as a (monoclonal) antibody. Thus the invention provides a non-viral gene delivery technology where endosomal escape enhancers (e.g. the glycosides of Table A1, Scheme I, embodiments of the invention), gene therapeutic product (oligonucleotides according to the invention such as a BNA) and targeting ligand or antibody (according to e.g. Table A2, A3, A4, embodiments of the invention) are all comprised by the conjugate of the invention. Such a conjugate of the invention thus provides therapeutic opportunities for current and future macromolecule drugs for a broad range of diseases and large patient groups. With the application of such a conjugate of the invention comprising at least one saponin, at least one oligonucleotide and at least one specific cell-targeting moiety such as an immunoglobulin, the problem is addressed which is apparent for current methods of applying endosomal escape enhancers and gene therapeutic product separately, which current methods do not ensure that both compounds are at the same time at the site of interaction. This problem is now overcome by using the conjugate of the invention. That is to say, such a conjugate of the invention provides a non-viral gene delivery technology with increased synchronization (in time and place) of both compounds, i.e. the saponin and the gene product such as a BNA.

Gene therapies could help with hereditary, previously incurable diseases such as cystic fibrosis, chorea, Huntington's disease or hemophilia. However, currently some problems have not been overcome: for example, the therapeutic genes must precisely reach specific target cells in the body. On the other hand, the therapeutic genes should be absorbed by the targeted cells, but the therapeutic genes should not be destroyed. The current gene therapy approaches use viruses as a ferry for genes. However, these procedures involve considerable risks and cannot be transferred to the introduction of other biomolecules. An embodiment is the conjugate of the invention comprising (plant-derived) glycosides for use a platform technology that allows not only delivery of genes when comprised by the conjugate as the carrier molecule, but also allows for the delivery of different therapeutic biomolecules to be introduced into target cells. Therefore, the conjugate of the invention is used for developing treatments based on nucleic acids for cystic fibrosis, chorea, Huntington's disease or hemophilia. Herewith, with the conjugate of the invention, a new gene therapy strategy is available for improving the health of patients with genetic diseases, including those patients with cystic fibrosis, Huntington's disease, and hemophilia. As part of the invention, a non-viral gene delivery technology is developed that combines plant-derived endosomal escape enhancers (glycosides), gene therapeutic products, and a targeting ligand that are all comprised in a single conjugate. The resulting non-viral gene therapy based on the conjugate of the invention displays about 40 times increased delivery efficiency at a lower dosage over currently available strategies. Herewith, the conjugate of the invention is for use in clinical applications such as for the repair or replacement of defective genes, like in cystic fibrosis patients, and for the targeted delivery of specific genes, for instance, to destroy cancer cells. In fact, the conjugate of the invention is suitable for application in treatment regimens for any disease caused by a genetic defect—such as cystic fibrosis, Huntington's disease and hemophilia and which are currently incurable. Gene therapy which makes use of the conjugate of the invention helps in overcoming two current problems: Firstly, it is possible with the conjugate of the invention to deliver therapeutic genes to specific target cells in the body; Secondly, the therapeutic genes enter the interior of these cells, but are not destroyed, due to the presence of saponin(s), the oligonucleotide product and a targeting moiety such as an antibody for binding a target cell, all covalently linked together in the conjugate of the invention, for example by using an oligomeric or polymeric scaffold of the invention.

The present invention also provides a method of treating cancer, the method comprising administering a medicament comprising a therapeutic conjugate according to the invention to a patient in need thereof, preferably administering an effective dose of said medicament to a patient in need thereof, preferably a human cancer patient.

Considerations concerning forms suitable for administration are known in the art and include toxic effects, solubility, route of administration, and maintaining activity. For example, pharmacological compositions injected into the bloodstream should be soluble.

Suitable dosage forms, in part depend upon the use or the route of entry, for example transdermal or by injection. Such dosage forms should allow the compound to reach a target cell whether the target cell is present in a multicellular host. Other factors are known in the art, and include considerations such as toxicity and dosage form which retard the compound or composition from exerting its effect.

An aspect of the invention relates to a kit comprising a container containing an endosomal escape enhancing conjugate according to the invention the kit further comprising instructions for using the conjugate.

TABLE A1

Saponins displaying (late) endosomal/lysosomal escape enhancing activity, and saponins comprising a structure reminiscent to such saponins displaying (late) endosomal/lysosomal escape enhancing activity

| Saponin Name | Aglycon core | Carbohydrate substituent at the C-3beta-OH | Carbohydrate substituent at the C-28-OH group group |
|---|---|---|---|
| NP-005236 | 2alpha-Hydro-xyoleanolic acid | GlcA- | Glc/Gal- |
| AMA-1 | 16alpha-Hydro-xyoleanolic acid | Glc- | Rha-(1→2)-[Xyl-(1→4)]-Rha- |
| AMR | 16alpha-Hydro-xyoleanolic acid | Glc- | Rha-(1→2)-[Ara-(1→3)-Xyl-(1→4)]-Rha- |

TABLE A1-continued

Saponins displaying (late) endosomal/lysosomal escape enhancing activity, and saponins comprising a structure reminiscent to such saponins displaying (late) endosomal/lysosomal escape enhancing activity

| Saponin Name | Aglycon core | Carbohydrate substituent at the C-3beta-OH | Carbohydrate substituent at the C-28-OH group group |
|---|---|---|---|
| alpha-Hederin | Heder-agenin (23-Hydro-xyoleanolic acid) | Rha-(1→2)-Ara- | — |
| NP-012672 | 16alpha, 23-Dihydro-xyoleanolic acid | Ara/Xyl-(1→4)-Rha/Fuc-(1→2)-Glc/Gal-(1→2)-Rha/Fuc-(1→2)-GlcA- | Ara/Xyl- |
| NP-017777 | Gypsogenin | Gal-(1→2)-[Xyl-(1→3)]-GlcA- | Xyl-(1→4)-Rha-(1→2)-[R-(→4)]-Fuc- (R = 4E-Methoxycinnamic acid) |
| NP-017778 | Gypsogenin | Gal-(1→2)-[Xyl-(1→3)]-GlcA- | Xyl-(1→4)-Rha-(1→2)-[R-(→4)]-Fuc- (R = 4Z-Methoxycinnamic acid) |
| NP-017774 | Gypsogenin | Gal-(1→2)-[Xyl-(1→3)]-GlcA- | Xyl-(1→4)-[Gal-(1→3)]-Rha-(1→2)-4-OAc-Fuc- |
| NP-018110[c], NP-017772[d] | Gypsogenin | Gal-(1→2)-[Xyl-(1→3)]-GlcA- | Xyl-(1-4)-[Glc-(1→3)]-Rha-(1→2)-3,4-di-OAc-Fuc- |
| NP-018109 | Gypsogenin | Gal-(1→2)-[Xyl-(1→3)]-GlcA- | Xyl-(1→4)-[Glc-(1→3)]-Rha-(1→2)-[R-(→4)]-3-OAc-Fuc- (R = 4E-Methoxy-cinnamic acid) |
| NP-017888 | Gypsogenin | Gal-(1→2)-[Xyl-(1→3)]-GlcA- | Glc-(1→3)-Xyl-(1→4)-[Glc-(1→3)]-Rha-(1→2)-4-OAc-Fuc- |
| NP-017889 | Gypsogenin | Gal-(1→2)-[Xyl-(1→3)]-GlcA- | Glc-(1→3)-Xyl-(1→4)-Rha-(1→2)-4-OAc-Fuc- |
| NP-018108 | Gypsogenin | Gal-(1→2)-[Xyl-(1→3)]-GlcA- | Ara/Xyl-(1→3)-Ara/Xyl-(1→4)-Rha/Fuc-(1→2)-[4-OAc-Rha/Fuc-(1→4)]-Rha/Fuc- |
| SA1641[a], AE X55[b] | Gypsogenin | Gal-(1→2)-[Xyl-(1→3)]-GlcA- | Xyl-(1→3)-Xyl-(1→4)-Rha-(1→2)-[Qui-(1→4)]-Fuc- |
| NP-017674 | Quillaic acid | Gal-(1→2)-[Xyl-(1→3)]-GlcA- | Api-(1→3)-Xyl-(1→4)-[Glc-(1→3)]-Rha-(1→2)-Fuc- |
| NP-017810 | Quillaic acid | Gal-(1→2)-[Xyl-(1→3)]-GlcA- | Xyl-(1→4)-[Gal-(1→3)]-Rha-(1→2)-Fuc- |
| AG1 | Quillaic acid | Gal-(1→2)-[Xyl-(1→3)]-GlcA- | Xyl-(1→4)-[Gal-(1→3)]-Rha-(1→2)-Fuc- |
| NP-003881 | Quillaic acid | Gal-(1→2)-[Xyl-(1→3)]-GlcA- | Ara/Xyl-(1→4)-Rha/Fuc-(1→4)-[Glc/Gal-(1→2)]-Fuc- |
| NP-017676 | Quillaic acid | Gal-(1→2)-[Xyl-(1→3)]-GlcA- | Api-(1→3)-Xyl-(1→4)-[Glc-(1→3)]-Rha-(1→2)-[R-(→4)]-Fuc- (R = 5-O-[5-O-Ara/Api-3,5-dihydroxy-6-methyl-octanoyl]-3,5-dihydroxy-6-methyl-octanoic acid) |
| NP-017677 | Quillaic acid | Gal-(1→2)-[Xyl-(1→3)]-GlcA- | Api-(1→3)-Xyl-(1→4)-Rha-(1→2)-[R-(→4)]-Fuc- (R = 5-O-[5-O-Ara/Api-3,5-dihydroxy-6- |

TABLE A1-continued

Saponins displaying (late) endosomal/lysosomal escape enhancing activity, and saponins comprising a structure reminiscent to such saponins displaying (late) endosomal/lysosomal escape enhancing activity

| Saponin Name | Aglycon core | Carbohydrate substituent at the C-3beta-OH | Carbohydrate substituent at the C-28-OH group group |
|---|---|---|---|
| | | | methyl-octanoyl]-3,5-dihydroxy-6-methyl-octanoic acid) |
| NP-017706 | Quillaic acid | Gal-(1→2)-[Xyl-(1→3)]-GlcA- | Api-(1→3)-Xyl-(1→4)-Rha-(1→2)-[Rha-(1→3)]-4-OAc-Fuc- |
| NP-017705 | Quillaic acid | Gal-(1→2)-[Xyl-(1→3)]-GlcA- | Api-(1→3)-Xyl-(1→4)-Rha-(1→2)-[Rha-(1→3)]-4-OAc-Fuc- |
| NP-017773 | Quillaic acid | Gal-(1→2)-[Xyl-(1→3)]-GlcA- | 6-OAc-Glc-(1→3)-Xyl-(1→4)-Rha-(1→2)-[3-OAc-Rha-(1→3)]-Fuc- |
| NP-017775 | Quillaic acid | Gal-(1→2)-[Xyl-(1→3)]-GlcA- | Glc-(1→3)-Xyl-(1→4)-Rha-(1→2)-[3-OAc-Rha-(1→3)]-Fuc- |
| SA1657 | Quillaic acid | Gal-(1→2)-[Xyl-(1→3)]-GlcA- | Xyl-(1→3)-Xyl-(1→4)-Rha-(1→2)-[Qui-(1→4)]-Fuc- |
| AG2 | Quillaic acid | Gal-(1→2)-[Xyl-(1→3)]-GlcA- | Glc-(1→3)-[Xyl-(1→4)]-Rha-(1→2)-[Qui-(1→4)]-Fuc- |
| SO1861 | Quillaic acid | Gal-(1→2)-[Xyl-(1→3)]-GlcA- | Glc-(1→3)-Xyl-(1→4)-Rha-(1→2)-[Xyl-(1→3)-4-OAc-Qui-(1→4)]-Fuc- |
| GE1741 | Quillaic acid | Gal-(1→2)-[Xyl-(1→3)]-GlcA- | Xyl-(1→3)-Xyl-(1→4)-Rha-(1→2)-[3,4-di-OAc-Qui-(1→4)]-Fuc- |
| SO1542 | Quillaic acid | Gal-(1→2)-[Xyl-(1→3)]-GlcA- | Glc-(1→3)-[Xyl-(1→4)]-Rha-(1→2)-Fuc- |
| SO1584 | Quillaic acid | Gal-(1→2)-[Xyl-(1→3)]-GlcA- | 6-OAc-Glc-(1→3)-[Xyl-(1→4)]-Rha-(1→2)-Fuc- |
| SO1658 | Gypsogenin | Gal-(1→2)-[Xyl-(1→3)]-GlcA- | Glc-(1→3)-[Xyl-(1→3)-Xyl-(1→4)]-Rha-(1→2)-Fuc- |
| SO1674 | Quillaic acid | Gal-(1→2)-[Xyl-(1→3)]-GlcA- | Glc-(1→3)-[Xyl-(1→3)-Xyl-(1→4)]-Rha-(1→2)-Fuc- |
| SO1832 | Quillaic acid | Gal-(1→2)-[Xyl-(1→3)]-GlcA- | Xyl-(1→3)-Xyl-(1→4)-Rha-(1→2)-[Xyl-(1→3)-4-OAc-Qui-(1→4)]-Fuc- |
| QS-7 (also referred to as QS1861) | Quillaic acid | Gal-(1→2)-[Xyl-(1→3)]-GlcA- | Api/Xyl-(1→3)-Xyl-(1→4)-[Glc-(1→3)]-Rha-(1→2)-[Rha-(1→3)]-4OAc-Fuc- |
| QS-7 api (also referred to as QS1862) | Quillaic acid | Gal-(1→2)-[Xyl-(1→3)]-GlcA- | Api-(1→3)-Xyl-(1→4)-[Glc-(1→3)]-Rha-(1→2)-[Rha-(1→3)]-4OAc-Fuc- |
| QS-17 | Quillaic acid | Gal-(1→2)-[Xyl-(1→3)]-GlcA- | Api/Xyl-(1→3)-Xyl-(1→4)-[Glc-(1→3)]-Rha-(1→2)-[R-(→4)]-Fuc-(R = 5-O-[5-O-Rha-(1→2)-Ara/Api-3,5-dihydroxy-6-methyl-octanoyl]-3,5-dihydroxy-6-methyl-octanoic acid) |
| QS-18 | Quillaic acid | Gal-(1→2)-[Xyl-(1→3)]-GlcA- | Api/Xyl-(1→3)-Xyl-(1→4)-[Glc-(1→3)]-Rha-(1→2)-[R-(→4)]-Fuc-(R = 5-O-[5-O-Ara/Api-3,5-dihydroxy-6-methyl-octanoyl]-3,5-dihydroxy-6-methyl-octanoic acid) |

TABLE A1-continued

Saponins displaying (late) endosomal/lysosomal escape enhancing activity, and saponins comprising a structure reminiscent to such saponins displaying (late) endosomal/lysosomal escape enhancing activity

| Saponin Name | Aglycon core | Carbohydrate substituent at the C-3beta-OH | Carbohydrate substituent at the C-28-OH group group |
|---|---|---|---|
| QS-21 A-apio | Quillaic acid | Gal-(1→2)-[Xyl-(1→3)]-GlcA- | Api-(1→3)-Xyl-(1→4)-Rha-(1→2)-[R-(→4)]-Fuc-(R = 5-O-[5-O-Ara/Api-3,5-dihydroxy-6-methyl-octanoyl]-3,5-dihydroxy-6-methyl-octanoic acid) |
| QS-21 A-xylo | Quillaic acid | Gal-(1→2)-[Xyl-(1→3)]-GlcA- | Xyl-(1→3)-Xyl-(1→4)-Rha-(1→2)-[R-(→4)]-Fuc-(R = 5-O-[5-O-Ara/Api-3,5-dihydroxy-6-methyl-octanoyl]3,5-dihydroxy-6-methyl-octanoic acid) |
| QS-21 B-apio | Quillaic acid | Gal-(1→2)-[Xyl-(1→3)]-GlcA- | Api-(1→3)-Xyl-(1→4)-Rha-(1→2)-[R-(→3)]-Fuc-(R = 5-O-[5-O-Ara/Api-3,5-dihydroxy-6-methyl-octanoyl]3,5-dihydroxy-6-methyl-octanoic acid) |
| QS-21 B-xylo | Quillaic acid | Gal-(1→2)-[Xyl-(1→3)]-GlcA- | Xyl-(1→3)-Xyl-(1→4)-Rha-(1→2)-[R-(→3)]-Fuc-(R = 5-O-[5-O-Ara/Api-3,5-dihydroxy-6-methyl-octanoyl]3,5-dihydroxy-6-methyl-octanoic acid) |
| beta-Aescin (described: Aescin Ia) | Proto-aescigenin-21(2-methylbut-2-enoate)-22-acetat | Glc-(1→2)-[Glc-(1→4)]-GlcA- | — |
| Teaseed saponin I | 23-Oxo-barring-togenol C -21,22-bis(2-methylbut-2-enoate) | Glc-(1→2)-Ara-(1→3)-[Gal-(1→2)]-GlcA- | — |
| Teaseed-saponin J | 23-Oxo-barring-togenol C -21,22-bis(2-methylbut-2-enoate) | Xyl-(1→2)-Ara-(1→3)-[Gal-(1→2)]-GlcA- | — |
| Assam-saponin F | 23-Oxo-barring-togenol C -21(2-methylbut-2-enoate)-16,22-diacetat | Glc-(1→2)-Ara-(1→3)-[Gal-(1→2)]-GlcA- | — |
| Digitonin | Digitogenin | Glc-(1→3)-Gal-(1→2)-[Xyl-(1→3)]-Glc-(1→4)-Gal- | — |
| Primula acid 1 | 3,16,28-Trihydro-xyoleanan-12-en | Rha-(1→2)-Gal-(1→3)-[Glc-(1→2)]-GlcA- | — |

TABLE A1-continued

Saponins displaying (late) endosomal/lysosomal escape enhancing activity, and saponins comprising a structure reminiscent to such saponins displaying (late) endosomal/lysosomal escape enhancing activity

| Saponin Name | Aglycon core | Carbohydrate substituent at the C-3beta-OH | Carbohydrate substituent at the C-28-OH group group |
|---|---|---|---|
| AS64R | Gypsogenic acid | —<br>Carbohydrate substituent at the C-23-OH group | Glc-(1→3)-[Glc-(1→6)]-Gal- |
| AS6.2 | Gypsogenic acid | Gal- | Glc-(1→3)-[Glc-(1→6)]-Gal- |

[a], [b]Different names refer to different isolates of the same structure

[c], [d]Different names refer to different isolates of the same structure

TABLE A2

ADCs which were previously investigated in the human clinical setting, and subsequently retracted from further clinical investigation

| Drug Name | Indication | Target | Last Devel-opment Stage |
|---|---|---|---|
| Monoclonal Antibody Conjugate to Target EGFR for Oncology | Oncology | Cells Expressing Epidermal Growth Factor Receptor (Proto Oncogene c ErbB 1 or Receptor Tyrosine Protein Kinase erbB 1 or HER1 or ERBB1 or EGFR or EC 2.7.10.1) | Dis-covery |
| Affilutin | Multiple Myeloma (Kohler Disease) | | Dis-covery |
| IMGN-779 | Myelodys-plastic Syndrome | Cells Expressing Myeloid Cell Surface Antigen CD33 (Sialic Acid Binding Ig Like Lectin 3 or gp67 or CD33) | IND/CTA Filed |
| Neuradiab | Non-Hodgkin Lymphoma | Cells Expressing Tenascin (Cytotactin or GMEM or GP 150-225 or Glioma Associated Extracellular Matrix Antigen or Hexabrachion or JI or Myotendinous Antigen or Neuronectin or Tenascin C or TNC) | Phase I |
| IMGN-779 | Refractory Acute Myeloid Leukemia; Relapsed Acute Myeloid Leukemia | Cells Expressing Myeloid Cell Surface Antigen CD33 (Sialic Acid Binding Ig Like Lectin 3 or gp67 or CD33) | Phase I |
| AGS-67E | Acute Myelocytic Leukemia (AML, Acute Myeloblas-tic Leukemia) | Cells Expressing Leukocyte Antigen CD37 (Tetraspanin 26 or CD37) | Phase I |

TABLE A2-continued

ADCs which were previously investigated in the human clinical setting, and subsequently retracted from further clinical investigation

| Drug Name | Indication | Target | Last Devel-opment Stage |
|---|---|---|---|
| AGS-67E | Hairy Cell Leukemia; Non-Hodgkin Lymphoma; Refractory Chronic Lymphocy-tic Leukemia (CLL); Relapsed Chronic Lymphocy-tic Leukemia (CLL); T-Cell Leukemia | Cells Expressing Leukocyte Antigen CD37 (Tetraspanin 26 or CD37) | Phase I |
| ASG-15ME | Metastatic Transitional (Urothelial) Tract Cancer | Cells Expressing SLIT And NTRK Like Protein 6 (SLITRK6) | Phase I |
| vandortuzumab vedotin | Metastatic Hormone Refractory (Castration Resistant, Androgen-Indepen-dent) Prostate Cancer | Cells Expressing Metalloreductase STEAP1 (Six Transmembrane Epithelial Antigen Of The Prostate 1 or STEAP1 or EC 1.16.1.) | Phase I |
| CDX-014 | Ovarian Cancer | Cells Expressing Hepatitis A Virus Cellular Receptor 1 (Kidney Injury Molecule 1 or T Cell Immunoglobulin And Mucin Domain Containing Protein 1 or T-Cell Immunoglobulin Mucin Receptor 1 or T Cell Membrane Protein 1 or CD365 or HAVCR1) | Phase I |
| AGS-16M18 | Liver Cancer; Renal Cell Carcinoma | | Phase I |
| vorsetuzumab mafodotin | Non-Hodgkin Lymphoma; Renal Cell Carcinoma | Cells Expressing CD70 Antigen (CD27 Ligand or Tumor Necrosis Factor Ligand Superfamily Member 7 or CD70) | Phase I |
| denintuzumab mafodotin | Acute Lymph-ocytic Leukemia (ALL, Acute Lympho-blastic Leukemia); B-Cell Non-Hodgkin Lymphoma; Burkitt Lymphoma; Lympho-blastic Lymphoma; Mantle Cell Lymphoma | Cells Expressing B Lymphocyte Antigen CD19 (B Lymphocyte Surface Antigen B4 or Differentiation Antigen CD19 or T Cell Surface Antigen Leu 12 or CD19) | Phase I |
| SGN-CD70A | Diffuse Large B-Cell Lymphoma; Follicular Lymphoma; | Cells Expressing CD70 Antigen (CD27 Ligand or Tumor Necrosis Factor Ligand Superfamily Member | Phase I |

TABLE A2-continued

ADCs which were previously investigated in the human clinical setting, and subsequently retracted from further clinical investigation

| Drug Name | Indication | Target | Last Development Stage |
| --- | --- | --- | --- |
| | Mantle Cell Lymphoma; Metastatic Renal Cell Carcinoma; Non-Hodgkin Lymphoma | 7 or CD70) | |
| RG-7636 | Metastatic Melanoma | Endothelin B Receptor (Endothelin Receptor Non Selective Type or EDNRB) | Phase I |
| SC-006 | Metastatic Colorectal Cancer | | Phase I |
| MM-310 | Breast Cancer; Endome-trial Cancer; Esophageal Cancer; Gastric Cancer; Gastroeso-phageal (GE) Junction Carcino-mas; Head And Neck Cancer Squamous Cell Carcinoma; Non-Small Cell Lung Cancer; Ovarian Cancer; Pancreatic Ductal Adenocar-cinoma; Prostate Cancer; Small-Cell Lung Cancer; Soft Tissue Sarcoma; Solid Tumor; Transitional Cell Carcinoma (Urothelial Cell Carcinoma) | Ephrin Type A Receptor 2 (Epithelial Cell Kinase or Tyrosine Protein Kinase Receptor ECK or EPHA2 or EC 2.7.10.1) | Phase I |
| PF-06647263 | Metastatic Breast Cancer; Ovarian Cancer | Cells Expressing Ephrin A4 (EPH Related Receptor Tyrosine Kinase Ligand 4 or EFNA4) | Phase I |
| PF-06263507 | Solid Tumor | Cells Expressing Trophoblast Glycoprotein (M6P1 or 5T4 Oncofetal Antigen or 5T4 Oncofetal Trophoblast Glycoprotein or Wnt Activated Inhibitory Factor 1 or TPBG) | Phase I |
| PF-06650808 | Metastatic Breast Cancer; Non-Small Cell Lung Cancer; | Cells Expressing Neurogenic Locus Notch Homolog Protein 3 (NOTCH3) | Phase I |

TABLE A2-continued

ADCs which were previously investigated in the human clinical setting, and subsequently retracted from further clinical investigation

| Drug Name | Indication | Target | Last Development Stage |
| --- | --- | --- | --- |
| | Ovarian Cancer | | |
| XMT-1522 | Breast Cancer; Gastric Cancer; Non-Small Cell Lung Cancer | Receptor Tyrosine Protein Kinase ERBB 2 (Metastatic Lymph Node Gene 19 Protein or Proto Oncogene Neu or Proto Oncogene C ErbB 2 or Tyrosine Kinase Type Cell Surface Receptor HER2 or p185erbB2 or HER2 or CD340 or ERBB2 or EC 2.7.10.1); Tubulin | Phase I |
| AMG-595 | Anaplastic Astrocyto-ma; Recurrent Glioblasto-ma Multiforme (GBM) | Cells Expressing Epidermal Growth Factor Receptor (Proto Oncogene c ErbB 1 or Receptor Tyrosine Protein Kinase erbB 1 or HER1 or ERBB1 or EGFR or EC 2.7.10.1) | Phase I |
| pinatuzumab vedotin | Chronic Lymphocytic Leukemia (CLL) | Cells Expressing B Cell Receptor CD22 (B Lymphocyte Cell Adhesion Molecule or Sialic Acid Binding Ig Like Lectin 2 or T Cell Surface Antigen Leu 14 or CD22) | Phase I |
| cantuzumab ravtansine | Colorectal Cancer; Non-Small Cell Lung Cancer; Pancreatic Cancer; Solid Tumor | | Phase I |
| AVE-9633 | Acute Myelocytic Leukemia (AML, Acute Myeloblas-tic Leukemia) | Cells Expressing Myeloid Cell Surface Antigen CD33 (Sialic Acid Binding Ig Like Lectin 3 or gp67 or CD33) | Phase I |
| BIWI-1[(1)] | Breast Cancer; Carcino-mas; Esophageal Cancer; Head And Neck Cancer Squamous Cell Carcinoma | Cells Expressing CD44 Antigen (CDw44 or Epican or Extracellular Matrix Receptor III or GP90 Lymphocyte Homing/Adhesion Receptor or HUTCH I or Heparan Sulfate Proteoglycan or Hermes Antigen or Hyaluronate Receptor or Phagocytic Glycoprotein 1 or CD44) | Phase I |
| RG-7882 | Epithelial Ovarian Cancer; Fallopian Tube Cancer; Pancreatic Cancer; Peritoneal Cancer | Cells Expressing Mucin 16 (Ovarian Cancer Related Tumor Marker CA125 or Ovarian Carcinoma Antigen CA125 or MUC16) | Phase I |
| ASG-5ME | Adenocar-cinoma; Hormone Refractory | Cells Expressing Choline Transporter Like Protein 4 (Solute | Phase I |

TABLE A2-continued

ADCs which were previously investigated in the human clinical setting, and subsequently retracted from further clinical investigation

| Drug Name | Indication | Target | Last Development Stage |
|---|---|---|---|
| | (Castration Resistant, Androgen-Independent) Prostate Cancer; Metastatic Adenocarcinoma of The Pancreas | Carrier Family 44 Member 4 or SLC44A4) | |
| DCDS-0780A | B-Cell Non-Hodgkin Lymphoma | | Phase I |
| SC-004 | Endome-trial Cancer; Epithelial Ovarian Cancer; Fallopian Tube Cancer; Peritoneal Cancer | | Phase I |
| RG-7600 | Ovarian Cancer; Pancreatic Ductal Adenocarcinoma | | Phase I |
| sofituzumab vedotin | Epithelial Ovarian Cancer; Fallopian Tube Cancer; Ovarian Cancer; Pancreatic Cancer; Peritoneal Cancer | Cells Expressing Mucin 16 (Ovarian Cancer Related Tumor Marker CA125 or Ovarian Carcinoma Antigen CA125 or MUC16) | Phase I |
| IMGN-289 | Breast Cancer; Esophageal Cancer; Gastric Cancer; Head And Neck Cancer Squamous Cell Carcinoma; Non-Small Cell Lung Cancer; Solid Tumor | Cells Expressing Epidermal Growth Factor Receptor (Proto Oncogene c ErbB 1 or Receptor Tyrosine Protein Kinase erbB 1 or HER1 or ERBB1 or EGFR or EC 2.7.10.1) | Phase I |
| SAR-428926 | Breast Cancer; Colorectal Cancer; Gastric Cancer; Non-Small Cell Lung Cancer; Ovarian Cancer; Prostate Cancer; Solid Tumor | Cells Expressing Lysosome Associated Membrane Glycoprotein 1 (CD107 Antigen Like Family Member A or CD107a or LAMP1) | Phase I |
| SGNCD-19B | B-Cell Non-Hodgkin Lymphoma; Diffuse Large B-Cell Lymphoma; Follicular Lymphoma | Cells Expressing B Lymphocyte Antigen CD19 (B Lymphocyte Surface Antigen B4 or Differentiation Antigen CD19 or T Cell Surface Antigen Leu 12 or CD19) | Phase I |
| SGNCD-123A | Refractory Acute Myeloid Leukemia; Relapsed Acute Myeloid Leukemia | Cells Expressing Interleukin 3 Receptor Subunit Alpha (CD123 or IL3RA) | Phase I |
| SGNCD-352A | Refractory Multiple Myeloma; Relapsed Multiple Myeloma | Cells Expressing SLAM Family Member 6 (Activating NK Receptor or NK T B Antigen or CD352 or SLAMF6) | Phase I |
| RG-7841 | Breast Cancer; Non-Small Cell Lung Cancer; Solid Tumor | Cells Expressing Lymphocyte Antigen 6E (Retinoic Acid Induced Gene E Protein or Stem Cell Antigen 2 or Thymic Shared Antigen 1 or LY6E) | Phase I |
| IMGN-388 | Solid Tumor | Cells Expressing Integrin Alpha V (Vitronectin Receptor Subunit Alpha or CD51 or ITGAV) | Phase I |
| lorvotuzumab mertansine | Refractory Multiple Myeloma; Relapsed Multiple Myeloma | Cells Expressing Neural Cell Adhesion Molecule 1 (Antigen Recognized By Monoclonal Antibody 5.1H11 or CD56 or NCAM1) | Phase I |
| lorvotuzumab mertansine | Neuroendocrine Carcinoma; Neuroendocrine Tumors; Non-Small Cell Lung Cancer; Ovarian Cancer; Skin Cancer | Cells Expressing Neural Cell Adhesion Molecule 1 (Antigen Recognized By Monoclonal Antibody 5.1H11 or CD56 or NCAM1) | Phase I |
| BAY-794620 | Lung Cancer; Solid Tumor | Cells Expressing Carbonic Anhydrase 9 (Carbonate Dehydratase IX or pMW1 or Membrane Antigen MN or P54/58N or Renal Cell Carcinoma Associated Antigen G250 or CA9 or EC 4.2.1.1) | Phase I |
| RG-7598 | Refractory Multiple Myeloma; Relapsed Multiple Myeloma | | Phase I |
| Oncolysin B | B-Cell Leukemia; Lymphoma | Cells Expressing B Lymphocyte Antigen CD19 (B Lymphocyte Surface Antigen B4 or Differentiation Antigen CD19 or T Cell Surface Antigen Leu 12 or CD19) | Phase I |
| ADCT-502[(1)] | Bladder Cancer; Breast Cancer; Esophageal | Cells Expressing Receptor Tyrosine Protein Kinase ERBB 2 (Metastatic Lymph | Phase I |

TABLE A2-continued

ADCs which were previously investigated in the human clinical setting, and subsequently retracted from further clinical investigation

| Drug Name | Indication | Target | Last Devel-opment Stage |
|---|---|---|---|
| | Cancer; Gastric Cancer; Non-Small Cell Lung Cancer | Node Gene 19 Protein or Proto Oncogene Neu or Proto Oncogene C ErbB 2 or Tyrosine Kinase Type Cell Surface Receptor HER2 or p185erbB2 or HER2 or CD340 or ERBB2 or EC 2.7.10.1) | |
| AMG-172 | Renal Cell Carcinoma | Cells Expressing CD70 Antigen (CD27 Ligand or Tumor Necrosis Factor Ligand Superfamily Member 7 or CD70) | Phase I |
| ImmuRAIT-LL2 | B-Cell Non-Hodgkin Lymphoma | Cells Expressing B Cell Receptor CD22 (B Lymphocyte Cell Adhesion Molecule or Sialic Acid Binding Ig Like Lectin 2 or T Cell Surface Antigen Leu 14 or CD22) | Phase I/II |
| indusatumab vedotin | Adenocar-cinoma Of The Gastroe-sophageal Junction; Gastric Cancer | Cells Expressing Heat Stable Enterotoxin Receptor (Guanylyl Cyclase C or or Intestinal Guanylate Cyclase or GUCY2C or EC 4.6.1.2) | Phase I/II |
| clivatuzumab tetraxetan | Pancreatic Cancer | Cells Expressing Mucin 1 (Breast Carcinoma Associated Antigen DF3 or Episialin or H23AG or Krebs Von Den Lungen 6 or PEMT or Peanut Reactive Urinary Mucin or Polymorphic Epithelial Mucin or Tumor Associated Epithelial Membrane Antigen or Tumor Associated Mucin or CD227 or MUC1) | Phase I/II |
| depatuxizumab mafodotin[(2)] | Recurrent Malignant Glioma | Epidermal Growth Factor Receptor (Proto Oncogene c ErbB 1 or Receptor Tyrosine Protein Kinase erbB 1 or HER1 or ERBB1 or EGFR or EC 2.7.10.1) | Phase I/II |
| CDX-014 | Metastatic Renal Cell Carcinoma; Papillary Renal Cell Carcinoma | Cells Expressing Hepatitis A Virus Cellular Receptor 1 (Kidney Injury Molecule 1 or T Cell Immunoglobulin And Mucin Domain Containing Protein 1 or T-Cell Immunoglobulin Mucin Receptor 1 or T Cell Membrane Protein 1 or CD365 or HAVCR1) | Phase I/II |
| vadastuximab talirine(1) | Refractory Acute Myeloid Leukemia; Relapsed Acute Myeloid Leukemia | Cells Expressing Myeloid Cell Surface Antigen CD33 (Sialic Acid Binding Ig Like Lectin 3 or gp67 or CD33) | Phase I/II |
| vadastuximab talirine | Myelodys-plastic Syndrome | Cells Expressing Myeloid Cell Surface Antigen CD33 (Sialic Acid Binding Ig Like Lectin 3 or gp67 or CD33) | Phase I/II |
| MLN-2704 | Metastatic Hormone Refractory (Castration Resistant, Androgen-Indepen-dent) Prostate Cancer | Cells Expressing Glutamate Carboxypeptidase 2 (Folate Hydrolase 1 or Prostate Specific Membrane Antigen or PSMA or Pteroylpoly Gamma Glutamate Carboxypeptidase or Cell Growth Inhibiting Gene 27 Protein or FOLH1 or EC 3.4.17.21) | Phase I/II |
| Oncolysin B | AIDS-Related Lymphoma | Cells Expressing B Lymphocyte Antigen CD19 (B Lymphocyte Surface Antigen B4 or Differentiation Antigen CD19 or T Cell Surface Antigen Leu 12 or CD19) | Phase I/II |
| coltuximab ravtansine | Diffuse Large B-Cell Lymphoma | Cells Expressing B Lymphocyte Antigen CD19 (B Lymphocyte Surface Antigen B4 or Differentiation Antigen CD19 or T Cell Surface Antigen Leu 12 or CD19) | Phase II |
| coltuximab ravtansine | Acute Lymphocy-tic Leukemia Acute Lympho-blastic Leukemia) | (ALL, Cells Expressing B Lymphocyte Antigen CD19 (B Lymphocyte Surface Antigen B4 or Differentiation Antigen CD19 or T Cell Surface Antigen Leu 12 or CD19) | Phase II |
| coltuximab ravtansine | Diffuse Large B-Cell Lymphoma | Cells Expressing B Lymphocyte Antigen CD19 (B Lymphocyte Surface Antigen B4 or Differentiation Antigen CD19 or T Cell Surface Antigen Leu 12 or CD19) | Phase II |
| indusatumab vedotin[(2)] | Adenocar-cinoma Of The Gastroe-sophageal Junction; Gastric Cancer; Metastatic Adenocar-cinoma of The Pancreas | Cells Expressing Heat Stable Enterotoxin Receptor (Guanylyl Cyclase C or or Intestinal Guanylate Cyclase or GUCY2C or EC 4.6.1.2) | Phase II |
| depatuxizumab mafodotin | Squamous Non-Small Cell Lung | Epidermal Growth Factor Receptor (Proto Oncogene c ErbB 1 or Receptor Tyrosine | Phase II |

TABLE A2-continued

ADCs which were previously investigated in the human clinical setting, and subsequently retracted from further clinical investigation

| Drug Name | Indication | Target | Last Devel-opment Stage |
|---|---|---|---|
| | Cancer | Protein Kinase erbB 1 or HER1 or ERBB1 or EGFR or EC 2.7.10.1) | |
| depatuxizumab mafodotin[2] | Anaplastic Astrocyto-ma; Anaplastic Oligoastro-cytoma; Gliosar-coma; High-Grade Glioma; Oligoden-droglioma; Pediatric Diffuse Intrinsic Pontine Glioma; Recurrent Glioblasto-ma Multiforme (GBM) | Epidermal Growth Factor Receptor (Proto Oncogene c ErbB 1 or Receptor Tyrosine Protein Kinase erbB 1 or HER1 or ERBB1 or EGFR or EC 2.7.10.1) | Phase II |
| lifastuzumab vedotin | Non-Small Cell Lung Cancer | Sodium Dependent Phosphate Transport Protein 2B (Sodium Phosphate Transport Protein 2B or NaPi3b or Sodium/Phosphate Cotransporter 2B or NaPi 2b or Solute Carrier Family 34 Member 2 or SLC34A2) | Phase II |
| lifastuzumab vedotin | Ovarian Cancer | Sodium Dependent Phosphate Transport Protein 2B (Sodium Phosphate Transport Protein 2B or NaPi3b or Sodium/Phosphate Cotransporter 2B or NaPi 2b or Solute Carrier Family 34 Member 2 or SLC34A2) | Phase II |
| Bismab-A | Acute Myelocytic Leukemia (AML, Acute Myeloblas-tic Leukemia) | Cells Expressing Myeloid Cell Surface Antigen CD33 (Sialic Acid Binding Ig Like Lectin 3 or gp67 or CD33) | Phase II |
| denintuzumab mafodotin | Diffuse Large B-Cell Lymphoma; Follicular Lymphoma | Cells Expressing B Lymphocyte Antigen CD19 (B Lymphocyte Surface Antigen B4 or Differentiation Antigen CD19 or T Cell Surface Antigen Leu 12 or CD19) | Phase II |
| Avicidin[1] | Colorectal Cancer; Prostate Cancer | Cells Expressing Epithelial Cell Adhesion Molecule (Adenocarcinoma Associated Antigen or Cell Surface Glycoprotein Trop 1 or Epithelial Cell Surface Antigen or Epithelial Glycoprotein 314 or KS 1/4 Antigen or KSA or Tumor Associated Calcium Signal Transducer 1 or CD326 or EPCAM) | |
| pinatuzumab vedotin | Diffuse Large B-Cell Lymphoma; Follicular Lymphoma | Cells Expressing B Cell Receptor CD22 (B Lymphocyte Cell Adhesion Molecule or Sialic Acid Binding Ig Like Lectin 2 or T Cell Surface Antigen Leu 14 or CD22) | Phase II |
| SGN-15 | Metastatic Breast Cancer; Non-Small Cell Lung Cancer; Ovarian Cancer; Prostate Cancer | Cells Expressing Lewis Y Antigen (CD174) | Phase II |
| cantuzumab ravtansine | Gastric Cancer; Gastroe-sophageal (GE) Junction Carcino-mas | | Phase II |
| ASP-6183 | Ovarian Cancer | | Phase II |
| SAR-566658 | Metastatic Breast Cancer | Cells Expressing Sialoglycotope CA6 Antigen | Phase II |
| Oncolysin S | Small-Cell Lung Cancer | Cells Expressing Neural Cell Adhesion Molecule 1 (Antigen Recognized By Monoclonal Antibody 5.1H11 or CD56 or NCAM1) | Phase II |
| lorvotuzumab mertansine | Small-Cell Lung Cancer | Cells Expressing Neural Cell Adhesion Molecule 1 (Antigen Recognized By Monoclonal Antibody 5.1H11 or CD56 or NCAM1) | Phase II |
| glembatumumab vedotin | Metastatic Melanoma; Metastatic Uveal Melanoma; Osteosar-coma; Squamous Non-Small Cell Lung Cancer | Cells Expressing Transmembrane Glycoprotein NMB (Transmembrane Glycoprotein HGFIN or GPNMB) | Phase II |
| MM-302 | Metastatic Breast Cancer | Cells Expressing Receptor Tyrosine Protein Kinase ERBB 2 (Metastatic Lymph Node Gene 19 Protein or Proto Oncogene Neu or Proto Oncogene C ErbB 2 or Tyrosine Kinase | Phase II/III |

TABLE A2-continued

ADCs which were previously investigated in the human clinical setting, and subsequently retracted from further clinical investigation

| Drug Name | Indication | Target | Last Development Stage |
|---|---|---|---|
| | | Type Cell Surface Receptor HER2 or p185erbB2 or HER2 or CD340 or ERBB2 or EC 2.7.10.1) | |
| Neuradiab | Brain Cancer; Glioblasto-ma Multiforme (GBM) | Cells Expressing Tenascin (Cytotactin or GMEM or GP 150-225 or Glioma Associated Extracellular Matrix Antigen or Hexabrachion or JI or Myotendinous Antigen or Neuronectin or Tenascin C or TNC) | Phase III |
| clivatuzumab tetraxetan | Metastatic Adenocar-cinoma of The Pancreas | Cells Expressing Mucin 1 (Breast Carcinoma Associated Antigen DF3 or Episialin or H23AG or Krebs Von Den Lungen 6 or PEMT or Peanut Reactive Urinary Mucin or Polymorphic Epithelial Mucin or Tumor Associated Epithelial Membrane Antigen or Tumor Associated Mucin or CD227 or MUC1) | Phase III |
| depatuxizumab mafodotin(2) | Glioblasto-ma Multiforme (GBM) | Epidermal Growth Factor Receptor (Proto Oncogene c ErbB 1 or Receptor Tyrosine Protein Kinase erbB 1 or HER1 or ERBB1 or EGFR or EC 2.7.10.1) | Phase III |
| vadastuximab talirine(1) | Acute Myelocytic Leukemia (AML, Acute Myeloblas-tic Leukemia) | Cells Expressing Myeloid Cell Surface Antigen CD33 (Sialic Acid Binding Ig Like Lectin 3 or gp67 or CD33) | Phase III |
| glembatumumab vedotin(2) | Metastatic Breast Cancer | Cells Expressing Transmembrane Glycoprotein NMB (Transmembrane Glycoprotein HGFIN or GPNMB) | Phase III |
| Oncolysin B | B-Cell Leukemia; Lymphoma | Cells Expressing B Lymphocyte Antigen CD19 (B Lymphocyte Surface Antigen B4 or Differentiation Antigen CD19 or T Cell Surface Antigen Leu 12 or CD19) | Phase III |
| ImmuRAIT-LL2 | B-Cell Leukemia | Cells Expressing B Cell Receptor CD22 (B Lymphocyte Cell Adhesion Molecule or Sialic Acid Binding Ig Like Lectin 2 or T Cell Surface Antigen Leu 14 or CD22) | Pre-clinical |

TABLE A2-continued

ADCs which were previously investigated in the human clinical setting, and subsequently retracted from further clinical investigation

| Drug Name | Indication | Target | Last Development Stage |
|---|---|---|---|
| indusatumab vedotin | Metastatic Colorectal Cancer | Cells Expressing Heat Stable Enterotoxin Receptor (Guanylyl Cyclase C or or Intestinal Guanylate Cyclase or GUCY2C or EC 4.6.1.2) | Pre-clinical |
| ASG-15ME | Lung Cancer | Cells Expressing SLIT And NTRK Like Protein 6 (SLITRK6) | Pre-clinical |
| HTI-1511 | Bile Duct Cancer (Cholangio-carcinoma) ; Breast Cancer; Colorectal Cancer; Non-Small Cell Lung Cancer | Cells Expressing Epidermal Growth Factor Receptor (Proto Oncogene c ErbB 1 or Receptor Tyrosine Protein Kinase erbB 1 or HER1 or ERBB1 or EGFR or EC 2.7.10.1) | Pre-clinical |
| ZW-33 | Gastric Cancer; Metastatic Breast Cancer | Cells Expressing Receptor Tyrosine Protein Kinase ERBB 2 (Metastatic Lymph Node Gene 19 Protein or Proto Oncogene Neu or Proto Oncogene C ErbB 2 or Tyrosine Kinase Type Cell Surface Receptor HER2 or p185erbB2 or HER2 or CD340 or ERBB2 or EC 2.7.10.1) | Pre-clinical |
| ZW-33 | Ovarian Cancer | Cells Expressing Receptor Tyrosine Protein Kinase ERBB 2 (Metastatic Lymph Node Gene 19 Protein or Proto Oncogene Neu or Proto Oncogene C ErbB 2 or Tyrosine Kinase Type Cell Surface Receptor HER2 or p185erbB2 or HER2 or CD340 or ERBB2 or EC 2.7.10.1) | Pre-clinical |
| SGNCD-352A | Non-Hodgkin Lymphoma | Cells Expressing SLAM Family Member 6 (Activating NK Receptor or NK T B Antigen or CD352 or SLAMF6) | Pre-clinical |
| HuMax-CD74-ADC | Oncology | Cells Expressing HLA Class II Histocompatibility Antigen Gamma Chain (HLA DR Antigens Associated Invariant Chain or la Antigen Associated Invariant Chain or p33 or CD74) | Pre-clinical |
| sacituzumab govitecan | Pancreatic Ductal Adenocar-cinoma | Cells Expressing Tumor Associated Calcium Signal Transducer 2 (Cell Surface Glycoprotein Trop 2 or Membrane Component Chromosome 1 Surface Marker 1 or Pancreatic | |

TABLE A2-continued

ADCs which were previously investigated in the human clinical setting, and subsequently retracted from further clinical investigation

| Drug Name | Indication | Target | Last Development Stage |
|---|---|---|---|
| | | Carcinoma Marker Protein GA733-1 or TACSTD2) | |
| sacituzumab govitecan | Adenocarcinoma; Colorectal Cancer; Endome-trial Cancer; Epithelial Ovarian Cancer; Esophageal Cancer; Follicular Thyroid Cancer; Gastric Cancer; Glioblasto-ma Multiforme (GBM); Head And Neck Cancer Squamous Cell Carcinoma; Hepato-cellular Carcinoma; Kidney Cancer (Renal Cell Cancer); Metastatic Hormone Refractory (Castration Resistant, Androgen-Indepen-dent) Prostate Cancer; Metastatic Transitional (Urothelial) Tract Cancer; Transitional Cell Cancer (Urothelial Cell Cancer) | Cervical Cancer; Cells Expressing Tumor Associated Calcium Signal Transducer 2 (Cell Surface Glycoprotein Trop 2 or Membrane Component Chromosome 1 Surface Marker 1 or Pancreatic Carcinoma Marker Protein GA733-1 or TACSTD2) | |
| sacituzumab govitecan | Hepato-cellular Carcinoma | Cells Expressing Tumor Associated Calcium Signal Transducer 2 (Cell Surface Glycoprotein Trop 2 or Membrane Component Chromosome 1 Surface Marker 1 or Pancreatic Carcinoma Marker Protein GA733-1 or TACSTD2) | |
| sacituzumab govitecan | Metastatic Breast Cancer; Transitional Cell Cancer (Urothelial Cell Cancer) | Cells Expressing Tumor Associated Calcium Signal Transducer 2 (Cell Surface Glycoprotein Trop 2 or Membrane Component Chromosome 1 Surface Marker 1 or Pancreatic Carcinoma Marker Protein GA733-1 or TACSTD2) | |
| sacituzumab govitecan | Non-Small Cell Lung Cancer; Small-Cell Lung Cancer | Cells Expressing Tumor Associated Calcium Signal Transducer 2 (Cell Surface Glycoprotein Trop 2 or Membrane Component Chromosome 1 Surface Marker 1 or Pancreatic Carcinoma Marker Protein GA733-1 or TACSTD2) | |
| sacituzumab govitecan | Metastatic Breast Cancer | Cells Expressing Tumor Associated Calcium Signal Transducer 2 (Cell Surface Glycoprotein Trop 2 or Membrane Component Chromosome 1 Surface Marker 1 or Pancreatic Carcinoma Marker Protein GA733-1 or TACSTD2) | |

(1) Discontinued due to adverse events
(2) Discontinued due to lack of efficacy

TABLE A3

ADCs that reached phase III clinical development

| Drug Name | Indication | Development Stage | Last Development Stage | Reason for Discontinuation |
|---|---|---|---|---|
| trastuzumab emtansine | Gastric Cancer | Marketed | Phase II/III | Unspecified |
| MM-302 | Metastatic Breast Cancer | Discontinued | Phase II/III | Business/Strategic Decision |
| trastuzumab emtansine | Metastatic Breast Cancer | Marketed | Phase III | Unspecified |

TABLE A3-continued

ADCs that reached phase III clinical development

| Drug Name | Indication | Development Stage | Last Development Stage | Reason for Discontinuation |
|---|---|---|---|---|
| trastuzumab emtansine | Gastric Cancer | Marketed | Phase III | Unspecified |
| ibritumomab tiuxetan | Diffuse Large B-Cell Lymphoma | Marketed | Phase III | |
| inotuzumab ozogamicin | Follicular Lymphoma | Marketed | Phase III | |
| inotuzumab ozogamicin | Diffuse Large B-Cell Lymphoma; Non-Hodgkin Lymphoma | Marketed | Phase III | Lack of Efficacy |
| rovalpituzumab tesirine | Small-Cell Lung Cancer | Phase III | Phase III | |
| rovalpituzumab tesirine | Small-Cell Lung Cancer | Phase III | Phase III | |
| Neuradiab | Brain Cancer; Glioblastoma Multiforme (GBM) | Inactive | Phase III | Unspecified |
| clivatuzumab tetraxetan | Metastatic Adenocarcinoma of The Pancreas | Inactive | Phase III | Unspecified |
| depatuxizumab mafodotin | Glioblastoma Multiforme (GBM) | Inactive | Phase III | Lack of Efficacy |
| vadastuximab talirine | Acute Myelocytic Leukemia (AML, Acute Myeloblastic Leukemia) | Discontinued | Phase III | Adverse Events |
| glembatumumab vedotin | Metastatic Breast Cancer | Discontinued | Phase III | Lack of Efficacy |
| Oncolysin B | B-Cell Leukemia; Lymphoma | Discontinued | Phase III | Business/Strategic Decision |

TABLE A4

Tumor-specific cell-surface receptor targets which can be targeted by a cell-surface molecule targeting molecule of the invention such as immunoglobulins according to the invention, and antibodies that can be used for the AOC-saponin conjugates of the invention, ADC-saponin conjugates of the invention (not presented as a limitation; further immunoglobulins are equally suitable for the invention)

| Target cell-surface receptor | Example monoclonal antibodies |
|---|---|
| HER2 | anti-HER2 monoclonal antibody such as trastuzumab and pertuzumab |
| CD20 | anti-CD20 monoclonal antibody such as rituximab, ofatumumab, tositumomab and ibritumomab |
| CA125 | anti-CA125 monoclonal antibody such as oregovomab |
| EpCAM (17-1A) | anti-EpCAM (17-1A) monoclonal antibody such as edrecolomab |
| EGFR | anti-EGFR monoclonal antibody such as cetuximab, panitumumab and nimotuzumab |
| CD30 | anti-CD30 monoclonal antibody such brentuximab |
| CD33 | anti-CD33 monoclonal antibody such as gemtuzumab and huMy9-6 |
| vascular integrin alpha-v beta-3 | anti-vascular integrin alpha-v beta-3 monoclonal antibody such as etaracizumab |
| CD52 | anti-CD52 monoclonal antibody such as alemtuzumab |
| CD22 | anti-CD22 monoclonal antibody such as epratuzumab |
| CEA | anti-CEA monoclonal antibody such as labetuzumab |
| CD44v6 | anti-CD44v6 monoclonal antibody such as bivatuzumab |
| FAP | anti- FAP monoclonal antibody such as sibrotuzumab |
| CD19 | anti-CD19 monoclonal antibody such as huB4 |
| CanAg | anti-CanAg monoclonal antibody such as huC242 |
| CD56 | anti-CD56 monoclonal antibody such huN901 |
| CD38 | anti-CD38 monoclonal antibody such as daratu-mumab |
| CA6 | anti-CA6 monoclonal antibody such as DS6 |
| IGF-IR | anti-IGF-IR monoclonal antibody such as cixutumumab and 3B7 |
| integrin | anti-integrin monoclonal antibody such as CNTO 95 |
| syndecan-1 | anti-syndecan-1 monoclonal antibody such as B-B4 |

TABLE A5

RIPs from plants*

| Plant Family | Plant Species | Proteins | Classification |
|---|---|---|---|
| Adoxaceae | *Sambucus ebulus L.* | Ebulitin α, Ebulitin β, Ebulitin γ | RIP 1 |
| | | Ebulin f, Ebulin l, Ebulin r1, Ebulin r2, SEA | RIP 2 |
| | | SEAII, SELfd, SELld, SELlm | lectin |

TABLE A5-continued

| RIPs from plants* | | | |
|---|---|---|---|
| Plant Family | Plant Species | Proteins | Classification |
| | *Sambucus nigra L.* | α-Nigritin, β-Nigritin, γ-Nigritin, Nigritin f1, Nigritin f2 | RIP 1 |
| | | basic Nigrin b, Nigrin b = SNA-V, Nigrin f = SNA-Vf, Nigrin l1, Nigrin l2, Nigrin s, SNA-I, SNA-I', SNA-If, SNAflu-I, SNLRP1, SNLRP2 | RIP 2 |
| | | SNA-ld, SNA-lm, SNA-II, SNA-III, SNA-IV = SNA-IVf, SNA-IVl, SNApol-I, SNApol-II, TrSNA-I, TrSNA-If | lectin |
| | *Sambucus racemosa L.* | basic racemosin b, SRA | RIP 2 |
| | | SRLbm = SRAbm | lectin |
| | *Sambucus sieboldiana* (Miq.) Blume ex Graebn. | SSA = SSA-b-1, Sieboldin-b = SSA-b-2 | RIP 2 |
| | | SSA-b-3, SSA-b-4 | lectin |
| Aizoaceae | *Mesembryanthe-mum crystallinum L.* | RIP1 | RIP 1 |
| Amaranthaceae | *Amaranthus caudatus L.* | Amaranthin = ACA | lectin |
| | *Amaranthus cruentus L.* | ACL | lectin |
| | *Amaranthus hypochondriacus L.* [Syn.: *Amaranthus leucocarpus* S. Watson] | *A. leucocarpus* lectin | lectin |
| | *Amaranthus mangostanus L.* | Amaramangin | RIP 1 |
| | *Amaranthus* tricolor L. | AAP-27 | RIP 1 |
| | *Amaranthus viridis L.* | Amaranthin | RIP 1 |
| | Beta *vulgaris L.* | Beetin-27 = BE27, Beetin-29 = BE29, Betavulgin | RIP 1 |
| | *Celosia argentea L.* [Syn.: *Celosia cristata L.*] | CCP-25, CCP-27 | RIP 1 |
| | Chenopodium album L. | CAP30 | RIP 1 |
| | *Spinacia oleracea L.* | SoRIP1 = BP31 | RIP 1 |
| | | SoRIP2 | RIP 1 candidate |
| Araliaceae | *Aralia elata* (Miq.) Seem. | Aralin | RIP 2 |
| | Panax ginseng C.A. Mey | Panaxagin | peculiar RIP 1 candidate/RNase |
| | *Panax quinquefolius L.* | Quinqueginsin | peculiar RIP 1 candidate/RNase |
| Asparagaceae | *Asparagus officinalis L.* | Asparin 1, Asparin 2 | RIP 1 |
| | *Drimia maritima* (L.) Stearn [Syn.: *Charybdis maritima* (L.) Speta] | Charybdin | RIP 1 |
| | *Muscari armeniacum* Leichtlin ex Baker | Musarmin 1, Musarmin 2, Musarmin 3, Musarmin 4 | RIP 1 |
| | *Polygonatum multiflorum* (L.) All. | PMRIPm, PMRIPt | RIP 2 |
| | *Yucca gloriosa* var. *tristis* Carrière [Syn.: *Yucca recurvifolia* Salisb.] | *Yucca* leaf protein = YLP | RIP 1 |
| Basellaceae | *Basella rubra L.* | Basella RIP 2a, Basella RIP 2b, Basella RIP 3 | RIP 1 |
| Caryophyllaceae | *Agrostemma githago L.* | Agrostin 2, Agrostin 5, Agrostin 6, Agrostin | RIP 1 |
| | *Dianthus barbatus L.* | Dianthin 29 | RIP 1 |
| | *Dianthus caryophyllus L.* | Dianthin 30, Dianthin 32 | RIP 1 |
| | *Dianthus chinensis L.* [Syn.: *Dianthus sinensis* Link] | *D. sinensis* RIP | RIP 1 |
| | *Gypsophila elegans* M. Bieb. | Gypsophilin | RIP 1 |
| | *Silene chalcedonica (L.)* E.H.L. Krause [Syn.: *Lychnis chalcedonica L.*] | Lychnin | RIP 1 |
| | *Silene glaucifolia* Lag. [Syn.: *Petrocoptis glaucifolia* (Lag.) Boiss.] | Petroglaucin 1, Petroglaucin 2 | RIP 1 |
| | *Silene laxipruinosa* Mayol & Rosselló [Syn.: *Petrocoptis grandiflora* Rothm.] | Petrograndin | RIP 1 |
| | *Saponaria ocymoides L.* | Ocymoidin | RIP 1 |
| | *Saponaria officinalis L.* | Saporin-L1 = SO-L1, Saporin-L2 = SO-L2, Saporin-L3 = SO-L3, Saporin-I = SO-I = SO-4, Saporin-R1 = SO-R1, Saporin-R2 = SO-R2, Saporin-R3 = SO-R3, SO3a, SO3b, Saporin-S5 = Saporin 5 = SO-S5, Saporin-S6 = Saporin 6 = SO-6 = SO-S6, Saporin-S8 = SO-S8, Saporin-S9 = Saporin 9 = SO-S9, SAP-C, SAP-S | RIP 1 |
| | *Myosoton aquaticum* (L.) Moench [Syn.: *Stellaria aquatica* (L.) Scop.] | Stellarin | RIP 1 |
| | *Stellaria media* (L.) Vill. | RIP Q3 | RIP 1 |
| | *Vaccaria hispanica* (Mill.) Rauschert [Syn.: *Vaccaria pyramidata* Medik.] | Pyramidatin | RIP 1 |

TABLE A5-continued

RIPs from plants*

| Plant Family | Plant Species | Proteins | Classification |
|---|---|---|---|
| Cucurbitaceae | *Benincasa hispida* (Thunb.) Cogn. | Hispin | RIP 1 |
| | | α-benincasin, β-benincasin | sRIP 1 |
| | *Bryonia cretica* subsp. *dioica* (Jacq.) Tutin. [Syn.: *Bryonia dioica L.*] | Bryodin 1 = BD1, Bryodin 2, Bryodin-L, Bryodin-R | RIP 1 |
| | | BDA | lectin/RIP 2 like |
| | *Citrullus colocynthis* (L.) Schrad. | Colocin 1, Colocin 2 | RIP 1 |
| | *Cucurbita foetidissima* Kunth | Foetidissimin | peculiar RIP 2 |
| | | Foetidissimin II | RIP 2 |
| | *Cucumis ficifolius* A. Rich. [Syn.: *Cucumis figarei Delile* ex Naudin] | *Cucumis figarei* RIP = CF-RIP | RIP 1 candidate |
| | *Cucurbita maxima* Duchesne | Cucurmoschin | sRIP 1 candidate |
| | *Cucurbita moschata* Duchesne [Syn.: *Cucurbita moschata* (Duchesne ex Lam.) Duchesne ex Poir.] | Cucurmosin, Cucurmosin 2, C. moschata RIP, Moschatin, PRIP 1, PRIP 2 | RIP 1 |
| | | α-moschin, β-moschin | sRIP 1 candidate |
| | *Cucurbita pepo L.* | Pepocin | RIP 1 |
| | *Cucurbita pepo* var. *texana* (Scheele) D.S. Decker [Syn.: *Cucurbita texana* (Scheele) A. Gray] | Texanin | RIP 1 |
| | *Gynostemma pentaphyllum* (Thunb.) Makino | Gynostemmin | RIP 1 |
| | *Lagenaria siceraria* (Molina) Standl. | Lagenin | RIP 1 candidate |
| | *Luffa acutangula* (L.) Roxb. | Luffaculin-1, Luffaculin-2 | RIP 1 |
| | | Luffangulin | sRIP 1 |
| | | Luffa acutangula fruit lectin | lectin |
| | *Luffa cylindrica* (L.) M. Roem [Syn.: *Luffa aegyptiaca* Mill] | Luffin, Luffin-a, Luffin-b, α-luffin, β-luffin, LRIP | RIP 1 |
| | | Luffacylin, Luffin P1 | sRIP 1 |
| | | Luffin-S, LuffinS(1), LuffinS(2) = luffin S2, LuffinS(3) | sRIP 1 candidate |
| | *Marah oreganus* (Torr. & A. Gray) Howell | MOR-I, MOR-II | RIP 1 |
| | *Momordica balsamina L.* | Balsamin, MbRIP-1, Momordin II | RIP 1 |
| | *Momordica charantia L.* | MAP 30, α-momorcharin = α-MC = α-MMC, β-momorcharin = β-MC = β-MMC, δ-momorcharin = δ-MMC, Momordin, Momordin = *Momordica charantia* inhibitor, Momordin II, Momordin-a, Momordin-b | RIP 1 |
| | | γ-momorcharin = γ-MMC, Charantin | sRIP 1 |
| | | RIP 1 candidate | RIP 1 candidate |
| | | MCL = *M. charantia* lectin, anti-H Lectin, *Momordica* agglutinin, Momordin, protein fraction 1, protein fraction 2 | lectin |
| | | MCL = *Momordica charantia* seed lectin = *Momordica charantia* lectin, MCL1 | RIP 2 |
| | *Momordica cochinchinensis* Spreng. | Cochinin B, Momorcochin, Momorcochin-S | RIP 1 |
| | *Siraitia grosvenorii* (Swingle) C. Jeffrey ex A.M. Lu & Zhi Y. Zhang [Syn.: *Momordica grosvenorii Swingle*] | Momorgrosvin | RIP 1 |
| | *Sechium edule* (Jacq.) Sw | *Sechiumin* | RIP 1 |
| | | *Sechium edule* fruit lectin | lectin |
| | *Trichosanthes anguina L.* | *Trichoanguin* | RIP 1 |
| | | SGSL | lectin/RIP 2 like |
| | *Trichosanthes cordata* Roxb. | TCA-I, TCA-II | lectin |
| | *Trichosanthes cucumerina L.* | TCSL | lectin/RIP 2 candidate |
| | *Trichosanthes cucumeroides* (Ser.) Maxim. | β-trichosanthin = β-TCS | RIP 1 |
| | *Trichosanthes kirilowii* Maxim. | α-kirilowin, β-kirilowin, TAP 29, TK-35, Trichobitacin, Trichokirin, Trichomislin = TCM, Trichosanthin = *Trichosanthes* antiviral protein = TAP = TCS = α-trichosanthin = α-TCS = GLQ223, Trichosanthin, β-trichosanthin = β-TCS, γ-trichosanthin = γ-TCS | RIP 1 |
| | | Trichokirin S1, S-Trichokirin, Trichosanthrip | sRIP 1 |
| | | TKL-1 = *Trichosanthes kirilowii* lectin-1 | lectin/RIP 2 candidate |
| | | TK-I, TK-II, TK-III, *Trichosanthes kirilowii* lectin | lectin |
| | *Trichosanthes kirilowii Maximovicz* var. *japonica* (Miguel) Kitamura | Karasurin-A, Karasurin-B, Karasurin-C | RIP 1 |

TABLE A5-continued

RIPs from plants*

| Plant Family | Plant Species | Proteins | Classification |
|---|---|---|---|
| | *Trichosanthes lepiniate* | Trichomaglin | RIP 1 |
| | *Trichosanthes dioica* Roxb. | TDSL | lectin/RIP 2 candidate |
| | *Trichosanthes* sp. Bac Kan 8-98 | Trichobakin | RIP 1 |
| Cupressaceae | *Thuja occidentalis L.* | Arborvitae RIP | RIP candidate |
| Euphorbiaceae | *Croton tiglium L.* | Crotin I | RIP 1 candidate |
| | | Crotin 2 | RIP 1 |
| | *Euphorbia characias L.* | *E. characias* lectin | lectin |
| | *Suregada multiflora* (A. Juss.) Baill. [Syn.: *Gelonium multiflorum* A. Juss.] | Gelonin = GAP 31 | RIP 1 |
| | *Hura Crepitans L.* | *Hura crepitans* RIP, *Hura crepitans* RIP-5 | RIP 1 |
| | | *Hura crepitans* latex lectin | RIP 2 |
| | | Crepitin, Hurin, *Hura crepitans* seed lectin | lectin |
| | *Jatropha curcas L.* | Curcin, Curcin 2, Curcin-L, Jc-SCRIP | RIP 1 |
| | *Manihot palmata* Müll. Arg. | Mapalmin | RIP 1 |
| | *Manihot esculenta* Crantz. [Syn.: *Manihot utilissima* Pohl] | Manutin 1, Manutin | 2 RIP 1 |
| | *Ricinus communis L.* | Ricin = crystalline Ricin = Ricin D, Ricin E, RCA = *Ricinus communis* agglutinin = RCAI = RCA120 = R. communis hemagglutinin = RCB-PHA I, RCAII = RCA60 = RCB-PHA II | RIP 2 |
| | *Ricinus communis,* USA | Ricin 1, Ricin 2, Ricin 3 | RIP 2 |
| | *Ricinus communis,* India | Ricin I, Ricin II, Ricin III | RIP 2 |
| | *Ricinus sanguienus,* France | $Ricin_{11}$, $Ricin_{12}$, $Ricin_2$ | RIP 2 |
| Fabaceae | *Abrus precatorius L.* | Abrin, Abrin-a = Abrin C = Abrin-III, Abrin-b, Abrin-c = Abrin A = Abrin-I, Abrin-d, Abrin-II, APA = *Abrus precatorius* agglutinin = Abrus lectin = AAG, APA-I, APA-II | RIP 2 |
| | *Abrus pulchellus Thwaites* | Pulchellin, Pulchellin PI, Pulchellin PII, Pulchellin PIII | RIP 2 |
| | *Pisum sativum* subsp. *sativum L.* [Syn.: *Pisum sativum* var. *arvense* (L.) Poir.] | α-pisavin, β-pisavin | RIP 1 |
| | *Pisum sativum* var. macrocarpon | Sativin | RIP 1 candidate |
| Iridaceae | *Iris hollandica* var. Professor Blaauw | IrisRIP = IRIP, IrisRIP.A1, IrisRIP.A2, IrisRIP.A3 | RIP 1 |
| | | IRA, IRAb, IRAr | RIP 2 |
| Lamiaceae | *Clerodendrum aculeatum* (L.) Schltdl. | CA-SRI | RIP 1 candidate |
| | *Clerodendrum inerme* (L.) Gaertn. | CIP-29 | RIP 1 |
| | | CIP-34 | RIP 1 candidate |
| | *Leonurus japonicus* Houtt. | Leonurin | RIP candidate |
| Lauraceae | *Cinnamomum bodinieri* H. Lév. | Bodinierin | RIP 2 |
| | *Cinnamomum camphora* (L.) J. Presl | Camphorin | RIP 1 |
| | | Cinnamomin, Cinnamomin 1, Cinnamomin 2, Cinnamomin 3 | RIP 2 |
| | | Cinphorin | sRIP 2 |
| | *Cinnamomum* parthenoxylon (Jack) Meisn. [Syn.: *Cinnamomum porrectum* (Roxb.) Kosterm] | Porrectin | RIP 2 |
| Malvaceae | *Abelmoschus esculentus* (L.) Moench | Abelesculin | RIP 1 |
| Nyctaginaceae | *Boerhaavia diffusa L.* | *Boerhaavia* inhibitor | RIP 1 candidate |
| | *Bougainvillea spectabilis* Willd. | BAP I, Bouganin = *Bougainvillea* RIP I | RIP 1 |
| | *Bougainvillea* × *buttiana cv.* Enid Lancester | BBP-24, BBP-28 | RIP 1 |
| | *Bougainvillea* × *buttiana cv. Mahara* | BBAP1 | RIP 1 |
| | *Mirabilis expansa* (Ruiz & Pav.) Standl. | ME1, ME2 | RIP 1 |
| | *Mirabilis jalapa L.* | MAP, MAP-2, MAP-3, MAP-4, MAP-S | RIP 1 |
| Olacaceae | *Malania oleifera* Chun & S. K. Lee | Malanin | lectin/RIP 2 candidate |
| | *Ximenia americana L.* | Riproximin = Rpx, Rpx-I, Rpx-II | RIP 2 |
| Passifloraceae | *Adenia digitata* (Harv.) Engl. | Modeccin = Modeccin 4B, Modeccin 6B | RIP 2 |
| | *Adenia ellenbeckii* Harms | *A. ellenbeckii* lectin | RIP 2 candidate |
| | *Adenia fruticosa* Burtt Davy | *A. fruticosa* lectin | lectin |

TABLE A5-continued

RIPs from plants*

| Plant Family | Plant Species | Proteins | Classification |
|---|---|---|---|
| | *Adenia glauca* Schinz | *A. glauca* lectin | RIP 2 candidate |
| | *Adenia goetzei* Harms (unresolved name) | *A. goetzei* lectin | RIP 2 |
| | *Adenia keramanthus* Harms | *A. keramanthus* lectin | RIP 2 candidate |
| | *Adenia lanceolata* Engl. | Lanceolin | RIP 2 |
| | *Adenia racemosa* W. J. de Wilde | *A. racemosa* lectin | lectin |
| | *Adenia spinosa* Burtt Davy | *A. spinosa* lectin | RIP 2 candidate |
| | *Adenia stenodactyla* Harms | Stenodactylin | RIP 2 |
| | *Adenia venenata* Forssk. | *A. venenata* lectin | RIP 2 candidate |
| | *Adenia volkensii* Harms | Volkensin | RIP 2 |
| Phytolaccaceae | *Phytolacca americana L.* | α-PAP, PAP = *Phytolacca americana* protein = pokeweed antiviral protein, PAP-I, PAP-II, PAP-III, PAP-C, PAP-H, PAP-R, PAP-S, PAP-S1, PAP-S2 | RIP 1 |
| | *Phytolacca dioica L.* | Diocin 1, Diocin 2, PD-L1, PD-L2, PD-L3, PD-L4, PD-S1, PD-S2, PD-S3 | RIP 1 |
| | *Phytolacca dodecandra* L'Hér. | Dodecandrin, Dodecandrin C | RIP 1 |
| | *Phytolacca heterotepala* H. Walter | Heterotepalin 4, Heterotepalin 5b | RIP 1 |
| | *Phytolacca insularis Nakai* | Insularin = PIP = *Phytolacca insularis* antiviral protein, PIP2 = *P. insularis* antiviral protein 2 | RIP 1 |
| Poaceae | *Hordeum vulgare L.* | Barley toxin = Barley translation inhibitor = Barley Protein Synthesis Inhibitor = BPSI = RIP 30, Barley toxin I= Barley translation inhibitor I, Barley toxin II = Barley translation inhibitor II = Barley Protein Synthesis Inhibitor II = BPSI II, Barley toxin III = Barley translation inhibitor III, JIP60 | RIP 1 |
| | *Oryza sativa L.* | *Oryza sativa* RIP | RIP 1 |
| | *Secale cereale L.* | RPSI | RIP 1 |
| | *Triticum aestivum L.* | Tritin, Tritin 1, Tritin 2, Tritin 3, Tritin-S, Tritin-L | RIP 1 |
| | *Zea mays L.* | b-32 = maize RIP = maize proRIP1, Maize proRIP2 | RIP 3/peculiar RIP 1 |
| Ranunculaceae | *Eranthis hyemalis* (L.) Salisb. | EHL | RIP 2 |
| Santalaceae | *Phoradendron californicum* Nutt. | PCL | RIP 2 |
| | *Viscum album L.* (Himalayan mistletoe) | HmRip, HmRip 1, HmRip 2, HmRip 3, HmRip 4 | RIP 2 |
| | *Viscum album L.* (European mistletoe) | ML-I = Mistletoe lectin I= Viscumin = Eu-ML = EML-1 = VAA-I, ML-II = Mistletoe lectin II = VAA-II, ML-III = Mistletoe lectin III = VAA-III | RIP 2 |
| | *Viscum articulatum Burm. f.* | Articulatin-D | RIP 2 |
| | *Viscum coloratum* (Kom.) Nakai [Syn.: Viscum album subsp. *coloratum* Kom.] | KML, KML-C, KML-IIL, KML-IIU, VCA | RIP 2 |
| Solanaceae | *Nicotiana tabacum L.* | CIP31 | RIP-like protein |
| | | TRIP | RIP 1 candidate |
| Thymelaeaceae | *Phaleria macrocarpa* (Scheff.) Boerl. | *P. macrocarpa* RIP | RIP candidate |

*Schrot J, Weng A, Melzig MF, et al. Ribosome-inactivating and related proteins. Toxins (Basel). 2015 May 8;7(5):1556-615.

It is part of the invention that the therapeutic conjugate is further combined with a covalent conjugate (complex) of a binding molecule or a binding moiety and a saponin, or is further combined with a pharmaceutical compound, an antibody, etc., therewith providing a composition comprising two or even three or more enhancers, pharmaceutically active ingredients, etc., e.g. a conjugate of the invention combined with a binding moiety complexed with an effector molecule, further optionally combined with a pharmaceutical, which is either or not linked to a saponin, and which is either or not coupled to a ligand such as a targeting immunoglobulin, a domain or a fragment thereof. Furthermore, an embodiment is the therapeutic conjugate of the invention, wherein the cell-surface molecule targeting molecule is provided with two or more effector moieties such as a toxin or immunotoxin, wherein the two or more effector moieties are the same or different.

EXEMPLARY EMBODIMENTS

An embodiment is the endosomal escape enhancing conjugate of the invention, wherein the saponin is a bisdesmosidic triterpene saponin belonging to the type of a 12,13-dehydrooleanane with an aldehyde function, in position 23, and wherein the saponin is preferably a saponin that can be isolated from *Gypsophila* or *Saponaria* species, more preferably the saponin SO1861 or any of its diastereomers.

An embodiment is the endosomal escape enhancing conjugate of the invention, wherein the cell-surface molecule targeting molecule is at least a ligand, such as an immunoglobulin, with at least an effector moiety bound thereto.

An embodiment is the endosomal escape enhancing conjugate of the invention, wherein the cell-surface molecule targeting molecule is an immunoglobulin or at least a binding domain thereof for binding to a cell surface molecule, wherein preferably the cell surface molecule is selected from any of HER2, EGFR, CD20, CD22, Folate receptor 1, CD146, CD56, CD19, CD138, CD27L, PSMA, CanAg, integrin-alphaV, CA6, CD33, mesothelin, Cripto, CD3, CD30, CD33, CD239, CD70, CD123, CD352, DLL3, CD25, ephrinA4, MUC1, Trop2, CEACAM5, HER3, CD74, PTK7, Notch3, FGF2, C4.4A, FLT3, CD71.

An embodiment is the endosomal escape enhancing conjugate of the invention, wherein a linker is coupled to the saponin via a cleavable bond, and wherein the cell-surface molecule targeting molecule is an immunoglobulin, wherein preferably said cleavable bond is subject to cleavage under acidic, reductive, enzymatic or light-induced conditions, and preferably the cleavable bond is a covalent bond, preferably an imine bond, a hydrazone bond, an oxime bond, a 1,3-dioxolane bond or an ester bond, wherein preferably the cleavable bond is a disulfide bond or a peptide bond.

An embodiment is the endosomal escape enhancing conjugate of the invention, wherein the saponin moiety is a terminal saponin, preferably the saponin SO1861, the linker is a chemical linker covalently linking the saponin to the cell-surface molecule targeting molecule of the conjugate of the invention, and the cell-surface molecule targeting molecule is an immunoglobulin such as trastuzumab or cetuximab, the linker preferably providing a cleavable bond between the terminal saponin moiety and the cell-surface molecule targeting molecule comprised by the conjugate.

An embodiment is the conjugate according to the invention, wherein the saponin is a bisdesmosidic triterpene.

An embodiment is the conjugate according to the invention, wherein the saponin is a bisdesmosidic triterpene saponin.

An embodiment is the conjugate according to the invention, wherein the saponin is a bisdesmosidic triterpene saponin belonging to the type of a 12,13-dehydrooleanane with an aldehyde function in position 23.

An embodiment is the conjugate according to the invention, wherein the saponin is a saponin that can be isolated from *Gypsophila* or *Saponaria* species.

An embodiment is the conjugate according to the invention, wherein the saponin is a SO1861 or any of its diastereomers.

An embodiment is the conjugate according to the invention, wherein the at least one saponin is bound to the cell-surface molecule targeting molecule (binding site for the epitope on the cell-surface molecule) via a cleavable bond, wherein preferably said cleavable bond is subject to cleavage under acidic, reductive, enzymatic or light-induced conditions, and wherein the cleavable bond preferably is a disulfide bond or a peptide bond.

An embodiment is the conjugate according to the invention, wherein the cleavable bond is a covalent bond, preferably an imine bond, a hydrazone bond, an oxime bond, a 1,3-dioxolane bond or an ester bond.

An embodiment is the conjugate according to the invention, wherein the endosomal escape enhancing conjugate comprises a defined number of glycosides or a defined range.

An embodiment is the conjugate according to the invention, wherein the defined range is between 1-30 glycoside(s), preferably between 1-20, more preferably between 1-10, more preferably between 1-6, more preferably between 2-6, more preferably between 2-5, more preferably between 3-5, more preferably between 3-4 glycosides.

An embodiment is the conjugate according to the invention, wherein the effector moiety is a pharmaceutically active substance, such as a toxin such as a proteinaceous toxin, a drug, a polypeptide or a polynucleotide.

An embodiment is the conjugate according to the invention, wherein the target cell is a diseased cell or a disease-related cell, preferably a tumor cell or a tumor-associated cell (e.g. tumor vascular cell), or an immune cell (e.g. a T regulatory cell), or an autoimmune cell.

An embodiment is the conjugate according to the invention, wherein the at least one effector moiety is bound to the cell-surface molecule targeting molecule comprised by the conjugate via a cleavable bond, wherein preferably said cleavable bond is subject to cleavage under acidic, reductive, enzymatic or light-induced conditions, and/or wherein the cleavable bond is a disulfide bond or a peptide bond.

An embodiment is the conjugate according to the invention, wherein the saponin is capable of augmenting endosomal escape of the effector molecule.

An embodiment is the conjugate according to the invention, for use as a medicament.

An embodiment is the pharmaceutical composition comprising a conjugate according to the invention (previous embodiments) and a pharmaceutically acceptable excipient.

An embodiment is the pharmaceutical composition according to the invention, further comprising at least one further active pharmaceutically ingredient, such as a further immunoglobulin.

An embodiment is the conjugate for use according to the invention, or pharmaceutical composition according to the invention, for use in a method of treating cancer or an autoimmune disease.

An embodiment is a method of treating cancer, the method comprising administering a conjugate according to the invention to a patient in need thereof.

An embodiment is the method of treating cancer, the method comprising administering a pharmaceutical composition according to the invention, to a patient in need thereof.

An embodiment is a kit comprising a container containing an endosomal escape enhancing conjugate according to the invention, the kit further comprising instructions for using the binding molecules.

The scaffold comprising at least one saponin according to the invention is suitable for use as a semi-finished product for the manufacture of a functionalized ADC or a functionalized AOC wherein the functionalized ADC or the functionalized OAC comprises at least one covalently coupled saponin of the invention and at least one effector moiety of the invention. An embodiment is the scaffold of the invention further comprising a payload or effector moiety of the invention such as a toxin or an oligonucleotide covalently bound to the scaffold of the invention, either directly or via a linker of the invention, preferably a cleavable linker of the invention. Such functionalized scaffold can be used for the manufacture of an ADC-saponin conjugate or an AOC-saponin conjugate comprising said scaffold with covalently bound scaffold thereto and with an effector moiety bound thereto. For example, such a functionalized ADC or OAC comprises 2-4 saponins covalently coupled to e.g. a cysteine side chain in the conjugate according to the invention such as covalently coupled to the cell-surface molecule targeting molecule which is for example a ligand or an antibody (fragment), either directly or via a (cleavable) linker, or such a functionalized ADC or OAC comprises for example a dendron, such as a G4-dendron, the dendron comprising 1-16 covalently coupled saponins bound thereto, the dendron covalently coupled to e.g. a cysteine side chain and/or a lysine side chain of the cell-surface molecule targeting molecule comprised by the conjugate according to the invention.

An aspect of the invention relates to a pharmaceutical composition comprising the conjugate of the invention and optionally a pharmaceutically acceptable excipient and/or a pharmaceutically acceptable diluent.

An aspect of the invention relates to a conjugate of the invention or relates to the pharmaceutical composition of the invention, for use as a medicament.

An aspect of the invention relates to a conjugate of the invention or relates to the pharmaceutical composition of the invention, for use in the treatment or prevention of a cancer or an autoimmune disease.

The invention is further illustrated by the following examples, which should not be interpreted as limiting the present invention in any way.

Examples

Example A—Treating a Mammalian Tumor-Bearing Animal with a Conjugate of the Invention in Combination with an ADC Results in Survival and Tumor Regression Female Balb/c nude mice were injected subcutaneously with a suspension of human A431 tumor cells. Under the skin of the mice, a human epidermal carcinoma developed in the xenograft animal tumor model. After injection of the tumor cells, the xenograft tumor was allowed to develop to a size of approximately 170-180 $mm^3$. The A431 tumor cells have the following characteristics: high EGFR expressors, medium CD71 expressors, low HER2 expressors. The A431 tumor-cell based tumor model is an aggressive model since amongst others the tumor is rapidly growing.

In Table A, the results of the treatment of control mice and tumor-bearing mice are presented. Tumor-bearing mice were treated with the indicated antibodies directed to either human Her2/neu, human EGFR, or human CD71, which are cell-surface receptors on the xenograft tumor. Cetuximab was covalently conjugated with saponin SO1861. The SO1861 was first provided with the linker EMCH (N-ε-maleimidocaproic acid hydrazide), which EMCH is a maleimide-and-hydrazide crosslinker for covalently conjugating sulfhydryls (reduced cysteines of the antibody)) to carbonyls (aldehyde or ketones; here the carbonyl of the aldehyde at position C-23 of the saponin). The saponin-EMCH was covalently coupled to reduced cysteines of the Cetuximab, forming a covalent thio-ether bond between the EMCH and the cysteine side chain. The ADCs trastuzumab-saporin (covalent conjugate) and anti-CD71 mAb (OKT-9, IgG)-saporin (covalent conjugate) were tested for their tumor-attacking efficacy in the mice, measured as tumor volume in time after start of the treatment with the ADCs. The dose of the ADCs was sub-optimal in the tumor model. That is to say, from previous experiments, it was established at which sub-optimal dose of the ADCs no tumor-regression or arrest of tumor growth would be observable.

TABLE A

RESULTS OF TREATING A MAMMALIAN TUMOR-BEARING ANIMAL WITH A CONJUGATE OF THE INVENTION IN COMBINATION WITH AN ADC RESULTS IN SURVIVAL AND TUMOR REGRESSION

| Treatment group | Patient/healthy animal | treatment | tumor size (volume in $mm^3$ or '+' for growth, '−' for regression, and 'stable' for growth nor regression) |
|---|---|---|---|
| 1 | xenograft | vehicle | 2000 $mm^3$ (death/euthanasia) |
| 2 | xenograft | Trastuzumab-saporin | 2000 $mm^3$ (death/euthanasia) |
| 3 | xenograft | Anti-CD71 mAb OKT-9 − saporin (covalent conjugate) | 2000 $mm^3$ (death/euthanasia) |
| 4 | xenograft | Cetuximab-SO1861 (covalent conjugate) | 2000 $mm^3$ (death/euthanasia) |
| 5 | xenograft | Cetuximab | >170 $mm^3$, but <2000 $mm^3$ (death/euthanasia) |
| 6 | xenograft | Trastuzumab-saporin (covalent conjugate) + Cetuximab-SO1861 conjugate (covalent | Tumor regression from 180 $mm^3$ at the start of treatment back to 80 $mm^3$ (survival) |
| 7 | xenograft | Anti-CD71 mAb OKT-9 − saporin (covalent conjugate) + Cetuximab-SO1861 (covalent conjugate) | Tumor regression from 180 $mm^3$ at the start of treatment back to 40 $mm^3$ (survival) |

These results demonstrate that the combination therapy of an ADC at a dose which is ineffective when treatment of tumor-bearing mice with the ADC alone is considered (tumor growths, death of the mice is not prevented (euthanasia)), with a conjugate of the invention consisting of a tumor-cell specific receptor targeting antibody covalently bound to a saponin, i.e. SO1861, the covalent conjugate administered to the mice suffering from cancer, at a non-effective dose when administered alone (tumor growths, death of the mice is not prevented (euthanasia)), provides an efficient and efficacious treatment regimen, expressed as tumors in regression and prolonged survival of the treated animals (beyond the duration of the experiment). The sub-optimal dose of ADC combined with a covalently bound saponin-comprising conjugate of the invention which has no anti-tumor activity when administered alone, thus provide for an effective treatment option for cancer patients, wherein a relative low dose of the ADC is efficacious. A lower dose of ADC bears the promise of less risk for adverse events, or even no side effects at all. In addition, the stimulatory effect of the saponin-bearing conjugate of the invention when the efficacy of the ADC is considered, shows that ADCs which previously have proven to lack efficacy when tumor patient treatment is concerned, may gain renewed attention and value, since ADC efficacy is improved in combination therapy setting, as the current example demonstrated. Reference is made to Table A2 and Table A3, summarizing ADCs which were previously investigated in the human clinical setting, but then were for some ADCs retracted from further clinical investigation. Especially the ADCs for which clinical development was terminated due to observed lack of efficacy and/or due to occurrence of unacceptable adverse event are ADCs which may gain renewed value for cancer patients when combined with a covalently bound saponin-comprising conjugate of the invention, such as the cetuximab-saponin tested.

Example B—Saponins Mixture of *Quillaja saponaria* Comprising QS-21, with Endosomal/Lysosomal Escape Enhancing Activity Scheme I displays the common molecular structure of a series of QS-21 saponins (in part adapted from: Conrado Pedebos, Laércio Pol-Fachin, Ramon Pons, Cilaine V. Teixeira Hugo Verli, Atomic Model and Micelle Dynamics of QS-21 Saponin, Molecules 2014, 19, 3744-3760). A mixture of water-soluble saponins obtained from *Quillaja saponaria* (Sigma-Aldrich, product No. S4521; Roth, Item No. 6857; InvivoGen, product 'Quil-A') may be applied in the endosomal/lysosomal escape enhancing conjugate, composition, combination of the invention, based on endosomal/lysosomal escape enhancing properties of at least one individual saponin present in the mixture, e.g. QS-21, or based on a combination of two or more of the saponins comprised by the mixture, such as QS-21 and QS-7.

The inventors demonstrated that the mixture of saponins from *Quillaja saponaria* at 2.5 microgram/ml dose was capable of enhancing endosomal escape of dianthin, as tested with mammalian tumor cells in a cell-based bioassay. The effector moiety exposed to the cells was dianthin covalently coupled to the ligand EGF: EGF-dianthin. Cells tested were tumor cell lines HeLa for free saponins, and A431, MDA-MB-468, CaSki and A2058 for testing the saponins when covalently coupled to cetuximab.

Example 1

Figure 1:
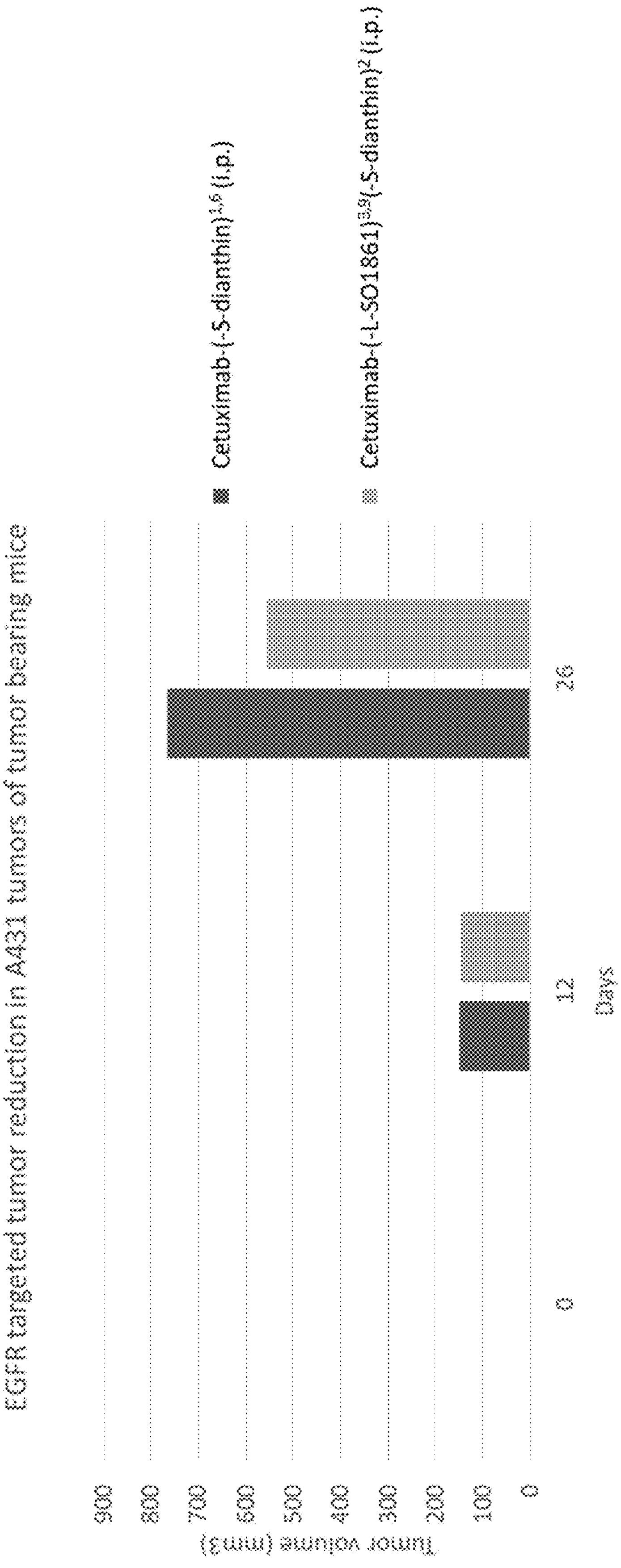
FIG. 1. Tumor targeted protein toxin delivery results in tumor volume reduction and tumor growth inhibition, in tumor bearing mice. A) Dose escalation (intraperitoneal, i.p.) of cetuximab-(Cys-L-SO1861)$^{3,9}$(Lys-S-dianthin)$^{2}$ in A431 tumor bearing mice reveals tumor volume reduction, compared to the control. B, C) Dose escalation (intraperitoneal, i.p. (B) or intravenous i.v. (C)) of cetuximab-(Cys-L-SO1861)$^{3,9}$(Lys-L-dianthin)$^{2}$ in A431 tumor bearing mice reveals tumor growth reduction, compared to the controls.
Figure 1:
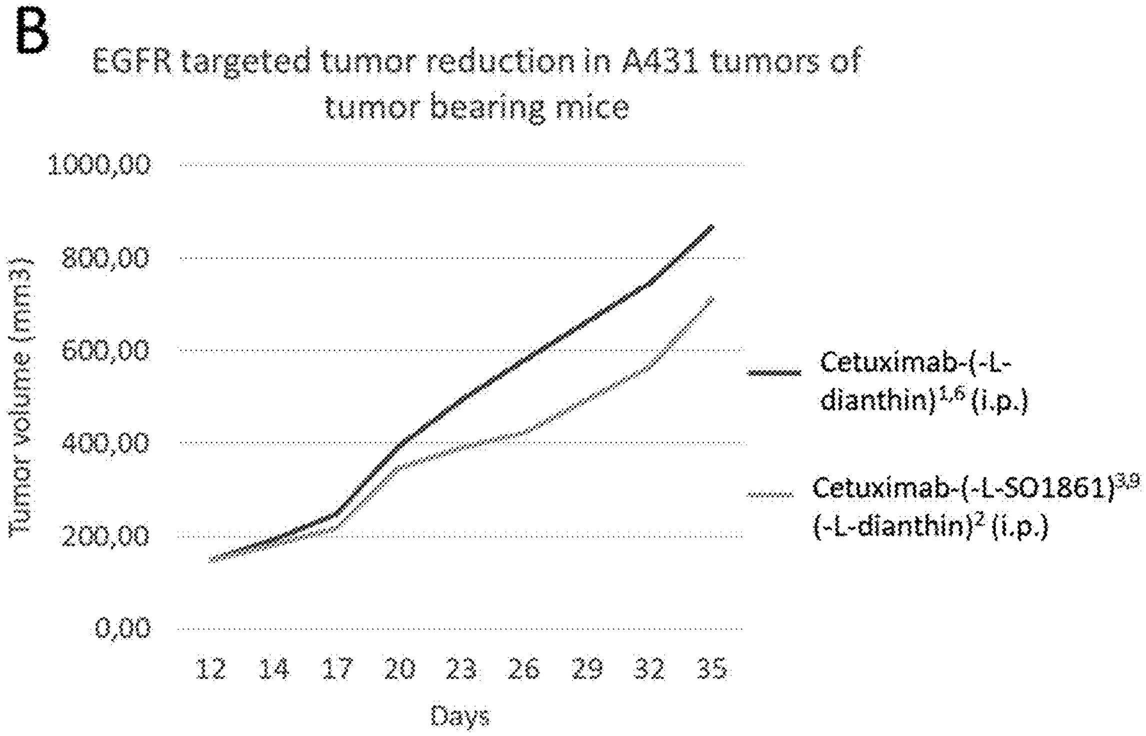
Figure 1:
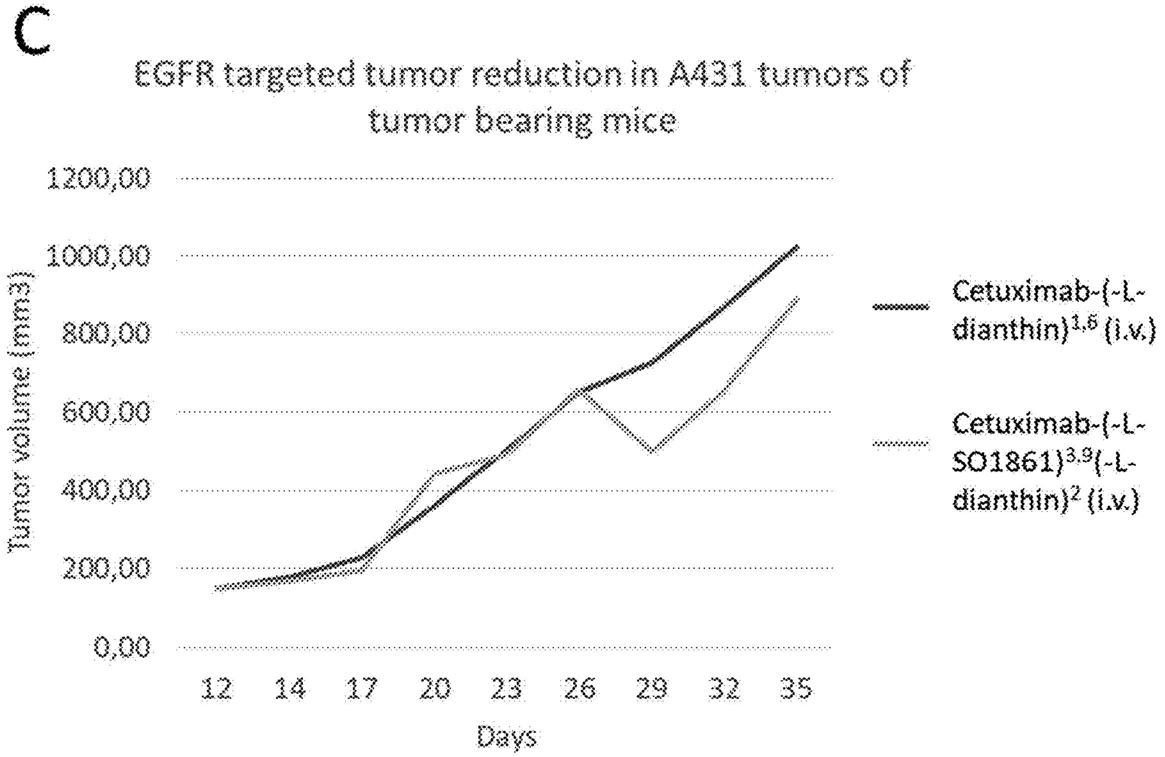
Figure 9:
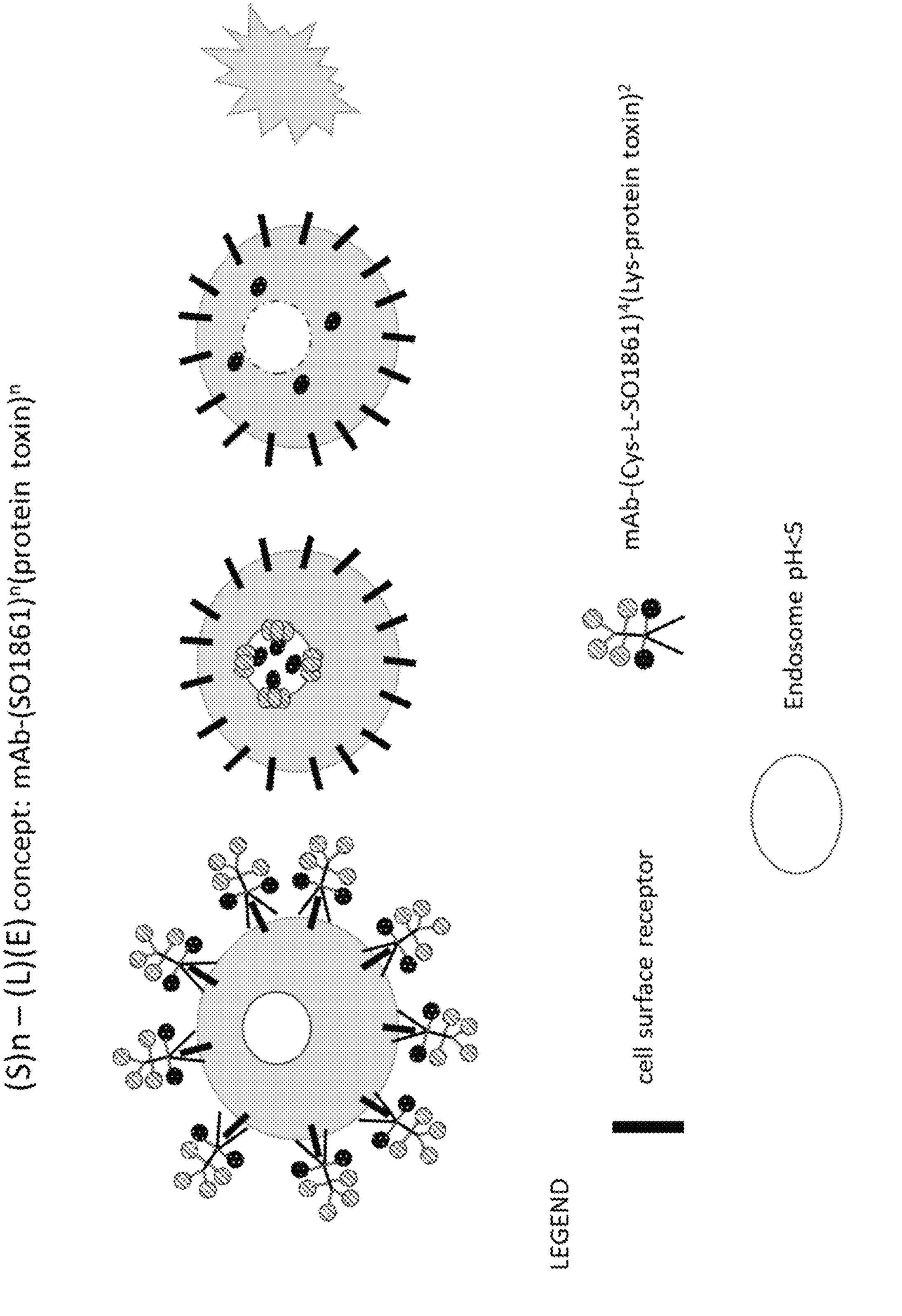
FIG. 9: (S)n-(L)(E) concept: mAb-(SO1861)$^{n}$(protein toxin)$^{n}$. Both, SO1861 at the cysteine residues (Cys) and protein toxin (ribosomal inactivating protein) at the lysine residues are conjugated to the same antibody (mAb) for delivery and internalization into the target cells. 1) mAb-(Cys-L-SO1861)$^{4}$(Lys-protein toxin)$^{2}$ bind to its corresponding cell surface receptor, 2) receptor-mediated endocytosis the conjugate occurs, 3) at low endolysosomal pH and appropriate concentration, SO1861 becomes active to enable endolysosomal escape, 4) release of toxin into cytoplasm occurs and 5) toxin induces cell death

SO1861 was conjugated (labile) via cysteine residues (Cys) and dianthin (protein toxin) was conjugated (stable) via lysine residues (Lys) to cetuximab (monoclonal antibody recognizing and binding human EGFR), resulting in the production of: Cetuximab-(Cys-L-SO1861)$^{3,9}$(Lys-S-dianthin)$^{2}$. The conjugate was tested in a A431 (EGFR$^{++}$) xenograph mouse tumor model for EGFR tumor targeted cell killing as illustrated in FIG. 9. Dosings started at day 12 when tumors reached ~150 mm$^3$ in size and tumor volume was determined after every dosing. Mice (n=3) were treated (intraperitoneal; i.p.; dose escalation) at day 12: 0.5 mg/kg; day 15: 1 mg/kg and day 24: 1.5 mg/kg with cetuximab-(Cys-L-SO1861)$^{3,9}$(Lys-S-dianthin)$^{2}$ or cetuximab-(Lys-S-dianthin)$^{1,6}$. At day 26, compared to the control group, tumor volume reduction could be observed in the tumor bearing mice treated with cetuximab-(Cys-L-SO1861)$^{3,9}$(Lys-S-dianthin)$^{2}$ (FIG. 1A). This shows that labile conjugation of SO1861 to an antibody-protein toxin (stable) conjugate can enhance the targeted therapeutic efficacy of the tumor targeted antibody-protein toxin, thereby inducing a more effective tumor targeted therapy.

Next, SO1861 was conjugated (labile) via cysteine residues (Cys) and dianthin (protein toxin) was conjugated (labile) via lysine residues (Lys) to cetuximab (monoclonal antibody recognizing and binding human EGFR), resulting in the production of: Cetuximab-(Cys-L-SO1861)$^{3,9}$(Lys-L-dianthin)$^{2}$. The conjugate was tested in a A431 (EGFR$^{++}$) xenograph mouse tumor model for EGFR tumor targeted cell killing as illustrated in FIG. 9. Dosings started at day 12 when tumors reached ~150 mm$^3$ in size and tumor volume was determined after every dosing. Mice (n=3) were treated (intraperitoneal; i.p.; dose escalation) at day 12: 0.5 mg/kg; day 15: 1 mg/kg, day 24: 1.5 mg/kg with cetuximab-(Cys-L-SO1861)$^{3,9}$(Lys-L-dianthin)$^{2}$ or cetuximab-(Lys-L-dianthin)$^{1,6}$. This revealed that after 35 days compared to the control, tumor bearing mice treated with cetuximab-(Cys-L-SO1861)$^{3,9}$(Lys-L-dianthin)$^{2}$ showed tumor growth inhibition (FIG. 1B). When mice (n=3; were treated (intravenous, i.v.; dose escalation) day 12: 0.5 mg/kg; day 15: 1 mg/kg, day 18: 2 mg/kg, day 24: 2.5 mg/kg with the cetuximab-(Cys-L-SO1861)$^{3,9}$(Lys-L-dianthin)$^{2}$ according to the invention also tumor growth inhibition could be observed compared to the control (data represents 1 mice, since 2 mice died during the treatments). This shows that labile conjugation of SO1861 to an antibody-protein toxin (labile) conjugate can enhance the targeted therapeutic efficacy of the tumor targeted antibody-protein toxin, thereby inducing a more effective tumor targeted therapy.

Figure 10:
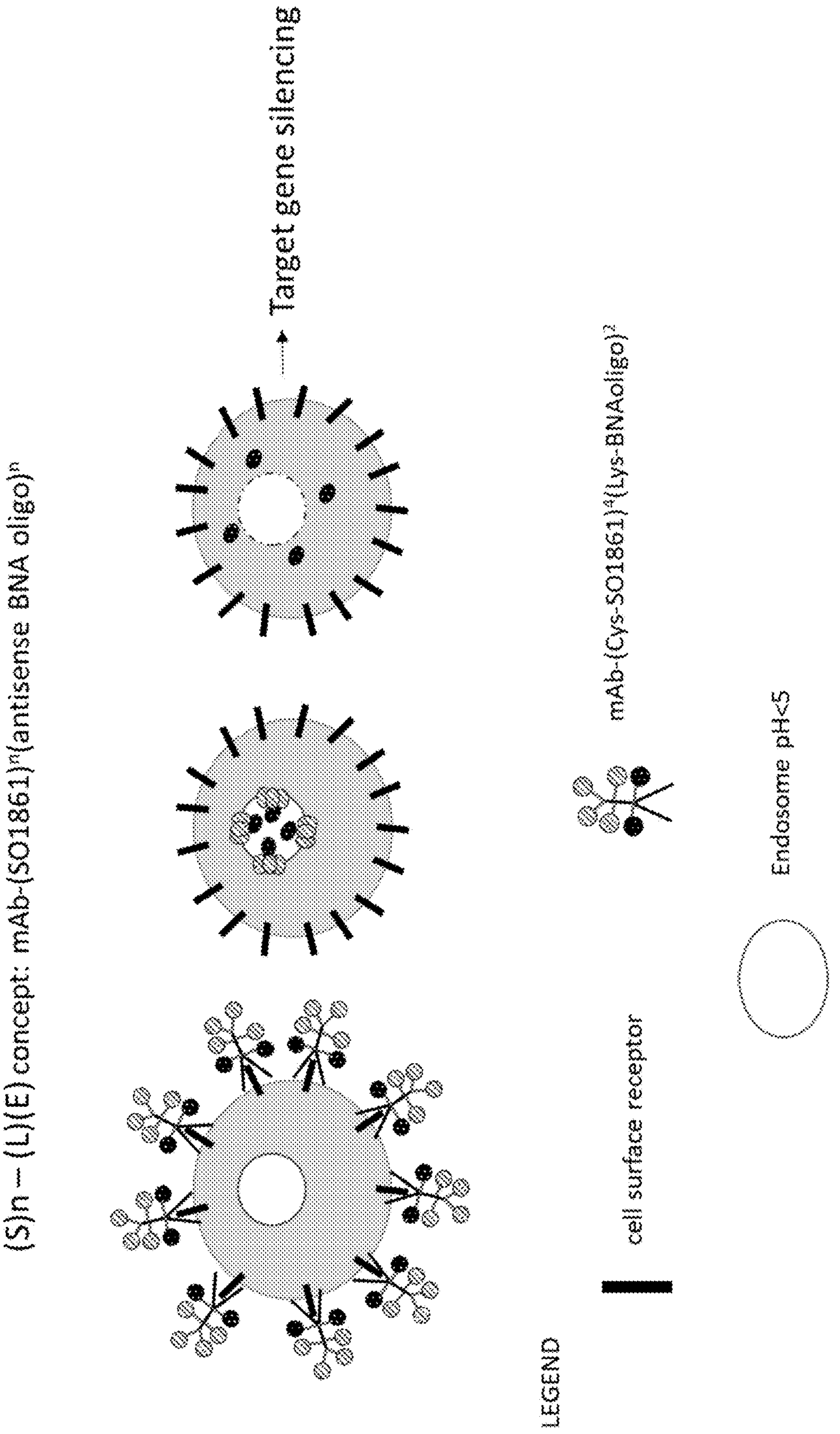
FIG. 10: (S)n-(L)(E) concept: mAb-(SO1861)$^{n}$(antisense BNA oligo)$^{n}$. Both, SO1861, at the cysteine residues (Cys) and the antisense BNA oligo nucleotide, at the lysine residues are conjugated to the same antibody (mAb) for delivery and internalization into the target cells. 1) mAb-(Cys-SO1861)$^{4}$(Lys-BNAoligo)$^{2}$ bind to its corresponding cell surface receptor, 2) receptor-mediated endocytosis of both conjugates occurs, 3) at low endolysosomal pH and appropriate concentration, SO1861 becomes active to enable endolysosomal escape, 4) release of BNA oligo into cytoplasm occurs and 5) target gene silencing is induced.
Figure 11:
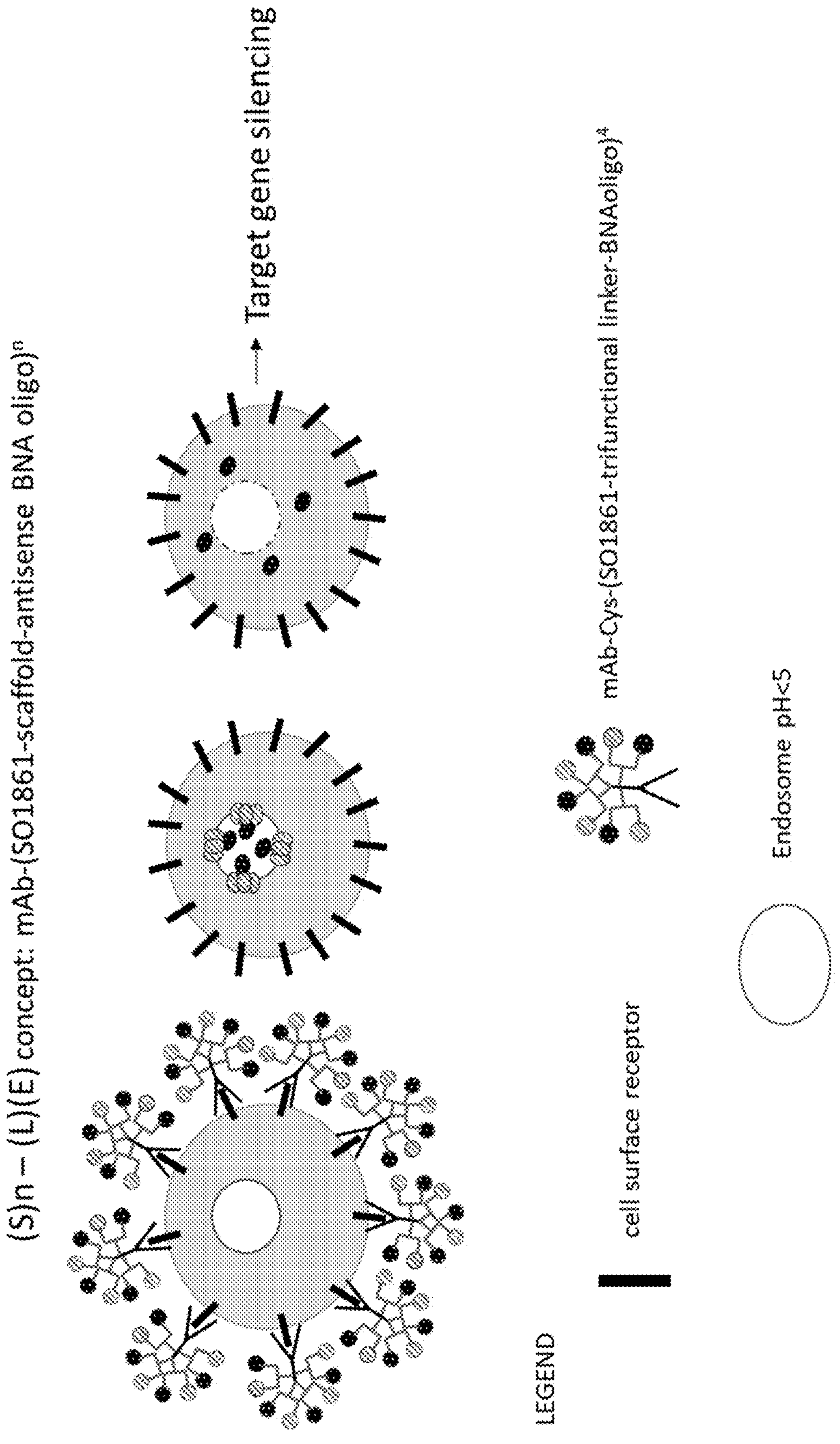
FIG. 11: (S)n-(L)(E) concept: mAb-(SO1861-scaffold-antisense BNA oligo)$^{n}$. the (SO1861-trifunctional linker-BNAoligo)$^{n}$ is conjugated to an antibody (mAb) for delivery and internalization into the target cells. 1) mAb-(SO1861-trifunctional linker-BNAoligo)$^4$ binds to its corresponding cell surface receptor, 2) receptor-mediated endocytosis of both conjugates occurs, 3) at low endolysosomal pH and appropriate concentration, SO1861 becomes active to enable endolysosomal escape, 4) release of BNA oligo into cytoplasm occurs and 5) target gene silencing is induced.

Next, SO1861-EMCH was conjugated via cysteine residues (Cys) to cetuximab (monoclonal antibody recognizing and binding human EGFR), with a DAR 3,9 and the antisense HSP27BNA oligo nucleotide (targeting and inducing degradation of the onco-target hsp27 mRNA (gene silencing) in cancer cells) via a labile (L) linker to the lysine residues (Lys) of the antibody, with a DAR 1,8 resulting in the production of cetuximab-(Cys-L-SO1861)$^{3,9}$(Lys-L-HSP27BNA)$^{1,8}$. Cetuximab-(Cys-L-SO1861)$^{3,9}$(Lys-L-HSP27BNA)$^{1,8}$ was tested in a A431 xenograph 'nude' mouse tumor model for EGFR-mediated tumor targeted HSP27 gene silencing, according to the invention as illustrated in FIG. 10. Dosing started at day 12 when tumors reached ~150 mm$^3$ in size and HSP27 mRNA expression was determined. For this, tumor samples were collected at 72 h after the first dosing and analysed for HSP27 gene expression levels compared to cellular control mRNA expression levels (reference genes). Tumor bearing mice (n=3) treated (intraperitoneal; i.p.) with 30 mg/kg cetuximab-(Cys-L-SO1861)$^{3,9}$(Lys-L-HSP27BNA)$^{1,8}$ showed after 1 dosing 40% reduction in HSP27 mRNA expression in the tumors compared to single dosing of cetuximab-(Cys-L-SO1861)$^{3,8}$ or cetuximab-(Lys-L-HSP27BNA)$^{1,5}$ (FIG. 2). Compared to the tumor of the vehicle control a reduction of 25% HSP27 gene expression was observed. This shows and enables that conjugation of SO1861 and HSP27BNA to the same targeting antibody, according to the invention, efficiently induces SO1861-mediated enhanced cytoplasmic delivery of a therapeutic antisense oligo nucleotide in solid tumors of tumor bearing mice, inducing tumor targeted gene silencing. In another example, a trifunctional linker scaffold was designed and produced with 3 specific chemical end groups for conjugation with SO1861 on one arm and the HSP27BNA on the other arm to produce SO1861-L-trifunctional linker-L-HSP27BNA. Next, SO1861-L-trifunctional linker-L-HSP27BNA was conjugated with its third arm to cysteine residues (Cys) of the anti-EGFR antibody, cetuximab (cetuximab-Cys-(SO1861-L-trifunctional linker-L-HSP27BNA)$^{3,7}$) and tested in a A431 xenograph 'nude' mouse tumor model for EGFR-mediated tumor targeted gene silencing activity, according to the invention as illustrated in FIG. 11. Dosings started at day 12 when tumors reached ~150 mm$^3$ in size and HSP27 mRNA expression was determined. For this, tumor samples were collected at 72 h after the first dosing and analysed for HSP27 gene expression levels compared to cellular control mRNA expression levels (reference genes). This revealed that 1 dosing of 30 mg/kg cetuximab-Cys-(SO1861-L-trifunctional linker-L-HSP27BNA)$^{3,7}$ resulted in a 40% reduction in HSP27 gene expression in the tumors compared to single dosing of 25 mg/kg cetuximab-(Cys-L-SO1861)$^{3,8}$ or 25 mg/kg cetuximab-(Lys-L-HSP27BNA)$^{4}$ mono therapies (FIG. 3). Compared to the vehicle control tumors, a reduction of 25% HSP27 gene expression was observed in tumor bearing mice treated with 1 dosing of cetuximab-Cys-(SO1861-L-trifunctional linker-L-HSP27BNA)$^{3,7}$. This shows and enables that cetuximab-Cys-(SO1861-L-trifunctional linker-L-HSP27BNA)$^{3,7}$ efficiently induces SO1861-mediated enhanced cytoplasmic delivery of a therapeutic antisense oligo nucleotide in a solid tumor of tumor bearing mice, inducing targeted gene silencing, in vivo.

Example 2

Figure 4:
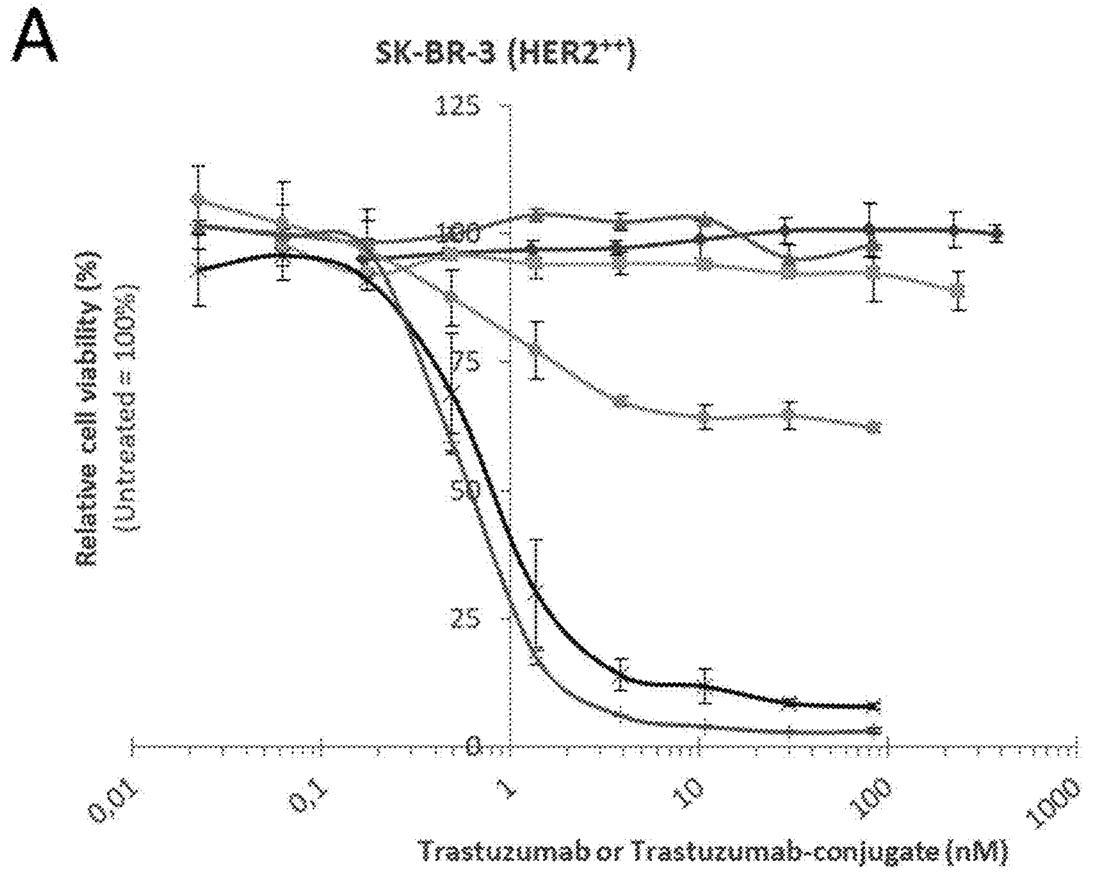
FIG. 4: HER2 or EGFR targeted protein toxin delivery and cell killing in cancer cells, according to the invention. A, B) Trastuzumab-(Cys-L-SO1861)$^{3,8}$(Lys-L-dianthin)$^{1,7}$ or Trastuzumab-(Cys-L-SO1861)$^{3,8}$(Lys-S-dianthin)$^{1,7}$ treatment and controls on SK-BR-3 cells ($HER2^{++}$) and MDA-MB-468 cells ($HER2^{-}$). C, D) Cetuximab-(Cys-L-SO1861)$^{3,8}$(Lys-L-dianthin)$^{1,7}$ or Cetuximab-(Cys-L-SO1861)$^{3,8}$(Lys-S-dianthin)$^{1,7}$ treatment and controls on A431 cells ($EGFR^{++}$) and A2058 cells ($EGFR^{-}$). Remark: For target receptor expression data of each cell line (determined by FACS analysis) see table 23.
Figure 4:
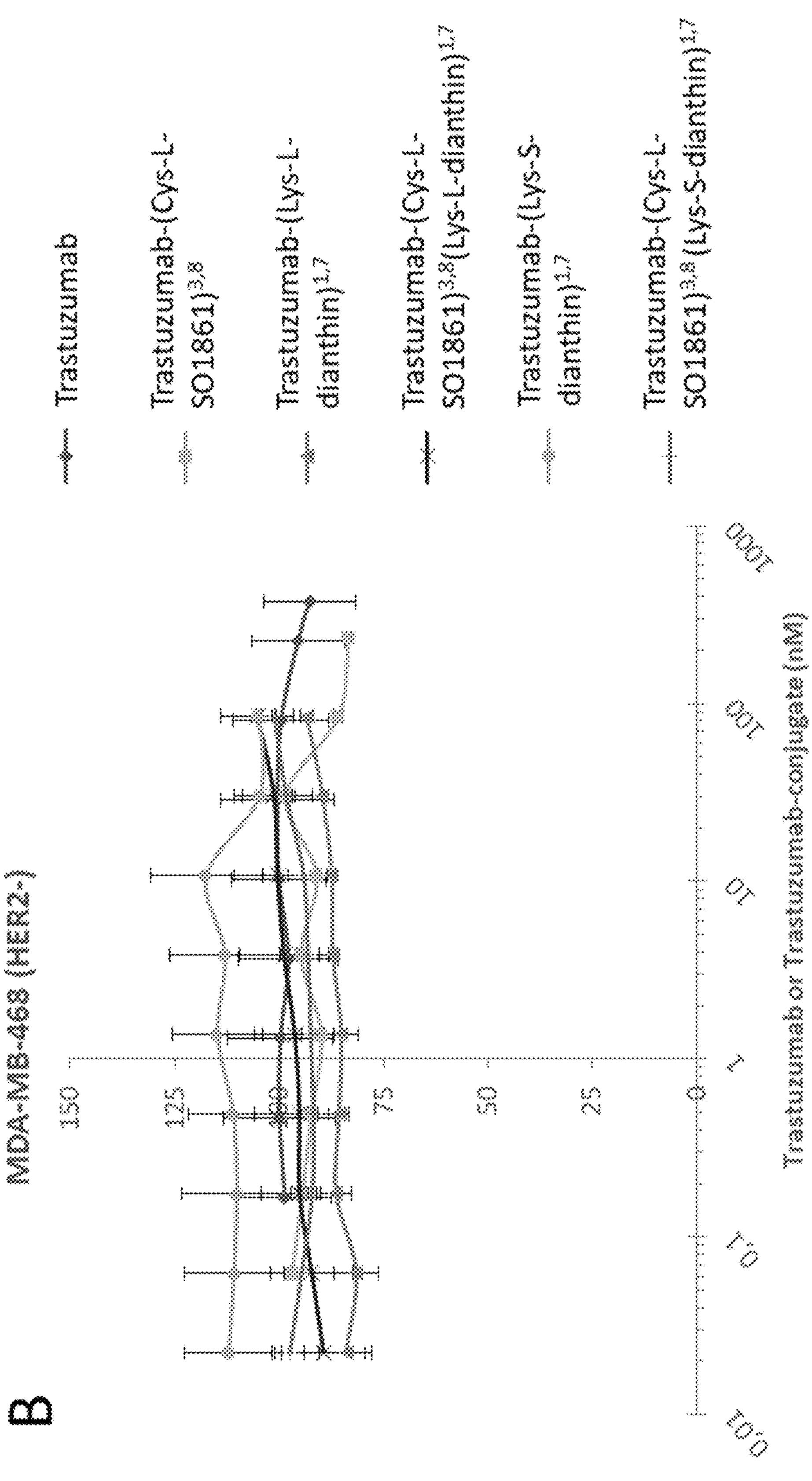
Figure 4:
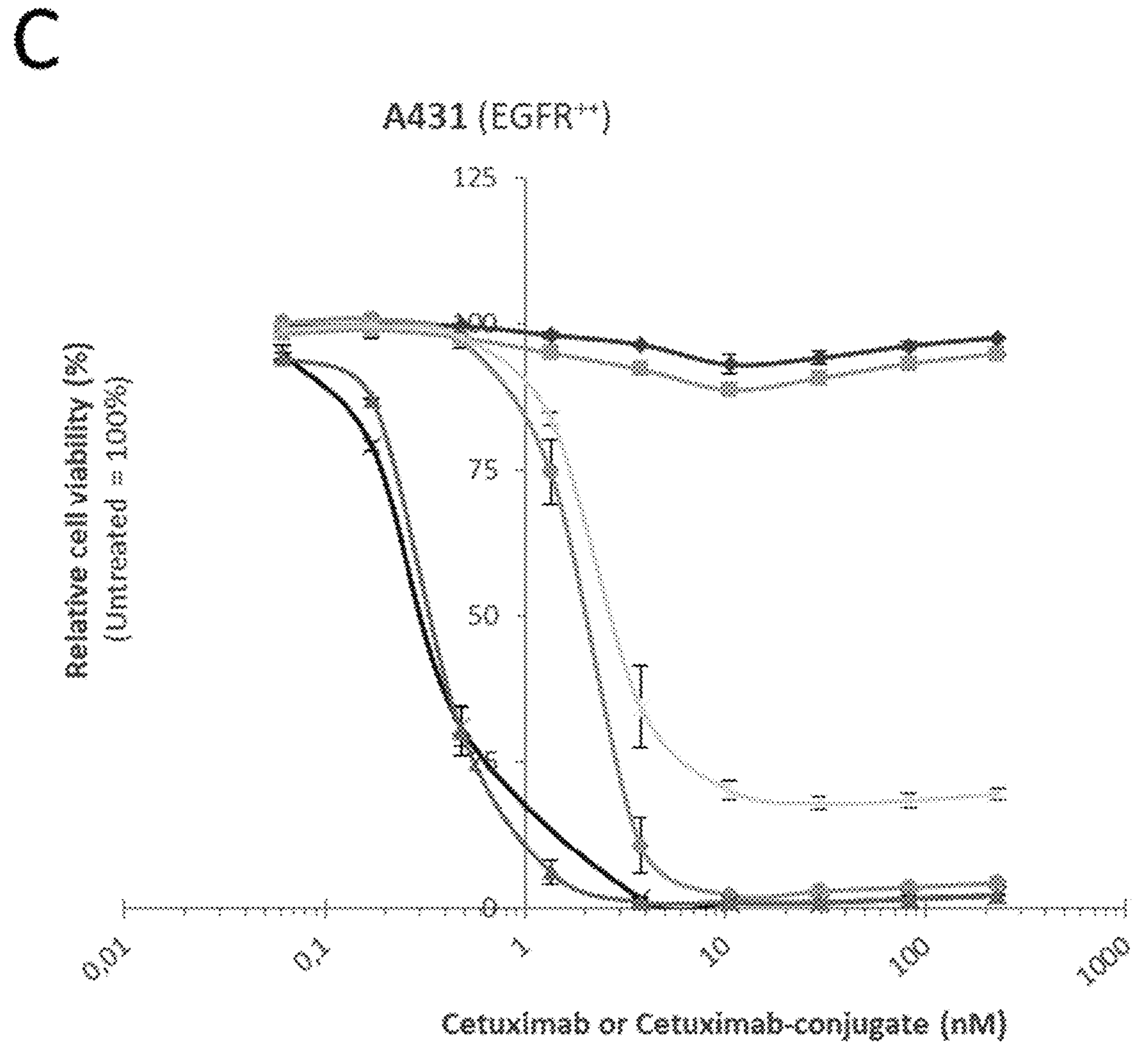
Figure 4:
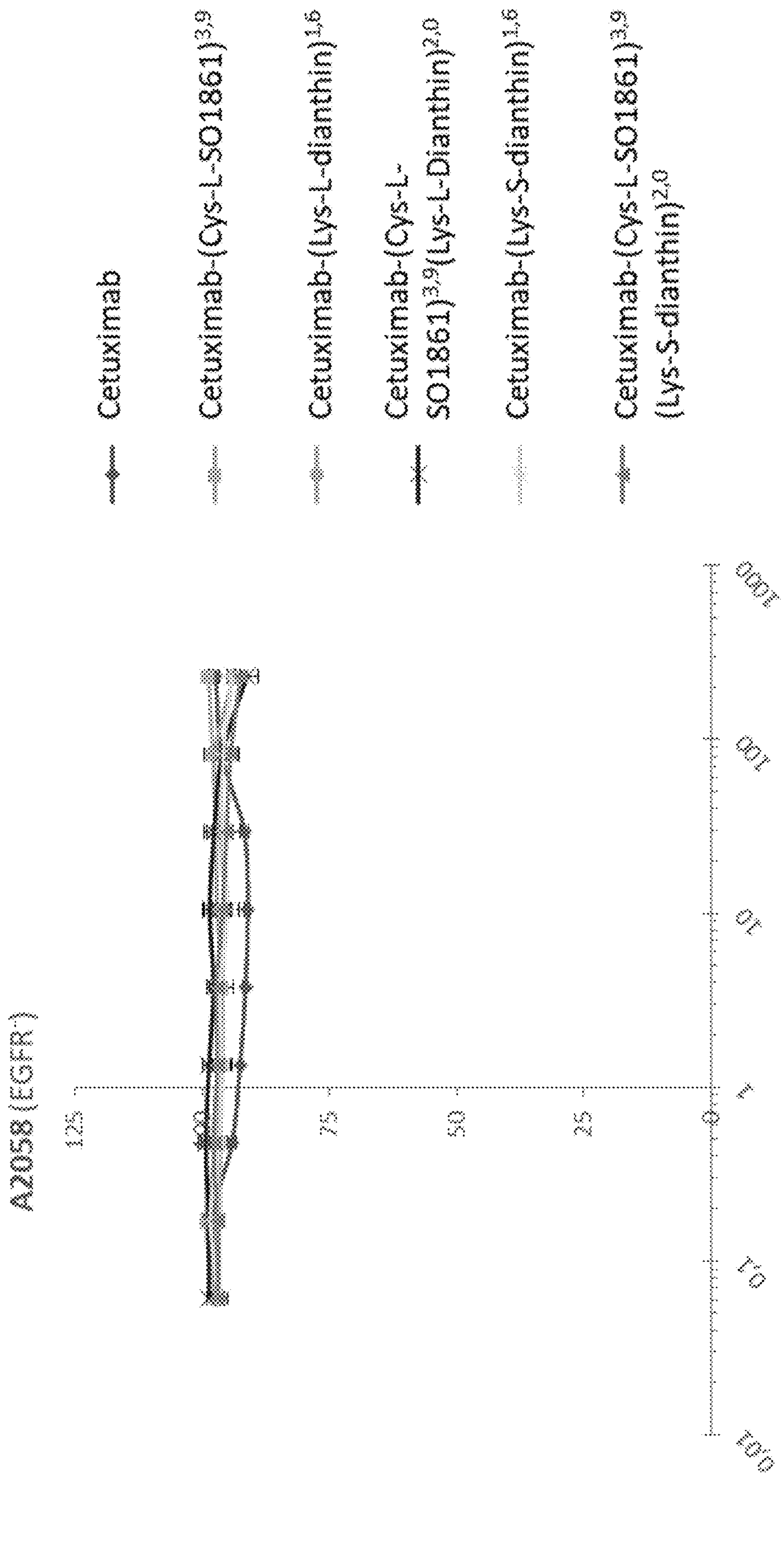

In another example according to the invention, SO1861 (labile) and the protein toxin, dianthin (labile or stable) were conjugated to the HER2 targeting antibody, trastuzumab. Trastuzumab-(Cys-L-SO1861)$^{3,8}$(Lys-L-dianthin)$^{1,7}$ or trastuzumab-(Cys-L-SO1861)$^{3,8}$(Lys-S-dianthin)$^{1,7}$, were produced and tested for enhanced cell killing in SK-BR-3 (HER2$^{++}$) and MDA-MB-468 (HER2$^{-}$) cells as illustrated in FIG. 9. Both, trastuzumab-(Cys-L-SO1861)$^{3,8}$(Lys-L-dianthin)$^{1,7}$ (IC50=0.8 nM) and trastuzumab-(Cys-L-SO1861)$^{3,8}$(Lys-S-dianthin)$^{1,7}$ (IC50=0.8 nM) efficiently induces cell killing of SK-BR-3 cells (HER2$^{++}$) (FIG. 4A). This was not observed in SK-BR-3 cells treated with trastuzumab, trastuzumab-(Lys-L-dianthin)$^{1,7}$, trastuzumab-(Lys-S-dianthin)$^{1,7}$ or trastuzumab-(L-SO1861)$^{3,8}$ alone (FIG. 4A). In MDA-MB-468 cells (HER2$^{-}$) no cell killing activity can be observed for any of the conjugates, according to the invention (FIG. 4B). This shows that conjugation of SO1861 to an HER targeting antibody-protein toxin conjugate, efficiently induces SO1861-mediated enhanced cytoplasmic delivery of the protein toxin in the target cell resulting in target cell death.

In another example according to the invention, SO1861 (labile) and the protein toxin, dianthin (labile or stable) were conjugated to the EGFR targeting antibody, cetuximab. Cetuximab-(Cys-L-SO1861)$^{3,9}$(Lys-L-dianthin)$^{2}$ or cetuximab-(Cys-L-SO1861)$^{3,9}$(Lys-S-dianthin)$^{2}$, was tested for enhanced cell killing in A431 cells (EGFR$^{++}$) and A2058 cells (EGFR$^{-}$) as illustrated in FIG. 9. Both, cetuximab-(Cys-L-SO1861)$^{3,9}$(Lys-L-dianthin)$^{2}$ (IC50=0.3 nM) and cetuximab-(Cys-L-SO1861)$^{3,8}$(Lys-S-dianthin)$^{1,7}$ (IC50=0.3 nM) showed enhanced cell killing in A431 cells (EGFR$^{++}$) compared to cetuximab-(Lys-L-dianthin)$^{1,6}$ (IC50=2 pM), cetuximab-(Lys-S-dianthin)$^{1,6}$ (IC5=2 pM) alone (FIG. 4C). In A2058 cells (EGFR$^{-}$) the combination according to the invention did not show any cell killing activity (IC50>200 nM; FIG. 4D). This shows that conjugation of SO1861 to an EGFR targeting antibody-protein toxin conjugate, efficiently enhances SO1861-mediated cytoplasmic delivery of the protein toxin in the target cell resulting in enhanced target cell death.

Example 3

Figure 5:
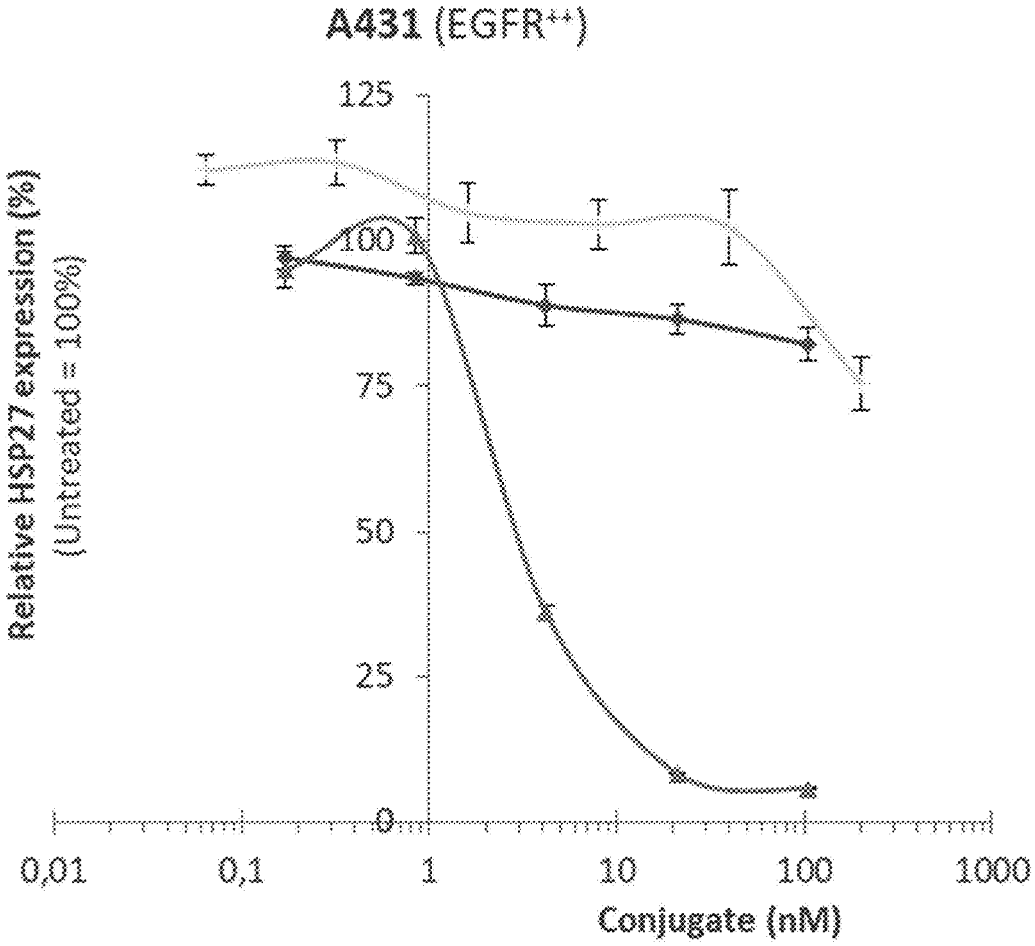
FIG. 5: EGFR targeted antisense BNA oligo delivery and gene silencing in cancer cells, according to the invention. A,B) Cetuximab-(Cys-L-SO1861)$^{3,8}$(Lys-L-HSP27BNA)$^{1,7}$ treatment and controls on A431 cells ($EGFR^{++}$) and A2058 cells ($EGFR^{-}$). Remark: For target receptor expression data of each cell line (determined by FACS analysis) see table 23.
Figure 5:
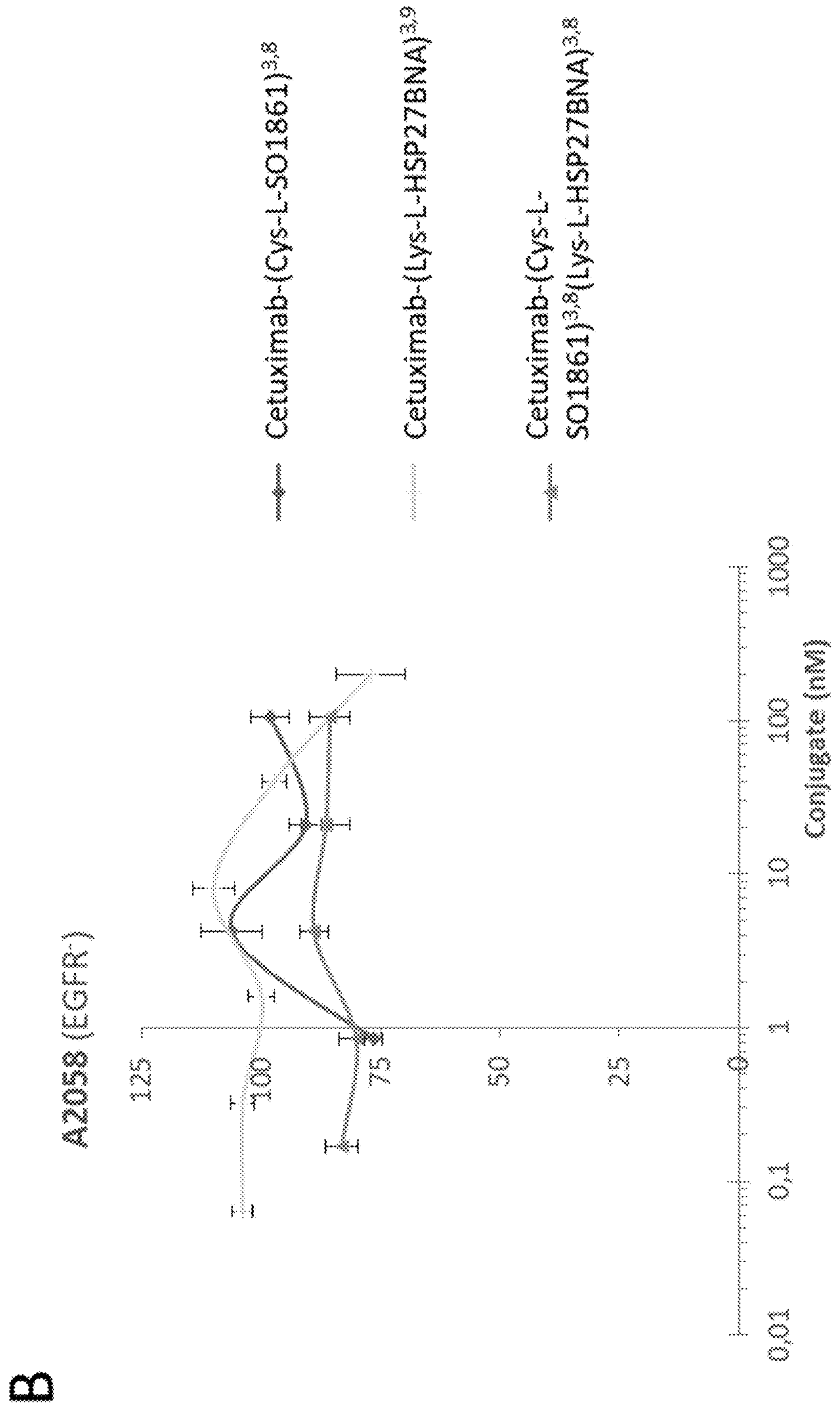

In another example according to the invention, SO1861 (labile) and the HSP27BNA oligo (labile) were conjugated to the EGFR targeting antibody, cetuximab. Cetuximab-(Cys-L-SO1861)$^{3,8}$(Lys-L-HSP27BNA)$^{3,8}$ was tested for enhanced HSP27 gene silencing in A431 cells (EGFR$^{++}$) and A2058 (EGFR$^{-}$) cells, according to the invention as illustrated in FIG. 10. Cetuximab-(Cys-L-SO1861)$^{3,8}$(Lys-L-HSP27BNA)$^{3,8}$ efficiently induces HSP27 gene silencing in A431 cells (IC50=3 nM) compared to cetuximab, cetuximab-(Lys-L-HSP27BNA)$^{3,9}$ or cetuximab-(Cys-L-SO1861)$^{3,8}$ alone (FIG. 5A). In A2058 cells (EGFR$^{-}$) no gene silencing activity can be observed with cetuximab-(Cys-L-SO1861)$^{3,8}$(Lys-L-HSP27BNA)$^{3,8}$ (IC50>100 nM; FIG. 5B). This shows and enables that conjugation of SO1861 and HSP27BNA to the same targeting antibody, according to the invention, efficiently induces SO1861-mediated enhanced cytoplasmic delivery of a therapeutic antisense oligo nucleotide in the target cells, inducing targeted gene silencing.

Figure 6:
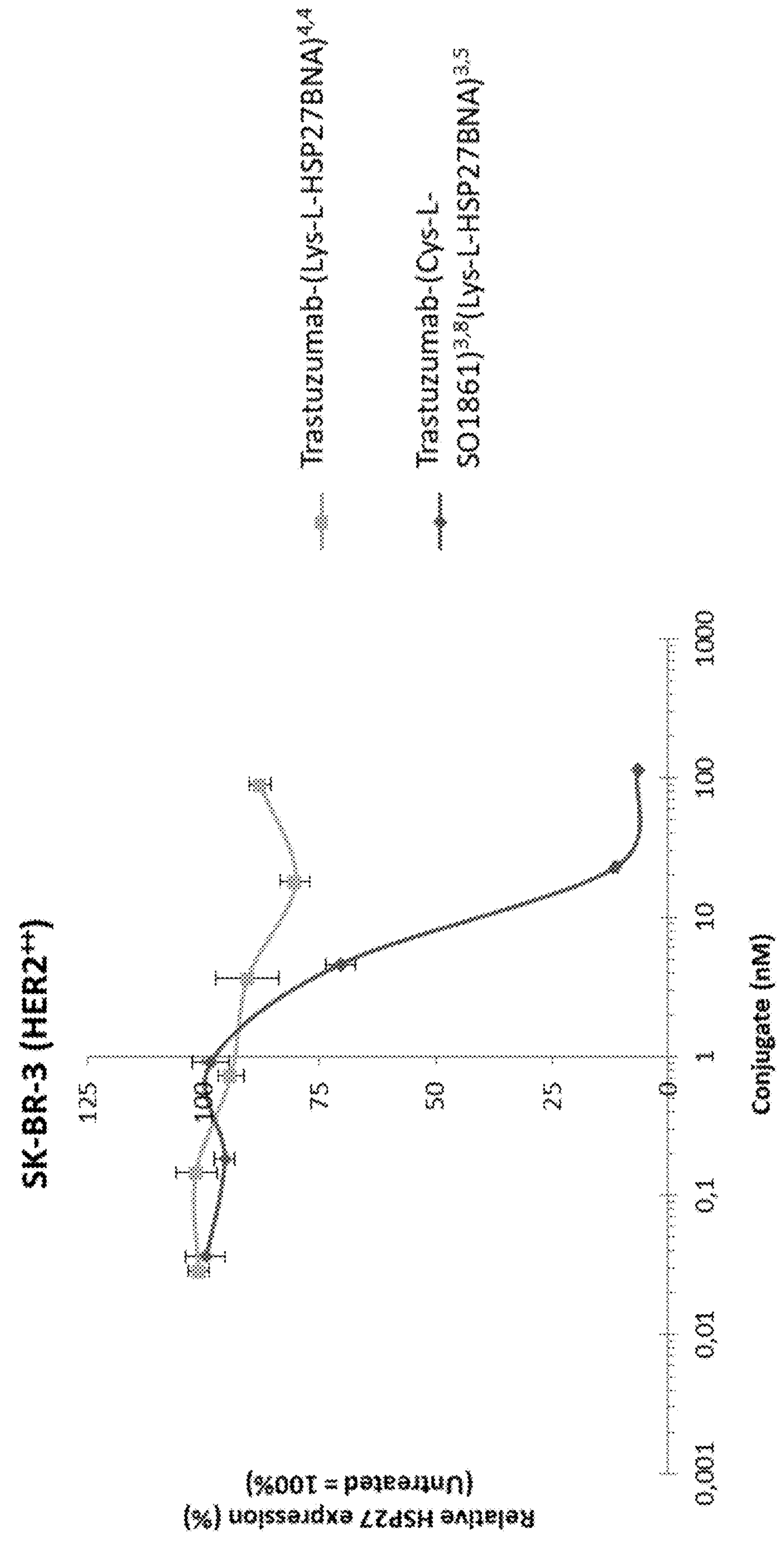
FIG. 6: HER2 targeted antisense BNA oligo delivery and gene silencing in cancer cells, according to the invention. Trastuzumab-(Cys-L-SO1861)$^{3,8}$(Lys-L-HSP27BNA)$^{3,5}$ treatment and controls on SK-BR-3 cells ($HER2^{++}$). Remark: For target receptor expression data of each cell line (determined by FACS analysis) see table 23.

In another example according to the invention, SO1861 (labile) and the HSP27BNA oligo (labile) were conjugated to the HER2 targeting antibody, trastuzumab. Trastuzumab-(Cys-L-SO1861)$^{3,8}$(Lys-L-HSP27BNA)$^{3,5}$ was tested for enhanced HSP27 gene silencing in SK-BR-3 cells (HER2$^{++}$) cells, according to the invention as illustrated in FIG. 10. Trastuzumab-(Cys-L-SO1861)$^{3,8}$(Lys-L-HSP27BNA)$^{3,5}$ efficiently induces HSP27 gene silencing in SK-BR-3 cells (IC50=9 nM) compared to trastuzumab-(Lys-L-HSP27BNA)$^{44}$ alone (FIG. 6). This shows and enables that conjugation of SO1861 and HSP27BNA to an HER2 targeting antibody, according to the invention, efficiently induces SO1861-mediated enhanced cytoplasmic delivery of a therapeutic antisense oligo nucleotide in the target cells, inducing targeted gene silencing.

Figure 7:
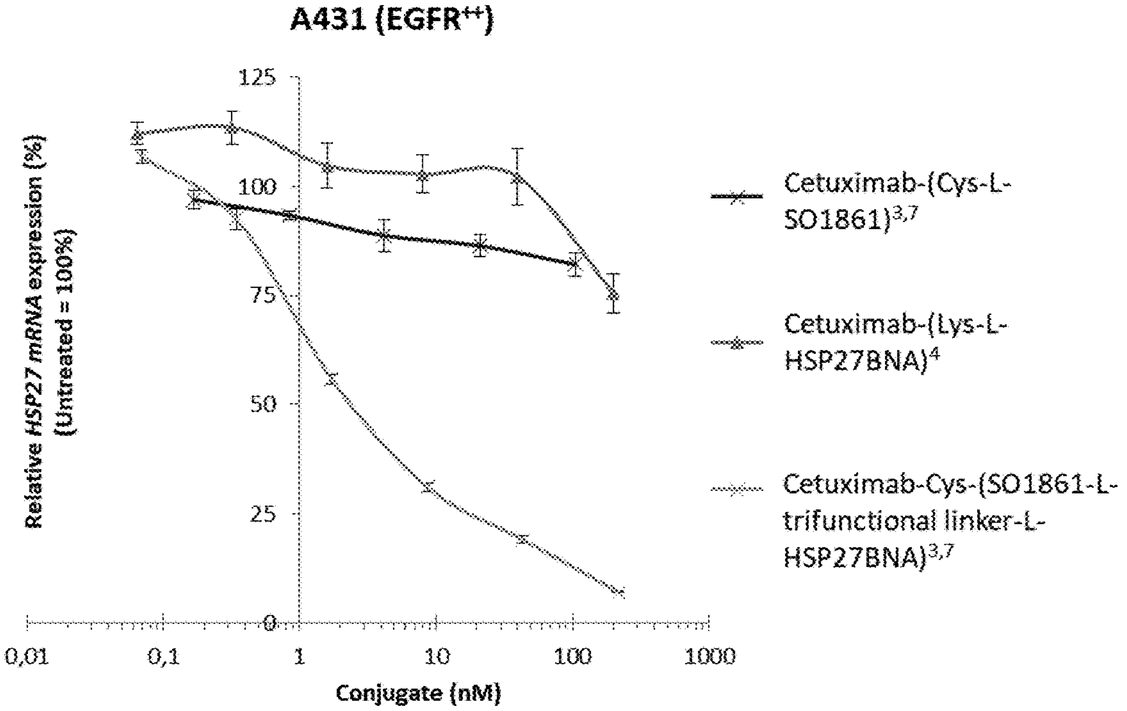
FIG. 7: EGFR targeted antisense BNA oligo delivery and gene silencing in cancer cells, according to the invention. A,B) Cetuximab-Cys-(SO1861-L-trifunctional linker-L-HSP27BNA)$^{3,7}$ treatment and controls on A431 cells ($EGFR^{++}$) and A2058 cells ($EGFR^{-}$). Remark: For target receptor expression data of each cell line (determined by FACS analysis) see table 23.
Figure 7:
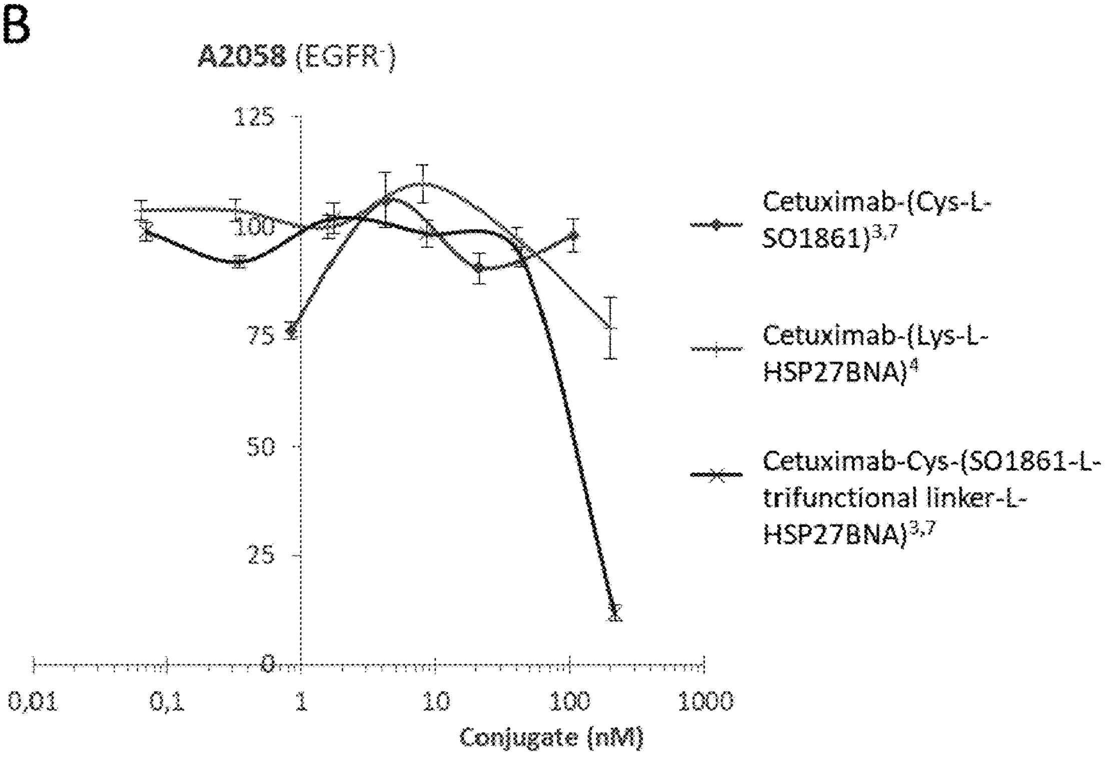

In another example, cetuximab-Cys-(SO1861-L-trifunctional linker-L-HSP27BNA)$^{3,7}$ was tested for enhanced HSP27 gene silencing in A431 (EGFR$^{++}$) and A2058 (EGFR$^{-}$) cells according to the invention as illustrated in FIG. 11. Cetuximab-Cys-(SO1861-L-trifunctional linker-L-HSP27BNA)$^{3,7}$ efficiently induces HSP27 gene silencing in A431 cells (IC50=2 nM) compared to Cetuximab-(Lys-L-HSP27BNA)$^{4}$ or Cetuximab-(Cys-L-SO1861)$^{3,7}$ alone (FIG. 7A). In A2058 cells (EGFR$^{-}$) gene silencing activity was only observed at high (>80 nM) concentrations of Cetuximab-Cys-(SO1861-L-trifunctional linker-L-HSP27BNA)$^{3,7}$ (IC50=100 nM; FIG. 7B). This shows and enables that in high EGFR expressing cells cetuximab-Cys-(SO1861-L-trifunctional linker-L-HSP27BNA)$^{3,7}$ efficiently induces SO1861-mediated enhanced cytoplasmic delivery of a therapeutic antisense oligo nucleotide in the target cells, inducing targeted gene silencing.

Example 4

FIG. 8A-D displays the relative cell viability when trastuzumab (FIG. 8A), cetuximab (FIG. 8B) or T-DM1 (FIG. 8C), unconjugated protein toxins, saporin, dianthin and saporin conjugated to a (non-cell binding) IgG antibody (FIG. 8D) are administrated to various cancer cell lines SK-BR-3, JIMT-1, MDA-MB-468, A431, CaSki, HeLa, A2058.

Trastuzumab and cetuximab do not or hardly influence cell viability when exposed to most of the cell lines, with some effect on cell growth inhibition via blocking the function of the HER2 growth factor receptor when trastuzumab is exposed to SK-BR-3 cells at relatively high dose and with some effect on cell growth inhibition via blocking the function of the EGFR growth factor receptor when cetuximab is exposed to MDA-MB-468 cells at relatively high dose.

Figure 8:
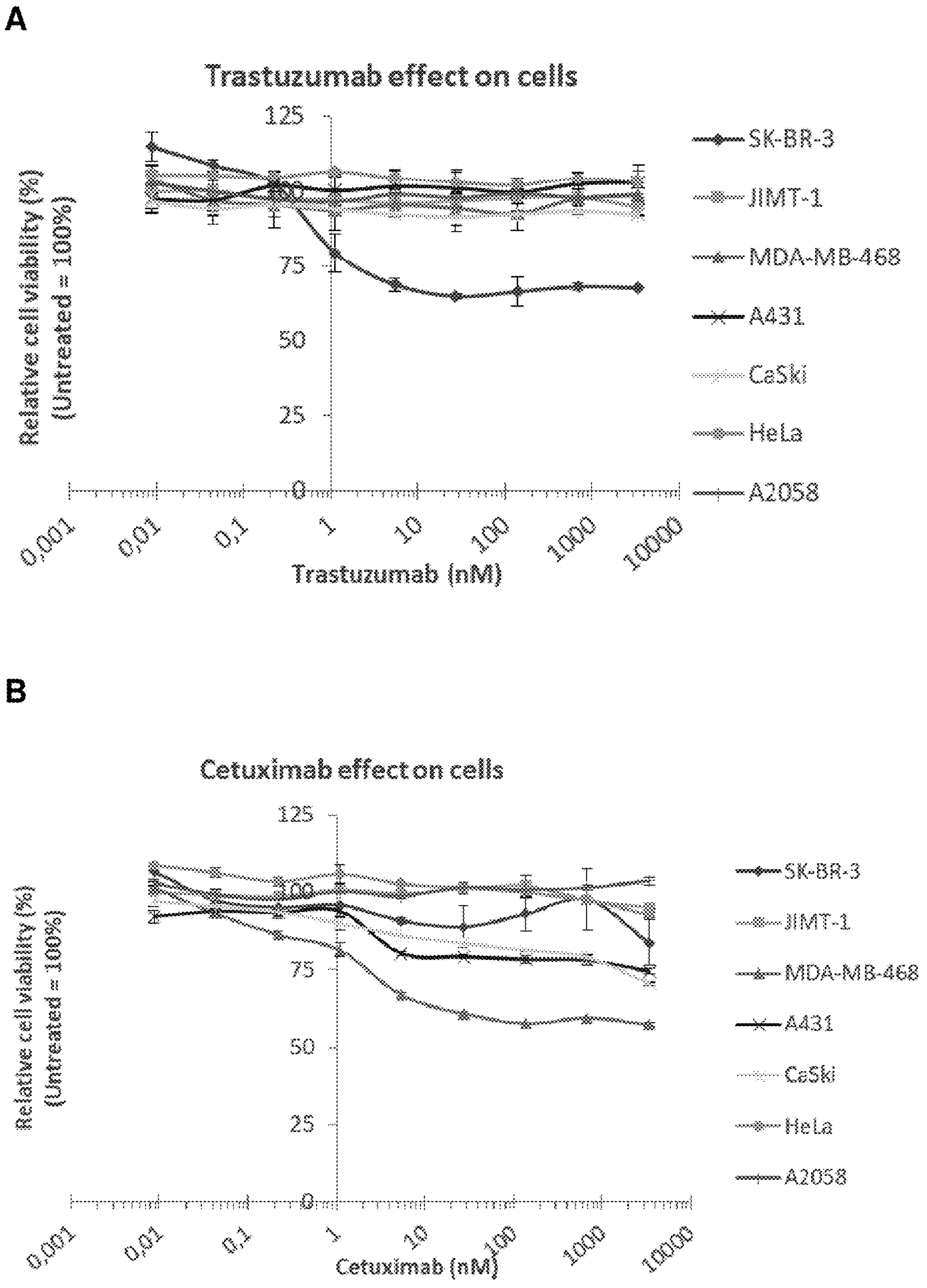
FIG. 8 Control treatments on all cell lines. A-D) Cell viability when trastuzumab (A), cetuximab (B), T-DM1, (C) free toxins: saporin and dianthin (D) or saporin coupled to a non-cell binding IgG (D) are treated with the indicated cell lines SK-BR-3, JIMT-1, MDA-MB-468, A431, CaSki, HeLa, A2058, BT-474. Remark: For target receptor expression data of each cell line (determined by FACS analysis) see table 23.
Figure 8:
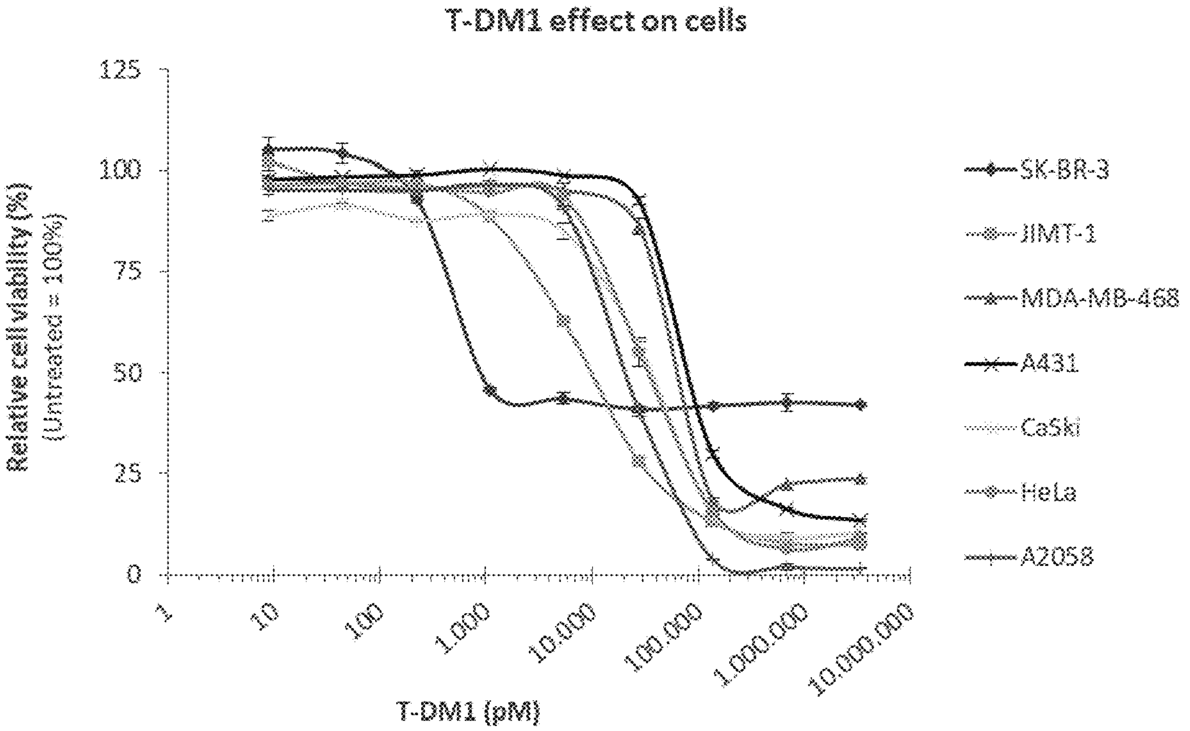
Figure 8:
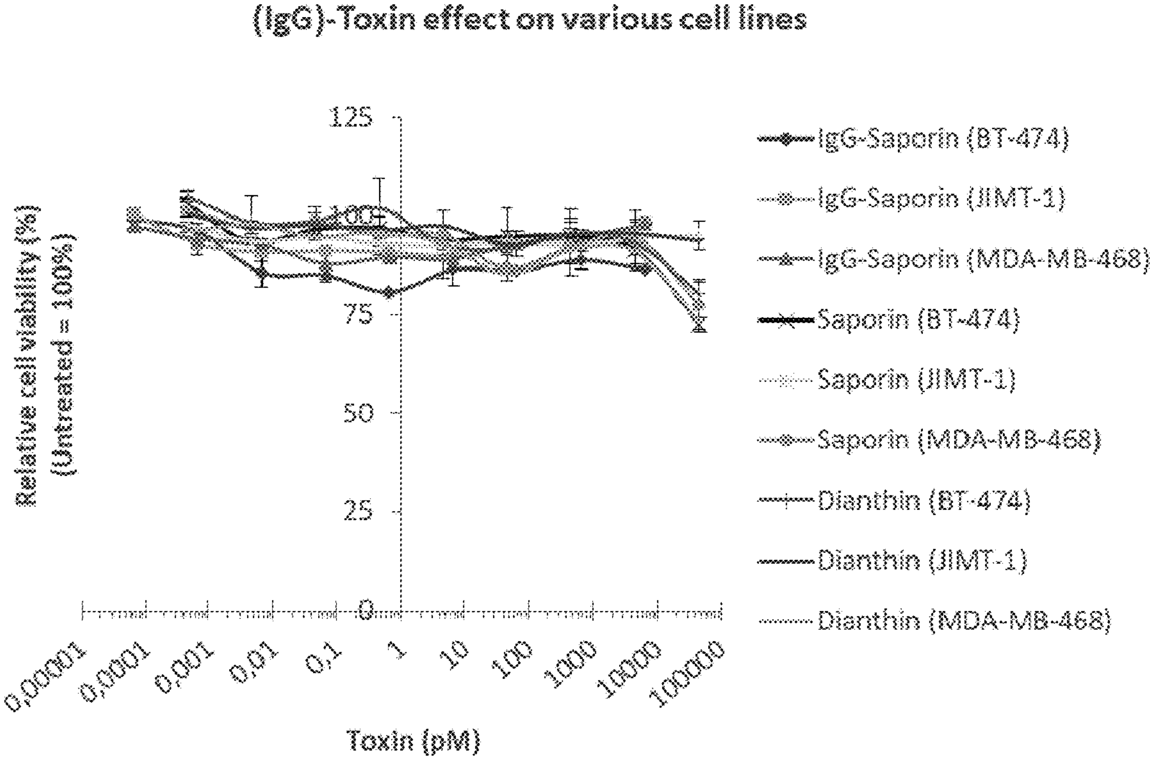

TDM-1, or ado-trastuzumab emtansine, is a targeted therapy approved by the U.S. Food and Drug Administration to treat: HER2-positive metastatic breast cancer that has previously been treated with Herceptin (chemical name: trastuzumab) and taxane chemotherapy; early-stage HER2-positive breast cancer after surgery if residual disease was found after neoadjuvant (before surgery) treatment with Herceptin and taxane chemotherapy. The TDM-1 is a combination of Herceptin (Trastuzumab) and the chemotherapy medicine emtansine. FIG. 8C shows that the TDM-1 results in decreased cell viability for all cell lines tested at >1000 pM concentrations The free toxins saporin and dianthin and the toxin saporin coupled to a control IgG with no affinity for any of the cell surface molecules on the cell lines tested, do not or hardly have any influence on cell viability over a wide range of concentrations toxin tested, up to 100.000 pM (FIG. 8D).

Example 5

Dendron(-L-SO1861)$^n$ Synthesis (FIG. 13, 14, 15)

Materials and Methods

Abbreviations

DCM dichloromethane
DIPEA N,N-diisopropylethylamine
DMF N,N-dimethylformamide
EDCl·HCl 3-((Ethylimino)methyleneamino)-N,N-dimethylpropan-1-aminium chloride
EMCH·TFA N-(ε-maleimidocaproic acid) hydrazide, trifluoroacetic acid salt
min minutes
r.t. retention time
TCEP tris(2-carboxyethyl)phosphine hydrochloride
Temp temperature
TFA trifluoroacetic acid
THF tetrahydrofuran Analytical Methods LC-MS Method 1,[1]

Apparatus: Agilent 1200 Bin. Pump: G1312A, degasser; autosampler, ColCom, DAD: Agilent G1316A, 210, 220 and 220-320 nm, PDA: 210-320 nm, MSD: Agilent LC/MSD G6130B ESI, pos/neg 100-1000; ELSD Alltech 3300 gas flow 1.5 ml/min, gas temp: 40° C.; column: Waters XSelect™ CSH C18, 30×2.1 mm, 3.5 μm, Temp: 35° C., Flow: 1 mL/min, Gradient: $t_0$=5% A, $t_{1.6min}$=98% A, $t_{3min}$=98% A, Posttime: 1.3 min, Eluent A: 0.1% formic acid in acetonitrile, Eluent B: 0.1% formic acid in water.

LC-MS Method 2,[2]

Apparatus: Agilent 1260 Bin. Pump: G7112B, Multisampler, Column Comp, DAD: Agilent G7115A, 210, 220 and 220-320 nm, PDA: 210-320 nm, MSD: Agilent LC/MSD G6130B ESI, mass ranges depending on the molecular weight of the product:

[A]pos/neg 100-1000

[B]pos/neg 100-1400;

ELSD Alltech 3300 gas flow 1.5 ml/min, gas temp: 40° C.; column: Waters XSelect™ C18, 30×2.1 mm, 3.5 μm, Temp: 40° C., Flow: 1 mL/min, Gradient: $t_0$=5% A, $t_{1.6min}$=98% A, $t_{3min}$=98% A, Posttime: 1.3 min, Eluent A: 0.1% formic acid in acetonitrile, Eluent B: 0.1% formic acid in water.

LC-MS Method 3, 3

Apparatus: Waters IClass; Bin. Pump: UPIBSM, SM: UPISMFTN with SO; UPCMA, PDA: UPPDATC, 210-320 nm, SQD: ACQ-SQD2 ESI, pos/neg 800-1500; ELSD: gas pressure 40 psi, drift tube temp: 50° C.; column: Waters XSelect™ CSH C18, 50×2.1 mm, 2.5 μm Temp: 25° C., Flow: 0.6 mL/min, Gradient: $t_0$=5% A, $t_{2.0min}$=98% A, $t_{2min}$=98% A, Posttime: 0.3 min, Eluent A: acetonitrile, Eluent B: 10 mM ammonium bicarbonate in water (pH=9.5).

LC-MS Method 4, 4

Apparatus: Waters IClass; Bin. Pump: UPIBSM, SM: UPISMFTN with SO; UPCMA, PDA: UPPDATC, 210-320 nm, SQD: ACQ-SQD2 ESI, pos/neg 1500-2500; ELSD: gas pressure 40 psi, drift tube temp: 50° C.; column: Waters XSelect™ CSH C18, 50×2.1 mm, 2.5 μm Temp: 25° C., Flow: 0.6 mL/min, Gradient: $t_0$=15% A, $t_{2.0min}$=60% A, $t_{2min}$=98% A, Posttime: 0.3 min, Eluent A: acetonitrile, Eluent B: 10 mM ammonium bicarbonate in water (pH=9.5).

LC-MS Method 5, [5]

Apparatus: Waters IClass; Bin. Pump: UPIBSM, SM: UPISMFTN with SO; UPCMA, PDA: UPPDATC, 210-320 nm, SQD: ACQ-SQD2 ESI, mass ranges depending on the molecular weight of the product:

[A]pos/neg 1500-2500

[B]neg 2000-3000;

ELSD: gas pressure 40 psi, drift tube temp: 50° C.; column: Acquity C18, 50×2.1 mm, 1.7 μm Temp: 60° C., Flow: 0.6 mL/min, Gradient: $t_0$=2% A, $t_{5.0min}$=50% A, $t_{6.0min}$=98% A, Posttime: 1.0 min, Eluent A: acetonitrile, Eluent B: 10 mM ammonium bicarbonate in water (pH=9.5).

Preparative Methods

Preparative MP-LC Method 1, [1]

Instrument type: Reveleris™ prep MPLC; column: Waters XSelect™ CSH C18 (145×25 mm, 10μ); Flow: 40 mL/min; Column temp: room temperature; Eluent A: 10 mM ammoniumbicarbonate in water pH=9.0); Eluent B: 99% acetonitrile+1% 10 mM ammoniumbicarbonate in water; Gradient: $t_{0min}$=5% B, $t_{1min}$=5% B, $t_{2min}$=10% B, $t_{17min}$=50% B, $t_{18min}$=100% B, $t_{23min}$=100% B; Detection UV: 210, 225, 285 nm.

Preparative MP-LC Method 2, [2]

Instrument type: Reveleris™ prep MPLC; Column: Phenomenex LUNA C18(3) (150×25 mm, 10μ); Flow: 40 mL/min; Column temp: room temperature; Eluent A: 0.1% (v/v) Formic acid in water, Eluent B: 0.1% (v/v) Formic acid in acetonitrile; Gradient: $t_{0min}$=5% B, $t_{1min}$=5% B, $t_{2min}$=10% B, $t_{17min}$=50% B, $t_{18min}$=100% B, $t_{23min}$=100% B; Detection UV: 210, 225, 285 nm.

Preparative LC-MS Method 1, [3]

MS instrument type: Agilent Technologies G6130B Quadrupole; HPLC instrument type: Agilent Technologies 1290 preparative LC; Column: Waters XSelect™ CSH (C18, 100×30 mm, 10μ); Flow: 25 ml/min; Column temp: room temperature; Eluent A: 100% acetonitrile; Eluent B: 10 mM ammonium bicarbonate in water pH=9.0; lin. gradient depending on the polarity of the product:

[A]$t_0$=20% A, $t_{2min}$=20% A, $t_{8.5min}$=60% A, $t_{10min}$=100% A, $t_{13min}$=100% A

[B]$t_0$=5% A, $t_{2min}$=5% A, $t_{8.5min}$=40% A, $t_{10min}$=100% A, $t_{13min}$=100% A

[C]$t_0$=10% A, $t_{2min}$=10% A, $t_{8.5min}$=50% A, $t_{10min}$=100% A, $t_{13min}$=100% A;

Detection: DAD (220-320 nm); Detection: MSD (ESI pos/neg) mass range: 100-800; Fraction collection based on DAD.

Preparative LC-MS Method 2, [4]

MS instrument type: Agilent Technologies G6130B Quadrupole; HPLC instrument type: Agilent Technologies 1290 preparative LC; column: Waters XBridge Shield (C18, 150×19 mm, 5μ); Flow: 25 ml/min; Column temp: room temperature; Eluent A: 100% acetonitrile; Eluent B: 10 mM ammonium bicarbonate in water pH=9.0; lin. gradient: $t_0$=5% A, $t_{2.5min}$=5% A, $t_{11min}$=40% A, $t_{13min}$=100% A, $t_{17min}$=100% A; Detection: DAD (220-320 nm); Detection: MSD (ESI pos/neg) mass range: 100-800; Fraction collection based DAD Flash Chromatography Grace Reveleris X2© C-815 Flash; Solvent delivery system: 3-piston pump with auto-priming, 4 independent channels with up to 4 solvents in a single run, auto-switches lines when solvent depletes; maximum pump flow rate 250 mL/min; maximum pressure 50 bar (725 psi); Detection: UV 200-400 nm, combination of up to 4 UV signals and scan of entire UV range, ELSD; Column sizes: 4-330 g on instrument, luer type, 750 g up to 3000 g with optional holder.

SO1861-EMCH Synthesis (FIG. 13)

To SO1861 (121 mg, 0.065 mmol) and EMCH·TFA (110 mg, 0.325 mmol) was added methanol (extra dry, 3.00 mL) and TFA (0.020 mL, 0.260 mmol). The reaction mixture stirred at room temperature. After 1.5 hours the reaction mixture was subjected to preparative MP-LC.[1] Fractions corresponding to the product were immediately pooled together, frozen and lyophilized overnight to give the title compound (120 mg, 90%) as a white fluffy solid. Purity based on LC-MS 96%.

LRMS (m/z): 2069 $[M-1]^{1-}$

LC-MS r.t. (min): 1.084

Dendron(-L-SO1861)$^4$ Synthesis (FIG. 14)

Intermediate 1 di-tert-butyl (((6-azidohexanoyl)azanediyl)bis(ethane-2,1-diyl))dicarbamate 6-azidohexanoic acid (0.943 g, 6.00 mmol), EDCl·HCl (1.21 g, 6.30 mmol) and Oxyma Pure (0.938 g, 6.60 mmol) were dissolved in DMF (10.0 mL) and the mixture was stirred for 5 min. Next a solution of di-tert-butyl (azanediylbis(ethane-2,1-diyl))dicarbamate (1.82 g, 6.00 mmol) in DMF (5.00 mL) was added and the reaction mixture was stirred at room temperature. After 5 hours the reaction mixture was evaporated in vacuo and the residue was dissolved in ethyl acetate (50 mL). The resulting solution was washed with 1N potassium bisulphate solution (50 mL), saturated sodium bicarbonate solution (2×50 mL) and brine (50 mL), dried over $Na_2SO_4$, filtered and evaporated in vacuo. The residue was purified by flash chromatography (ethyl acetate-heptane gradient, 10:90 rising to 100:0) to give the title compound (2.67 g, 100%) as a white solid. Purity based on LC-MS 98%.

LRMS (m/z): 287/343/465 $[M-155/M-99/M+23]^{1+}$

LC-MS r.t. (min): $2.02^{2A}$

Intermediate 2

N,N-bis(2-aminoethyl)-6-azidohexanamide dihydrochloride

To di-tert-butyl (((6-azidohexanoyl)azanediyl)bis(ethane-2,1-diyl))dicarbamate (2.66 g, 6.00 mmol) was added HCl in isopropanol (5-6 N, 20.0 mL, 110 mmol) and the reaction mixture was stirred at room temperature. After 4 hours, the reaction mixture was evaporated in vacuo and the resulting crude product was co-evaporated with DCM (3×20 mL) to give the crude title product (1.49 g, 79%) as a white solid.

LRMS (m/z): 243 $[M+1]^{1+}$

Intermediate 3 tetra-tert-butyl ((5S,5'S)-((((6-azidohexanoyl) azanediyl)bis(ethane-2,1-diyl))bis(azanediyl))bis(6-oxohexane-6,1,5-triyl))tetracarbamate To a solution of N,N-bis(2-aminoethyl)-6-azidohexanamide dihydrochloride (1.19 g, 3.76 mmol) in DMF (30.0 mL) and DIPEA (2.62 mL, 15.1 mmol) was added Boc-Lys (Boc)-ONp (3.69 g, 7.90 mmol) and the mixture was stirred at room temperature overnight. The reaction mixture was evaporated in vacuo and the residue was dissolved in ethyl acetate (100 mL). The resulting solution was washed with 1N potassium bisulphate solution (100 mL) and saturated sodium bicarbonate solution (5×100 mL), dried over $Na_2SO_4$, filtered and evaporated in vacuo. The residue was purified by flash chromatography (DCM-methanol/DCM (1/9, v/v) gradient 100:0 rising to 0:100) to give the give the title product (3.07 g, 91%) as a slightly yellowish solid. Purity based on LC-MS 94%.

LRMS (m/z): 800/900/922 $[M-99/M+1/M+23]^{1+}$

LC-MS r.t. (min): $2.17^{2A}$

Intermediate 4

4-nitrophenyl 3-(acetylthio)propanoate

4-Nitrophenyl trifluoroacetate (5.17 g, 22.0 mmol) and 3-(Acetylthio)propionic Acid (2.96 g, 20.0 mmol) were dissolved in DCM (50.0 mL). Next, DIPEA (6.97 mL, 40.0 mmol) was added and the reaction mixture was stirred at room temperature overnight. The reaction mixture was evaporated in vacuo and the residue was dissolved in ethyl acetate (50 mL). The resulting solution was washed with 1N potassium bisulphate solution (50 mL), saturated sodium bicarbonate solution (5×50 mL) and brine (50 mL), dried over $Na_2SO_4$, filtered and evaporated in vacuo. The residue was purified by flash chromatography (DCM-methanol/DCM (1/9, v/v) gradient 100:0 rising to 0:100) to give the give the title product (4.90 g, 91%) as a slightly yellowish solid. Purity based on LC-MS 99%.

LRMS (m/z): 292 $[M+23]^{1+}$

LC-MS r.t. (min): $1.94^{2A}$

Intermediate 5

(S)-2,6-diamino-N-(2-(6-azido-N-(2-((S)-2,6-diaminohexanamido)ethyl)hexanamido)ethyl)hexanamide tetrahydrochloride tetra-tert-butyl ((5S,5'S)-((((6-azidohexanoyl)azanediyl) bis(ethane-2,1-diyl))bis(azanediyl))bis(6-oxohexane-6,1,5-triyl))tetracarbamate (1.80 g, 2.00 mmol) was dissolved in HCl in isopropanol (5-6N, 50.0 ml, 275 mmol) and the reaction mixture was stirred at room temperature overnight. The reaction mixture was evaporated in vacuo and the resulting crude product was co-evaporated with DCM (3×20 mL) to give the crude title product as a white solid.

LRMS (m/z): 250 $[M+2]^{2+}$, 500 $[M+1]^{1+}$

Intermediate 6

(2S)-2,6-bis[3-(acetylsulfanyl)propanamido]-N-[2-(6-azido-N-{2-[(2S)-2,6-bis[3-(acetylsulfanyl)propanamido]hexanamido]ethyl}hexanamido)ethyl] hexanamide To a solution of (S)-2,6-diamino-N-(2-(6-azido-N-(2-((S)-2,6-diaminohexanamido)ethyl)hexanamido) ethyl) hexanamide tetrahydrochloride (1.29 g, 2.00 mmol) in DMF (30 mL) and DIPEA (3.48 mL, 20.0 mmol) was added 4-nitrophenyl 3-(acetylthio)propanoate (2.26 g, 8.40 mmol) and the reaction mixture was stirred at room temperature over the weekend. The reaction mixture was evaporated in vacuo and the residue was dissolved in DCM/methanol (95:5, v/v, 100 mL). The resulting solution was washed with 1N potassium bisulphate solution (100 mL), 1 N sodium hydroxide solution (3×100 mL) and brine (100 mL), dried over $Na_2SO_4$, filtered and evaporated in vacuo. The residue was purified by flash chromatography (DCM-methanol/DCM (1/9, v/v) gradient 100:0 rising to 0:100) to give the title product (1.33 g, 65%) as a white solid. On LC-MS an impurity (15%) was found with m/z values corresponding to the product with one deprotected thioacetate group. The impurity was formed during or after work-up. Purity based on LC-MS 85%.

LRMS (m/z): 510 $[M+2]^{2+}$, 1019/1041 $[M+1/M+23]^{1+}$

LC-MS r.t. (min): 1.86[2B]

Intermediate 7

N,N'-((9S,19S)-14-(6-aminohexanoyl)-1-mercapto-9-(3-mercaptopropanamido)-3,10,18-trioxo-4,11,14,17-tetraazatricosane-19,23-diyl)bis(3-mercaptopropanamide) formate Scaffold 2 (102 mg, 0.100 mmol) was dissolved in methanol (1.00 ml). Next, a freshly prepared 1 N Sodium hydroxide solution (0.440 ml, 0.440 mmol) was added and the reaction mixture was stirred at room temperature. After 30 min a 1.0 M trimethylphosphine solution in THE (0.500 ml, 0.500 mmol) was added and the resulting mixture was stirred at room temperature. After 30 min the reaction mixture was evaporated in vacuo and co-evaporated with methanol (2×10 mL). The residue was dissolved in a mixture of methanol/water (9:1, v/v, 1.00 mL) and the resulting solution was subjected to preparative MP-LC.[2] Fractions corresponding to the product were immediately pooled together, frozen and lyophilized overnight to give the title compound (75.6 mg, 87%) as a colorless sticky oil. Purity based on LC-MS 96%.

LRMS (m/z): 513 $[M+2]^{2+}$, 825 $[M+1]^{1+}$

LC-MS r.t. (min): 1.42[2A]

Intermediate 8

Dendron(-L-SO1861)$^4$-Amine

N,N'-((9S,19S)-14-(6-aminohexanoyl)-1-mercapto-9-(3-mercaptopropanamido)-3,10,18-trioxo-4,11,14,17-tetraazatricosane-19,23-diyl)bis(3-mercaptopropanamide) formate (2.73 mg, 3.13 μmol) was dissolved in a mixture of 20 mM $NH_4HCO_3$ with 0.5 mM TCEP/acetonitrile (3:1, v/v, 3.00 mL). Next, SO1861-EMCH (29.2 mg, 0.014 mmol) was added and the reaction mixture was stirred at room temperature. After 1.5 hours the reaction mixture was subjected to preparative LC-MS.[3B] Fractions corresponding to the product were immediately pooled together, frozen and lyophilized overnight to give the title compound (12.3 mg, 43%) as a white fluffy solid. Purity based on LC-MS 97%.

LRMS (m/z): 1517 $[M-6]^{6-}$, 1821 $[M-5]^{5-}$, 2276 $[M-4]^{4-}$

LC-MS r.t. (min): 4.39[5A]

Intermediate 9

Dendron(-L-SO1861)$^4$-Azide

Dendron(SO1861)$_4$-amine (6.81 mg, 0.748 μmol) and 2,5-dioxopyrrolidin-1-yl 1-azido-3,6,9,12-tetraoxapentadecan-15-oate (2.90 mg, 7.48 μmol) were dissolved in DMF (1.00 mL). Next, DIPEA (1.302 μL, 7.48 μmol) was added and the mixture was shaken for 1 min and left standing at room temperature. After 2 hours the reaction mixture was subjected to preparative LC-MS.[3C] Fractions corresponding to the product were immediately pooled together, frozen and lyophilized overnight to give the title compound (5.86 mg, 84%) as a white fluffy solid. Purity based on LC-MS 90%.

LRMS (m/z): 2344 $[M-4]^{4-}$

LC-MS r.t. (min): 4.78[5B]

Intermediate 10

Dendron(-L-SO1861)$^4$-Maleimide1

Dendron(SO1861)$_4$-amine (8.12 mg, 0.891 μmol) and 2,5-dioxopyrrolidin-1-yl 1-(2,5-dioxo-2,5-dihydro-1H-pyrrol-1-yl)-3,6,9,12-tetraoxapentadecan-15-oate (3.94 mg, 8.91 μmol) were dissolved in DMF (1.00 mL). Next, DIPEA (1.55 μL, 8.91 μmol) was added and the mixture was shaken for 1 min and left standing at room temperature. After 3 hours the reaction mixture was subjected to preparative LC-MS.[3C] Fractions corresponding to the product were immediately pooled together, frozen and lyophilized overnight to give the title compound (6.76 mg, 80%) as a white fluffy solid. Purity based on LC-MS 66%.

LRMS (m/z): 2358 $[M-4]^{4-}$

LC-MS r.t. (min): 2.13[6C]

Intermediate 11

Dendron(-L-SO1861)$^4$-Maleimide2

Scaffold 2 (5.10 mg, 5.00 μmol) was dissolved in methanol (100 μL). Next, a freshly prepared 1 N Sodium hydroxide solution (22.0 μL, 22.0 μmol) was added and the mixture was shaken for 1 min and left standing at room temperature. After 30 min a 1.0 M trimethylphosphine solution in THF (25.0 μL, 25.0 μmol) was added and the resulting mixture was shaken for 1 min and left standing at room temperature. After 30 min the reaction mixture was evaporated in vacuo and co-evaporated with methanol (2×5 mL). The resulting residue was dissolved in a mixture of 20 mM $NH_4HCO_3$ with 0.5 mM TCEP/acetonitrile (3:1, v/v, 3.242 mL). From this solution, directly, 1000 μL was added to SO1861-EMCH (14.4 mg, 6.94 μmol, 4.5 equiv. compared to the scaffold) and the mixture was shaken for 1 min and left standing at room temperature. After 10 min the reaction mixture was lyophilized overnight. To the resulting residue 2,5-Dioxopyrrolidin-1-yl 3-(2-(2-(3-(2,5-dioxo-2h-pyrrol-1(5h)-yl)propanamido)ethoxy)ethoxy)propanoate (5.84 mg, 0.014 mmol) and DMF (1.00 mL) were added. Next, DIPEA (2.39 μL, 0.014 mmol) was added and the suspension was shaken for 1 min and left standing at room temperature. After 2 hours the reaction mixture was subjected to preparative LC-MS.[3C] Fractions corresponding to the product were immediately pooled together, frozen and lyophilized overnight to give the title compound (10.9 mg, 85%) as a white fluffy solid. Purity based on LC-MS 80%.

LRMS (m/z): 2354 $[M-4]^{4-}$

LC-MS r.t. (min): 4.16[5B]

Dendron(-L-SO1861)$^8$ Synthesis (FIG. 15)

Intermediate 1 tert-butyl N-[(1S)-1-{[(1S)-1-{[2-(6-azido-N-{2-[(2S)-2,6-bis[(2S)-2,6-bis({[(tert-butoxy)carbonyl]amino})hexanamido]hexanamido]ethyl}hexanamido)ethyl]carbamoyl}-5-[(2S)-2,6-bis({[(tert-butoxy)carbonyl]amino})hexanamido]pentyl]carbamoyl}-5-{[(tert-butoxy)carbonyl]amino}pentyl]carbamate (S)-2,6-diamino-N-(2-(6-azido-N-(2-((S)-2,6-diaminohexanamido)ethyl)hexanamido)ethyl)hexanamide tetrahydrochloride (964 mg, 1.50 mmol) was dissolved in DMF (25.0 mL) and triethylamine (2.08 mL, 15.0 mmol). Next, Boc-Lys(Boc)-ONp (3.36 g, 7.18 mmol) was added and the reaction mixture was stirred at room temperature overnight. The reaction mixture was evaporated in vacuo and the residue was purified by flash chromatography (DCM-methanol/DCM (1/9, v/v) gradient 100:0 rising to 0:100) to give the title product (2.71 g, 100%) as a white solid. Purity based on

LC-MS 97%.

LRMS (m/z): 807 $[M-198]^{2+}$

LC-MS r.t. (min): 2.35[2B]

Intermediate 2

(2S,2'S)—N,N'-((5S,15S,22S)-22,26-diamino-10-(6-azidohexanoyl)-15-((S)-2,6-diaminohexanamido)-6,14,21-trioxo-7,10,13,20-tetraazahexacosane-1,5-diyl)bis(2,6-diaminohexanamide) octahydrochloride Intermediate 1 (2.71 g, 1.50 mmol) was dissolved in HCl in isopropanol (5-6N, 25.0 ml, 138 mmol) and the reaction mixture was stirred at room temperature overnight. Next, the reaction mixture was evaporated in vacuo and the resulting crude product was co-evaporated with DCM (3×20 mL) to give the crude title product as a white solid.

LRMS (m/z): 203/254 $[M-200/M+4]^{4}$+, 338 $[M+3]^{3}$+, 507 $[M+2]^{2+}$, 1012 $[M+1]^{1+}$

Intermediate 3

(2S)-2,6-bis[3-(acetylsulfanyl)propanamido]-N-[(1S)-1-{[2-(6-azido-N-{2-[(2S)-2,6-bis[(2S)-2,6-bis[3-(acetylsulfanyl)propanamido]hexanamido]hexanamido]ethyl}hexanamido)ethyl]carbamoyl}-5-[(2S)-2,6-bis[3-(acetylsulfanyl)propanamido]hexanamido]pentyl]hexanamide To (2S,2'S)—N,N'-((5S,15S,22S)-22,26-diamino-10-(6-azidohexanoyl)-15-((S)-2,6-diaminohexanamido)-6,14,21-trioxo-7,10,13,20-tetraazahexacosane-1,5-diyl)bis(2,6-diaminohexanamide) octahydrochloride (300 mg, 0.230 mmol) was added DMF (20.0 mL), triethylamine (320 μl, 2.30 mmol) and 4-nitrophenyl 3-(acetylthio)propanoate (595 mg, 2.21 mmol). The resulting suspension was sonicated at 60° C. for 30 min and left stirring at room temperature overnight. The reaction mixture was evaporated in vacuo and the residue was purified by first performing flash chromatography (DCM-methanol/DCM (1/9, v/v) gradient 100:0 rising to 0:100), followed by preparative MP-LC[2] to give the title product (70 mg, 15%) as a white solid. Purity based on

LC-MS 100%.

LRMS (m/z): 685 $[M+3]^{3+}$

LC-MS r.t. (min): 1.91[2A]

Intermediate 4

(2S)—N-[(1S)-1-{[2-(6-amino-N-{2-[(2S)-2,6-bis[(2S)-2,6-bis(3-sulfanylpropanamido)hexanamido]hexanamido]ethyl}hexanamido)ethyl]carbamoyl}-5-[(2S)-2,6-bis(3-sulfanylpropanamido)hexanamido]pentyl]-2,6-bis(3-sulfanylpropanamido)hexanamide formate Scaffold 4 (10.0 mg, 4.87 μmol) was dissolved methanol (200 μL). Next, a freshly prepared 1 N Sodium hydroxide solution (42.9 μL, 0.043 mmol) was added and the resulting mixture was shaken for 1 min and left standing at room temperature. After 30 min a 1.0 M trimethylphosphine solution in THE (24.4 μL, 0.024 mmol) was added and the resulting mixture was shaken for 1 min and left standing at room temperature. After 30 min the reaction mixture was diluted with water (1 mL) and directly subjected to preparative MP-LC.[2] Fractions corresponding to the product were immediately pooled together, frozen and lyophilized overnight to give the title compound (4.02 mg, 48%) as a white fluffy solid.

LRMS (m/z): 564 $[M+3]^{3}$+, 846 $[M+2]^{2+}$

LC-MS r.t. (min): 1.54[2C]

Intermediate 5

Dendron(-L-SO1861)[8]-Amine

Scaffold 5 (0.52 mg, 0.299 μmol) and SO1861-EMCH (29.2 mg, 0.014 mmol) were dissolved in a mixture of 20 mM $NH_4HCO_3$ with 0.5 mM TCEP/acetonitrile (3:1, v/v, 1.00 mL) and the resulting mixture was shaken for 1 min and left standing at room temperature. After 30 min TCEP (0.30 mg, 1.05 μmol) was added and the reaction mixture was shaken for 1 min. Next, the mixture was directly subjected to preparative LC-MS.[3B] Fractions corresponding to the product were immediately pooled together, frozen and lyophilized overnight to give the title compound (2.17 mg, 40%) as a white fluffy solid. Purity based on LC-MS 97%.

LRMS (m/z): 2282 $[M-8]^{8-}$, 2607 $[M-7]^{7-}$

LC-MS r.t. (min): 4.41[5A]

Example 6

SO1861-Trifunctional Linker-BNAoligo Synthesis (FIG. 16)

Materials and Methods

Trifunctional Linker

Trifunctional linker (DBCO, TCO, maleimide) was ordered at Bio-Synthesis Inc. (Lewisville, Texas).

HSP27BNA Oligo

HSP27BNA(-thiol) oligos (sequence 5'-GGCacagccagtgGCG-3') (Zhang et al., 2011) were purchased at Bio-synthesis Inc. (Lewisville, Texas)

Intermediate 1

SO1861-Azide

To SO1861 60 mg, 0.032 mmol)) and 1-azido-3,6,9,12-tetraoxapentadecane-15-hydrazide (39.3 mg, 0.129 mmol) was added methanol (extra dry, 1.00 mL) and TFA (9.86 μl, 0.129 mmol) and the reaction mixture was shaken for 1 min and left standing at room temperature. After 2 hours the reaction mixture was subjected to preparative MP-LC.[1] Fractions corresponding to the product were immediately pooled together, frozen and lyophilized overnight to give the title compound (58.4 mg, 84%) as a white fluffy solid. Purity based on LC-MS 100%.

LRMS (m/z): 2150 $[M-1]^{1-}$

LC-MS r.t. (min): 1.10[3B]

Intermediate 2

SO1861-Trifunctional Linker

SO1861-azide (45 mg, 0.021 mmol) and trifunctional linker (26.5 mg, 0.022 mmol) were dissolved in DMF (2.50 mL) and the resulting mixture was shaken for 1 min and left standing at room temperature. After 30 min the reaction mixture was subjected to preparative LC-MS.[3C] Fractions corresponding to the product were immediately pooled together, frozen and lyophilized overnight to give the title compound (58.4 mg, 84%) as a white fluffy solid. Purity based on LC-MS 89%.

LRMS (m/z): 1677 $[M-2]^{2-}$

LC-MS r.t. (min): 2.54[6A]

Intermediate 3

(E)-1-(4-((2-(6-(2,5-dioxo-2,5-dihydro-1H-pyrrol-1-yl)hexanoyl)hydrazineylidene)methyl)benzamido)-N-(4-(6-methyl-1,2,4,5-tetrazin-3-yl)benzyl)-3,6,9,12-tetraoxapentadecan-15-amide To 1-(4-formylbenzamido)-N-(4-(6-methyl-1,2,4,5-tetrazin-3-yl)benzyl)-3,6,9,12-tetraoxapentadecan-15-amide (28.0 mg, 0.048 mmol) and EMCH·TFA (24.5 mg, 0.072 mmol) was added methanol (extra dry, 2.00 mL) and TFA (11.1 μL, 0.145 mmol) and the reaction mixture stirred at 50° C. After 30 min the reaction mixture was evaporated in vacuo and the resulting residue was purified by MP-LC.[1] Fractions corresponding to the product were immediately pooled together, frozen and lyophilized overnight to give the title compound (33.4 mg, 88%) as a bright purple fluffy solid. Purity based on LC-MS 92%.

LRMS (m/z): 394 $[M+2]^{2+}$, 789 $[M+1]^{1+}$

LC-MS r.t. (min): 1.28[7A]

Intermediate 4

Methyltetrazine-BNA Oligo

To HSP27 BNA oligo disulfide (70.0 mg, 0.012 mmol) was dissolved in 20 mM $NH_4HCO_3$ (20.0 mL). Next, TCEP (14.3 mg, 0.050 mmol) was added and the reaction mixture was shaken for 1 min and left standing at room temperature. The reaction mixture was filtered by using a centrifugal filter with a molecular weight cut-off of 3000 Da (5000×g for 30 min). Next, a solution of 20 mM $NH_4HCO_3$ with 2.5 mM TCEP (20.0 mL) was added to the residue solution and the resulting mixture was filtered again under the same conditions described above. The residue solution was diluted with 20 mM $NH_4HCO_3$ (30.0 mL) and the resulting mixture was added to a solution of (E)-1-(4-((2-(6-(2,5-dioxo-2,5-dihydro-1H-pyrrol-1-yl)hexanoyl)hydrazineylidene)methyl)benzamido)-N-(4-(6-methyl-1,2,4,5-tetrazin-3-yl)benzyl)-3,6,9,12-tetraoxapentadecan-15-amide (14.8 mg, 18.8 μmol) in acetonitrile (10.0 mL). The reaction mixture was shaken for 1 min and left standing at room temperature. After 30 min the reaction mixture was frozen and lyophilized over the weekend to yield the crude title product as a pink fluffy solid. To the crude product was added a solution of 20 mM $NH_4HCO_3$ (20.0 mL) and the resulting suspension was filtered over a 0.45 μm syringe filter. The filtrate was filtered using a centrifugal filter with the same conditions as described above. Next, again a solution of 20 mM $NH_4HCO_3$ (20.0 mL) was added to the residue solution and the resulting mixture was again filtered by using a centrifugal filter with the same conditions described above. The residue solution was diluted with 20 mM $NH_4HCO_3$ (20.0 mL) and the resulting mixture was lyophilized overnight to yield the title product (90.0 mg, 115%) as a pink fluffy solid. Purity based on LC-MS 91%.

LRMS (m/z): 1631 $[M-4]^{4-}$, 2174 $[M-3]^{3-}$

LC-MS r.t. (min): 0.73[7B]

Intermediate 5

SO1861-Trifunctional Linker-BNA Oligo

Methyltetrazine-BNA oligo (90.0 mg, 0.014 mmol) and SO1861-trifunctional linker (48.6 mg, 0.014 mmol) were dissolved in a mixture of water/acetonitrile (4:1, v/v, 12.0 mL). The reaction mixture was shaken for 1 min and left standing at room temperature. After 15 min the mixture was subjected to preparative LC-MS.[4A] Fractions corresponding to the product were immediately pooled together, frozen and lyophilized overnight to give the title compound (82.0 mg, 60%) as a white fluffy solid. Purity based on LC-MS 92% (2 peaks with both m/z values corresponding to the title compound).

LRMS (m/z): 1641 $[M-6]^{6-}$, 1970 $[M-5]^{5-}$

LC-MS r.t. (min): 3.24 and 3.40[6B]

Intermediate 1

SO1861-Azide

To SO1861 60 mg, 0.032 mmol)) and 1-azido-3,6,9,12-tetraoxapentadecane-15-hydrazide (39.3 mg, 0.129 mmol) was added methanol (extra dry, 1.00 mL) and TFA (9.86 μl, 0.129 mmol) and the reaction mixture was shaken for 1 min and left standing at room temperature. After 2 hours the reaction mixture was subjected to preparative MP-LC.[1] Fractions corresponding to the product were immediately pooled together, frozen and lyophilized overnight to give the title compound (58.4 mg, 84%) as a white fluffy solid. Purity based on LC-MS 100%.

LRMS (m/z): 2150 $[M-1]^{1-}$

LC-MS r.t. (min): 1.10[3B]

Intermediate 2

SO1861-Trifunctional Linker

SO1861-azide (45 mg, 0.021 mmol) and trifunctional linker (26.5 mg, 0.022 mmol) were dissolved in DMF (2.50 mL) and the resulting mixture was shaken for 1 min and left standing at room temperature. After 30 min the reaction mixture was subjected to preparative LC-MS.[3C] Fractions corresponding to the product were immediately pooled together, frozen and lyophilized overnight to give the title compound (58.4 mg, 84%) as a white fluffy solid. Purity based on LC-MS 89%.

LRMS (m/z): 1677 $[M-2]^{2-}$

LC-MS r.t. (min): 2.54[6A]

Intermediate 3

(E)-1-(4-((2-(6-(2,5-dioxo-2,5-dihydro-1H-pyrrol-1-yl)hexanoyl)hydrazineylidene)methyl)benzamido)-N-(4-(6-methyl-1,2,4,5-tetrazin-3-yl)benzyl)-3,6,9,12-tetraoxapentadecan-15-amide To 1-(4-formylbenzamido)-N-(4-(6-methyl-1,2,4,5-tetrazin-3-yl)benzyl)-3,6,9,12-tetraoxapentadecan-15-amide (28.0 mg, 0.048 mmol) and EMCH·TFA (24.5 mg, 0.072 mmol) was added methanol (extra dry, 2.00 mL) and TFA (11.1 μL, 0.145 mmol) and the reaction mixture stirred at 50° C. After 30 min the reaction mixture was evaporated in vacuo and the resulting residue was purified by MP-LC.[1] Fractions corresponding to the product were immediately pooled together, frozen and lyophilized overnight to give the title compound (33.4 mg, 88%) as a bright purple fluffy solid. Purity based on LC-MS 92%.

LRMS (m/z): 394 $[M+2]^{2+}$, 789 $[M+1]^{1+}$

LC-MS r.t. (min): 1.28[7A]

Intermediate 4

Methyltetrazine-BNA Oligo

To HSP27 BNA oligo disulfide (70.0 mg, 0.012 mmol) was dissolved in 20 mM $NH_4HCO_3$ (20.0 mL). Next, TCEP (14.3 mg, 0.050 mmol) was added and the reaction mixture was shaken for 1 min and left standing at room temperature. The reaction mixture was filtered by using a centrifugal filter with a molecular weight cut-off of 3000 Da (5000×g for 30 min). Next, a solution of 20 mM $NH_4HCO_3$ with 2.5 mM TCEP (20.0 mL) was added to the residue solution and the resulting mixture was filtered again under the same conditions described above. The residue solution was diluted with 20 mM $NH_4HCO_3$ (30.0 mL) and the resulting mixture was added to a solution of (E)-1-(4-((2-(6-(2,5-dioxo-2,5-dihydro-1H-pyrrol-1-yl)hexanoyl)hydrazineylidene)methyl) benzamido)-N-(4-(6-methyl-1,2,4,5-tetrazin-3-yl)benzyl)-3,6,9,12-tetraoxapentadecan-15-amide (14.8 mg, 18.8 μmol) in acetonitrile (10.0 mL). The reaction mixture was shaken for 1 min and left standing at room temperature. After 30 min the reaction mixture was frozen and lyophilized over the weekend to yield the crude title product as a pink fluffy solid. To the crude product was added a solution of 20 mM $NH_4HCO_3$ (20.0 mL) and the resulting suspension was filtered over a 0.45 μm syringe filter. The filtrate was filtered using a centrifugal filter with the same conditions as described above. Next, again a solution of 20 mM $NH_4HCO_3$ (20.0 mL) was added to the residue solution and the resulting mixture was again filtered by using a centrifugal filter with the same conditions described above. The residue solution was diluted with 20 mM $NH_4HCO_3$ (20.0 mL) and the resulting mixture was lyophilized overnight to yield the title product (90.0 mg, 115%) as a pink fluffy solid. Purity based on LC-MS 91%.

LRMS (m/z): 1631 $[M-4]^{4-}$, 2174 $[M-3]^{3-}$

LC-MS r.t. (min): $0.73^{7B}$

Intermediate 5

SO1861-Trifunctional Linker-BNA Oligo

Methyltetrazine-BNA oligo (90.0 mg, 0.014 mmol) and SO1861-trifunctional linker (48.6 mg, 0.014 mmol) were dissolved in a mixture of water/acetonitrile (4:1, v/v, 12.0 mL). The reaction mixture was shaken for 1 min and left standing at room temperature. After 15 min the mixture was subjected to preparative LC-MS.[4A] Fractions corresponding to the product were immediately pooled together, frozen and lyophilized overnight to give the title compound (82.0 mg, 60%) as a white fluffy solid. Purity based on LC-MS 92% (2 peaks with both m/z values corresponding to the title compound).

LRMS (m/z): 1641 $[M-6]^{6-}$, 1970 $[M-5]^{5-}$

LC-MS r.t. (min): 3.24 and $3.40^{6B}$

Example 7

SO1861-BNA Oligo Conjugation

HSP27 BNA oligo disulfide (1.10 mg, 0.187 μmol) was dissolved in 20 mM $NH_4HCO_3$ with 1.0 mM TCEP (500 μL) and the mixture was shaken for 1 min and left standing at room temperature. After 1 hour the reaction mixture was filtered by using a centrifugal filter with a molecular weight cut-off of 3000 Da (14000×g for 30 min). The residue solution was diluted with 20 mM $NH_4HCO_3$ with 1.0 mM TCEP (500 μL) and the resulting mixture was filtered again under the same conditions described above. The residue solution was diluted with 20 mM $NH_4HCO_3$/acetonitrile (3:1, v/v, 1.00 mL) and the resulting mixture was added to SO1861-EMCH (3.54 mg, 0.375 μmol). The reaction mixture was shaken for 1 min and left standing at room temperature. After 10 min the reaction mixture was subjected to preparative LC-MS.[4A] Fractions corresponding to the product were immediately pooled together, frozen and lyophilized overnight to give the title compound (1.25 mg, 85%) as a white fluffy solid. Purity based on LC-MS 100%.

LRMS (m/z): 1561 $[M-5]^{5-}$, 1951 $[M-4]^{4-}$

LC-MS r.t. (min): $2.46^{6B}$

Dendron(SO1861)$^4$-BNA Oligo Conjugation (FIG. 17)

HSP27 BNA oligo disulfide (1.1 mg, 0.187 μmol) was dissolved in 20 mM $NH_4HCO_3$ with 1.0 mM TCEP (500 μL) and the mixture was shaken for 1 min and left standing at room temperature. After 1 hour the reaction mixture was filtered by using a centrifugal filter with a molecular weight cut-off of 3000 Da (14000×g for 30 min). The residue solution was diluted with 20 mM $NH_4HCO_3$ with 1.0 mM TCEP (500 μL) and the resulting mixture was filtered again under the same conditions described above. The residue solution was diluted with 20 mM $NH_4HCO_3$/acetonitrile (3:1, v/v, 1.0 mL) and the resulting mixture was added to dendron(SO1861)$^4$-maleimide1 (3.54 mg, 0.375 μmol). The reaction mixture was shaken for 1 min and left standing at room temperature. After 10 min the reaction mixture was subjected to preparative LC-MS.[4A] Fractions corresponding to the product were immediately pooled together, frozen and lyophilized overnight to give the title compound (1.25 mg, 85%) as a white fluffy solid. Purity based on LC-MS 94%

LRMS (m/z): 1896 $[M-8]^{8-}$, 2167 $[M-7]^{7-}$

LC-MS r.t. (min): $3.77^{6B}$

Dendron(NEM)$^4$ Synthesis (FIG. 18)

To benzyl bis(2-((S)-2,6-bis(3-mercaptopropanamido) hexanamido)ethyl)carbamate (1.69 mg, 2.00 μmol) and N-Ethylmaleimide (1.05 mg, 8.40 μmol) was added a mixture of 20 mM $NH_4HCO_3$/acetonitrile (3:1, v/v, 2.00 mL) and the reaction mixture was stirred at room temperature. After 2 hours, the reaction mixture was lyophilized overnight. The resulting residue was purified by using preparative LC-MS[3A] to give the title compound (1.53 mg, 57%) as a white fluffy solid. Purity based on LC-MS 98%.

LRMS (m/z): 1346 $[M+1]^{1+}$

LC-MS r.t. (min): $1.43^{3A}$

Example 8

A431 Mouse Tumor Mouse Model and Vitro and Vivo Gene Silencing Studies

Materials and Methods

HSP27BNA with linkers oligos (sequence 5'-GGCacagccagtgGCG-3') (Zhang et al., 2011) were purchased at Bio-Synthesis Inc. (Lewisville, Texas)

Vitro RNA Isolation and Gene Expression Analyses

RNA from cells was isolated and analysed according to standard protocols (Biorad)

Vivo Mouse Tumor Model

The mouse study was performed at CrownBio (China) according to standard protocols and procedures. Model: Subcutaneous A431 Human Epidermoid Carcinoma Xenograft Model in female BALB/c nude Mice. Tumor volume was monitored and tumor samples were collected for gene silencing analysis (see below)

RNA Isolation and Gene Expression Analyses of Tumor Samples from Mice

Total RNA was isolated from tumors using TriZol (Thermo Fisher) according to the manufacturer's instructions. Isolated RNA was resuspended in nuclease-free water (NFW). RNA samples were checked for their RNA integrity on the gel. To prepare cDNA, first 100 ng total RNA was mixed with Random Hexamers (Qiagen; final concentration 2 μM) in a final volume of 12.5 μl in NFW, denatured for 5 min at 70° C. and immediately cooled on ice. Next, 7.5 μl of a cDNA synthesis mix was added, consisting of 4 μl 5×RT Buffer (Promega), 0.4 μl 25 mM dNTPs (Promega), 1 μl 200 U/μL MMLV RT-enzyme (Promega), 0.5 μL 40 U/μL RNAse Inhibitor (Promega) and 1.6 μL NFW. The following cDNA synthesis protocol was used: 1) 10 minutes 25° C. 2) 60 minutes 37° C. 3) 5 minutes 85° C. 4) ∞ 4° C.

For a single qPCR reaction the following mix was prepared: 1 μL cDNA, 0.05 μL forward primer (250 μM), 0.05 μL reverse primer (250 μM), 8.9 μl LNFW, 10 μl SYBR Green (Bio-Rad). The following qPCR protocol was used: 1 cycle: 5 minutes 95° C., 40 cycles: 15 s 95° C.+30 s 60° C.

HSP27 gene expression was calculated using $2^{-(Ct_{HSP27}-GEOMEAN(Ct_{ref1};Ct_{ref2};Ct_{ref3};Ct_{ref4}))}$, where ref1, ref2, ref3 and ref4 are the reference genes IMMT, EIF2S2, GUSB and UBC for the analysis of the tumors.

Four reference genes were chosen based on the performance of a GeNORM analysis among nine reference genes tested to choose the most ideal and stable reference gene for this tumor samples. To do so, qPCR results were imported in Qbase+ software program by which two quality measures are calculated: the coefficient of variation of the normalized reference gene expression levels (V); and the geNorm stability M-value (M)1. A reference gene with an M<0.2 and a V<0.15 is considered very stable. Based on this analysis IMMT and EIF2S2 were chosen as the most stable reference genes. However, UBC and GUSB were also added to the group of reference genes to further enhance the accuracy of the normalization. Each sample was analyzed as technical triplicate on a CFX96 Real-Time qPCR machine (Bio-Rad).

TABLE 1

Primers used in qPCR are shown below:

| Gene | Primer | Sequence (5'-3') |
|---|---|---|
| UBC | Forward | CAGCCGGGATTTGGGTCG |
| | Reverse | CACGAAGATCTGCATTGTCAAGT |
| GUSB | Forward | TGCGTAGGGACAAGAACCAC |
| | Reverse | GGGAGGGGTCCAAGGATTTG |
| IMMT | Forward | AACCCACACCTGCACTTTCA |
| | Reverse | TTTTCCTGTTGTGCAAGGCG |
| EIF2S2 | Forward | CCACAAGTCGTCCGAGTAGG |
| | Reverse | GGAGATGTTTGGGCTGACGA |
| HSP27 | Forward | GCAGTCCAACGAGATCACCA |
| | Reverse | TAAGGCTTTACTTGGCGGCA |

Example 9

Conjugate Synthesis

Monoclonal Antibodies, SO1861, QS Saponins

Trastuzumab (Herceptin®), cetuximab (Erbitux®) and T-DM1 (Kadcyla®) were purchased from the pharmacy (Charite, Berlin). CD71 monoclonal antibody was purchased from BioCell (Okt9, #BE0023). SO1861 was isolated and purified by Analyticon Discovery GmbH from raw plant extract obtained from *Saponaria officinalis* L. *Quillaja Saponaria* saponin extract (QSmix) was purchased (Sigma Aldrich, #S4521)

Materials

Trastuzumab (Tras, Herceptin®, Roche), Cetuximab (Cet, Erbitux®, Merck KGaA), Tris(2-carboxyethyl)phosphine hydrochloride (TCEP, 98%, Sigma-Aldrich), 5,5-Dithiobis (2-nitrobenzoic acid) (DTNB, Ellman's reagent, 99%, Sigma-Aldrich), Zeba™ Spin Desalting Columns (2 mL, Thermo-Fisher), NuPAGE™ 4-12% Bis-Tris Protein Gels (Thermo-Fisher), NuPAGE™ MES SDS Running Buffer (Thermo-Fisher), Novex™ Sharp Pre-stained Protein Standard (Thermo-Fisher), PageBlue™ Protein Staining Solution (Thermo-Fischer), Pierce™ BCA Protein Assay Kit (Thermo-Fisher), N-Ethylmaleimide (NEM, 98%, Sigma-Aldrich), 1,4-Dithiothreitol (DTT, 98%, Sigma-Aldrich), Sephadex G25 (GE Healthcare), Sephadex G50 M (GE Healthcare), Superdex 200P (GE Healthcare), Isopropyl alcohol (IPA, 99.6%, VWR), Tris(hydroxymethyl)aminomethane (Tris, 99%, Sigma-Aldrich), Tris(hydroxymethyl)aminomethane hydrochloride (Tris·HCL, Sigma-Aldrich), L-Histidine (99%, Sigma-Aldrich), D-(+)-Trehalose dehydrate (99%, Sigma-Aldrich), Polyethylene glycol sorbitan monolaurate (TWEEN 20, Sigma-Aldrich), Dulbecco's Phosphate-Buffered Saline (DPBS, Thermo-Fisher), Guanidine hydrochloride (99%, Sigma-Aldrich), Ethylenediaminetetraacetic acid disodium salt dihydrate ($EDTA-Na_2$, 99%, Sigma-Aldrich), sterile filters 0.2 μm and 0.45 μm (Sartorius), Succinimidyl 4-(N-maleimidomethyl)cyclohexane-1-carboxylate (SMCC, Thermo-Fisher), Dianthin-Cys (Dia-Cys, Dianthin mutant with a single C-terminal cysteine function, Proteogenix), Vivaspin T4 and T15 concentrator (Sartorius), Superdex 200PG (GE Healthcare), Tetra(ethylene glycol) succinimidyl 3-(2-pyridyldithio)propionate ($PEG_4$-SPDP, Thermo-Fisher), HSP27 BNA disulfide oligonucleotide (Biosynthesis), [O-(7-Azabenzotriazol-1-yl)-N,N,N,N-tetramethyluronium-hexafluorphosphat] (HATU, 97%, Sigma-Aldrich), Dimethyl sulfoxide (DMSO, 99%, Sigma-Aldrich), N-(2-Aminoethyl)maleimide trifluoroacetate salt (AEM, 98%, Sigma-Aldrich), L-Cysteine (98.5%, Sigma-Aldrich), deionized water (DI) was freshly taken from Ultrapure Lab Water Systems (MilliQ, Merck), Nickel-nitrilotriacetic acid agarose (Ni-NTA agarose, Protino), Glycine (99.5%, VWR), 5,5-Dithiobis(2-nitrobenzoic acid (Ellman's reagent, DTNB, 98%, Sigma-Aldrich), S-Acetylmercaptosuccinic anhydride Fluorescein (SAMSA reagent, Invitrogen) Sodium bicarbonate (99.7%, Sigma-Aldrich), Sodium carbonate (99.9%, Sigma-Aldrich), PD MiniTrap desalting columns with Sephadex G-25 resin (GE Healthcare), PD10 G25 desalting column (GE Healthcare), Zeba Spin Desalting Columns in 0.5, 2, 5, and 10 mL (Thermo-Fisher), Vivaspin Centrifugal Filters T4 10 kDa MWCO, T4 100 kDa MWCO, and T15 (Sartorius), Biosep s3000 aSEC column (Phenomenex), Vivacell Ultrafiltration Units 10 and 30 kDa MWCO (Sartorius), Nalgene Rapid-Flow filter (Thermo-Fisher), Methods

MALDI-TOF-MS

Matrix-assisted laser desorption/ionization time of flight (MALDI-TOF) spectra were recorded on a MALDI-Mass Spectrometer (Bruker Ultrafex III). Typically, the sample dissolved in MilliQ water in nanomole to micromole range was spotted on the target (MTP 384 target plate polished steel T F, Bruker Daltons) using either super-DHB (99%, Fluka) or sinapinic acid (SA, 99%, Sigma-Aldrich) as the matrix that was dissolved in acetonitrile (MADLI-TOF-MS tested, Sigma)/0.1% TFA (7:3 v/v) via the dried-droplet-method. PepMix (Peptide Calibration Standard, Bruker Daltons) or ProteoMass (Protein Calibration Standard, Sigma-Aldrich) served as calibration standards. RP mode refers to reflector positive mode. RN mode refers to reflector negative mode. LP mode refers to linear positive mode.

Dialysis

Regenerated cellulose membranes: MWCO=1 and 2 kDa (Spectra/Por), and MWCO=12-14 kDa (Carl Roth) were used to perform dialysis. Typically, dialysis was carried out for 24 h with 1 L of solvent that was exchanged after first 6 h of the process.

Lyophilization

Freeze-drying was performed on an Alpha 1-2 LD plus (Martin Christ Gefriertrocknungsanlagen GmbH). Typically, samples were frozen with liquid nitrogen and placed into the freeze-dryer at high vacuum.

UV-Vis

Absorbance measurements were performed on a Perkin Elmer Lambda 25 UV-Vis or on a Thermo NanoDrop ND-2000 spectrophotometer in the spectral range of 200-750 nm.

Concentrations were determined using a Thermo Nanodrop 2000 or Lambda 25 spectrometer using the following parameters:

Trastuzumab $OD_{280}$=1.5 $(mg/ml)^{-1}$ $cm^{-1}$

Cetuximab $OD_{280}$=1.4 $(mg/ml)^{-1}$ $cm^{-1}$

HSP27 Oligonucleotide $OD_{260}$=153,000 $M^{-1}$ $cm^{-1}$; $Rz_{260/280}$=1.819

Dia-Cys $OD_{280}$=0.57 $(mg/ml)^{-1}$ $cm^{-1}$ $PEG_4$-SPDP (PDT) $OD_{343}$=8,080 $M^{-1}$ $cm^{-1}$

SAMSA-Fluorescein $OD_{495}$=64,500 $M^{-1}$ $cm^{-1}$; $Rz_{280:495}$=0.232

Ellmans (TNB) $OD_{412}$=14,150 $M^{-1}$ $cm^{-1}$

Immobilized Metal Ion Affinity Chromatography (IMCA)

Nickel-nitrilotriacetic acid (Ni-NTA) chromatography was performed to purify histidine-tagged protein and protein-conjugates. Briefly, Ni-NTA agarose (10 mL) was pipetted into a gravity flow column for 5 mL bed volume. The resin was washed with 20 mL deionized water and recharged with 5 mL of 100 mM NiSO4 solution. The resin was washed again five times with 5 mL deionized water and equilibrated five times with DPBS. The protein solution was incubated with the washed Ni-NTA agarose rotating at 4° C. for 30 min. Afterwards, the Ni-NTA protein solution was pipetted back into the gravity flow column. The flow through was collected and the resin was washed three times with 5 mL DPBS. The immobilized sample was then eluted by increasing the imidazole concentration from 50 mL of 125 mM, pH 8 to 50 mL of 250 mM, pH 8. Elution fractions were dialyzed against PBS pH 7.4 to obtain the purified sample.

Size Exclusion Chromatography

Size exclusion chromatography (SEC) was carried out on an AKTA purifier. Samples were analyzed by SEC using either a Biosep SEC-S3000 column or an Sephadex G50M column (10×40 cm) eluting with TBS/isopropyl alcohol solution (85:15 v/v). Sample purities were determined by integration of the antibody sample peak with respect to the trace aggregate peaks.

Ellman's Assay

Ellman's test (or Ellman's assay) was carried out to quantitatively determine thiol concentration in a sample via spectrophotometry. Presence of thiols was indicated via the stoichiometric release of the 2-nitro-5-thiobenzoate (TNB) from Ellman's reagent in the presence of thiols. TNB obtains an absorption maximum at 412 nm and an extinction coefficient of $OD_{412}$=14,150 $M^{-1}$ $cm^{-1}$ in buffered systems. Briefly, 2 µL of a 0.5 mg/mL solution of the Ellman's reagent (5,5-Dithiobis(2-nitrobenzoic acid), DTNB) in phosphate buffer (0.1 M, 1 mM EDTA, pH 7.4) was mixed with 20 µL of a thiol containing sample in buffer. The mixture was vortexed for 5 sec. Then, UV-Vis absorbance at 412 nm was measured on a Thermo Nanodrop 2000 to determine TNB concentration and thus thiol content of the sample.

Dianthin Production

Dianthin was expressed in a bacterium culture and the protein was purified following conventional cell culturing and protein purification steps known in the art.

Production of Saporin Conjugates

Custom trastuzumab-saporin cetuximab-saporin, CD71mab-saporin conjugates were produced and purchased from Advanced Targeting Systems (San Diego, CA). IgG-saporin and saporin was purchased from Advanced Targeting Systems Antibody-(Cys-Dendron-(L-SO1861)$^n$)$^n$ Synthesis Trastuzumab and Cetuximab are referred hereafter as "Ab". Ab was conjugated to dendritic saponin [dendron-(L-SO1861)$_4$-maleimide]via a tetra(ethylene glycol) succinimidyl 3-(2-pyridyldithio)propionate ($PEG_4$-SPDP) linker conducting a thiole-ene Michael-type reaction between Ab and dendritic saponin. The procedure is exemplary described for Cetuximab-(S-dendron-(L-SO1861)$_4$)$_4$:

Cetuximab was desalted into DPBS pH 7.5 buffer and then normalized to 2.50 mg/ml. To an aliquot of Ab (9.19 mg, 61 nmol) was added an aliquot of freshly prepared $PEG_4$-SPDP solution (5.0 mg/ml, 6.70 mole equivalents, 411 nmol), the mixture vortexed briefly then incubated for 60 minutes at 20° C. with roller-mixing. After incubation, the reaction was quenched with the addition of glycine (20 mg/ml, 7.7 µl), then the SPDP moiety reduced in situ by the addition of TCEP (5.0 mg/ml, 4.0 mole equivalents per SPDP, 1.64 µmol). This mixture was roller-mixed for 15 minutes at 20° C. with roller-mixing. The resulting Ab-SH was purified by gel filtration using a zeba spin desalting column into TBS pH 7.5. The Ab-SH was characterized by UV-vis analysis and Ellman's assay (thiol to Ab ratio=5.4). To the bulk Ab-SH (7.41 mg, 1.93 mg/ml, 49 nmol) was added an aliquot of freshly prepared dendron-(L-SO1861)$^4$-maleimide solution in DMSO (10 mg/ml, 8.0 mole equivalents per Ab, 0.4 µmol, 3.16 mg, 0.32 ml), the mixture vortexed briefly then incubated overnight at 20° C. Besides the conjugation reaction, two aliquots of the desalted Ab-SH (0.25 mg, 1.67 nmol) were removed prior to conjugation, and were reacted with NEM (8.0 mole equivalents per Ab, 13.3 nmol, 6.7 µl of a 0.25 mg/ml solution) or TBS pH 7.5 buffer (6.7 µl) overnight at 20° C., as positive and negative controls, respectively. After incubation for 18 hours (prior to addition of NEM), the crude conjugate mixture was centrifuged briefly and 100 µl aliquot removed for analysis by UV-vis and alongside positive and negative controls were characterized by Ellman's assay to obtain dendron-(L-SO1861)$_4$ incorporation. To the bulk Ab-dendron-(L-SO1861)$_4$ mixture was added an aliquot of freshly prepared NEM solution (2.5 mg/ml, 5.0 mole equivalents, 0.25 µmol) and the mixture purified by 1.6×30 cm Sephadex G50 column eluting with DPBS pH 7.5 to give purified Cetuximab-(S-dendron-(L-SO1861)$_4$)$_4$ conjugate. The product was filtered to 0.2 µm to clarify and then concentrated carefully to ca. 3 mg/ml using a vivaspin T15 concentrator (3,000 g, 5 minute intervals, 5° C.) to give the final Cetuximab-(S-dendron(L-SO1861)$_4$)$_4$ conjugate. Yield: 4.41 mg, 48%. Dendron-(L-SO1861)$_4$ to Ab ratio=4.4.

TABLE 2

| Summarized reaction outcomes | | | | | | |
|---|---|---|---|---|---|---|
| Batch | Ab feed (mg) | $PEG_4$-SPDP mol equivalents | Dendron(SO1861)$^4$-maleimide mol equivalents | Obtained DAR | Purity by analytical SEC | Yield |
| Trastuzumab-(Cys-dendron-(L-SO1861)$^4$)$^4$ | 9.0 | 6.81 | 8 | 4.7 | 99.2% | 2.34 mg (26%) |
| Cetuximab-(Cys-dendron-(L-SO1861)$^4$)$^4$ | 9.2 | 6.7 | 8 | 4.4 | 96.7% | 4.41 mg (48%) |

Antibody-(L-SO1861)$^n$ (as Illustrated in FIG. 12)

Trastuzumab, Cetuximab, are referred hereafter as "Ab". Ab was conjugated to the saponin S018161-EMCH via Michael-type thiol-ene conjugation reaction at DARs of 1, 2, 3, 4, 5, and 6. The SO1861-EMCH molecule obtains a labil (L) hydrazone bond between its structure and its maleimide function generating a labil bond between the saponin and Ab. The procedure is exemplary described for Trastuzumab-(L-SO1861)$^4$:

To a solution of Cetuximab (40 mg, 8.0 ml) was added 10 μl/ml each of Tris concentrate (127 mg/ml, 1.05M), Tris·HCl concentrate (623 mg/ml, 3.95M) and EDTA-$Na_2$ concentrate (95 mg/ml, 0.26M) to give a 50 mM TBS, 2.5 mM EDTA buffer pH 7.5.

To Cetuximab divided into four portions (each of 9.73 mg, 4.864 mg/ml, 65 nmol) was added an aliquot of freshly prepared TCEP solution (0.5-2.0 mg/ml, 1.15-7.02 mole equivalents, 75-455 nmol), the mixtures vortexed briefly then incubated for 300 minutes at 20° C. with roller-mixing. After incubation (prior to addition of SO1861-EMCH), a ca. 1 mg (0.210 ml) aliquot of Ab-SH was removed from each mixture and purified by gel filtration using a zeba spin desalting column into TBS pH 7.5. These aliquots were characterized by UV-vis analysis and Ellman's assay (thiol to Ab ratio=2.0, 4.2, 5.9 and 6.8 respectively). To each of the bulk Ab-SH was added an aliquot of freshly prepared SO1861-EMCH solution (2 mg/ml, 1.3 mole equivalents per 'thiol', 0.15-0.61 μmol, 0.16-0.63 ml), the mixtures vortexed briefly then incubated for 120 minutes at 20° C. Besides each conjugation reaction, two aliquots of desalted Ab-SH (0.25 mg, 1.67 nmol) were reacted with NEM (1.3 mole equivalents per 'thiol', 4.3-17.4 nmol, 2.2-8.7 μl of a 0.25 mg/ml solution) or TBS pH 7.5 buffer (2.2-8.7 μl) for 120 minutes at 20° C., as positive and negative controls, respectively. After incubation (prior to addition of NEM), a 0.200 ml aliquot of Ab-SO1861-EMCH mixture was removed and purified by gel filtration using zeba spin desalting column into TBS pH 7.5. This aliquot was characterized by UV-vis and alongside positive and negative controls were characterized by Ellman's assay to obtain SO1861-EMCH incorporations. To the bulk Ab-SO1861-EMCH mixture was added an aliquot of freshly prepared NEM solution (2.5 mg/ml, 2.5-10 mole equivalents, 0.15-0.58 μmol) and the mixtures purified by zeba spin desalting columns eluting with DPBS pH 7.5 to give purified Cetuximab-(L-SO1861) conjugates. The products were normalized to 2.5 mg/ml and filtered to 0.2 μm prior to dispensing for biological evaluation.

TABLE 3

| Summarized reaction conditions and results for Trastuzumab-L-SO1861 conjugates | | | | | | |
|---|---|---|---|---|---|---|
| Batch | Ab feed | TCEP feed mole equivalents | SO1861-EMCH feed | Obtained DAR | Purity by analytical SEC (%) | Yield (%) |
| Tras-(L-SO1861)$_2$ | 9.91 mg 66 nmol | 1.10 | 0.15 μmol | 1.6 | 99.2 | 79 |
| Tras-(L-SO1861)$_3$ | 9.91 mg 66 nmol | 2.35 | 0.31 μmol | 3.0 | 99.0 | 81 |
| Tras-(L-SO1861)$_4$ | 9.91 mg 66 nmol | 3.83 | 0.46 μmol | 4.0 | 98.4 | 81 |
| Tras-(L-SO1861)$_5$ | 9.91 mg 66 nmol | 5.77 | 0.62 μmol | 5.3 | 98.5 | 79 |

TABLE 4

Summarized reaction conditions and results for Cetuximab-L-SO1861 conjugates

| Batch | Ab feed | TCEP feed mole equivalents | SO1861-EMCH feed | Obtained DAR | Purity by analytical SEC (%) | Yield (%) |
|---|---|---|---|---|---|---|
| Cet-(L-SO1861)$_1$ | 9.73 mg 65 nmol | 1.15 | 0.15 μmol | 1.4 | 99.7 | 74 |
| Cet-(L-SO1861)$_3$ | 9.73 mg 65 nmol | 2.49 | 0.31 μmol | 2.8 | 99.6 | 80 |
| Cet-(L-SO1861)$_4$ | 9.73 mg 65 nmol | 4.19 | 0.46 μmol | 4.1 | 99.0 | 77 |
| Cet-(L-SO1861)$_6$ | 9.73 mg 65 nmol | 7.02 | 0.61 μmol | 5.6 | 98.3 | 80 |

Antibody-(S-SO1861)$^n$ Synthesis

SO1861-S-Mat Synthesis

SO1861 from *Saponaria officinalis* L (15.4 mg, 8.28 μmol) and HATU (140 mg, 368 μmol, 44.5 mole equivalents) were placed as solid into a 20 mL glass vial with magnetic stirrer and 5 mL DMSO was added to dissolve the materials. The dissolved mixture was stirred for 30 min at room temperature. After 30 min, 1 mL of freshly prepared AEM solution (65 mg, 256 μmol, 31 mole equivalents) in DMSO was added to the stirring SO1861-HATU mixture. The reaction mixture was stirred for 17 hours at room temperature. After stirring for 17 hours, the mixture was diluted with deionized water and dialyzed extensively for 24 h against deionized water using regenerated cellulose membrane tubes (Spectra/Por 7) with a MWCO of 1 kDa. After dialysis, the solution was lyophilized to obtain a white powder.

Yield: 7.22 mg (44%).

Dried aliquots were further used for characterization via MALDI-TOF-MS.

MALDI-TOF-MS (RN mode) (Figure x a): m/z 1983 Da ($[M-H]^-$, 501861-S-Mal conjugate), 2136 Da ($[M-H]^-$, saponin-S-Mal conjugate).

MALDI-TOF-MS (RP mode) (Figure x b): m/z 2007 Da ($[M+Na]^+$, SO1861-S-Mal conjugate), 2107 Da ($[M-Na]^+$, saponin-S-Mal conjugate).

Maleimide functionality was verified by mixing the purified SO1861-S-Mal with a freshly prepared L-cysteine solution (1000 mole excess) and observing the expected mass shift in MALDI-TOF-MS (Figure x) yielding a cysteine-conjugate at m/z 2103 Da.

Antibody Conjugation

Trastuzumab and Cetuximab are referred hereafter as "Ab". Ab was conjugated to the saponin S018161-S-Mal via Michael-type thiol-ene conjugation reaction. The saponin obtains a stable (S) amide bond between its structure and its maleimide function generating a stable bond between the saponin and Ab.

5 mg of Ab dissolved in phosphate buffer saline (PBS) was buffer exchanged into tris(hydroxymethyl)-aminomethan buffer saline (TBS) pH 7.5 via zeba spin desalting column and normalized to a concentration of 3 mg/mL. To Ab was added an aliquot of freshly prepared tris(2-carboxyethyl)phosphine (TCEP) solution (0.25 mg/mL, 2.92 mole equivalents), the mixture vortexed briefly then incubated for 90 min at 20° C. After, the resulting Ab-SH was purified by gel filtration using zeba spin desalting column into TBS pH 7.5. An aliquot was analyzed by Ellman's assay to ascertain sulfhydryl content. The Ab-SH obtained was split into a single portion for conjugation and two aliquots of 0.25 mg for controls. To the main portion of AB-SH was added an aliquot of freshly prepared SO1861-S-Mal solution (2 mg/mL, 2 mol equivalents with respect to sulfhydryl content), to the second control aliquot was added buffer TBS pH 7.5. Each mixture was vortexed briefly then incubated for 2 hours at 20° C. After, an aliquot from each was analyzed by Ellman's assay to ascertain sulfhydryl content remaining in the conjugate with respect to controls. After purification by gel filtration via zeba spin desalting column into Dulbecco's PBS pH 7.1, Ab-S-SO1861 was obtained. The conjugate was further analyzed by SEC to ascertain % purity. For the Trastuzumab-(S-SO1861)$^4$ sample a purity of 99% was determined. For the Cetuximab-(S-SO1861)$^4$ sample a purity of 98.3% was determined. Retention volumes for Trastuzumab-(S-SO1861)$^4$ (9.1 mL) and Cetuximab-(S-SO1861)$^4$ (8.8 mL) were noted to be similar and are consistent with a non-modified Ab (e.g. IgG).

Antibody-(L-HSP27 BNA)$^n$

Trastuzumab-(L-HSP27)$^4$, Cetuximab-(L-HSP27)$^4$, Synthesis Via $PEG_4$-SPDP with a DAR4 and Cetuximab-(L-HSP27)$^2$ Synthesis Via $PEG_4$-SPDP with a DAR2

Trastuzumab, Cetuximab, are referred hereafter as "Ab". Ab was conjugated to HSP27 BNA disulfide via a tetra (ethylene glycol) succinimidyl 3-(2-pyridyldithio)propionate ($PEG_4$-SPDP) linker forming a labil (L) disulfide bond between Ab and HSP27 BNA. The procedure is exemplary described for Trastuzumab-(L-HSP27 BNA)$_4$:

HSP27 BNA disulfide oligo (2.7 mg, 470 nmol, 6.10 mg/ml) was reacted with TCEP (10 mole equivalents, 4.7 μmol, 1.34 mg, 50 mg/ml) for 30 minutes at 20° C. with roller mixing. After, the oligo-SH was purified by PD10 G25 desalting column eluting into TBS pH 7.5 and used promptly. Oligo-SH was obtained (2.48 mg, 90%, 1.24 mg/ml, SH to oligo ratio=0.8) Trastuzumab (1.5 mg, 10.3 nmol, 2.50 mg/ml) was reacted with an aliquot of freshly prepared $PEG_4$-SPDP solution (6.81 mole equivalents, 70.1 nmol, 39 μg) in DMSO (1 mg/ml) for 60 minutes at 20° C. with roller mixing. After, the reaction was quenched with glycine (15.1 μl of 2 mg/ml freshly prepared solution in TBS pH 7.5) and then desalted via zeba desalting column eluting with TBS pH 7.5. An aliquot of the resulting Tras-S-$PEG_4$-SPDP was taken out and tested by UV-Vis analysis. SPDP incorporation was determined using TCEP to liberate pyridiyl-2-thione (PDT) and by UV-vis analysis at 343 nm (SPDP to Ab ratio: 4). The remaining Tras-(S-$PEG_4$-SPDP)$_4$ was reacted with an aliquot of freshly prepared HSP27 oligonucleotide (oligo-SH) (8 mole equivalents, 82.4 nmol, 1.24 mg/ml) and incubated overnight at 20° C. with roller mixing. After 17 hours, the conjugate was analysed by UV-vis analysis to ascertain incorporation of HSP27 by displacement of pyridiyl-2-thione (PDT) at 343 nm. The crude conjugate was purified using a 1.6×33 cm Sephadex G50 column eluting with DPBS pH 7.5. The resulting Trastuzumab-(L-HSP27)$^4$ was obtained as a single fraction. Yield: n.d. Purity: 96%, HSP27 BNA to Ab ratio=4.4

TABLE 5

| Summarized reaction conditions and results | | | | | |
|---|---|---|---|---|---|
| Batch | $PEG_4$-SPDP mol equivalents | HSP27 (oligo-SH) mol equivalents | Obtained DAR | Purity by analytical SEC (%) | Yield (%) |
| Tras-(L-HSP27 BNA)$^4$ | 6.81 | 8 | 4.4 | 96.0 | n.d. |
| Cet-(L-HSP27 BNA)$^4$ | 6.70 | 8 | 3.9 | 93.9 | n.d. |
| Cet-(L-HSP27)$^2$ | 2.3 | 3.6 | 1.5 | 94.9 | 87 |

n.d. = not determined two aliquots of desalted Ab-SH (0.5 mg, 3.3 nmol) were reacted with NEM (1.3 mole equivalents per 'thiol', 17.3 nmol, 6.7 μl of a 0.25 mg/ml solution) or TBS pH 7.5 buffer (6.7 μl) for 120 minutes at 20° C., as positive and negative controls, respectively. After incubation (prior to addition of NEM), a 0.100 ml aliquot of Ab-HSP27 BNA mixture was removed and purified by gel filtration using zeba spin desalting column into TBS pH 7.5. This aliquot was characterized by UV-vis and alongside positive and negative controls was characterized by Ellman's assay to obtain HSP27 incorporation. To the bulk Ab-HSP27 mixture was added an aliquot of freshly prepared NEM solution (0.25 mg/ml, 2.5 mole equivalents, 89 nmol) and the mixture purified by gel filtration using a 1.6×30 cm Sephadex G50M eluting with DPBS pH 7.5 followed by repeated centrifugal filtration and washing using a 100 KDa MWCO concentrator to give purified Trastuzumab-(L-HSP27-L-blocked)$_4$ conjugate. The products were filtered to 0.2 μm prior to dispensing for biological evaluation.

TABLE 6

| Summarized reaction conditions and results | | | | | | |
|---|---|---|---|---|---|---|
| Batch | Ab-SH feed | Thiol to Ab ratio | HSP27-Mal feed | Obtained DAR | Purity by analytical SEC (%) | Yield (%) |
| Tras-(L-HSP27 BNA-L-blocked)$^4$ | 5.1 mg 35 nmol | 3.98 | 1.36 mg | 3.6 | 99.4 | 40 |
| Cet-(L-HSP27 BNA-L-blocked)$^4$ | 5.1 mg 35 nmol | 4.16 | 1.36 mg | 3.6 | 97.9 | 50 |

Antibody-(L-HSP27 BNA-L-Blocked)$^n$ Trastuzumab-(L-HSP27-L-Blocked)$^4$, Cetuximab-(L-HSP27-L-Blocked)

Trastuzumab and Cetuximab are referred hereafter as "Ab". Ab was conjugated a maleimido (Mal) bearing HSP27 derivate which is referred hereafter as "HSP27-Mal". Ab was conjugated to the HSP27-Mal via Michael-type thiol-ene conjugation reaction. The HSP17-Mal obtains a labile (L) hydrazone bond between its structure and its maleimide function generating a labile bond between the HSP27 BNA and Ab. The procedure is exemplary described for Trastuzumab-(L-HSP27 BNA-L-blocked)$^n$:

Trastuzumab was reconstituted to 21 mg/ml with deionized water (DI), then diluted to 5 mg/ml using histidine buffer pH 6. To a 20 mg (4.0 ml) aliquot was added 10 μl/ml each of Tris concentrate (127 mg/ml, 1.05M), Tris·HCl concentrate (623 mg/ml, 3.95M) and EDTA-$Na_2$ concentrate (95 mg/ml, 0.26M) to give a 50 mM TBS, 2.5 mM EDTA buffer pH 7.5. To Trastuzumab (20.30 mg, 4.920 mg/ml, 0.14 μmol) was added an aliquot of freshly prepared TCEP solution (1.00 mg/ml, 2.35 mole equivalents, 0.32 μmol), the mixture vortexed briefly then incubated for 90 minutes at 20° C. with roller-mixing. After incubation (prior to addition of HSP27-Mal), a ca. 2 mg (0.439 ml) aliquot of Ab-SH was removed from each mixture and purified by gel filtration using a zeba spin desalting column into TBS pH 7.5. This aliquot was characterized by UV-vis analysis and Ellman's assay (thiol to ab ratio=4.0). To the bulk Ab-SH (5.1 mg, 35 nmol) was added an aliquot of the HSP27-Mal derivative (freshly prepared in TBS pH 7.5, 2 mg/ml, 1.3 mole equivalents per 'thiol', 182 nmol), the mixture vortexed briefly then incubated for 120 minutes at 20° C. Besides the Trasuzumab-HSP27 BNA derivative conjugation reaction, Antibody-(Cys-Trifunctional Linker-(L-SO1861)-(L-HSP27 BNA))$^n$ Trastuzumab-[S-Tri-(L-SO1861)-(L-HSP27)]$^4$, Trastuzumab-[S-Tri-(Blocked)-(L-HSP27)]$^4$, Cetuximab-[S-Tri-(L-SO1861)-(L-HSP27)]$^4$, Cetuximab-[S-Tri-(Blocked)-(L-HSP27)]$^4$ Trastuzumab and Cetuximab are referred hereafter as "Ab". Ab was conjugated via Michael-type thiol-ene reaction to two different maleimide (Mal) bearing HSP27 BNA derivatives which are referred hereafter as "HSP27-Mal". These HSP27-Mal derivatives were namely: 1) Mal-Trifunctional linker-(L-SO1861)-(L-HSP27), 2) Mal-Trifunctional linker-(blocked)-(L-HSP27). The procedure is exemplary described for Trastuzumab-[S-Trifunctional linker-(L-SO1861)-(L-HSP27 BNA)]$^4$: Trastuzumab was reconstituted to 21 mg/ml with deionized water (DI), then diluted to 5 mg/ml using histidine buffer pH 6. To a 20 mg (4.0 ml) aliquot was added 10 μl/ml each of Tris concentrate (127 mg/ml, 1.05M), Tris·HCl concentrate (623 mg/ml, 3.95M) and EDTA-$Na_2$ concentrate (95 mg/ml, 0.26M) to give a 50 mM TBS, 2.5 mM EDTA buffer pH 7.5.

To Trastuzumab (20.30 mg, 4.920 mg/ml, 0.14 μmol) was added an aliquot of freshly prepared TCEP solution (1.00 mg/ml, 2.35 mole equivalents, 0.32 μmol), the mixture vortexed briefly then incubated for 90 minutes at 20° C. with roller-mixing. After incubation (prior to addition of construct), a ca. 2 mg (0.439 ml) aliquot of Ab-SH was removed from each mixture and purified by gel filtration using a zeba spin desalting column into TBS pH 7.5. These aliquots were characterized by UV-vis analysis and Ellman's assay (thiol to ab ratio=4.0). The bulk Ab-SH was split into two aliquots (1.1 mg, 7.6 nmol and 1.2 mg, 8.3 nmol), and to each aliquot was added an aliquot of each of the HSP27 BNA-Mal derivatives 1-2 (freshly prepared in TBS pH 7.5, 2 mg/ml, 1.3 mole equivalents per 'thiol', 40 nmol and 43 nmol), the mixtures vortexed briefly then incubated for 120 minutes at 20° C. Besides the Trastuzumab—HSP27 BNA derivatives 2 conjugation reaction, two aliquots of desalted Ab-SH (0.5 mg, 3.3 nmol) were reacted with NEM (1.3 mole equivalents per 'thiol', 17.3 nmol, 6.7 μl of a 0.25 mg/ml solution) or TBS pH 7.5 buffer (6.7 μl) for 120 minutes at 20° C., as positive and negative controls, respectively. After incubation (prior to addition of NEM), a 0.100 ml aliquot of Ab-construct 2 mixture was removed and purified by gel filtration using zeba spin desalting column into TBS pH 7.5. This aliquot was characterized by UV-vis and alongside positive and negative controls was characterized by Ellman's assay to obtain HSP27 BNA derivatives 2 incorporation. To each bulk Ab-construct mixture was added an aliquot of freshly prepared NEM solution (0.25 mg/ml, 2.5 mole equivalents, 19 and 21 nmol) and the mixtures purified by gel filtration using a 1.6×30 cm Sephadex G50M eluting with DPBS pH 7.5 followed by repeated centrifugal filtration and washing using a 100 KDa MWCO concentrator to give purified Trastuzumab-construct 1-2 conjugates. The products were filtered to 0.2 μm prior to dispensing for biological evaluation.

TABLE 7

Summarized reaction conditions and results

| Batch | Ab-SH feed | TCEP equivalents | Thiol to ab ratio | Purity by analytical SEC (%) | Yield (%) |
|---|---|---|---|---|---|
| Tras-[S-Trifunctional linker-(L-SO1861)-(L-HSP27 BNA)]$^4$ | 1.1 mg 7.6 nmol | 2.35 | 3.98 | 97.0 | 57 |
| Tras-[S-Trifunctional linker-(blocked)-(L-HSP27 BNA)]$^4$ | 1.2 mg 8.3 nmol | 2.35 | 3.98 | 96.6 | 33 |
| Cet-[S-Trifunctional linker-(L-SO1861)-(L-HSP27 BNA)]$^4$ | 1.1 mg 7.6 nmol | 2.72 | 4.16 | 98.9 | 47 |
| Cet-[S-Trifunctional linker-(blocked)-(L-HSP27 BNA)]$^4$ | 1.2 mg 8.3 nmol | 2.72 | 4.16 | 99.1 | 50 |

Antibody-(L-SO1861)$^n$-(L-HSP27 BNA)$^n$ Trastuzumab-(L-SO1861)$^4$-(L-HSP27)$^4$, Cetuximab-(L-SO1861)$^4$-(L-HSP27)$^4$ Synthesis Via $PEG_4$-SPDP with a DAR4 Cetuximab-(L-SO1861)$^4$-(L-HSP27)$^2$ (FBR703 STB17/7-8) Synthesis Via $PEG_4$-SPDP with a DAR2

Trastuzumab-(L-SO1861)$_4$, Cetuximab-(L-SO1861)$_4$ are referred hereafter as "Ab". Ab was conjugated to HSP27 BNA disulfide via a tetra(ethylene glycol) succinimidyl 3-(2 pyridyldithio)propionate ($PEG_4$-SPDP) linker forming a labil (L) disulfide bond between Ab and HSP27 BNA. The procedure is exemplary described for Trastuzumab-(L-SO1861)$_4$-(L-HSP27)$_4$:

HSP27 BNA disulfide oligo (2.7 mg, 470 nmol, 6.10 mg/ml) was reacted with TCEP (10 mole equivalents, 4.7 μmol, 1.34 mg, 50 mg/ml) for 30 minutes at 20° C. with roller mixing. After, the oligo-SH was purified by PD10 G25 desalting column eluting into TBS pH 7.5 and used promptly. Oligo-SH was obtained (2.48 mg, 90%, 1.24 mg/ml, SH to oligo ratio=0.8)

Trastuzumab-(L-SO1861)$_4$ (1.3 mg, 8.7 nmol, 2.50 mg/ml) was reacted with an aliquot of freshly prepared $PEG_4$-SPDP solution (9.26 mole equivalents, 80.3 nmol, 45 μg) in DMSO (1 mg/ml) for 60 minutes at 20° C. with roller mixing. After, the reaction was quenched with glycine (15.1 μl of 2 mg/ml freshly prepared solution in TBS pH 7.5) and then desalted via zeba desalting column eluting with TBS pH 7.5. An aliquot of the resulting Tras-(L-SO1861)-(L-$PEG_4$-SPDP) was taken out and tested by UV-Vis analysis. SPDP incorporation was determined using TCEP to liberate pyridiyl-2-thione (PDT) and by UV-vis analysis at 343 nm (SPDP to Ab ratio=4). The remaining Tras-(L-SO1861)-(L-$PEG_4$-SPDP) was reacted with an aliquot of freshly prepared HSP27 oligonucleotide (oligo-SH) (8 mole equivalents, 54.8 nmol, 0.32 mg, 1.24 mg/ml) and incubated overnight at 20° C. with roller mixing. After 17 hours, the conjugate was analyzed by UV-vis analysis to ascertain incorporation of HSP27 by displacement of pyridiyl-2-thione (PDT) at 343 nm. The crude conjugate was purified using a 1.6×33 cm Sephadex G50 column eluting with DPBS pH 7.5. The resulting Trastuzumab-(L-SO1861)$_4$-(L-HSP27 BNA)$_4$ was obtained as a single fraction. Yield: 0.47 mg, 45% (0.49 mg/ml), HSP27 to Ab ratio=3.5

TABLE 8

Summarized reaction conditions and results

| Batch | $PEG_4$-SPDP mol equivalents | HSP27 (oligo-SH) mol equivalents | Obtained DAR | Purity by analytical SEC (%) | Yield (%) |
|---|---|---|---|---|---|
| Tras-(L-SO1861)$^4$-(L-HSP27 BNA)$^4$ | 9.26 | 8 | 3.5 | 85.1 | 45 |
| Cet-(L-SO1861)$_4$-(L-HSP27 BNA)$^4$ | 7.21 | 8 | 3.8 | 80.8 | n.d. |
| Cet-(L-SO1861)$_4$-(L-HSP27 BNA)$^2$ | 3.34 | 3.6 | 1.8 | 76.2 | 81 |

n.d. = not determined

Antibody-(L-QS Mix)$^n$

Trastuzumab, Cetuximab, are referred hereafter as "Ab". Ab was conjugated to the saponin QS Mix-EMCH via Michael-type thiol-ene conjugation reaction. The procedure is exemplary described for Trastuzumab-L-QS Mix:

Trastuzumab ("Ab", 600 mg) was reconstituted to 21 mg/mL with deionized water (DI), then diluted to 5 mg/mL using freshly prepared histidine buffer pH 6 (5 mM histidine pH 6, 2% trehalose, 0.01% Tween 20). 10 μL/mL each of Tris concentrate (127 mg/mL, 1.05M), Tris·HCL concentrate (623 mg/mL, 3.95M) and EDTA-$Na_2$ concentrate (95 mg/ml, 0.26M) was added to give a 50 mM TBS, 2.5 mM EDTA buffer pH 7.5. To Trastuzumab (603.8 mg, 4.887 mg/mL, 4.0 μmol) was added an aliquot of freshly prepared TCEP solution (1 mg/mL, 2.35 mole equivalents, 9.5 μmol, 2.72 mg), the mixture swirled by hand to mix then incubated for 90 minutes at 20° C. with roller-mixing. After incubation (prior to addition of QS Mix-EMCH), a 2 mg (0.409 mL) aliquot of Ab-SH was removed and purified by gel filtration using zeba spin desalting column into TBS pH 7.5. This aliquot was characterized by UV-vis analysis and Ellman's assay. To the bulk Ab-SH was added an aliquot of freshly prepared QS Mix-EMCH solution (2 mg/mL, 5.2 mole equivalents, 21 μmol, 21.6 mL), the mixtures vortexed briefly then incubated for 120 minutes at 20° C. Besides the conjugation reaction, two aliquots of desalted Ab-SH (0.5 mg, 0.134 mL, 3.33 nmol) were reacted with NEM (8.00 equivalents, 26.6 nmol, 3.3 μg, 13.3 μL of a 0.25 mg/mL solution) or TBS pH 7.5 buffer (13.3 μL) for 120 minutes at 20° C., as positive and negative controls, respectively. After incubation (prior to addition of NEM), a ca. 2 mg (0.481 mL) aliquot of Ab-QS Mix-EMCH mixture was removed and purified by gel filtration using zeba spin desalting column into TBS pH 7.5. This aliquot was characterized by UV-vis and alongside positive and negative controls were characterized by Ellman's assay to obtain QS Mix-EMCH incorporations. To the bulk Ab-QS Mix-EMCH mixture was added an aliquot of freshly prepared NEM solution (2.5 mg/mL, 5 mole equivalents, 20 μmoL, 2.51 mg) and the mixture stored at 2-8° C. overnight. The conjugate was purified by 10×40 cm Sephadex G50M column eluting with DPBS pH 7.5 to give purified Trastuzumab-(L-QS Mix) conjugate. The product as a whole was concentrated then normalized to 5 mg/mL using a vivacell 100 concentrator (2,000 g, 4° C., 200 minutes). The product were filtered to 0.2 μm and dispensed for biological evaluation. Yield: n.d. QS Mix to Ab ratio=4.1.

TABLE 9

| Summarized reaction outcomes | | |
|---|---|---|
| Method | Measure | Result |
| Analytical SEC | Purity | n.d. |
| Yield | Mass (percent) | n.d. |
| Ellman's assay | QS Mix-EMCH incorpoation | 4.1 |

Antibody-(L-HSP27BNA-L-SO1861)$^n$ Trastuzumab-(L-HSP27BNA-L-SO1861)$^4$, Cetiximab-(L-HSP27BNA-L-SO1861)$^4$ with a DAR4

Trastuzumab and Cetuximab are referred hereafter as "Ab". Ab was conjugated a saponin SO1861 and maleimido (Mal) bearing HSP27 derivate which is referred hereafter as "HSP27-Mal". Ab was conjugated to the HSP27-Mal via Michael-type thiol-ene conjugation reaction. The HSP17-Mal obtains a labile (L) hydrazone bond between its structure and its maleimide function generating a labile bond between the HSP27 BNA and Ab. The procedure is exemplary described for Trastuzumab-(L-HSP27 BNA-L-SO1861)$_4$:

Trastuzumab was reconstituted to 21 mg/ml with deionized water (DI), then diluted to 5 mg/ml using histidine buffer pH 6. To a 20 mg (4.0 ml) aliquot was added 10 μl/ml each of Tris concentrate (127 mg/ml, 1.05M), Tris·HCl concentrate (623 mg/ml, 3.95M) and EDTA-$Na_2$ concentrate (95 mg/ml, 0.26M) to give a 50 mM TBS, 2.5 mM EDTA buffer pH 7.5. To Trastuzumab (20.30 mg, 4.920 mg/ml, 0.14 μmol) was added an aliquot of freshly prepared TCEP solution (1.00 mg/ml, 2.35 mole equivalents, 0.32 μmol), the mixture vortexed briefly then incubated for 90 minutes at 20° C. with roller-mixing. After incubation (prior to addition of HSP27-Mal), a ca. 2 mg (0.439 ml) aliquot of Ab-SH was removed from each mixture and purified by gel filtration using a zeba spin desalting column into TBS pH 7.5. This aliquot was characterized by UV-vis analysis and Ellman's assay (thiol to ab ratio=4.0). To the bulk Ab-SH (4.7 mg, 32 nmol) was added an aliquot of the HSP27-Mal derivative (freshly prepared in TBS pH 7.5, 2 mg/ml, 1.3 mole equivalents per 'thiol', 166 nmol), the mixture vortexed briefly then incubated for 120 minutes at 20° C. Besides the Trasuzumab-HSP27 BNA derivative conjugation reaction, two aliquots of desalted Ab-SH (0.5 mg, 3.3 nmol) were reacted with NEM (1.3 mole equivalents per 'thiol', 17.3 nmol, 6.7 μl of a 0.25 mg/ml solution) or TBS pH 7.5 buffer (6.7 μl) for 120 minutes at 20° C., as positive and negative controls, respectively. After incubation (prior to addition of NEM), a 0.100 ml aliquot of Ab-HSP27 BNA mixture was removed and purified by gel filtration using zeba spin desalting column into TBS pH 7.5. This aliquot was characterized by UV-vis and alongside positive and negative controls was characterized by Ellman's assay to obtain HSP27 incorporation. To the bulk Ab-HSP27 mixture was added an aliquot of freshly prepared NEM solution (0.25 mg/ml, 2.5 mole equivalents, 80 nmol) and the mixture purified by gel filtration using a 1.6×30 cm Sephadex G50M eluting with DPBS pH 7.5 followed by repeated centrifugal filtration and washing using a 100 KDa MWCO concentrator to give purified Trastuzumab-(L-HSP27 BNA-L-SO1861)$_4$ conjugate. The products were filtered to 0.2 μm prior to dispensing for biological evaluation.

TABLE 10

| Summarized reaction conditions and results | | | | | |
|---|---|---|---|---|---|
| Batch | Ab-SH feed | Thiol to Ab ratio | HSP27-Mal feed | Purity by analytical SEC (%) | Yield (%) |
| Tras-(L-H5P27 BNA-L-SO1861)$^4$ | 4.7 mg 32 nmol | 3.98 | 1.57 mg | 99.4 | 40 |
| Cet-(L-HSP27 BNA-L-SO1861)$^4$ | 4.7 mg 32 nmol | 4.16 | 1.57 mg | 97.9 | 50 |

Antibody-(L-SO1861)$^n$-(S-Dianthin)$^n$

Trastuzumab-(L-SO1861)$_4$—(S-Dianthin)$_2$ and Cetuximab-(L-SO1861)$_4$—(S-Dainthin)$_2$ synthesis via SMCC with a DAR2

Trastuzumab-L-SO1861 and Cetuximab-L-SO1861 are referred hereafter as "Ab". Ab was conjugated to Dianthin-Cys via a succinimidyl 4-(N-maleimidomethyl)cyclohexane-1-carboxylate (SMCC) linker providing a stable (S) amide bond between Ab and Dianthin. The procedure is exemplary described for Trastuzumab-(L-SO1861)$_4$—(S-Dianthin)$_2$:

Dianthin-Cys (7.8 mg, 261 nmol, 0.78 mg/ml) was reacted with TCEP (5 mole equivalents, 1.31 μmol, 0.37 mg, 1 mg/ml) for 30 minutes at 20° C. with roller mixing. After, the protein-SH was purified by zeba desalting column eluting into TBS pH 7.5 and used promptly. Protein-SH was obtained (5.2 mg, 67%, 0.52 mg/ml, SH to protein ratio=1±0.1).

Trastuzumab-(L-SO1861)$^4$ (1.5 mg, 10 nmol, 2.50 mg/ml) was reacted with an aliquot of freshly prepared SMCC solution (4.83 mole equivalents, 48.3 nmol, 16 μg) in DMSO (0.5 mg/ml) for 60 minutes at 20° C. with roller mixing. After, the reaction was quenched with glycine (18.1 μl of 1 mg/ml freshly prepared solution in TBS pH 7.5) and then desalted via zeba desalting column eluting with TBS pH 7.5. The resulting Tras-(L-SO1861)-(S-SMCC) (1.22 mg, 8.1 nmol, 2.03 mg/ml) was reacted with an aliquot of freshly reduced Dianthin-Cys (3.2 mole equivalents, 32.5 nmol, 0.97 mg, 0.52 mg/ml) and incubated overnight at 20° C. with roller mixing. After 17 hours, the conjugate was concentrated to 51 ml using a vivaspin T4 concentrator and purified using a 1.6×37 cm Superdex 200PG column eluting with DPBS pH 7.5. The resulting Tras-(L-SO1861)$_4$—(S-Dianthin)$_2$ conjugate was obtained as High-Molecular-Weight (HMW) (0.36 mg, 30%, 0.34 mg/ml, Dianthin to Ab ratio=not determined) and Low-Molecular-Weight (LMW) (0.49 mg, 40%, 0.30 mg/ml, Dianthin to Ab ratio=not determined) fractions. Yield: n.d. Purity: 79.3%.

TABLE 11

| Summarized reaction conditions and results | | | | | |
|---|---|---|---|---|---|
| Batch | SMCC mol equivalents | Dianthin-Cys mol equivalents | Obtained DAR | Purity by analytical SEC (%) | Yield (%) |
| Tras-(L-SO1861)$_4$-(S-Dianthin)$_x$ | 4.82 | 3.2 | n.d. | 79.3 | n.d. |
| Cet-(L-SO1861)$_4$-(S-Dianthin)$_2$ | 4.46 | 3.2 | 2.0 | 87.6 | 92 |

n.d. = not determined

12. Antibody-(S-Dianthin)$^n$

Trastuzumab-(S-Dianthin)$^2$, Cetuximab-(S-Dianthin)$^2$, Synthesis Via SMCC with a DAR2

Trastuzumab and Cetuximab are referred hereafter as "Ab". Ab was conjugated to Dianthin-Cys via a succinimidyl 4-(N-maleimidomethyl)cyclohexane-1-carboxylate (SMCC) linker providing a stable (S) amide bond between Ab and Dianthin. The procedure is exemplary described for Trastuzumab-(S-Dianthin)$_2$:

Dianthin-Cys (7.8 mg, 261 nmol, 0.78 mg/ml) was reacted with TCEP (5 mole equivalents, 1.31 μmol, 0.37 mg, 1 mg/ml) for 30 minutes at 20° C. with roller mixing. After, the protein-SH was purified by zeba desalting column eluting into TBS pH 7.5 and used promptly. Protein-SH was obtained (5.2 mg, 67%, 0.52 mg/ml, SH to protein ratio=1±0.1).

Trastuzumab (1.5 mg, 10 nmol, 2.50 mg/ml) was reacted with an aliquot of freshly prepared SMCC solution (3.16 mole equivalents, 31.6 nmol) in DMSO (0.5 mg/ml) for 60 minutes at 20° C. with roller mixing. After, the reaction was quenched with glycine (18.1 μl of 1 mg/ml freshly prepared solution in TBS pH 7.5) and then desalted via zeba desalting column eluting with TBS pH 7.5. The resulting Tras-(S-SMCC) (1.22 mg, 8.1 nmol, 2.03 mg/ml) was reacted with an aliquot of freshly reduced Dianthin-Cys (3.2 mole equivalents, 32.5 nmol, 0.97 mg, 0.52 mg/ml) and incubated overnight at 20° C. with roller mixing. After 17 hours, the conjugate was concentrated to 51 ml using a vivaspin T4 concentrator and purified using a 1.6×37 cm Superdex 200PG column eluting with DPBS pH 7.5.

Yield: n.d. Purity: 99%.

TABLE 12

| Summarized reaction conditions and results | | | | | |
|---|---|---|---|---|---|
| Batch | SMCC mol equivalents | Dianthin-Cys mol equivalents | Obtained DAR | Purity by analytical SEC (%) | Yield (%) |
| Tras-(S-Dianthin)$_x$ | 3.16 | 3.2 | n.d. | 99.0 | n.d. |
| Cet-(S-Dianthin)$_2$ | 3.70 | 3.2 | 1.6 | 97.2 | 93 |

n.d. = not determined

Antibody-(L-SO1861)$^n$-(L-Dianthin)$^n$

Trastuzumab-(L-SO1861)$_4$-(L-Dainthin)$_2$, and Cetuximab-(L-SO1861)$_4$-(L-Dainthin)$_2$ Synthesis Via PEG$_4$-SPDP with a DAR2

Trastuzumab-L-SO1861, and Cetuximab-L-SO1861 are referred hereafter as "Ab". Ab was conjugated to Dianthin-Cys via a tetra(ethylene glycol) succinimidyl 3-(2-pyridyldithio)propionate (PEG$_4$-SPDP) linker forming a labil (L) disulfide bond between Ab and Dianthin. The procedure is exemplary described for Trastuzumab-L-SO1861:

Dianthin-Cys (7.8 mg, 261 nmol, 0.78 mg/ml) was reacted with TCEP (5 mole equivalents, 1.31 μmol, 0.37 mg, 1 mg/ml) for 30 minutes at 20° C. with roller mixing. After, the protein-SH was purified by zeba desalting column eluting into TBS pH 7.5 and used promptly. Protein-SH was obtained (5.2 mg, 67%, 0.52 mg/ml, SH to protein ratio=1±0.1).

Trastuzumab-(L-SO1861)$^4$ (0.75 mg, 5 nmol, 2.50 mg/ml) was reacted with an aliquot of freshly prepared PEG$_4$-SPDP solution (4.95 mole equivalents, 24.75 nmol, 14 μg) in DMSO (1 mg/ml) for 60 minutes at 20° C. with roller mixing. After, the reaction was quenched with glycine (18.1 μl of 1 mg/ml freshly prepared solution in TBS pH 7.5) and then desalted via zeba desalting column eluting with TBS pH 7.5. An aliquot of the resulting Tras-(L-SO1861)-(S-PEG$_4$-SPDP) was taken out and tested by UV-Vis analysis. SPDP incorporation was determined using TCEP to liberate pyridiyl-2-thione (PDT) and by UV-vis analysis at 343 nm (SPDP to Ab ratio=2.4). The remaining Tras-(L-SO1861)-(S-PEG$_4$-SPDP) was reacted with an aliquot of freshly prepared Dianthin-Cys (protein-SH) (4 mole equivalents, 20 nmol, 0.6 mg, 0.52 mg/ml) and incubated overnight at 20° C. with roller mixing. After 17 hours, an aliquot of the conjugate was analyzed by UV-vis analysis to ascertain incorporation of Dianthin-Cys by displacement of PDT. After, the conjugate was concentrated to 51 ml using a vivaspin T4 concentrator and purified using a 1.6×37 cm Superdex 200PG column eluting with DPBS pH 7.5. Dianthin to Ab ratio=2). Yield: n.d. Purity: 60.5%.

TABLE 13

| Summarized reaction conditions and results | | | | | |
|---|---|---|---|---|---|
| Batch | PEG$_4$-SPDP mol equivalents | Dianthin-Cys mol equivalents | Obtained DAR | Purity by analytical SEC (%) | Yield (%) |
| Tras-(L-SO1861)$_4$-(L-Dianthin)$_2$ | 4.95 | 4 | 1.7 | 60.5 | n.d. |
| Cet-(L-SO1861)$_4$-(L-Dianthin)$_2$ | 4.95 | 4 | 2.1 | 85.2 | 89 |

n.d. = not determined

Antibody-(L-Dianthin)$^n$

Trastuzumab-(L-Dianthin)$_2$, Cetuximab-(L-Dianthin)$_2$ and Synthesis Via PEG$_4$-SPDP with a DAR2

Trastuzumab and Cetuximab are referred hereafter as "Ab". Ab was conjugated to Dianthin-Cys via a tetra(ethylene glycol) succinimidyl 3-(2-pyridyldithio)propionate (PEG$_4$-SPDP) linker forming a labil (L) disulfide bond between Ab and Dianthin. The procedure is exemplary described for Trastuzumab-L-SO1861:

Dianthin-Cys (7.8 mg, 261 nmol, 0.78 mg/ml) was reacted with TCEP (5 mole equivalents, 1.31 μmol, 0.37 mg, 1 mg/ml) for 30 minutes at 20° C. with roller mixing. After, the protein-SH was purified by zeba desalting column eluting into TBS pH 7.5 and used promptly. Protein-SH was obtained (5.2 mg, 67%, 0.52 mg/ml, SH to protein ratio=1±0.1).

Trastuzumab (0.75 mg, 5 nmol, 2.50 mg/ml) was reacted with an aliquot of freshly prepared PEG$_4$-SPDP solution (3.35 mole equivalents, 16.75 nmol) in DMSO (1 mg/ml) for 60 minutes at 20° C. with roller mixing. After, the reaction was quenched with glycine (18.1 μl of 1 mg/ml freshly prepared solution in TBS pH 7.5) and then desalted via zeba desalting column eluting with TBS pH 7.5. An aliquot of the resulting Tras-(S-PEG$_4$-SPDP) was taken out and tested by UV-Vis analysis. SPDP incorporation was determined using TCEP to liberate pyridiyl-2-thione (PDT) and by UV-vis analysis at 343 nm. The remaining Tras-(S-$PEG_4$-SPDP) was reacted with an aliquot of freshly prepared Dianthin-Cys (protein-SH) (4 mole equivalents, 20 nmol, 0.6 mg, 0.52 mg/ml) and incubated overnight at 20° C. with roller mixing. After 17 hours, an aliquot of the conjugate was analyzed by UV-vis analysis to ascertain incorporation of Dianthin-Cys by displacement of PDT. After, the conjugate was concentrated to 51 ml using a vivaspin T4 concentrator and purified using a 1.6×37 cm Superdex 200PG column eluting with DPBS pH 7.5. Dianthin to Ab ratio=2). Yield: n.d. Purity: 67.7%.

TABLE 14

| Summarized reaction conditions and results | | | | | |
|---|---|---|---|---|---|
| Batch | $PEG_4$-SPDP mol equivalents | Dianthin-Cys mol equivalents | Obtained DAR | Purity by analytical SEC (%) | Yield (%) |
| Tras-(L-Dianthin)$_2$ | 3.35 | 4 | 1.6 | 67.7 | n.d. |
| Cet-(L-Dianthin)$_2$ | 3.35 | 4 | 1.6 | 95.2 | 88 |

n.d. = not determined

Example 10

Materials and Methods

In our current work, we investigated a model scaffold consisting of four molecular arms for saponin binding via a Schiff base (imine) and one arm for click chemistry. The polymeric structure (FIG. 19) is a pentavalent polyethylene glycol-based dendrimer of the first generation (i.e. number of repeated branching cycles) that was purchased from Iris Biotech GmbH (Marktredwitz, Germany). The saponin (in this example SA1641) was purified from a saponin composite raw extract from *Gypsophila* species called Saponinum album obtained from Merck (Darmstadt, Germany). The powdered raw extract (2.5 g) was hydrolyzed in water (100 mL) with sodium hydroxide (0.2 g). The solution was stirred for 20 h at 40° C. and then supplemented with glacial acetic acid until pH 5.0 was reached. To remove tannins, the solution was shaken in a separatory funnel with 30 mL butanol. The aqueous phase was recaptured and butanol extraction repeated two times. The butanol phases were supplemented with anhydrous sodium sulfate, filtered and pooled. Butanol was evaporated and the remaining saponin powder resolved in 20% methanol to a final concentration of 30 mg/mL. After short sonication, different saponins were separated by high performance liquid chromatography (HPLC). Tubes (excluding column) were rinsed with warm water (40° C.) at a flow of 1.5 mL/min and then including Eurospher RP-C18-column (5 µm, 250×8 mm) with isopropanol (100%). Saponins were applied to the column and eluted with a methanol gradient (20% methanol to 70% methanol within 30 min at 1.5 mL/min in water supplemented with 0.01% trifluoroacetic acid followed by 70% methanol for further 60 min) (Sama et al, 2018). Aliquots of the fractions were analyzed for their SA1641 content by electrospray ionization mass spectrometry (ESI-MS). Fractions containing pure SA1641 were pooled and methanol evaporated. The aqueous solution was frozen as a thin film in a rotating round-bottom flask by use of dry ice. After storage for 16 h at −80° C., the sample was lyophilized. To produce the scaffold as defined in the invention, the polymeric structure (0.2 mM) and SA1641 (3.2 mM) were solved in water (approx. pH 8) and equal volumes mixed and shaken for 24 h at 26° C. Then sodium cyanoborohydride ($NaCNBH_3$; 0.1 M) was added in 4-fold molar excess referred to SA1641 and the sample incubated for further 24 h. The structure was then verified by ultra performance liquid chromatography (UPLC)/ESI-MS. The samples were applied to a RP-C4-column and eluted with a methanol gradient (25% methanol to 80% methanol within 15 min in water supplemented with 0.01% trifluoroacetic acid followed by 80% methanol for further 10 min). The fractions were analyzed by use of LockSpray™ that is an ion source designed specifically for exact mass measurement with electrospray ionization using LC-time-of-flight (LC-TOF) mass spectrometers from Waters Corporation.

Results

The inset of FIG. 20 shows the theoretically expected mass spectrum obtained from a calculation with the isotope pattern calculator enviPat Web 2.0. The pattern considers the charge of the molecule and the natural occurrence of isotopes, which is the reason that more than one peek is expected for a single substance. The experimental data (FIG. 20) obtained by UPLC/ESI-MS show almost exactly the same peaks at m/z 758-760 with same intensity as predicted, thus proving successful SA1641 coupling to the polymeric structure.

Example 11

Materials and Methods

As an example for a pharmaceutical active substance, we used the targeted toxin dianthin-Epidermal Growth Factor (dianthin-EGF). The plasmid His-dianthin-EGF-pET11d (Weng et al, 2009) (100 ng) was added to 20 µL *Escherichia coli* Rosetta™ 2 (DE3) pLysS Competent Cells (Novagen, San Diego, CA, USA). Cells were transformed by a heat-shock (30 min on ice, 90 s at 42° C. and 1 min on ice). Thereafter, 300 µL lysogeny broth (LB) was added and the suspension incubated for 1 h at 37° C. while shaking at 200 rpm. A preheated lysogeny broth agar plate with 50 µg/mL ampicillin was inoculated with 100 µl bacteria suspension and the plate incubated overnight at 37° C. Lysogeny broth (3 mL) with 50 µg/mL ampicillin was inoculated with a colony from the plate and the bacteria were incubated for 8 h at 37° C. and 200 rpm. The suspension (50 µL) was added to 500 mL of lysogeny broth with 50 µg/mL ampicillin and incubated overnight at 37° C. and 200 rpm. Subsequently, the volume was scaled-up to 2.0 L and bacteria grew under the same conditions until an optical density at wavelength 600 nm of 0.9 was reached. Thereafter, protein expression was induced by the addition of isopropyl β-D-1-thiogalactopyranoside (IPTG) at a final concentration of 1 mM. Protein expression lasted for 3 h at 37° C. and 200 rpm. Finally, the bacterial suspension was centrifuged at 5,000×g and 4° C. for 5 min, resuspended in 20 mL PBS (137 mM NaCl, 2.7 mM KCl, 8.1 mM $Na_2HPO_4$, 1.47 mM $KH_2PO_4$) and stored at −20° C. until use. For purification, bacterial suspensions were thawed and lysed by sonication. Lysates were centrifuged (15,800×g, 4° C., 30 min) and imidazole added to a final concentration of 20 mM. The supernatant was incubated with 2 mL of Ni-nitrilotriacetic acid agarose under continuous shaking for 30 min at 4° C. in the presence of 20 mM imidazole. Subsequently, the material was poured into a 20-mL-column and washed three times with 10 mL wash buffer (50 mM $NaH_2PO_4$, 300 mM NaCl, 20 mM imidazole) and dianthin-EGF eluted by 10-mL-portions of increasing concentrations of imidazole (31, 65, 125 and 250 mM) in wash buffer. Eluate fractions (2 mL) were dialyzed overnight at 4° C. against 2.0 L PBS. Desalted dianthin-EGF was concentrated by an Amicon® Ultra-15 (10 kDa) and the protein concentration quantified.

To introduce a suitable click chemistry group into dianthin-EGF, alkyne-$PEG_5$-N-hydroxysuccinimidyl ester in 8-fold molar excess referred to dianthin-EGF was solved in dimethyl sulfoxide and added to 9 volumes of dianthin-EGF (1 mg in 0.2 M $NaH_2PO_4$/$Na_2HPO_4$, pH 8). After incubation at room temperature for 4 h, non-bound alkyne was separated by use of a PD10 column (GE-Healthcare, Freiburg, Germany). Click chemistry with the polymeric structure was conducted by copper(I)-catalyzed alkyne-azide cycloaddition. Alkyne-dianthin-EGF (0.02 mM), dendrimer (0.05 mM), $CuSO_4$ (0.1 mM), tris(3-hydroxypropyltriazolylmethyl)amine (0.5 mM) and sodium ascorbate (5 mM) were incubated under gentle agitation for 1 h at room temperature in 0.1 M $NaH_2PO_4$/$Na_2HPO_4$, pH 8. Low molecular mass substances were then separated using a PD10 column.

To test the efficacy of the invention, we conducted a viability assay with HER14 cells. These cells are fibroblasts stably transfected with the human epidermal growth factor receptor and therefore target cells for the targeted toxin dianthin-EGF. HER14 cells (2,000 cells/100 μL/well) were seeded into wells of 96-well-cell culture plates and incubated for 24 h in DMEM medium supplemented with 10% fetal calf serum and 1% penicillin/streptomycin at 37° C., 5% $CO_2$ and 98% humidity. The different test substances (see results and FIG. 21) were then added in triplicates in a volume of 25 μL and supplemented with further 25 μL of medium. After an incubation of 72 h, 30 μL 3-(4,5-dimethylthiazol-2-yl)-2,5-diphenyltetrazolium bromide (0.5 mg/mL in water) was added per well and incubated for 2 h. Thereafter, the medium was carefully removed and replaced by an aqueous solution containing 10% (v/v) isopropanol, 5% (w/v) sodium dodecyl sulfate and 400 mM HCl, and incubated for 5 min. Solubilized formazan was photometrically quantitated at 570 nM in a microplate reader (Spectra MAX 340 PC, Molecular Devices, Sunnyvale, CA, USA). Untreated cells were normalized to 1 and all samples referred to the untreated control. Significance was determined by unpaired two-sample t-tests.

Results

The polymeric structure, in the example a pentameric dendrimer (pentrimer), does not have any cytotoxic effect on the target cells, neither in absence nor in presence of SA1641 (FIG. 27, column 2 and 3). In the absence of the scaffold, the targeted toxin (dianthin-EGF) shows half maximal toxicity at a concentration of 0.1 nM (column 4). In the presence of SA1641 the same concentration results in death of all cells indicating the general ability of SA1641 to act as an enhancer of the endosomal escape (column 5). The presence of the polymeric structure does not affect the toxicity of dianthin-EGF neither in the presence nor in the absence of SA1641 (columns 6 and 7), indicating that the scaffold does not affect the toxicity of dianthin-EGF. To couple the model polymeric structure via click chemistry to the example pharmaceutically active substance of dianthin-EGF, the substance had to be coupled with an alkyne group before. In consequence of this modification, dianthin-EGF lost some activity (compare columns 8 and 9 with 6 and 7, respectively), however, the undirected alkyne modification does not affect the idea of the invention and is also not required in future applications. We had to introduce the alkyne in an undirected way for test purposes only with the risk to impede the pharmaceutically active center of the toxin. A manufacturer of a pharmaceutically active substance can introduce the click position during synthesis directly into the substance at a position of his choice where the activity of the substance remains unaffected. There was no additional loss of activity when clicking the alkyne-modified pharmaceutically active substance to the polymeric structure indicating that the polymeric structure itself was not toxic (column 10 and 11).

Example 12

Materials

The following chemicals were used as purchased: methanol (MeOH, LiChrosolv, Merck), N-ε-maleimidocaproic acid hydrazide (EMCH, 95%, TCI Chemicals), trifluoroacetic acid (TFA, 99.8%, Carl Roth), 2-mercaptoethanol (98%, Sigma-Aldrich), poly(amidoamine) (PAMAM dendrimer, ethylenediamine core, generation 5.0 solution, Sigma-Aldrich), cyanine 3 carboxylic acid (Cy3-COOH, 95%, Lumiprobe), 1-[Bis(dimethylamino)methylene]-1H-1,2,3-triazolo[4,5-b]pyridinium 3-oxid hexafluorophosphate, N-[(Dimethylamino)-1H-1,2,3-triazolo-[4,5-b]pyridin-1-ylmethylene]-N-methylmethanaminium hexafluorophosphate N-oxide (HATU, 97%, Sigma-Aldrich), bovine serum albumin fraction V (BSA, Carl Roth), dimethylsulfoxide (DMSO, 99%, Carl Roth), 2-Iminothiolane hydrochloride (98%, Sigma-Aldrich), rhodamine b (RhodB, 95%, Merck), Dulbecco's phosphate buffered saline (PBS, Gibco), hydrochloric acid (HCl, 37%, Merck), NHS-$PEG_{13}$-DBCO (Click Chemistry Tools), Alexa Fluor™ 488 5-TFP (Thermo-Fischer), azido-PEG3-SS-NHS (Conju-Probe), sodium cyanoborohydride ($NaCNBH_3$, 95%, Sigma-Aldrich), ammonium persulfate (APS, 98%, Sigma-Aldrich), N,N,N',N'-tetramethylethylenediamine (TMEDA, 99%, Sigma-Aldrich), customized peptide SESDDAMFCDAMDESDSK (95%, PeptideSynthetics), azido-dPEG12-NHS (95%, Quanta Biodesign), PFd-G4-Azide-NH-BOC Dendron (G4-dendron, 95%, Polymer Factory), Cyanin5-DBCO (Cy5-DBCO, 95%, Lumiprobe), Chloroform ($CHCl_3$, 99.5%, Sigma), Amicon Ultra 0.5 mL centrifugal filters (3 kDa MWCO, Sigma), mPEG-SCM ($mPEG_{2k}$-NHS, 95.6%, Creative PEG Works), Amicon Ultra 15 mL centrifugal filters (10 kDa MWCO, Sigma).

Methods

MALDI-TOF-MS

MALDI-TOF spectra were recorded on a MALDI-Mass Spectrometer (Bruker Ultrafex III). Typically, the sample dissolved in MilliQ water in nanomolar to micromolar range was spotted on the target (MTP 384 target plate polished steel T F, Bruker Daltons) using either super-DHB (99%, Fluka) or sinapinic acid (SA, 99%, Sigma-Aldrich) as the matrix dissolved in acetonitrile (MADLI-TOF-MS tested, Sigma)/0.1% TFA (7:3 v/v) via the dried-droplet-method. PepMix (Peptide Calibration Standard, Bruker Daltons) or ProteMass (Protein Calibration Standard, Sigma-Aldrich) served as calibration standards. RP mode refers to reflector positive mode. RN mode refers to reflector negative mode. LP mode refers to linear positive mode.

H-NMR $^1H$ NMR analysis was performed using a Bruker 400 MHz NMR spectrometer. The sample preparation, in which 2 mg of sample had been dissolved in 0.8 mL of methanol-$D_4$ (99%, Deutero), was performed 24 h prior to the measurement.

UV-Vis

UV-Vis measurements were performed on a NanoDrop ND-1000 spectrophotometer in the spectral range of 200-750 nm.

Size Exclusion Chromatography

Size exclusion chromatography (SEC) was performed with Sephadex G 25 Superfine from GE Healthcare and on prepacked PD10 columns (GE Healthcare, Sephadex G 25 M). The material was activated by swelling in the respective eluent prior to performing chromatography.

Dialysis

Regenerated cellulose membranes: MWCO=1 and 2 kDa (Spectra/Por), and MWCO=12-14 kDa (Carl Roth) were used to perform dialysis. Typically, dialysis was carried out for 24 h with 1 L of solvent that was exchanged after first 6 h of the process.

Lyophilization

Freeze-drying was performed on an Alpha 1-2 LD plus (Martin Christ Gefriertrocknungsanlagen GmbH). Typically, samples were frozen with liquid nitrogen and placed into the freeze-dryer at high vacuum.

SO1861-EMCH Synthesis

SO1861 from *Saponaria officinalis* L (59 mg, 31.7 μmol) and EMCH (301 mg, 888 μmol) were placed in a round flask with stirrer and dissolved in 13 mL methanol. TFA (400 μL, cat.) was added to the solution and the reaction mixture was stirred for 3 h at 800 rpm and room temperature on a RCT B magnetic stirrer (IKA Labortechnik). After stirring for 3 h, the mix was diluted either with MilliQ water or PBS and dialyzed extensively for 24 h against either with MilliQ water or PBS using regenerated cellulose membrane tubes (Spectra/Por 7) with a MWCO of 1 kDa. After dialysis, the solution was lyophilized to obtain a white powder. Yield 62.4 mg (95%). Dried aliquots were further used for characterization via $^1$H NMR and MALDI-TOF-MS.

$^1$H NMR (400 MHz, methanol-$D_4$) (FIG. 22 A, SO1861): δ=0.50-5.50 (m, saponin triterpenoid and sugar backbone protons), 9.43 (1H, s, aldehyde proton of saponin, $H^a$).

$^1$H NMR (400 MHz, methanol-$D_4$) (FIG. 22 B. SO1861-EMCH, PBS workup): δ=0.50-5.50 (m, saponin triterpenoid and sugar backbone protons), 6.79 (2H, s, maleimide protons, H), 7.62-7.68 (1H, m, hydrazone proton, $H^b$).

MALDI-TOF-MS (RP mode) (FIG. 23 A): m/z 2124 Da ($[M+K]^+$, saponin-EMCH), m/z 2109 Da ($[M+K]^+$, SO1861-EMCH), m/z 2094 Da ($[M+Na]^+$, SO1861-EMCH)

MALDI-TOF-MS (RN mode) (FIG. 28 C): m/z 2275 Da ($[M-H]^-$, saponin-EMCH conjugate), 2244 Da ($[M-H]^-$, saponin-EMCH conjugate), 2222 Da ($[M-H]^-$, saponin-EMCH conjugate), 2178 Da ($[M-H]^-$, saponin-EMCH conjugate), 2144 Da ($[M-H]^-$, saponin-EMCH conjugate), 2122 Da ($[M-H]^-$, saponin-EMCH conjugate), 2092 Da ($[M-H]^-$, saponin-EMCH conjugate), 2070 Da ($[M-H]^-$, SO1861-EMCH), 2038 Da ($[M-H]^-$, S01832-EMCH), 1936 Da ($[M-H]^-$, S01730-EMCH), 1861 Da ($[M-H]^-$, SO1861).

SO1861-EMCH-Mercaptoethanol

To SO1861-EMCH (0.1 mg, 48 nmol) 200 μL mercaptoethanol (18 mg, 230 μmol) was added and the solution was shaken for 1 h at 800 rpm and room temperature on a ThermoMixer C (Eppendorf). After shaking for 1 h, the solution was diluted with methanol and dialyzed extensively for 4 h against methanol using regenerated cellulose membrane tubes (Spectra/Por 7) with a MWCO of 1 kDa. After dialysis, an aliquot was taken out and analyzed via MALDI-TOF-MS.

MALDI-TOF-MS (FIG. 23B) (RP mode): m/z 2193 Da ($[M+K]^+$, SO1861-EMCH-mercaptoethanol), m/z 2185 Da ($[M+K]^+$, SO1861-EMCH-mercaptoethanol), m/z 2170 Da ($[M+Na]^+$, SO1861-EMCH-mercaptoethanol).

BSA-SO1861 Synthesis 2-iminothiolane (231 μg, 1.1 μmol) dissolved in 47 μL PBS was added to a BSA-RhodB solution (10 mg, 0.15 μmol) in 200 μL PBS and the mix was shaken for 40 min at 800 rpm and room temperature on a ThermoMixer C (Eppendorf). After shaking for 40 min, the reaction mix was immediately run through a Sephadex G25 superfine size exclusion column (16 mL column volume) and SO1861-EMCH (1 mg, 0.5 μmol) dissolved in 100 μL PBS was added to the collected BSA-SH fraction. The reaction mixture was shaken for 12 h at 800 rpm and room temperature on a ThermoMixer C (Eppendorf). After shaking for 12 h the BSA-SO1861 concentrated using centrifugal filtration at 4,000 rpm (15° C.) via Amicon Ultra 15 filters with a MWCO of 3 kDa. The conjugate was stored as solution in the fridge and aliquots were taken for analysis. Yield: not determined.

MALDI-TOF-MS (FIG. 15 A) (LP mode): m/z 74.2 kDa ($[M+H]^+$, BSA-SO1861 with 4 SO1861 attached), 72.2 kDa ($[M+H]^+$, BSA-SO1861 with 3 SO1861 attached), 70.2 kDa ($[M+H]^+$, BSA-SO1861 with 2 SO1861 attached), 37.0 kDa ($[M+H]^{2+}$, BSA-SO1861 with 4 SO1861 attached), 35.9 kDa ($[M+H]^{2+}$, BSA-SO1861 with 3 SO1861 attached), 34.7 kDa ($[M+H]^{2+}$, BSA-SO1861 with 2 SO1861 attached).

Cy3-PAMAM

720 μL PAMAM dissolved in methanol (30 mg, 1.04 μmol) was placed into a 250 mL round flask and methanol was removed via a rotary evaporator (20 mbar, 60° C.). Remaining PAMAM was dissolved in 9 mL DMSO. HATU (7.6 mg, 20 μmol) dissolved in 0.5 mL DMSO was added to a Cy3-COOH (0.6 mg, 1.2 μmol) solution in DMSO and the mix was shaken for 1 h at 800 rpm at room temperature on a ThermoMixer C (Eppendorf). After shaking for 1 h, the HATU-Cy3 solution was added to the stirring PAMAM solution and the reaction mix was stirred for 12 h at room temperature. After stirring for 12 h, the reaction mix was diluted with MilliQ water and dialyzed extensively for 24 h against MilliQ water using regenerated cellulose membrane tubes (Spectra/Por 6) with a MWCO of 2 kDa. After dialysis, the volume of the conjugate solution was reduced via a rotary evaporator (20 mbar, 60° C.) and the concentrated conjugate solution was run through a Sephadex G25 superfine size exclusion column (16 mL column volume). The first fraction was collected and lyophilized to obtain the viscous pink PAMAM-Cy3 conjugate. PAMAM-Cy3 conjugate formation was confirmed by chromatography on thin layer chromatography (methanol/water, v/v 1:1), and the appearance of a faster band on a Sephadex G 25 superfine column. Yield 21.3 mg (63%). The dye per PAMAM molar ratio determined by UV-Vis spectrophotometry was 0.43.

MALDI-TOF-MS (FIG. 33 A) (LP mode): m/z 28.0 kDa ($[M+H]^+$, Cy3-PAMAM).

Cy3-PAMAM-SO1861 Synthesis

Procedure is described exemplary for Cy3-PAMAM-$(SO1861)_5$. 2-iminothiolane (1 mg, 6.7 μmol) dissolved in 250 μL MilliQ water was added to a PAMAM-Cy3 solution (0.5 mg, 17 nmol) in 125 μL MilliQ water and the mix was shaken for 40 min at 800 rpm and room temperature on a ThermoMixer C (Eppendorf). After shaking for 40 min, the reaction mix was immediately run through a Sephadex G25 superfine size exclusion column (16 mL column volume) and SO1861-EMCH (176 μg, 85 nmol) dissolved in 40 μL MilliQ water was added to the collected Cy3-PAMAM-SH fraction. The reaction mixture was shaken for 12 h at 800 rpm and room temperature on a ThermoMixer C (EppendorD. After shaking for 12 h, the reaction mix was diluted with MilliQ water and dialyzed extensively for 24 h against MilliQ water using regenerated cellulose membrane tubes (ZelluTrans, Carl Roth) with a MWCO of 12-14 kDa. After dialysis, the Cy3-PAMAM-SO1861 solution was concentrated using centrifugal filtration at 4000 rpm (15° C.) via Amicon Ultra 15 filters with a MWCO of 3 kDa. The conjugate was stored as solution in the fridge and aliquots were taken for analysis. Yield: 0.5 mg (75%).

MALDI-TOF-MS spectra are illustrated in FIGS. 33 B-D, and FIG. 34. MALDI-TOF-MS of Cy3-PAMAM-$(SP1861)_6$ (FIG. 33 B) (LP mode): m/z 38.4 kDa ($[M+H]^+$, Cy3-PAMAM-SO1861), 17.9 kDa ($[M+H]^{2+}$, Cy3-PAMAM-SO1861).

The synthesis of Cy3-PAMAM-$(SO1861)_5$, Cy3-PAMAM-$(SO1861)_{13}$, Cy3-PAMAM-$(SO1861)_{51}$, and Cy3-PAMAM-$(SC1861)_{27}$, has been performed via the above described methodology but differ in the feed equivalents of the starting materials 2-iminothiolane and (1861-EMCH. The respective feed equivalents of the starting materials and the respective mass of the conjugates are highlighted in Table 15.

TABLE 15

Reaction parameter for Cy3-PAMAM-SO1861 synthesis.

| 2-Iminothiolane feed equivalents to Cy3-PAMAM | SO1861-EMCH feed equivalents to Cy3-PAMAM | Mass of conjugate via MALDI-TOF-MS | SO1861 molecules attached per PAMAM | Resulting conjugate |
|---|---|---|---|---|
| 384 | 6 | 38.7 kDa | ~5 | Cy3-PAMAM-$(SO1861)_6$, FIG. 33 B |
| 384 | 20 | 53.9 kDa | ~13 | Cy3-PAMAM-$(SO1861)_{13}$, FIG. 33 C |
| 384 | 57 | 133.9 kDa | ~51 | Cy3-PAMAM-$(SO1861)_{51}$, FIG. 33 D |
| 8 | 5 | 37.7 kDa | ~5 | Cy3-PAMAM-$(SO1861)_5$, FIG. 34 A |
| 32 | 30 | 87.0 kDa | ~27 | Cy3-PAMAM-$(SO1861)_{27}$, FIG. 34 B |

Cy3-PAMAM-NC-SO1861 Synthesis

Cy3-PAMAM (0.5 mg, 18 nmol), SO1861 (2.3 mg, 1.24 µmol), and HATU (64.6 mg, 170 µmol) were dissolved separately in 200 µL DMSO. SO1861 and HATU solutions were mixed and shaken for 20 min at 800 rpm and room temperature on a ThermoMixer C (Eppendorf. After shaking for 20 min, Cy3-PAMAM solution was added to the shaking SO1861-HATU solution and the reaction mixture was allowed to shake for 12 h at 800 rpm and room temperature on a ThermoMixer C (Eppendorf). After shaking for 12 h, the reaction mix was diluted with MilliQ water and dialyzed extensively for 24 h against MilliQ water using regenerated cellulose membrane tubes (ZelluTrans, Carl Roth) with a MWCO of 12-14 kDa. After dialysis, the Cy3-PAMAM-NC-SO1861 solution was concentrated using centrifugal filtration at 4,000 rpm (15° C.) via Amicon Ultra 15 filters with a MWCO of 3 kDa. The Cy3-PAMAM-NC-$(SO1861)^{17}$ conjugate was stored as solution in the fridge and aliquots were taken for analysis. Yield: 0.77 mg (69%).

MALDI-TOF-MS (FIG. 35) (LP mode): m/z 62.3 kDa ($[M+H]^+$, Cy3-PAMAM-NC-SO1861), 35.7 kDa ($[M+H]^{2+}$, Cy3-PAMAM-NC-SO1861).

G4-Dendron Dye Labeling and Deprotection

PFd-G4-Azide-NH-BOC (G4-dendron) (9.75 mg, 2.11 µmol) was placed into a 2 mL reaction tube (Eppendorf) and dissolved in 200 µL DMSO. 100 µL of a Cy5-DBCO solution in DMSO (1.72 µmol*$mL^{-1}$, 170 nmol) was added to the G4-dendron solution and the mix was shaken for 12 hours at room temperature and 800 rpm on a ThermoMixer C (Eppendorf). After shaking for 12 h, the reaction mix was diluted with MilliQ water and dialyzed extensively for 24 h against MilliQ water using regenerated cellulose membrane tubes (Spectra/Por 7) with a MWCO of 1 kDa. After dialysis, the solution was lyophilized to obtain a blue powder. The crude product was used as obtained from lyophilization for the deprotection step.

Partially Cy5 labeled lyophilized G4-dendron was dissolved in 12 mL $CHCl_3$ in 50 mL round flask with stirrer. 12 mL TFA was added and the reaction mix was stirred for 3 h at 800 rpm and room temperature on a RCT B magnetic stirrer (IKA Labortechnik). After stirring for 3 h, the solvent was removed under reduced pressure (50° C., 30 mbar) on a rotary evaporator (Heidolph WB 2000). After evaporation, the batch was dissolved in MilliQ water and run through a PD10 size exclusion column. G4-dendron conjugate formation was confirmed by chromatography on thin layer chromatography (methanol/water, v/v 1:1), and the appearance of a faster band on a PD10 column. Obtained fraction of size exclusion chromatography was lyophilized to obtain a blue powder.

Yield 5.7 mg (93%). The dye per G4-dendron molar ratio determined by UV-Vis spectrophotometry was 0.012.

MALDI-TOF-MS (FIG. 32 B) (RP mode): m/z 3956 Da ($[M+Na]^+$, Cy5-G4-dendron+$PF_6^-$ counterion), 3820 Da ($[M+Na]^+$, Cy5-G4-dendron-$PF_6^-$ counterion), 3617 Da ($[M+H]^+$, G4-dendron impurity), 3017 ($[M+H]^+$, G4-dendron).

G4-dendron-SO1861 Synthesis

Procedure is described exemplary for the lowest G4-dendron to SO1861-EMCH ratio. 2-iminothiolane (2.65 mg, 19.2 µmol) dissolved in 300 µL MilliQ water was added to a partially Cy5 labeled G4-dendron solution (0.577 mg, 192 nmol) in 252 µL MilliQ water and the mix was shaken for 40 min at 800 rpm and room temperature on a ThermoMixer C (Eppendorf). After shaking for 40 min, the reaction mix was immediately run through a PD10 size exclusion column and SO1861-EMCH (1.19 mg, 575 nmol) dissolved in 100 µL MilliQ water was added to the collected G4-dendron-SH fraction. The reaction mixture was shaken for 12 h at 800 rpm and room temperature on a ThermoMixer C (Eppendorf). After shaking for 12 h, the reaction mix was concentrated via centrifugal filtration using Amicon Ultra centrifugal filters (3 kDa MWCO). The conjugate was stored as solution in the fridge and aliquots were taken for analysis. Yield: 90 nmol (47%).

MALDI-TOF-MS spectra are illustrated in FIG. 33. MALDI-TOF-MS of G4-dendron-SO1861 (FIG. 33 C) (LP mode): m/z 10.19 kDa ($[M+H]^+$, Cy5-G4-dendron-$[SO1861]_3$), 9.27 kDa ($[M+H]^+$, G4-dendron-$[SO1861]_3$), 7.92 kDa ($[M+H]^+$, Cy5-G4-dendron-$[SO1861]_2$), 7.14 kDa ($[M+H]^+$, G4-dendron-$[SO1861]_2$), 5.86 kDa ($[M+H]^+$, Cy5-G4-dendron-$[SO1861]_1$), 5.07 kDa ($[M+H]^+$, G4-dendron-$[SO1861]_1$).

The synthesis of other G4-dendron-$(SO1861)_n$ conjugates has been performed via the above described methodology but differs in the feed equivalents of the starting material SO1861-EMCH. The respective feed equivalents of the starting materials and the respective mass of the conjugates are highlighted in Table 16.

TABLE 16

Reaction parameter for G4-dendron-SO1861 synthesis.

| 2-Iminothiolane feed equivalents to G4-dendron | SO1861-EMCH feed equivalents to G4-dendron | Mass of conjugates via MALDI-TOF-MS | SO1861 molecules attached per G4-dendron | Resulting MS spectrum |
|---|---|---|---|---|
| 100 | 3 | 5.07-10.18 kDa | ~1-3 | FIG. 49 C |
| 100 | 10 | 5.07-11.64 kDa | ~1-4 | FIG. 49 B |
| 100 | 22 | 6.20-22.02 kDa | ~1-9 | FIG. 49 A |

PAMAM Thiolation

Procedure is described exemplary for the highest PAMAM to 2-iminothiolane ratio. To a PAMAM (333 µg, 12.8 nmol) solution dissolved in 30 µL methanol 2-iminothiolane (0.53 mg, 3.84 µmol) dissolved in 128 µL MilliQ water was added. The reaction mixture was shaken for 12 h at 800 rpm and room temperature on a ThermoMixer C (Eppendorf. After shaking for 12 h, the reaction mix was washed 4 times with MilliQ water via centrifugal filtration using Amicon Ultra centrifugal filters (3 kDa MWCO) at 15° C. and 13500 rpm. After washing the sample was lyophilized to obtain a white solid. Yield was not determined.

MALDI-TOF-MS spectra are illustrated in FIG. 51. MALDI-TOF-MS of PAMAM-$(SH)_{108}$ (FIG. 51 C) (LP mode): m/z 41.5 kDa ($[M+H]^+$, PAMAM-$[SH]_{108}$).

The synthesis of other PAMAM-iminothiolane conjugates has been performed via the above described methodology but differs in the feed equivalents of the starting material 2-iminothiolane. For the lowest 2-iminothiolane feed reaction Cy3-PAMAM has been used.

The respective feed equivalents of the starting materials and the respective mass of the conjugates are highlighted in Table 17.

TABLE 17

Reaction parameter for PAMAM-SH synthesis.

| 2-Iminothiolane feed equivalents to PAMAM | Mass of conjugates via MALDI-TOF-MS | Iminothiolane molecules attached per PAMAM | Resulting MS spectrum |
|---|---|---|---|
| 50 | 34.4 kDa | ~16 | FIG. 51 C |
| 100 | 35.9 kDa | ~65 | FIG. 51 D |
| 300 | 41.5 kDa | ~108 | FIG. 51 E |

PAMAM PEGylation

Procedure is described exemplary for the lowest PAMAM to $mPEG_{2k}$ ratio. To a PAMAM (333 µg, 12.8 nmol) solution dissolved in 10 µL DMSO $mPEG_{2k}$-NHS (0.268 mg, 128 nmol) dissolved in 13 µL DMSO was added. The reaction mixture was shaken for 12 h at 800 rpm and room temperature on a ThermoMixer C (Eppendorf). After shaking for 12 h, the reaction mix was diluted with MilliQ water and dialyzed extensively for 24 h against MilliQ water using regenerated cellulose membrane tubes (Spectra/Por 6) with a MWCO of 2 kDa. After dialysis, the batch was concentrated via centrifugal filtration using Amicon Ultra 15 mL centrifugal filters (10 kDa MWCO). The concentrated batch was run through a PD10 size exclusion column followed by lyophilization to obtain a white fluffy powder. Yield was not determined.

MALDI-TOF-MS spectra are illustrated in FIG. 52. MALDI-TOF-MS of PAMAM-$(mPEG_{2k})_3$ (FIG. 52 C) (LP mode): m/z 33.46 kDa ($[M+H]^+$, PAMAM-$[mPEG_{2k}]_3$).

The synthesis of other PAMAM-$mPEG_{2k}$ conjugates has been performed via the above described methodology but differs in the feed equivalents of the starting material $mPEG_{2k}$-NHS. The respective feed equivalents of the starting materials and the respective mass of the conjugates are highlighted in Table 18.

TABLE 18

Reaction parameter for PAMAM-$mPEG_{2k}$ synthesis.

| $mPEG_{2k}$-NHS feed equivalents to PAMAM | Mass of conjugates via MALDI-TOF-MS | $mPEG_{2k}$ molecules attached per PAMAM | Resulting MS spectrum |
|---|---|---|---|
| 10 | 28.5 kDa | ~3 | FIG. 52 C |
| 20 | 43.0 kDa | ~8 | FIG. 52 D |
| 100 | 62.8 kDa | ~18 | FIG. 52 E |

Cy3-PAMAM-SO1861-DBCO Synthesis

Procedure is described exemplary for Cy3-PAMAM-$(SO1861)_{27}$-$(DBCO)_{10}$. Cy3-PAMAM-$(SO1861)_{27}$ (0.41 mg, 4.71 nmol) was freeze-fried and dissolved in 100 µL DMSO. DBCO-$PEG_{13}$-NHS ester (0.197 mg, 188 nmol) dissolved in DMSO was added to the Cy3-PAMAM-SO1861 solution and the mixture was shaken at 800 rpm and room temperature on a ThermoMixer C (Eppendorf). After shaking for 3 h, the reaction mix was diluted with MilliQ water and dialyzed extensively for 24 h against MilliQ water using regenerated cellulose membrane tubes (ZelluTrans, Carl Roth) with a MWCO of 12-14 kDa. After dialysis, the Cy3-PAMAM-SO1861-DBCO solution was concentrated using centrifugal filtration at 4,000 rpm (15° C.) via Amicon Ultra 15 filters with a MWCO of 3 kDa. The conjugate was stored as solution in the fridge and aliquots were taken for analysis. Yield: 0.1 mg (22%).

MALDI-TOF-MS (FIG. 36 D) (LP mode): m/z 92.5 kDa ($[M+H]^+$, Cy3-PAMAM-SO1861-DBCO), 53.0 kDa ($[M+H]^{2+}$, Cy3-PAMAM-SO1861-DBCO).

The synthesis of Cy3-PAMAM-$(SO1861)_5$-$(DBCO)_{38}$, and Cy3-PAMAM-$(SO1861)_{27}$-$(DBCO)_{10}$, have been performed via the above described methodology. The respective feed equivalents of the starting material and the respective mass of the conjugates are highlighted in Table 19.

TABLE 19

Reaction parameter for Cy3-PAMAM-SO1861-DBCO synthesis.

| Used Cy3-PAMAM-saponin batch | DBCO-PEG13-NHS feed equivalents | Mass via MALDI-TOF-MS | DBCO molecules attached per PAMAM | Resulting conjugate |
|---|---|---|---|---|
| Cy3-PAMAM-$(SO1861)_5$ | 40 | 76.3 kDa | ~38 | Cy3-PAMAM-$(SO1861)_5$-$(DBCO)_{38}$, FIG. 36 C |
| Cy3-PAMAM-$(SO1861)_{27}$ | 40 | 92.5 kDa | ~10 | Cy3-PAMAM-$(SO1861)_{27}$-$(DBCO)_{10}$, FIG. 36 D |

Cy3-PAMAM-NC-SO1861-DBCO Synthesis

Cy3-PAMAM-NC-$(SO1861)_{17}$ (0.3 mg, 4.8 nmol) was freeze-fried and dissolved in 100 µL DMSO. DBCO-$PEG_{13}$-NHS ester (0.202 mg, 194 nmol) dissolved in DMSO was added to the Cy3-PAMAM-NC-SO1861 solution and the mixture was shaken at 800 rpm and room temperature on a ThermoMixer C (Eppendorf). After shaking for 3 h, the reaction mix was diluted with MilliQ water and dialyzed extensively for 24 h against MilliQ water using regenerated cellulose membrane tubes (ZelluTrans, Carl Roth) with a MWCO of 12-14 kDa. After dialysis, the Cy3-PAMAM-SO1861-DBCO solution was concentrated using centrifugal filtration at 4,000 rpm (15° C.) via Amicon Ultra 15 filters with a MWCO of 3 kDa. The conjugate was stored as solution in the fridge and aliquots were taken for analysis. Yield: 0.1 mg (22%).

Mass spectrometry indicates the conjugation of 30 DBCO moieties per PAMAM molecule.

MALDI-TOF-MS (FIG. 36 B) (LP mode): m/z 93.2 kDa ($[M+H]^+$, Cy3-PAMAM-NC-SO1861-DBCO), 49.6 kDa ($[M+H]^{2+}$, Cy3-PAMAM-NC-SO1861-DBCO).

EGFDianthin and Dianthin Expression

Plasmid-DNA (His-dianthin-EGF-pET11d or His-dianthin-pET11d) [20] was transformed into chemically competent *Escherichia coli* NiCo21 (DE3) (New England Biolabs®, Inc.) and grown in 3 mL lysogeny broth supplemented with 50 μg/mL ampicillin at 37° C. for 5 h at 200 rpm. These bacteria were used to inoculate 500 mL lysogeny broth supplemented with 50 μg/mL ampicillin for overnight culture at 37° C. Subsequently, the culture volume was scaled up to 2 L and bacteria were grown until an optical density (A600) of 0.9. Protein expression was induced by the addition of isopropyl β-D-1-thiogalactopyranoside (IPTG) at a final concentration of 1 mM. Cells were further grown for 3 h at 37° C. and 200 rpm. After centrifugation (5 min, 5,000 g, 4° C.) cell pellets were resuspended in 20 mL phosphate buffered saline (Dulbecco's phosphate-buffered saline (PBS) with $Ca^{2+}$ and $Mg^{2+}$, pH 7.4) and stored at −20° C. After thawing, proteins were released by ultrasound device (Branson Sonifier 250, G. Heinemann). The solution was centrifuged (15,800×g, 30 min, 4° C.) and adjusted to 20 mM imidazole concentration. The construct contained an N-terminal His-tag and was purified by nickel nitrilotriacetic acid chromatography (Ni-NTA Agarose, Qiagen, Hilden, Germany). After elution with imidazole (20-250 mM) the eluates were analyzed by sodium dodecyl sulfate polyacrylamide gel electrophoresis (SDS-PAGE) (12%). Fractions containing dianthin-EGF or dianthin were dialyzed against 2 L chitin binding domain buffer (20 mM tris(hydroxymethyl)-aminomethane/HCl, 500 mM NaCl, 1 mM EDTA, 0.1% Tween-20, pH 8.0) at 4° C. Further purification by chitin column affinity chromatography served to remove bacterial proteins with binding activity for Ni-NTA agarose. After elution with chitin binding domain buffer, the fractions were analyzed by SDS-PAGE (12%). Fractions containing dianthin-EGF or dianthin were dialyzed against 5 L PBS at 4° C. Purified proteins were concentrated by Amicon centrifugal filter devices (10 kDa, Millipore, Eschborn, Germany). The protein concentration was determined by a bicinchoninic acid assay (Pierce, Rockford, USA).

Dianthin-EGF-Alexa488 Synthesis

Dianthin-EGF (240 μg, 6.7 nmol) solution in PBS was placed into an Amicon Ultra 15 filter with a MWCO of 3 kDa and centrifuged at 4,000 rpm and 4° C. for 30 min three times. After each cycle, the Amicon filter was refilled with 0.1 M sodium carbonate buffer at pH 9. After the third centrifugation cycle, the volume was reduced to 0.5 mL via centrifugation. The dianthin-EGF sodium carbonate solution was placed into a 2 mL reaction tube and Alexa Fluor™ 488 5-TFP (50 μg, 56 nmol) dissolved in 10 μL DMSO was added to the protein solution. The mix was shaken at 800 rpm and room temperature on a ThermoMixer C (Eppendorf) for 80 min. After shaking, the mix was run through a Sephadex G25 M size exclusion column (GE Healthcare, PD10 column). The dianthin-EGF-Alexa488 conjugate was stored in solution in 0.1 M sodium carbonate buffer at pH 9 in the fridge and aliquots were taken for analysis.

Yield: 210 μg (85%).

MALDI-TOF-MS (FIG. 37 D) (LP mode): m/z 36.8 kDa ($[M+H]^+$, dianthin-EGF-Alexa488), m/z 33.6 kDa ($[M+H]^+$, dianthin-EGF-Alexa488), 18.8 kDa ($[M+H]^{2+}$, dianthin-EGF-Alexa488), 16.6 kDa ($[M+H]^{2+}$, dianthin-EGF-Alexa488).

Dianthin-Alexa488 Synthesis

Dianthin (184 μg, 6.2 nmol) solution in PBS was placed into an Amicon Ultra 15 filter with a MWCO of 3 kDa and centrifuged at 4,000 rpm and 4° C. for 30 min three times. After each cycle, the Amicon filter was refilled with 0.1 M sodium carbonate buffer at pH 9. After the third centrifugation cycle, the volume was reduced to 0.5 mL via centrifugation. The dianthin sodium carbonate solution was placed into a 2 mL reaction tube and Alexa Fluor™ 488 5-TFP (16.7 μg, 19 nmol) dissolved in 3.5 μL DMSO was added to the protein solution. The mix was shaken at 800 rpm and room temperature on a ThermoMixer C (Eppendorf) for 80 min. After shaking, the mix was run through a Sephadex G25 M size exclusion column (GE Healthcare, PD 10 column). The dianthin-Alexa488 conjugate was stored in solution in 0.1 M sodium carbonate buffer at pH 9 in the fridge and aliquots were taken for analysis. Yield: not determined MALDI-TOF-MS (FIG. 38 D) (LP mode): m/z 30.7 kDa ($[M+H]^+$, dianthin-Alexa488).

Dianthin-EGF-Alexa488-S-S-PEG-$N_3$, and Dianthin-EGF-Alexa488-$PEG_{12}$-$N_3$ Synthesis Procedure is described exemplary for dianthin-EGF-Alexa488-S-S-PEG-$N_3$. Dianthin-EGF-Alexa488 (70 μg, 1.9 nmol) sodium carbonate solution was placed into a 2 mL reaction tube and azido-$PEG_3$-S-S-NHS (120 μg, 272 nmol) dissolved in 9 μL DMSO was added to the protein solution. The mix was shaken at 800 rpm and 15° C. on a ThermoMixer C (Eppendorf) for 12 h. After shaking, the reaction mix was diluted with PBS and was washed with PBS via centrifugal filtration at 4,000 rpm and 4° C. using Amicon Ultra 15 filter with a MWCO of 3 kDa.

Yield: 54 μg (70%).

MALDI-TOF-MS (FIG. 37 E) (LP mode): m/z 40.8 kDa ($[M+H]^+$, dianthin-EGF-Alexa488-S-S-PEG-$N_3$), m/z 37.5 kDa ($[M+H]^+$, dianthin-EGF-Alexa488-S-S-PEG-$N_3$).

The synthesis of dianthin-EGF-Alexa488-S-S-PEG-$N_3$, and dianthin-EGF-Alexa488-$PEG_{12}$-$N_3$ have been performed via the above described methodology but differed in the used azido-PEG linker. The respective azido-PEG linker, their feed equivalents, and the respective mass of the conjugates are highlighted in Table 20.

TABLE 20

Reaction parameter for dianthin-EGF-Alexa488-PEG-N3 synthesis

| Used toxin batch | Azido-PEG linker used | Azido-PEG linker feed equivalents | Mass of conjugate via MALDI-TOF-MS | Resulting conjugate |
|---|---|---|---|---|
| Dianthin-EGF-Alexa488 | Azido-$PEG_3$-S-S-NHS | 135 | 40.8 kDa | Dianthin-EGF-Alexa488-S-S-$PEG_3$-$N_3$ |
| Dianthin-EGF-Alexa488 | Azido-$PEG_{12}$-NHS | 135 | 43.3 kDa | Dianthin-EGF-Alexa488-$PEG_{12}$-$N_3$ |

Dianthin-Alexa488-S-S-PEG-$N_3$

Dianthin-Alexa488 (24.5 μg, 0.8 nmol) sodium carbonate solution was placed into a 2 mL reaction tube and azido-$PEG_3$-S-S-NHS (34 μg, 78 nmol) dissolved in 9 μL DMSO was added to the protein solution. The mix was shaken at 800 rpm and 15° C. on a ThermoMixer C (Eppendorf for 12 h. After shaking, the reaction mix was diluted with PBS and was washed with PBS via centrifugal filtration at 4,000 rpm and 4° C. using Amicon Ultra 15 filter with a MWCO of 3 kDa.

Yield: 10.3 μg (39%).

MALDI-TOF-MS (FIG. 38 E) (LP mode): m/z 32.9 kDa ($[M+H]^+$, dianthin-Alexa488-S-S-PEG-$N_3$).

Cy3-PAMAM-Saponin-Toxin Conjugate Synthesis

Procedure is described exemplary for Cy3-PAMAM-$(SO1861)_{27}$-DBCO. Cy3-PAMAM-$(SO1861)_{27}$-DBCO (17 μg, 0.184 nmol) solution in MilliQ water was mixed with a dianthin-EGF-Alexa488-SS-$PEG_3$-$N_3$ (3.6 μg, 0.089 nmol) solution in PBS in a 1.5 mL reaction tube and the reaction mix was shaken at 800 rpm and 15° C. on a ThermoMixer C (Eppendorf) for 2 h. After shaking, small aliquots were taken out for analysis via SODS-PAGE and fluorescence imaging on a Molecular Imager® VersaDoc™ MP 4000 imaging system (Bio-Rad) (FIG. 39).

The synthesis of Cy3-PAMAM-$(SO1861)_5$-S-S-Dianthin-EGF-Alexa488, Cy3-PAMAM-$(SO1861)_{27}$-S-S-Dianthin-EGF-Alexa488, Cy3-PAMAM-NC-$(SO1861)_{17}$-S-S-Dianthin-EGF-Alexa488, Cy3-PAMAM-NC-$(SO1861)_{17}$-S-S-Dianthin-Alexa488, and Cy3-PAMAM-NC-$(SO1861)_{17}$-Dianthin-EGF-Alexa488, have been performed via the above described methodology but differ in the used PAMAM-saponin-DBCO batch, the used azido-toxin batch, and their feed equivalents. The respective feed equivalents of the starting materials are highlighted in Table 21.

TABLE 21

Reaction parameter for Cy3-PAMAM-saponin-toxin synthesis.

| PAMAM-saponin-DBCO batch used | PAMAM-saponin-DBCO feed equivalents | Azido-toxin batch used | Azido-toxin feed equivalents | Resulting conjugate |
|---|---|---|---|---|
| Cy3-PAMAM-$(SO1861)_5$-$(DBCO)_{38}$ | 3 | Dianthin-EGF-Alexa488-S-S-$PEG_3$-$N_3$ | 1 | Cy3-PAMAM-$(SO1861)_5$-S-S-Dianthin-EGF-Alexa488 |
| Cy3-PAMAM-$(SO1861)_{27}$-$(DBCO)_{10}$ | 2.1 | Dianthin-EGF-Alexa488-S-S-$PEG_3$-$N_3$ | 1 | Cy3-PAMAM-$(SO1861)_{27}$-S-S-Dianthin-EGF-Alexa488 |
| Cy3-PAMAM-NC-$(SO1861)_{17}$-$(DBCO)_{30}$ | 2.3 | Dianthin-EGF-Alexa488-S-S-$PEG_3$-$N_3$ | 1 | Cy3-PAMAM-NC-$(SO1861)_{17}$-S-S-Dianthin-EGF-Alexa488 |
| Cy3-PAMAM-NC-$(SO1861)_{17}$-$(DBCO)_{30}$ | 7.1 | Dianthin-Alexa488-S-S-$PEG_3$-$N_3$ | 1 | Cy3-PAMAM-NC-$(SO1861)_{17}$-S-S-Dianthin-Alexa488 |
| Cy3-PAMAM-NC-$(SO1861)_{17}$-$(DBCO)_{30}$ | 2.3 | Dianthin-EGF-Alexa488-$PEG_{12}$-$N_3$ | 1 | Cy3-PAMAM-NC-$(SO1861)_{17}$-Dianthin-EGF-Alexa488 |

Cy3-PAMAM-NC-SO1861 Synthesis Via Reductive Amination Cy3-PAMAM (0.19 mg, 13 nmol) and SO1861 (0.73 mg, 0.39 μmol) were dissolved separately in 200 μL 0.1 M acetate buffer at pH 5. SO1861 and Cy3-PAMAM solutions were mixed and shaken for 20 min at 800 rpm and room temperature on a ThermoMixer C (Eppendorf. After shaking for 20 min, $NaCNBH_3$ (5 mg, 81 μmol) was added to the shaking reaction solution and the reaction mixture was allowed to shake for 12 h at 800 rpm and room temperature on a ThermoMixer C (Eppendorf). After shaking for 12 h, the reaction mix was diluted with MilliQ water and dialyzed extensively for 24 h against MilliQ water using regenerated cellulose membrane tubes (ZelluTrans, Carl Roth) with a MWCO of 12-14 kDa. After dialysis, the Cy3-PAMAM-NC-SO1861 solution was concentrated using centrifugal filtration at 4,000 rpm (15° C.) via Amicon Ultra 15 filters with a MWCO of 3 kDa. The conjugate was stored as solution in the fridge and aliquots were taken for analysis. Yield: not determined MALDI-TOF-MS (FIG. 40 B, C) (LP mode): m/z 88.7 kDa ($[M+H]^+$, Cy3-PAMAM-NC-SO1861), 49.2 kDa ($[M+H]^{2+}$, Cy3-PAMAM-NC-SO1861).

The synthesis of Cy3-PAMAM-NC-$(SO1861)_{30}$, and Cy3-PAMAM-NC-$(SO1861)_{10}$, have been performed via the above described methodology but differed in the time after which the reducing agent $NaCNBH_3$ was added to the reaction batch. The respective time of the $NaCNBH_3$ addition and the respective mass of the conjugates are highlighted in Table 22.

TABLE 22

Reaction parameter Cy3-PAMAM-NC-SO1861 synthesis via reductive amination.

| Time of shaking reaction mix before $NaCNBH_3$ addition | Mass via MALDI-TOF-MS | SO1861 molecules attached per PAMAM | Resulting conjugate |
|---|---|---|---|
| 20 min | 88.8 kDa | ~30 | Cy3-PAMAM-NC-$(SO1861)_{30}$, FIG. 40 C |
| 12 h | 48.0 kDa | ~10 | Cy3-PAMAM-NC-$(SO1861)_{10}$, FIG. 40 B |

Poly(SO1861) Synthesis

SO1861-EMCH (0.13 mg, 63 nmol) was dissolved in 30 μL degassed MilliQ water. APS (0.2 μg, 0.8 nmol) dissolved in 4 μL degassed MilliQ water was added to the SO1861-EMCH solution and the solution was placed into a ThermoMixer C (Eppendorf) at 60° C. Then, TMEDA (cat., 0.5 μL) was added to the mix and the mix was shaken at 800 rpm and 60° C. on a ThermoMixer C (Eppendorf for 2 h. After 2 h, a small aliquot was taken out for analysis via mass spectrometry.

MALDI-TOF-MS (FIG. 42 C) (LP mode): m/z 18.2 kDa ($[M+H]^+$, $poly(SO1861)_9$), 16.0 kDa ($[M+H]^+$, $poly(SO1861)_8$), 14.2 kDa ($[M+H]^+$, $poly(SO1861)_7$), 12.2 kDa ($[M+H]^+$, $poly(SO1861)_6$), 10.2 kDa ($[M+H]^+$, $poly(SO1861)_5$), 8.2 kDa ($[M+H]^+$, $poly(SO1861)_4$), 6.2 kDa ($[M+H]^+$, $poly(SO1861)_3$).

SO1861-EMCH Peptide Coupling

Customized peptide with the sequence SESDDAMFCDAMDESDSK (0.6 mg, 0.3 μmol) and SO1861-EMCH (0.8 mg, 0.39 μmol) were dissolved separately in 200 μL PBS. SO1861-EMCH and peptide solutions were mixed and shaken for 12 h at 800 rpm and room temperature on a ThermoMixer C (Eppendorf). After shaking small aliquots were taken out for analysis. Yield: not determined MALDI- TOF-MS (FIG. 45 B) (RN mode): m/z 4.05 kDa ($[M+H]^-$, peptide-SO1861), 3.92 kDa ($[M+H]^-$, peptide-SO1730), 1.98 kDa ($[M+H]^-$, peptide), 1.86 kDa ($[M+H]^-$, SO1861).

Cell Viability Assay

After treatment the cells were incubated for 72 hr at 37° C. before the cell viability was determined by a MTS-assay, performed according to the manufacturer's instruction (CellTiter 96® AQueous One Solution Cell Proliferation Assay, Promega). Briefly, the MTS solution was diluted 20× in DMEM without phenol red (PAN-Biotech GmbH) supplemented with 10% FBS (PAN-Biotech GmbH). The cells were washed once with 200 μL PBS per well, after which 100 μL diluted MTS solution was added per well. The plate was incubated for approximately 20-30 minutes at 37° C. Subsequently, the optical density at 492 nm was measured on a Thermo Scientific Multiskan FC plate reader (Thermo Scientific). For quantification the background signal of 'medium only' wells was subtracted from all other wells, before the ratio of untreated/treated cells was calculated, by dividing the background corrected signal of untreated wells over the background corrected signal of the treated wells.

FACS Analysis

HeLa cells were seeded in DMEM (PAN-Biotech GmbH) supplemented with 10% fetal calf serum (PAN-Biotech GmbH) and 1% penicillin/streptomycin (PAN-Biotech GmbH), at 500,000 c/plate in 10 cm dishes and incubated for 48 hrs (5% $CO_2$, 37° C.), until a confluency of 90% was reached. Next, the cells were trypsinized (TryplE Express, Gibco Thermo Scientific) to single cells. $0.75\times10^6$ Cells were transferred to a 15 mL falcon tube and centrifuged (1,400 rpm, 3 min). The supernatant was discarded while leaving the cell pellet submerged. The pellet was dissociated by gentle tapping the falcon tube on a vortex shaker and the cells were washed with 4 mL cold PBS ($Mg^{2+}$ and $Ca^{2+}$ free, 2% FBS). After washing the cells were resuspended in 3 mL cold PBS ($Mg^{2+}$ and $Ca^{2+}$ free, 2% FBS) and divided equally over 3 round bottom FACS tubes (1 mL/tube). The cells were centrifuged again and resuspended in 200 μL cold PBS ($Mg^{2+}$ and $Ca^{2+}$ free, 2% FBS) or 200 μL antibody solution; containing 5 μL antibody in 195 μL cold PBS ($Mg^{2+}$ and $Ca^{2+}$ free, 2% FBS). APC Mouse IgG1, κ Isotype Ctrl FC (#400122, Biolegend) was used as isotype control, and APC anti-human EGFR (#352906, Biolegend) was used to stain the EGFR receptor, HER2: APC anti-human CD340 (erbB2/HER-2) (324408, Biolegend). CD71: APC anti-human CD71 #334108, Biolegend. Samples were incubated for 30 min at 4° C. on a tube roller mixer. Afterwards, the cells were washed 3× with cold PBS ($Mg^{2+}$ and $Ca^{2+}$ free, 2% FBS) and fixated for 20 min at room temperature using a 2% PFA solution in PBS. Cells were washed 2× with cold PBS, and resuspended in 250-350 μL cold PBS for FACS analysis. Samples were analyzed with a BD FACSCanto II flow cytometry system (BD Biosciences) and FlowJo software.

TABLE 23

Expression levels of EGFR, HER2 and CD71 of various cells

| Cell line | EGFR expression level (MFI) | HER2 expression level (MFI) | CD71 expression level (MFI) |
|---|---|---|---|
| MDA-MB-468 | 1656 | 1 | 186 |
| A431 | 1593 | 10 | 322 |
| CaSki | 481 | 12 | 189 |
| SK-BR-3 | 28 | 1162 | 331 |
| JIMT-1 | 58 | 74 | 107 |
| HeLa | 91 | 7 | 312 |
| A2058 | 1 | 5 | 59 |

Results

Considering available chemical groups for conjugation reactions to the SO1861 molecule, four chemical groups have been identified. The alcohols and diols of the sugar residues, the aldehyde group on the triterpenoid backbone, the carboxylic acid on one of the sugar residues (glucuronic acid), and the alkene group on the triterpenoid backbone as highlighted in FIG. 24.

In view of the pros and cons of each identified chemical group (Table 24), the aldehyde and alcohol groups are best suitable for reversible conjugation reactions, while the alkene and the carboxylic acid (glucuronic acid) are the groups best suitable for irreversible/stable conjugation reactions. The aldehyde group within the molecule structure of SO1861, however, is the most suitable for reversible conjugation reactions over the alcohols. On the one hand, because there is only one aldehyde present in the structure that allows chemoselective reactions. On the other hand, because the aldehyde can perform reversible conjugation reactions with a variety of chemical groups such as amines, hydrazides, and hydroxylamines forming acid-cleavable moieties like imines, hydrazones, and oximes. This factor enables a freedom of choice over the chemical group for the desired reversible conjugation reaction. Contrary, the alcohols are good candidates for reversible conjugation reaction via the formation of acetals and ketals as well, but lack in chemoselectivity since they are present in a large quantity on the glycosidic structure.

For the formation of an irreversible and stable bond the carboxylic acid is the most suitable since it can form amides and esters with the common tools used in peptide chemistry (e.g. reaction with amines via carbodiimide mediated amide formation).

TABLE 24

Functional groups that are available for saponin conjugation reactions

| Functional Group | Pros | Cons |
|---|---|---|
| Alcohol (Diols) | Suitable for reversible acetal/ketal formation<br>Suitable for ester formations with activated carboxylic acids | Acetal/ketal formation without chemoselectivity<br>Ester formation without chemoselectivity |
| Aldehyde | Suitable for chemoselective reversible hydrazone formation with hydrazides<br>Suitable for chemoselective reversible imine formation with amines<br>Suitable for chemoselective reversible oxime formation with hydroxylamines | Not suitable for acetal formation in the presence of unprotected saponin sugar diols |
| Alkene | Suitable for chemoselective irreversible radical reactions | Not suitable for reversible conjugation reactions<br>Not suitable for reactions involving a hydrogenation step |

TABLE 24-continued

| Functional groups that are available for saponin conjugation reactions | | |
|---|---|---|
| Functional Group | Pros | Cons |
| Carboxylic acid | Suitable for chemoselective amide/ester formation with amines and alcohols after activation | Not suitable for reversible conjugation reactions under mild conditions |

Thus, for the development of an endosomal escape enhancing saponin (such as SO1861) a methodology has been established that allows the generation of a non-cleavable and cleavable 'ready to conjugate' saponins (FIG. 25) using the most suitable chemical groups present on SO1861.

For producing non-cleavable 'ready to conjugate' saponins the carboxylic group of SO1861 is activated via a reagent used in peptide coupling chemistry to generate an active ester (e.g. 1-[Bis(dimethylamino)methylene]-1H-1,2,3-triazolo[4,5-b]pyridinium 3-oxide hexafluorophosphate, HATU). The resulting active ester of SO1861 is able to react with amines forming stable amide bonded conjugates (FIG. 25 A).

For producing cleavable 'ready to conjugate' saponins the aldehyde group of SO1861 is reacted with an EMCH (ε-maleimidocaproic acid hydrazide) linker. The hydrazide group of EMCH forms an acid cleavable hydrazone bond with the aldehyde of SO1861. At the same time the EMCH linker presents a maleimide group that is thiol (sulfhydryl group) reactive and thus can be conjugated to thiols (FIG. 25 B).

The maleimide group of SO1861-EMCH performs a rapid and specific Michael addition reaction with thiols and thiol bearing polymeric structures when carried out in a pH range of 6.5-7.5 (FIG. 25 B). In addition, the acid sensitive hydrazone linkage between the SO1861 and EMCH can be utilized to perform saponin release from a scaffold in acidic environment (FIG. 26). Thus, the EMCH linker fulfills both the need for a pH cleavable strategy and a conjugation strategy to a polymeric structure.

Regarding an ideal EMCH spacer length for conjugation to a polymeric structure, computer simulation (PerkinElmer, ChemBio3D, Ver. 13.0.0.3015) shows that the maleimide group on SO1861-EMCH is located at the periphery of the molecule and thus should be accessible for thiol bearing polymeric structures (FIG. 27).

To synthesize the SO1861-EMCH, a strategy has been developed that allows the conversion of the aldehyde group on the SO1861 to EMCH (FIG. 28 A). The SO1861-EMCH conjugate was isolated and successfully characterized via nuclear magnetic resonance spectroscopy (see materials and methods section, FIG. 22B) and matrix-assisted laser desorption/ionization time-of-flight mass spectrometry (MALDI-TOF-MS) as shown in FIGS. 28 B and 28 C, and FIG. 23 A.

For testing the pH dependent hydrolysis of the hydrazone bond, SO1861-EMCH was dissolved in an HCl solution at pH 3 and MALDI-TOF-MS spectra were recorded at two different points in time (FIG. 29). As shown on FIGS. 29 A and 29 B, a clear decreasing tendency of the peak at m/z 2070 Da that corresponds to SO1861-EMCH is visible in FIG. 29 B. Since SO1861 is generated during hydrolysis, an increase of the peak at m/z 1861 Da was recorded that accompanied the decreasing tendency at m/z 2070 Da. These results show that the hydrazone bond is responsive towards hydrolysis and gets cleaved even if it is attached on SO1861.

In order to conjugate SO1861-EMCH to a polymeric structure, accessible amines of the polymeric structure are converted into thiols with the aid of the agent 2-iminothiolane. The generated free thiols on the polymeric structure act then as the nucleophile for the thiol-ene Michael-type addition to the maleimide group of SO1861-EMCH (FIG. 30). This developed methodology is suitable for the conjugation of SO1861-EMCH to any available polymeric structure that obtains accessible amine groups and allows furthermore a control over the number of conjugated SO1861 molecules depending on the polymeric structure, respectively.

First proof of concept for conjugation of 'ready-to conjugate saponins' to a polymeric structure was obtained by use of the amine of a protein (poly amino acid scaffold example), bovine serum albumin (BSA). After conjugation, mass spectrometry obtained the corresponding peaks of BSA-SO1861 at m/z~70, ~72, and ~74 kDa (FIG. 31 A). In comparison with the detected mass of BSA with m/z 66 kDa (FIG. 31 B), the obtained masses of BSA-SO1861 correspond to a mixture of BSA-SO1861 conjugates consisting of 2, 3, and 4 SO1861 molecules per BSA.

Next proof of concept for conjugation of 'ready-to conjugate saponins' to a polymeric structure was obtained by the use of the amine bearing generation 5 (G5) dendrimer poly(amidoamine) (PAMAM with covalently coupled red-fluorescent dye (Cy3)). PAMAM-Cy3 was utilized as the polymeric structure for the conjugation to both SO1861-EMCH and SO1861-HATU and served as a model for conjugation of SO1861 to a polymeric structure (FIG. 32).

All accessible amine groups of Cy3-PAMAM were converted into thiols using a 3 fold excess of 2-iminothiolane per Cy3-PAMAM amines followed by the reaction with SO1861-EMCH. Three different feed equivalents (5, 20 and 57) of SO1861-EMCH were used for the three reaction batches. After reaction, the recorded masses of the Cy3-PAMAM-SO1861 conjugates at MALDI-TOF-MS show an increment of the corresponding masses with increasing the SO1861-EMCH feed (FIG. 33). The three different feeds corresponded to an obtained mass of m/z 38.4 kDa, m/z 53.9 kDa and m/z 133.8 kDa for the Cy3-PAMAM-SO1861 conjugates that correspond to 6, 13 and 51 SO1861 molecules attached per PAMAM dendrimer as shown on FIG. 33 B-D.

In another reaction, only a certain number of PAMAM amines were converted into thiols prior to reaction with SO1861-EMCH. Here, two different feed equivalents of 2-Iminothiolane (8 and 32) and two different feed equivalents of SO1861-EMCH (5 and 30) were used, respectively. After reaction, the respective spectra of the Cy3-PAMAM-SO1861 conjugates at MALDI-TOF-MS show peaks at m/z 37.7 kDa (5 feed equivalents of SO1861-EMCH) and at m/z 87.0 kDa (30 feed equivalents of SO1861-EMCH) as shown in FIG. 34. The obtained masses at m/z 37.7 kDa and m/z 87.0 kDa correspond to Cy3-PAMAM-SO1861 conjugates with 5 and 30 SO1861 molecules attached and demonstrate that with this method almost all feed of SO1861-EMCH were conjugated.

For the generation of a non-pH-cleavable saponin conjugate the carboxylic acid of SO1861 was activated with HATU and then reacted with the amines of Cy3-PAMAM forming a pH stable amide bound between Cy3-PAMAM and SO1861. The resulting mass of the conjugate was detected via MALDI-TOF-MS with a mass of m/z 62.3 kDa that corresponds to Cy3-PAMAM-NC-SO1861 (NC=non-cleavable) conjugate with 17.5 SO1861 molecules attached per PAMAM (FIG. 32 B, FIG. 35).

Next, the saponin conjugated scaffolds were conjugated to linking points for a possible conjugation to targeted therapeutics (e.g. targeted toxins) via the so-called strain-promoted alkyne-azide cycloaddition (SPAAC, click chemistry) to obtain a functionalized scaffold. For this reaction, Cy3-PAMAM-SO1861 (FIG. 36 C, D) and Cy3-PAMAM-NC-SO1861 (FIG. 36 B) were conjugated to a heterobifunctional NHS-$PEG_{13}$-DBCO linker that generated a strained alkyne on the conjugates' surface (FIG. 36 A). The NHS (N Hydroxysuccinimide) moiety of the linker reacted with remaining amines of the PAMAM-saponin conjugates forming an amide bond between the scaffold and the linker. The resulting DBCO (dibenzocyclooctyne) moiety on the conjugates is able to perform SPAAC with corresponding azides on the targeted therapeutics.

Dianthin-EGF served as a model targeted toxin and dianthin served as a non-targeted toxin. Both toxins were labeled with Alexa Fluor™ 488 using the tetrafluorophenyl ester (TFP) derivative of the dye. The dye labeled proteins were then conjugated to a heterobifunctional NHS-SS-$PEG_3$-azide linker to obtain the corresponding chemical moiety for the SPAAC to the PAMAM-saponin conjugates. Maldi-TOF-MS measurements showed that one Alexa Fluor™ 488 dye and 9 NHS-SS-$PEG_3$-azide molecules were attached per dianthin-EGF molecule (FIG. 37, FIG. 38). Furthermore, Alexa Fluor™ 488 labeled dianthin-EGF was conjugated to a heterobifunctional NHS-$PEG_{12}$-azide linker that lacked the disulfide bond and would thus generate a non-toxin-cleavable construct.

The Cy3-PAMAM-NC-SO1861-DBCO and Cy3-PAMAM-SO1861-DBCO conjugates were reacted with Alexa Fluor™ 488 labeled azido-toxins to perform a strain-promoted alkyne-azide cycloaddition. The conjugation between the reacting agents was indicated via gel electrophoresis and the co-localization of the fluorescent signals of Cy3 that is only attached on the PAMAM polymer and Alexa Fluor™ 488 that is only attached on the toxins on a polyacrylamide gel after gel electrophoresis (FIG. 39).

As an alternative polymeric structure to the PAMAM dendrimer, a G4-dendron (PFd-G4-Azide-NH-BOC, Polymer Factory) with 16 functional amino end groups and an azido group at the focal point was utilized for the conjugation to SO1861 (FIG. 46). The advantage of using a dendron over a dendrimer is the focal point that the dendron structure is exhibiting. This focal point allows the direct conjugation to a targeted toxin without the need of its post-modification with orthogonal click functions (FIG. 47). As shown in FIG. 47, the dendron underwent the same methodology as described for the PAMAM dendrimer. Briefly, after partial dye labeling and deprotection (FIG. 48), the amino groups of the dendron were converted into thiols using the thiolating reagent 2-iminothiolane followed by conjugation to SO1861-EMCH. For the conjugation to SO1861-EMCH three different feed equivalents of SO1861-EMCH were used. The dendron-SO1861 conjugates were analyzed via MALDI-TOF-MS. As expected, the conjugate species of 1 and 2 SO1861 molecules per dendron molecule were obtained when low SO1861-EMCH feed equivalents of 3 and 10 were used (FIG. 49 B, C). Higher dendron-SO1861 conjugate species of up to 9 SO1861 molecules per dendron were obtained (FIG. 49 A) when using a feed equivalent of 22 SO1861-EMCH molecules per dendron molecule. In further experiments, the saponin functionalized dendron will be conjugated to targeted toxins over its focal point to yield a functionalized scaffold and will be evaluated biologically.

The previous examples demonstrate that a methodology has been developed that allows the conjugation of a determined amount of SO1861 molecules or other endosomal escape enhancer molecules to a polymeric structure for enhanced cytoplasmic delivery of therapeutic substances such as targeted toxins.

To further test other conjugation methodologies of SO1861 to a polymeric structure, the reductive amination pathway was used. For this, the aldehyde group of S1861 was directly conjugated to PAMAM amines forming an imine bound. The imine bond formation was followed a reductive amination step through the addition of the reductive agent sodium cyanoborohydride forming a pH-stable amine bond between SO1861 and PAMAM (FIG. 40 A). Similar to the EMCH and HATU approach, this methodology allows a control over the number of conjugated saponins per polymer as shown on FIG. 40 B, C. Here, PAMAM-saponin conjugates were produced which obtained a number of 10 (FIG. 40 B) and 30 (FIG. 40 C) SO1861 molecules per PAMAM.

Another approach for the development of a SO1861 scaffold among the discussed polymer, and protein approach is the poly(SO1861) approach. The idea of this approach is to generate a polymer that consists of SO1861 molecules only, with pH sensitive cleavable bonds that release the SO1861. In addition, the poly(SO1861) should be able to perform conjugation reactions to toxins and biopolymers. The main goal with this approach is to keep it as simple and cost effective as possible. Since a protocol for the generation of acid cleavable SO1861 has been developed already (SO1861-EMCH approach) it would be interesting to see if it is possible to polymerize the SO1861-EMCH through simple addition of a polymerization initiator without further modifying the SO1861 or identifying other conjugation sites on the SO1861 molecule. In the past, several papers have discussed the polymerization of maleimide groups by using radical initiators which attack the double bond of the maleimide group and thus initiate a radical polymerization along the double bonds of the maleimides (29-31). Since SO1861-EMCH reveals a maleimide group in its structure this group could potentially be explored for radical polymerization reactions to yield a poly(SO1861) with acid cleavable function. If the polymerization reaction has a reasonable reaction time the generated SO1861 polymers could be quenched with a radical quencher that not only quenches the reaction but also generates a functional group for toxin or biopolymer conjugation. Such a reaction scheme is illustrated in FIG. 41. Here, the system of ammonium persulfate (APS) and tetramethylethylenediamine (TMEDA) is shown in an exemplary way as radical generator and aminopropanethiol serves as a model radical quencher. Using aminopropanethiol as a quencher exemplary, the generated amine group could be specifically further modified to a click-able group or being used to directly conjugate the poly(SO1861) to a toxin.

In free radical polymerization the reaction conditions have a huge influence on the polymer properties and the reaction outcome. For instance, temperature, monomer concentration, and initiator concentration play a major role for forming the polymer and have to be fine-tuned according to the desired polymer properties. As radical polymerizations are usually carried out at temperatures above 50° C., the first reactions have been performed at a temperature of 60° C. It was interesting to see if the SO1861-EMCH polymerization can be initiated spontaneously and if APS and TMEDA would have an influence on the polymerization degree. Thus, three reactions have been carried out, using the same SO1861-EMCH concentration, but differ in their APS/TMEDA composition. In the first reaction only the SO1861-EMCH was heated up to 60° C. for 3 h, while the second reaction contained SO1861-EMCH and APS, and the third reaction contained SO1861-EMCH, APS, and TMEDA. (For these experiments the same amount and concentration of starting materials have been used which are mentioned in the Materials and Methods section "Poly(SO1861) synthesis"). The batches have been analyzed via MALDI-TOF-MS as shown on FIG. 42 A-C. Interestingly it has been shown that SO1861-EMCH started to form oligomers consisting of 2, 3, 4, 5, and 6 SO1861 molecules spontaneously when heated up to 60° C. (FIG. 42 A). The addition of $11^{-3}$ equivalents APS at the same temperature had no influence on this trend (FIG. 42 B). When using the initiator system of APS/TMEDA, however, SO1861 oligomers of up to 9 SO1861 molecules with a molecular weight of 18.2 kDa could be detected (FIG. 42 C). In addition, the obtained peaks for the oligomers seemed much bigger in comparison with the peaks in FIGS. 42 A and 42 B, indicating a higher consumption of SO1861-EMCH for this reaction. To further fine-tune the reaction conditions, other initiators such as azo-initiators like 2,2'-azobis[2-methyl-N-(2-hydroxyethyl) propionamide]and azobisisobutyronitrile will be tested, as well as other polymerization techniques such as controlled radical polymerization (atom-transfer radical-polymerization, reversible addition-fragmentation chain transfer, etc). Moreover, another hydrazide linker as a substitute for EMCH could be considered which obtains a functional group (such as an acryl or acrolyol residue) that is more suitable for radical polymerization than the maleimide group.

Another approach for the development of a SO1861 scaffold is the DNA approach. The idea of this approach is to utilize the concept of the so-called DNA-origami (Kolb et al, 2004; Bird et al, 1988). DNA-origami as the polymeric or assembled polymeric structure to conjugate saponins to it, can offer several inherent advantages including stability, scalability, and precise control of the final size and shape of the resulting DNA-saponin scaffold. Since these DNA nanocarriers are comprised of natural DNA, they are biocompatible and do not show toxicity to living cells, and can ease the release of cargo from internal cellular compartments. The multivalency of such a structure can further allow fine-tuning targeting capabilities and high capacity for a variety of payloads such as fluorophores and toxins. Thus, in this approach DNA strands are identified that offer chemical functional groups on the 3' and 5' endings respectively, and that are able to hybridize only in certain wanted areas of the sequence that allow a control over the final shape of the construct. The chemical groups should be utilized to couple saponins, for instance though a thiol-ene reaction between the already developed SO1861-EMCH and a thiol group on one of the 3' and 5' DNA strands. The complementary DNA strand can offer a click function group that can be used for coupling to a targeted toxin. The concept is illustrated in FIG. 43.

A similar approach is imaginable by using a specific peptide sequence instead of DNA strands that is able to bind and release saponins and that can be polymerized forming a large poly(peptide)-like structure. In this approach, a peptide sequence has been identified and purchased that has a length fitting the calculated size of a SO1861-EMCH molecule, that offers a cysteine residue in the middle of the sequence, and that obtains an amine group at both the N-terminus and C-terminus. The cysteine residue can be utilized to conjugate SO1861-EMCH via a thiol-ene reaction of the maleimide group of SO1861-EMCH and the thiol group of the cysteine residue. The two amine groups can be utilized to polymerize the peptide-SO1861 conjugate with a suitable crosslinker as shown on FIG. 44.

Conjugation studies have shown that the conjugation of SO1861-EMCH to the customized peptide (sequence: SESDDAMFCDAMDESDSK) was successful. The peptide that bears a maleimide reactive cysteine in the middle of the sequence and its conjugation to SO1861-EMCH was analyzed via MALDI-TOF-MS (FIG. 45). The MALDI-TOF-MS spectra shows the expected peak for the peptide-SO1861 conjugate at m/z 4053 Da and an additional peak at m/z 3821 Da which is the peptide-SO1861 conjugate of the corresponding saponin-EMCH of S01730. As SO1861-EMCH has been used in slight excess (1.3 equivalents) and no SO1861-EMCH peak was detected after reaction, it can be assumed that the conjugation was quantitative. For starting first polymerization reactions of the peptide-SO1861, disuccinimidyl tartrate will be utilized as the amine reactive cross-linker.

Since the endosomal escape enhancing properties of SO1861 are only exposed at low endosomal pH (<pH5), the scaffold or functionalized scaffold should not contain chemical groups that are able to interfere in acidification of the endosomes and thus block the activity of SO1861.

The amine containing polymeric structures of a G5 PAMAM (128 primary amines as well as approximately 126 tertiary amines) and G4-dendron (16 primary amines) were tested, in order to determine if these molecules inhibit the endosomal escape enhancing capacity of SO1861. Co-administration experiments of PAMAM (native or thiolated) or dendron (native) in combination with dianthin-EGF and various SO1861 concentrations on HeLa cells were performed. As control for the inhibition of endosomal acidification chloroquine was used.

HeLa cells show sufficient EGFR cell surface levels (FIG. 50 A). It is observed that both 'native' PAMAM and chloroquine inhibit the SO1861-mediated endosomal escape of the targeted toxin and subsequent cell killing in Hela cells (FIG. 50 B). PAMAM at 500 nM inhibits even to an equal extent as the endosomal acidification inhibitor chloroquine, while 667 nM dendron has no effect at all. To further address if the inhibitory activity of the 'native' PAMAM is due to the availability of amino groups in PAMAM, the primary amino groups of PAMAM were partially thiolated through reaction with 2-iminothiolane (FIG. 51), resulting in 16 of 128 (FIG. 51 C), 65/128 (FIG. 51 D), and 108/128 (FIG. 51 E) blocked primary amines. It is observed that thiolation of 65 and 108 primary amines overcomes the inhibition of SO1861-mediated endosomal escape, whereas thiolation of up to 16 amines groups still shows the inhibitory effects of SO1861-mediated endosomal escape of the targeted toxin (FIG. 50 C). The primary amino groups of PAMAM were also partially PEGylated through a reaction with mPEG2k-NHS (FIG. 52), resulting in 3 of 128 (FIG. 52 C), 8/128 (FIG. 52 D), and 18/128 (FIG. 52 E) blocked primary amines. Blocking only 3 primary amines by PEGylation is already sufficient to reverse the inhibition of SO1861-mediated endosomal escape (FIG. 51 D). The shielding effect of PEGylation most likely extends beyond the small number of amines that are converted, as PEGylation is known to introduce a hydration layer that can shield off an entire molecule, if a sufficient level is reached.

These results demonstrate that the presence of a certain number of free amino groups on polymeric structures, such as PAMAM, can block endosomal acidification and thus inhibit the endosomal escape activity of SO1861 or other glycosides. When the number of amino groups is lower, as shown for the G4-dendron, or if the amino groups have been shielded, such as thiolation or PEGylation, the inhibitory effect is reversed.

REFERENCES

Weng, A.; Thakur, M.; Beceren-Braun, F.; Bachran, D.; Bachran, C.; Riese, S. B.; Jenett-Siems, K.; Gilabert-Oriol, R.; Melzig, M. F.; Fuchs, H. The toxin component of targeted anti-tumor toxins determines their efficacy increase by saponins. Molecular oncology 2012, 6, 323-332. saponinum album in a synergistic way. Journal of immunotherapy 2009, 32, 713-725.

Sama, S.; Jerz, G.; Schmieder, P.; Joseph, J. F.; Melzig, M. F.; Weng, A. Plant derived triterpenes from *Gypsophila elegans* M.Bieb. enable non-toxic delivery of gene loaded nanoplexes. Journal of Biotechnology 2018, 284, 131-139

Kolb, H. C.; Finn, M. G.; Sharpless, K. B. Click Chemistry: Diverse Chemical Function from a Few Good Reactions. Angewandte Chemie 2001, 40, 2004-2021.

Bird, R. E.; Hardmann, K. D.; Jacobson, J. W.; Johnson, S.; Kaufman, B. M.; Lee, S. M.; Lee, T.; Pope, S. H.; Riordan, G. S.; Whitlow, M. Single-chain antigen-binding proteins. Science 1988, 242, 423-426.

Y Zhang, Z Qu, S Kim, V Shi, B Liao1, P Kraft, R Bandaru, Y Wu, L M Greenberger and I D Horak, Down-modulation of cancer targets using locked nucleic acid (LNA)-based antisense oligonucleotides without transfection, Gene Therapy (2011) 18, 326-333

The invention claimed is:

1. A conjugate comprising a cell-surface molecule targeting molecule and at least one effector moiety and further comprising at least one covalently bound saponin, wherein the at least one saponin is a triterpenoid saponin and/or a bisdesmosidic triterpene saponin belonging to the type of a 12,13-dehydrooleanane with an aldehyde function in position C-23 and comprising a glucuronic acid function in a carbohydrate substituent at the C-3beta-OH group of the saponin, and wherein the cell-surface molecule targeting molecule comprises or consists of an immunoglobulin, at least one binding domain of an immunoglobulin and/or at least one binding fragment of an immunoglobulin, an antibody, an IgG, a molecule comprising or consisting of a Vhh domain or Vh domain, a Fab, an scFv, an Fv, a dAb, an $F(ab)_2$, Fcab fragment, which can bind to the cell-surface molecule, and wherein the at least one effector moiety comprises or consists of any one or more of oligonucleotide, a nucleic acid and a xeno nucleic acid, or selected from any one or more of a vector, a gene, a cell suicide inducing transgene, deoxyribonucleic acid (DNA), ribonucleic acid (RNA), anti-sense oligonucleotide (ASO, AON), short interfering RNA (siRNA), microRNA (miRNA), DNA aptamer, RNA aptamer, mRNA, mini-circle DNA, peptide nucleic acid (PNA), phosphoramidate morpholino oligomer (PMO), locked nucleic acid (LNA), bridged nucleic acid (BNA), 2'-deoxy-2'-fluoroarabino nucleic acid (FANA), 2'-O-methoxyethyl-RNA (MOE), 2'-O,4'-aminoethylene bridged nucleic acid, 3'-fluoro hexitol nucleic acid (FHNA), a plasmid, glycol nucleic acid (GNA) and threose nucleic acid (TNA).

2. The conjugate of claim 1, wherein the at least one saponin is a saponin isolated from any one or more of a *Gypsophila* species and/or a *Saponaria* species and/or an *Agrostemma* species and/or a *Quillaja* species.

3. The conjugate according to claim 1, wherein the at least one saponin is one or more of the saponins selecting from a group consisting of SO1861, SA1657, GE1741, SA1641, QS-7, QS-17, QS-18, QS-21, QS-21A, QS-21 A-api, QS-21 A-xyl, QS-21B, QS-21 B-api, QS-21 B-xyl, QS-7-xyl, QS-7-api, QS-17-api, QS-17-xyl, QS1861, QS1862, Quillajasaponin, Saponinum album, QS-18, Quil-A, Gyp1, gypsoside A, AG1, AG2, S01542, S01584, S01658, S01674, S01832, NP-017777, NP-017778, NP-017774, NP-018110, NP-017772, NP-018109, NP-017888, NP-017889, NP-018108, NP-017674, NP-017810, NP-003881, NP-017676, NP-017677, NP-017706, NP-017705, NP-017773, NP-017775, any of their stereoisomers, and any combinations thereof.

4. The conjugate of claim 1, wherein the cell-surface molecule targeting molecule can bind to CD71.

5. The conjugate of claim 1, wherein the cell-surface molecule targeting molecule comprises or consists of an anti-CD71 antibody.

6. The conjugate of claim 1, wherein the at least one saponin is covalently bound to the cell-surface molecule targeting molecule, via an aldehyde function in the saponin, and/or to the at least one effector moiety, via an aldehyde function in the saponin.

7. The conjugate of claim 1, wherein the at least one saponin is covalently bound to an amino-acid residue of the cell-surface molecule targeting molecule and/or to the at least one effector moiety via said glucuronic acid function.

8. The conjugate of claim 1 wherein the at least one saponin is covalently bound to the cell-surface molecule targeting molecule and to the at least one effector moiety via at least one linker comprising a tri-functional linker to which tri-functional linker both the cell-surface molecule targeting molecule and the at least one effector moiety are bound.

9. The conjugate according to claim 8, wherein the at least one linker comprises at least one cleavable linker, wherein said cleavable linker is subject to cleavage under acidic, reductive, enzymatic or light-induced conditions.

10. The conjugate of claim 1, wherein the at least one saponin is covalently bound i. to a lysine side chain, forming an amide bond, or ii. to a cysteine side chain, forming a thio-ether linkage or a disulphide bond, or both i. and ii.;

wherein the lysine or cysteine is or both are comprised by the cell-surface molecule targeting molecule and the lysine or cysteine is or both are comprised by the at least one effector moiety, and wherein the at least one saponin is either directly bound to the lysine or cysteine or to the both, or is bound via at least one linker.

11. The conjugate of claim 1, wherein the at least one saponin is covalently bound to the cell-surface molecule targeting molecule and/or to the at least one effector moiety via at least one linker, wherein the linker is or comprises a scaffold comprising a polymeric or oligomeric structure and further comprising at least one fourth chemical group for covalently coupling of the scaffold to the cell-surface molecule targeting molecule and/or to the at least one effector moiety.

12. The conjugate according to claim 11, wherein the at least one saponin is covalently bound to the polymeric or oligomeric structure of the scaffold via a cleavable bond wherein the cleavable bond is subject to cleavage under any of acidic conditions, reductive conditions, enzymatic conditions and light-induced conditions.

13. The conjugate according to claim 11, wherein the polymeric or oligomeric structure of the scaffold comprises a linear, branched and/or cyclic polymer, oligomer, dendrimer, dendron, dendronized polymer, dendronized oligomer, a DNA, a polypeptide, poly-lysine, a poly-ethylene glycol, or an assembly of these polymeric or oligomeric structures.

14. The conjugate according to claim 1, wherein the at least one saponin is a defined number of saponins or a defined range of saponins.

15. The conjugate according to claim 1, wherein the conjugate comprises more than one saponin or wherein the conjugate comprises 1-100 saponins, or wherein the conjugate comprises any number of saponins therein between, covalently bound directly to an amino-acid residue of the cell-surface molecule targeting molecule and/or to the at least one effector moiety.

16. The conjugate according to claim 1, wherein the at least one saponin is covalently bound to the cell-surface molecule targeting molecule and to the at least one effector moiety via a tri-functional linker, the tri-functional linker comprising a second chemical group a with at least one saponin covalently bound thereto either directly or via a linker and/or via a scaffold comprising a polymeric or oligomeric structure and a fourth chemical group for covalently coupling of the scaffold to the tri-functional linker, the tri-functional linker further comprising a third chemical group for covalent binding to the cell-surface molecule targeting molecule and comprising a first chemical group for covalent binding to the at least one effector moiety, wherein the cell-surface molecule targeting molecule is bound to the third chemical group and/or the at least one effector moiety is bound to the first chemical group.

17. A pharmaceutical composition comprising the conjugate of claim 1 and a pharmaceutically acceptable excipient and/or a pharmaceutically acceptable diluent.

* * * * *

SEQUENCE LISTING

```
<160> NUMBER OF SEQ ID NOS: 12

<210> SEQ ID NO 1
<211> LENGTH: 16
<212> TYPE: DNA
<213> ORGANISM: Artificial Sequence
<220> FEATURE:
<223> OTHER INFORMATION: Antisense BNA (HSP27) oligo nucleic acid
      sequence

<400> SEQUENCE: 1

ggcacagcca gtggcg                                                     16


<210> SEQ ID NO 2
<211> LENGTH: 18
<212> TYPE: DNA
<213> ORGANISM: Artificial Sequence
<220> FEATURE:
<223> OTHER INFORMATION: UBC primer forward sequence

<400> SEQUENCE: 2

cagccgggat ttgggtcg                                                   18


<210> SEQ ID NO 3
<211> LENGTH: 23
<212> TYPE: DNA
<213> ORGANISM: Artificial Sequence
<220> FEATURE:
<223> OTHER INFORMATION: UBC primer reverse sequence

<400> SEQUENCE: 3

cacgaagatc tgcattgtca agt                                             23


<210> SEQ ID NO 4
<211> LENGTH: 20
<212> TYPE: DNA
<213> ORGANISM: Artificial Sequence
<220> FEATURE:
<223> OTHER INFORMATION: GUSB primer forward sequence

<400> SEQUENCE: 4

tgcgtaggga caagaaccac                                                 20


<210> SEQ ID NO 5
<211> LENGTH: 20
<212> TYPE: DNA
<213> ORGANISM: Artificial Sequence
<220> FEATURE:
<223> OTHER INFORMATION: GUSB primer reverse sequence

<400> SEQUENCE: 5
```

gggaggggtc caaggatttg 20

<210> SEQ ID NO 6
<211> LENGTH: 20
<212> TYPE: DNA
<213> ORGANISM: Artificial Sequence
<220> FEATURE:
<223> OTHER INFORMATION: IMMT primer forward sequence

<400> SEQUENCE: 6
aacccacacc tgcactttca 20

<210> SEQ ID NO 7
<211> LENGTH: 20
<212> TYPE: DNA
<213> ORGANISM: Artificial Sequence
<220> FEATURE:
<223> OTHER INFORMATION: IMMT primer reverse sequence

<400> SEQUENCE: 7
ttttcctgtt gtgcaaggcg 20

<210> SEQ ID NO 8
<211> LENGTH: 20
<212> TYPE: DNA
<213> ORGANISM: Artificial Sequence
<220> FEATURE:
<223> OTHER INFORMATION: EIF2S2 primer forward sequence

<400> SEQUENCE: 8
ccacaagtcg tccgagtagg 20

<210> SEQ ID NO 9
<211> LENGTH: 20
<212> TYPE: DNA
<213> ORGANISM: Artificial Sequence
<220> FEATURE:
<223> OTHER INFORMATION: EIF2S2 primer reverse sequence

<400> SEQUENCE: 9
ggagatgttt gggctgacga 20

<210> SEQ ID NO 10
<211> LENGTH: 20
<212> TYPE: DNA
<213> ORGANISM: Artificial Sequence
<220> FEATURE:
<223> OTHER INFORMATION: HSP27 primer forward sequence

<400> SEQUENCE: 10
gcagtccaac gagatcacca 20

<210> SEQ ID NO 11
<211> LENGTH: 20
<212> TYPE: DNA
<213> ORGANISM: Artificial Sequence
<220> FEATURE:
<223> OTHER INFORMATION: HSP27 primer reverse sequence

<400> SEQUENCE: 11
taaggcttta cttggcggca 20

<210> SEQ ID NO 12
<211> LENGTH: 18
<212> TYPE: PRT

-continued

```
<213> ORGANISM: Artificial Sequence
<220> FEATURE:
<223> OTHER INFORMATION: Customized peptide

<400> SEQUENCE: 12

Ser Glu Ser Asp Asp Ala Met Phe Cys Asp Ala Met Asp Glu Ser Asp
1               5                   10                  15

Ser Lys
```